United States Patent
Whalen et al.

(10) Patent No.: US 12,173,346 B2
(45) Date of Patent: Dec. 24, 2024

(54) ENZYMATIC PROCESS FOR PRODUCTION OF MODIFIED HOP PRODUCTS

(71) Applicant: KALAMAZOO HOLDINGS, INC., Kalamazoo, MI (US)

(72) Inventors: Katie Whalen, Charlottesville, VA (US); Donald Richard Berdahl, Lawton, MI (US); Brian Patrick Buffin, Yakima, WA (US); Matthew Blake Jones, Portage, MI (US); Katrina Williams, Riner, VA (US)

(73) Assignee: KALAMAZOO HOLDINGS, INC., Kalamazoo, MI (US)

( * ) Notice: Subject to any disclaimer, the term of this patent is extended or adjusted under 35 U.S.C. 154(b) by 0 days.

(21) Appl. No.: 18/171,737

(22) Filed: Feb. 21, 2023

(65) Prior Publication Data
US 2023/0313237 A1    Oct. 5, 2023

Related U.S. Application Data

(63) Continuation of application No. 17/147,579, filed on Jan. 13, 2021, now Pat. No. 11,591,625, which is a continuation-in-part of application No. 17/030,636, filed on Sep. 24, 2020, now abandoned, which is a continuation-in-part of application No. 16/583,762, filed on Sep. 26, 2019, now Pat. No. 10,961,550.

(60) Provisional application No. 62/736,555, filed on Sep. 26, 2018.

(51) Int. Cl.
C12P 7/38    (2006.01)

(52) U.S. Cl.
CPC ..................... *C12P 7/38* (2013.01)

(58) Field of Classification Search
CPC ...... C12N 1/20; C12P 7/38; C12P 7/02; C12P 7/26
See application file for complete search history.

(56) References Cited

U.S. PATENT DOCUMENTS

| | | |
|---|---|---|
| 2,433,411 A | 12/1947 | Wallerstein |
| 3,044,879 A | 7/1962 | Koth et al. |
| 5,624,701 A | 4/1997 | Maye et al. |
| 6,738,849 B2 | 5/2004 | Morgan et al. |
| 7,887,256 B2 | 2/2011 | Cimbel |
| 8,426,178 B2 | 4/2013 | Savile et al. |
| 10,961,550 B2 * | 3/2021 | Whalen ............... C12Y 101/01 |
| 11,591,625 B2 * | 2/2023 | Whalen .......... C12Y 101/01184 |
| 2004/0115290 A1 | 6/2004 | Tripp et al. |
| 2013/0177962 A1 | 7/2013 | Savile |
| 2020/0095619 A1 | 3/2020 | Whalen |
| 2021/0010038 A1 | 1/2021 | Whalen et al. |

FOREIGN PATENT DOCUMENTS

| | | |
|---|---|---|
| CN | 108418838 | 8/2018 |
| EP | 0924294 | 6/1998 |
| WO | WO 2004/882697 | 9/2004 |
| WO | WO 2009/029554 | 3/2009 |
| WO | WO 2009/977611 | 5/2009 |
| WO | WO 2011/859486 | 5/2011 |
| WO | WO 2018/02238 | 3/2018 |
| WO | WO 2020/069139 | 4/2020 |
| WO | WO 2021/061915 | 4/2021 |

OTHER PUBLICATIONS

De Keukeleire, Denis, "Fundamentais of beer and hop chemistry", Quimica Nova, 23(1), 2008, pp. 108-112.
Dishionno, Lidia, et al. , "Brewing with prolyi endopeptidase from Aspergillus nigeri the impact of enzymatic treatment on gluten levels, quality attributes and sensory profile", International Journal of Food Science & TECHNOLOGY, 52, Mar. 2017, pp. 1367-1374.
Ghos, Jaques, st el., "Enzymatic release of odourent polyfunctional thiols from cysteine conjugates in hop", 3. Inst. Boox. 2013, 139 (43, 223-227.
Hult, Karl, et al., "Enzyme promiscuity: mechanism and applications", Trends in Biotechnology, vol. 25, No. 5, pp. 231-238.
Haveere, et al., Photochem, Photobiol. Sci., 2884, 3, 854 -858.
International Search Report for PCT/US2019/853117 dated Feb. 4, 2020.
International Search Report for PCT/052019/853170 dated Mar. 23, 2020.
International Search Report for PCT/US2028/852396 dated Mar. 25, 2021,.
Nobeli, Irene, et al., "Protein promiscuity and its implications for biot biotechnology", vol. 27, No. 2, Feb. 2009, pp. 157-167.
Partial International Search Report for PCT/US2019/053170 dated Jan. 29, 2020.
Pozen, Morris, A., "Enzymes in brewing", Industrial and Engineering Chemistry, vol. 26, No. 11, Nov. 1934, pp. 1127-1133.
Praet, Tatiana, et al., "Biotransformations of hop-derived aroma compounds by Saccharomyces cerevisiae upon fermentation", Cerevisia 36, 2012, pp. 125-132.
Redthop product information, Jun. 8, 2020,.
Reduced Isolone product information (https://www.kalsec.com/hop-acids).
Robinson, Peter, K, "Enzymes; principles and biotechnological applications", Essays Biochem. , 59, 2815, pp. 1-43.
Safety Data Sheet for Sodium Borohydride, SIGMA-ALDRICH, Version 6.5, Jan. 2028, pp. 1-38.
Todo, et al., NBAA Tech. Quant., 1986, 33, 91-95.
Verzee, et al., 3. Inst. Brew., 1986, 92, 32-48.

\* cited by examiner

*Primary Examiner* — Tekchand Saidha
(74) *Attorney, Agent, or Firm* — HUESCHEN AND SAGE

(57) ABSTRACT

The present invention relates to a process for producing a beer bittering agent via enzyme catalyzed bioconversion of hop-derived isoalpha acids to dihydro-(rho)-isoalpha acids.

4 Claims, 6 Drawing Sheets
Specification includes a Sequence Listing.

Figure 1. Enzyme catalyzed reduction of a representative epimer of isoalpha acids.

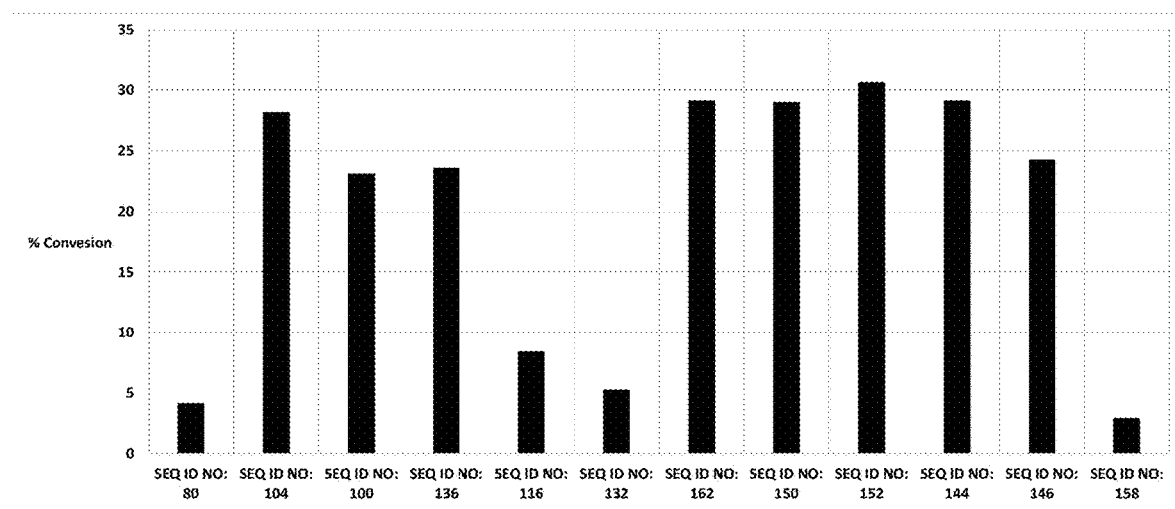
Figure 5 Improved KRED Activity

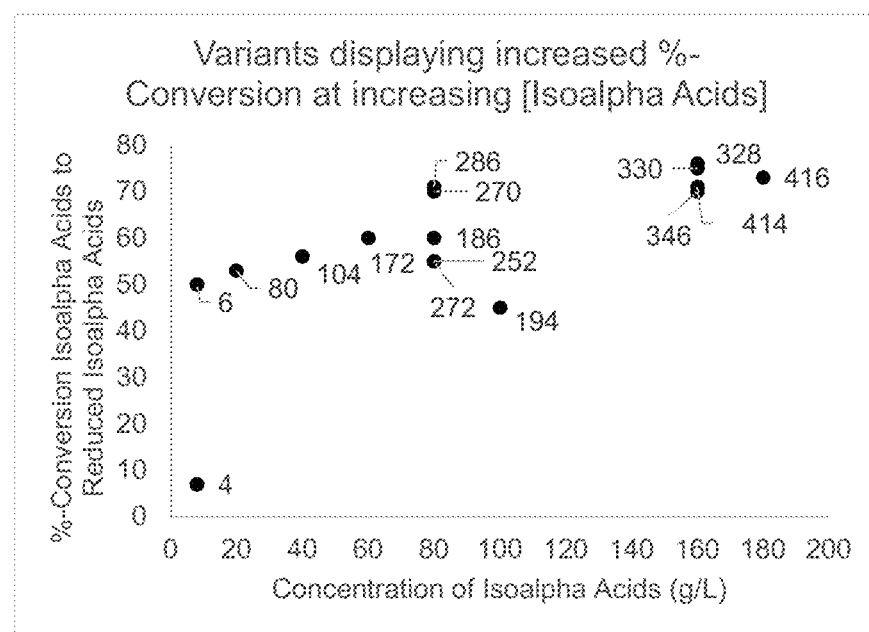
Figure 6 Improved KRED activity compared to SEQ ID NO: 4

ENZYMATIC PROCESS FOR PRODUCTION OF MODIFIED HOP PRODUCTS

REFERENCE TO SEQUENCE LISTING, TABLE OR COMPUTER PROGRAM

The Sequence Listing submitted under 37 CFR § 1.821 in a computer readable form (CRF) via PATENT CENTER as file name KALSEC_75_US_CIP_2_CONT_SEQ_LISTING_XML is herein incorporated by reference. The electronic copy of the Sequence Listing was created on 27 Apr. 2023, with a file size of 725 kilobytes.

FIELD OF THE INVENTION

The present invention relates to a process for producing a beer bittering agent via enzyme catalyzed bioconversion of hop-derived isoalpha acids to dihydro-(rho)-isoalpha acids. Dihydro-(rho)-isoalpha acids have superior characteristics which improve utility as a beverage additive. Consumers may prefer dihydro-(rho)-isoalpha acids produced via this process, which does not require the use of harsh chemical reagents and which utilizes enzymes which may be naturally occurring.

BACKGROUND OF THE INVENTION

Traditional methods of bittering beer use whole fresh hops, whole dried hops, or hop pellets added during the kettle boil. Hop extracts made by extracting hops with supercritical carbon dioxide, or isomerized hop pellets, made by heating hops in the presence of a catalyst are more recent bittering innovations that have also been adopted by brewers. Hop pellets can also be added later in the brewing process and in the case of dry hopping, hops are added to the finished beer prior to filtration. These methods suffer from a poor utilization of the bittering compounds present in the hops, which impacts the cost unfavorably. Beer or other malt beverages produced in this manner are unstable to light and must be packaged in dark brown bottles or cans or placed to avoid the light induced formation of 3-methyl-2-butene-1-thiol (3-MBT) which gives a pronounced light-struck or skunky aroma. Placing bottles in cardboard boxes or completely wrapping them in light-proof or light-filtering paper, foil, or plastic coverings is another expensive method of protecting these beverages from light-struck flavor and aroma.

Bitterness in traditionally brewed beer is primarily derived from isoalpha acids. These compounds are formed during the brewing process by the isomerization of the humulones, which are naturally occurring compounds in the lupulin glands of the hop plant. A consequence of this is, given the natural instability of the isoalpha acids towards photochemical reactions in beer, a beverage prone to the formation of light-struck or skunky flavor and aroma.

Fully light stable beers or other malt beverages can be prepared using so-called advanced or modified hop acids. Beers made using these bittering agents can be packaged in non-colored flint glass bottles without fear of forming skunky aromas. Dihydro-(rho)-isoalpha acids are reduction products of isoalpha acids which are light stable. To date, these compounds have not been found in nature. Traditionally, the portion of the isoalpha acids which is responsible for the photochemistry has been altered by reduction of a carbonyl group using sodium borohydride.

Sodium borohydride is an inorganic compound that can be utilized for the reduction of ketones. It is extremely hazardous in case of skin contact, eye contact, inhalation, or ingestion, with an oral LD50 of 160 mg/kg (rat). Sodium borohydride is also flammable, corrosive, and extremely reactive with oxidizing agents, acids, alkalis, and moisture (*Sodium Borohydride*; MSDS No. S9125; Sigma-Aldrich Co.: Saint Louis, MO Nov. 1, 2015.

Consumers are increasingly expressing a preference for natural materials over synthetic or semi-synthetic ones. Thus, a need exists not only to provide compositions employing natural materials as bittering agents for beer and other beverages, but also processes for more natural production of said materials.

Biocatalytic production is an emerging technology which provides highly selective, safe, clean, and scalable production of high value compounds. Biocatalytic production relies on naturally occurring enzymes to replace chemical catalysts.

Enzymes are naturally occurring proteins capable of catalyzing specific chemical reactions. Enzymes exist in nature that are currently capable of replacing chemical catalysts in the production of modified hop bittering compounds (Robinson, P. K., Enzymes: principles and biotechnological applications. Essays Biochem 2015, 59, 1-41).

Humulone is a natural secondary metabolite that would be exposed to fungi and bacteria cohabitating with the plant, *Humulus lupulus*. It is possible that soil- and plant-dwelling fungi and bacteria possess enzymes capable of modifying humulone for detoxification or scavenging purposes. Additionally, organisms may have evolved enzymes to modify humulone-like molecules, but because of promiscuous activity, these enzymes possess activity against the compounds of interest, isoalpha acids (Hult, K.; Berglund, P., Enzyme promiscuity: mechanism and applications. Trends Biotechnol. 2007, 25 (5), 231-238; Nobeli, I.; Favia, A. D.; Thornton, J. M., Protein promiscuity and its implications for biotechnology. Nat. Biotechnol. 2009, 27 (2), 157-167).

Enzymes which catalyze oxidation/reduction reactions, that is transfer of hydrogen and oxygen atoms or electrons from one substance to another, are broadly classified as oxidoreductases. More specifically, enzymes that reduce ketone groups to hydroxyl groups are known as ketoreductases or carbonyl reductases and depend on the supplementation of an exogenous source of reducing equivalents (e.g. the cofactors NADH, NADPH). Consistent with the existing naming of the enzymes characterized herein, the enzymes will be referred to as a "ketoreductases".

The cost of expensive cofactors (NADH, NADPH) can be reduced by including additional enzymes and substrates for cofactor recycling, for example glucose dehydrogenase and glucose, or by utilizing a ketoreductase that is also capable of oxidizing a low-cost and natural feedstock, such as ethanol.

Abundant precedence exists for the utility of enzymes in brewing and their favorable influence on the final character of beer (Pozen, M., Enzymes in Brewing. Ind. Eng. Chem, 1934, 26 (11), 1127-1133). The presence of yeast enzymes in the natural fermentation of beer is known to produce compounds that affect the flavor and aroma of the final beverage (Praet, T.; Opstaele, F.; Jaskula-Goiris, B.; Aerts, G.; De Cooman, L., Biotransformations of hop-derived aroma compounds by *Saccharomyces cerevisiae* upon fermentation. Cerevisia, 2012, 36, 125-132). Exogenously added enzymes provide a variety of improvements to the brewing process, such as reduced viscosity, increased fermentable sugars, chill-proofing and clarification (Wallerstein, L. (1947) Bentonite and Proteolytic Enzyme Treatment of Beer, U.S. Pat. No. 2,433,411; Ghionno, L.; Marconi, O.; Sileoni, V.; De Francesco, G.; Perretti, G., Brewing with prolyl endopeptidase from *Aspergillus niger*: the impact of enzymatic treatment on gluten levels, quality attributes, and sensory profile. Int. J. Food Sci. Technol, 2017, 52 (6), 1367-1374). Additionally, hop extracts have been specifically pretreated with enzymes for modifying hop-derived aroma compounds (Gros, J.; Tran, T. T. H.; Collin, S., Enzymatic release of odourant polyfunctional thiols from cysteine conjugates in hop. J. Inst. Brew. 2013, 119 (4), 221-227).

Prior to the present invention, however, enzymes capable of catalyzing the reduction of isoalpha acids to dihydro-(rho)-isoalpha acids have not been observed in nature, and thus have not been described in the literature. The process disclosed herein represents a novel enzymatic reaction.

OBJECT OF THE INVENTION

It is an object of the present invention to provide a process for enzymatic production of dihydro-(rho)-isoalpha acids, a modified version of natural bittering agents derived from the hop plant. The present process is designed to replace current production processes which utilize the chemical reagent, sodium borohydride.

SUMMARY OF THE INVENTION

The present invention relates to a process that can be scaled up to industrial levels for bioconversion of iso-alpha acids into dihydro-(rho)-isoalpha acids, which can then be used as a naturally derived and light stable bittering agent in beverages.

One aspect of the present invention is a process for the high-yield bioconversion of iso-alpha acids into dihydro-(rho)-isoalpha acids utilizing a ketoreductase enzyme or a microorganism expressing a gene that encodes said ketoreductase.

A further aspect of the invention relates to such a process for production of dihydro-(rho)-isoalpha acids, wherein the process is carried out in an aqueous system with mild temperature and pH conditions, making it an environmentally benign manufacturing process.

In an embodiment of the invention, bioconversion of isoalpha acids to dihydro-(rho)-isoalpha acids comprises the addition of purified ketoreductase enzyme and NADPH or NADP to a mixture of isoalpha acids followed by incubation until the desired yield is obtained.

In another embodiment of the invention, bioconversion of isoalpha acids to dihydro-(rho)-isoalpha acids comprises the addition of purified ketoreductase enzyme and NADPH or NADP to a mixture of isoalpha acids in the presence of isopropanol for cofactor recycling, followed by incubation until the desired yield is obtained.

In a further embodiment of the invention, the concentration of isoalpha acids, i.e. the substrate, is maximized to increase the volumetric productivity of the bioconversion.

In a further embodiment of the invention, the concentration of the cofactor NADPH or NADP in the mixture is minimized to improve the economics of the bioconversion.

In a further embodiment of the invention, the bioconversion is performed in a vessel purged of air with an inert gas such as nitrogen or argon to prevent the formation of degradation products.

In an embodiment of the invention, bioconversion of isoalpha acids to dihydro-(rho)-isoalpha acids comprises the addition of purified ketoreductase enzyme and NADPH or NADP to a mixture of isoalpha acids in the presence of another enzyme (such as glucose dehydrogenase) for cofactor recycling, followed by incubation until the desired yield is obtained.

In another embodiment of the invention, bioconversion of isoalpha acids to dihydro-(rho)-isoalpha acids comprises the addition of a whole cell biocatalyst to a mixture of isoalpha acids followed by incubation until the desired yield is obtained, wherein the whole cell biocatalyst is an immobilized microorganism expressing the gene which encodes a ketoreductase.

In another embodiment of the invention, bioconversion of isoalpha acids to dihydro-(rho)-isoalpha acids comprises the feeding of isoalpha acids to a growing microorganism expressing the gene which encodes a ketoreductase.

In another embodiment of the invention, bioconversion of alpha acids to dihydro-(rho)-isoalpha acids comprises the addition of thermostable ketoreductase enzyme to an extract of alpha acids wherein heat is applied, and the mixture is incubated until the desired yield of dihydro-(rho)-isoalpha acids is achieved.

In another embodiment of the invention, the ketoreductase employed in the process according to the present invention displays a preference for reducing the carbonyl group in the side chain at C (4) of the isoalpha acids, converting the light-sensitive acyloin group to a secondary alcohol, and producing a light-stable isoalpha acid derivative (FIG. 1).

In another embodiment of the invention, the ketoreductase employed in the process according to the present invention advantageously displays minimal or no preference for catalyzing reduction of any one particular member of the six major isoalpha acids: cis-isohumulone, trans-isohumulone, cis-isocohumulone, trans-isocohumulone, cis-isoadhumulone, and trans-isoadhumulone.

In another embodiment of the invention, the ketoreductase employed in the process according to the present invention specifically reduces cis-isohumulone, cis-isocohumulone, and cis-isoadhumulone.

In another embodiment of the invention, the ketoreductase employed in the process according to the present invention specifically reduces trans-isohumulone, trans-isocohumulone, and trans-isoadhumulone.

In another embodiment of the invention, a mixture of 2 or more ketoreductase enzymes displaying the above substrate specificity is employed in the process according to the present invention to reduce a mixture of cis- and trans-isoalpha acids, to their respective dihydroisoalpha acids.

In another embodiment of the invention, a mixture of 2 or more ketoreductase enzymes displaying substrate specificity can be added to a reaction mixture to produce a unique mixture of dihydroisoalpha acids that is distinct from that produced by chemical reducing agents, such as sodium borohydride.

In a further embodiment, the present invention relates to a process as defined above, wherein the commercially available ketoreductase is selected from KRED-P1-B05, KRED-P2-B02, KRED-P2-C02, KRED-P2-C11, KRED-P2-D11, KRED-P2-G03, KRED-P2-G09, KRED-101, KRED-119, KRED-130, KRED-NADH-110, KRED-430, KRED-431, KRED-432, KRED-433, KRED-434, KRED-435, and KRED-436.

A further embodiment of the invention relates to a ketoreductase enzyme which comprises the amino acid sequence of SEQ ID NO: 4, SEQ ID NO: 6, SEQ ID NO: 80, SEQ ID NO: 104, SEQ ID NO: 100, SEQ ID NO: 136, SEQ ID NO:

116, SEQ ID NO: 132, SEQ ID NO: 162, SEQ ID NO: 150, SEQ ID NO: 152, SEQ ID NO: 144, SEQ ID NO: 146 or SEQ ID NO: 158.

A further embodiment of the invention relates to a ketoreductase enzyme which comprises the amino acid sequence of SEQ ID NO: 172, SEQ ID NO: 186, SEQ ID NO: 194, SEQ ID NO: 196, SEQ ID NO: 252, SEQ ID NO: 270, SEQ ID NO: 272, SEQ ID NO: 286, SEQ ID NO: 300, SEQ ID NO: 328, SEQ ID NO: 330, SEQ ID NO: 346, SEQ ID NO: 348, SEQ ID NO: 356, SEQ ID NO: 414, and SEQ ID NO: 416.

In a further embodiment, the present invention relates to a process as defined above, wherein the ketoreductase enzyme comprises the amino acid sequence of SEQ ID NO: 4, SEQ ID NO: 6, SEQ ID NO: 80, SEQ ID NO: 104, SEQ ID NO: 100, SEQ ID NO: 136, SEQ ID NO: 116, SEQ ID NO: 132, SEQ ID NO: 162, SEQ ID NO: 150, SEQ ID NO: 152, SEQ ID NO: 144, SEQ ID NO: 146 or SEQ ID NO: 158.

In a further embodiment, the present invention relates to a process as defined above, wherein the ketoreductase enzyme or microorganism expressing a gene which encodes the ketoreductase enzyme can optionally have one or more differences at amino acid residues as compared to the ketoreductase enzyme which comprises the amino acid sequence of SEQ ID NO: 4, SEQ ID NO: 6, SEQ ID NO: 80, SEQ ID NO: 104, SEQ ID NO: 100, SEQ ID NO: 136, SEQ ID NO: 116, SEQ ID NO: 132, SEQ ID NO: 162, SEQ ID NO: 150, SEQ ID NO: 152, SEQ ID NO: 144, SEQ ID NO: 146 or SEQ ID NO: 158.

In a further embodiment, the present invention relates to a process as defined above, wherein the ketoreductase is 99, 95, 90, 85, 80, 75 or 70 percent homologous to the ketoreductase enzyme which comprises the amino acid sequence of SEQ ID NO: 4, SEQ ID NO: 6, SEQ ID NO: 80, SEQ ID NO: 104, SEQ ID NO: 100, SEQ ID NO: 136, SEQ ID NO: 116, SEQ ID NO: 132, SEQ ID NO: 162, SEQ ID NO: 150, SEQ ID NO: 152, SEQ ID NO: 144, SEQ ID NO: 146 or SEQ ID NO: 158.

In a further embodiment, the present invention relates to a process as defined above, wherein the ketoreductase enzyme comprises the amino acid sequence of SEQ ID NO: 172, SEQ ID NO: 186, SEQ ID NO: 194, SEQ ID NO: 196, SEQ ID NO: 252, SEQ ID NO: 270, SEQ ID NO: 272, SEQ ID NO: 286, SEQ ID NO: 300, SEQ ID NO: 328, SEQ ID NO: 330, SEQ ID NO: 346, SEQ ID NO: 348, SEQ ID NO: 356, SEQ ID NO: 414, or SEQ ID NO: 416.

In a further embodiment, the present invention relates to a process as defined above, wherein the ketoreductase enzyme or microorganism expressing a gene which encodes the ketoreductase enzyme can optionally have one or more differences at amino acid residues as compared to the ketoreductase enzyme which comprises the amino acid sequence of SEQ ID NO: 172, SEQ ID NO: 186, SEQ ID NO: 194, SEQ ID NO: 196, SEQ ID NO: 252, SEQ ID NO: 270, SEQ ID NO: 272, SEQ ID NO: 286, SEQ ID NO: 300, SEQ ID NO: 328, SEQ ID NO: 330, SEQ ID NO: 346, SEQ ID NO: 348, SEQ ID NO: 356, SEQ ID NO: 414, or SEQ ID NO: 416.

In a further embodiment, the present invention relates to a process as defined above, wherein the ketoreductase is 99, 95, 90, 85, 80, 75 or 70 percent homologous to the ketoreductase enzyme which comprises the amino acid sequence of SEQ ID NO: 172, SEQ ID NO: 186, SEQ ID NO: 194, SEQ ID NO: 196, SEQ ID NO: 252, SEQ ID NO: 270, SEQ ID NO: 272, SEQ ID NO: 286, SEQ ID NO: 300, SEQ ID NO: 328, SEQ ID NO: 330, SEQ ID NO: 346, SEQ ID NO: 348, SEQ ID NO: 356, SEQ ID NO: 414, or SEQ ID NO: 416.

BRIEF DESCRIPTION OF THE DRAWINGS

FIG. 5 shows improved KRED Activity of SEQ ID NO: 80, 104, 100, 136, 116, 132, 162, 150, 152, 144, 146 and 158 at High Substrate and low NADP Concentration.

FIG. 6 shows improved KRED activity of SEQ ID NO: 6, SEQ ID NO: 80, SEQ ID NO: 104, SEQ ID NO: 172, SEQ ID NO: 186, SEQ ID NO: 194, SEQ ID NO: 252, SEQ ID NO: 270, SEQ ID NO: 272, SEQ ID NO: 286, SEQ ID NO: 328, SEQ ID NO: 330, SEQ ID NO: 346, SEQ ID NO: 414 and SEQ ID NO: 416 compared to SEQ ID NO: 4 where %-conversion increases at increasing concentrations of isoalpha acids (substrate).

DETAILED DESCRIPTION OF THE INVENTION

Figure 1:
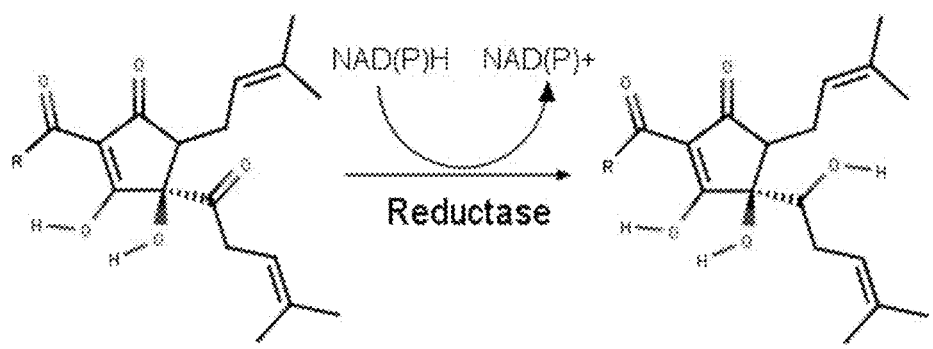
FIG. 1 shows the enzyme catalyzed reduction of a representative epimer of isoalpha acids.

In this invention, a ketoreductase enzyme replaces the function of sodium borohydride and allows a more natural production method for the beverage additive, dihydro-(rho)-isoalpha acids. The enzyme may be any ketoreductase specifically reducing a ketone group to a hydroxy group of any or all isomers of isoalpha acid (co-, n-ad-, and cis/trans-). The enzyme may be derived from, but not limited to, bacteria, fungi, or plants. The enzyme may be cofactor dependent (NADH or NADPH) or independent.

Herein, "isoalpha acids", "hop isoalpha acids", and "hop-derived isoalpha acids" may be used interchangeably.

Isoalpha acid solution is subjected to enzymatic treatment using a purified enzyme or a mixture containing an enzyme and optionally additional enzymes for cofactor recycling. The amount of enzyme depends on the incubation parameters including duration, temperature, amount and concentration of substrate.

Alternatively, an isoalpha acid solution is subjected to enzymatic treatment using a mixture containing a microorganism expressing said enzyme. The invention furthermore provides a process for reducing isoalpha acids according to the invention, which comprises cultivating a ketoreductase-producing microorganism, if appropriate inducing the expression of the ketoreductase. Intact cells can be harvested and added directly to a reaction, in place of isolated enzyme, for the reduction of isoalpha acids as described above. Furthermore, the harvested cells can be immobilized prior to addition to a reduction reaction. The microorganism can be cultivated and fermented by known methods. The microorganism can be bacteria or fungi.

A mixture of cis- and trans-isoalpha acids may be incubated with a single ketoreductase displaying the capacity to reduce both isomers. Alternatively, a mixture of cis- and trans-isoalpha acids may be incubated with 2 or more ketoreductases showing varying specificity where the resulting product is a mixture of cis- and trans-dihydroisoalpha acids.

Alternatively, a solution containing only cis-isoalpha acids may be incubated with a ketoreductase specific for the cis-isomer, and the resulting product is a solution of cis-dihydroisoalpha acids. A solution of only cis-dihydroisoalpha acids may display advantageous bitterness and/or thermal stability properties.

Alternatively, a solution containing only trans-isoalpha acids may be incubated with a ketoreductase specific for the trans-isomer, and the resulting product is a solution of trans-dihydroisoalpha acids. A solution of only trans-dihydroisoalpha acids may display advantageous bitterness properties.

Customized blends of trans- and cis-isoalpha acids may be incubated with 1 or more ketoreductases displaying variable substrate specificity, to produce unique blends of dihydroisoalpha acids otherwise unattainable.

An isoalpha acid mixture may be subjected to an enzymatic reaction using a ketoreductase enzyme in addition to enzymes for catalyzing additional desired modifications, such as but not limited to, dehydrogenases, isomerases, hydratases and lyases. Enzymes of varying activity may be combined in a one pot reaction or added sequentially.

A suitable solvent to use in the enzyme incubation includes water and mixtures of water with another solvent compatible with the enzyme, such as ethanol or isopropanol. Enzymatic activity benefits from buffering of aqueous solutions. Buffering agents include, but are not limited to: tris(hydroxymethyl)aminomethane (aka. Tris), 4-(2-hydroxyethyl) piperazine-1-ethanesulfonic acid (aka. HEPES), sodium phosphate, and potassium phosphate.

The enzyme and isoalpha acids are incubated within a suitable pH range, for example pH 6 to 10, and temperature range, for example 10 to 90° C., and held at this temperature for a sufficient time to convert isoalpha acids to the desired dihydro-(rho)-isoalpha acids yield. Continuous stirring will ensure a constant temperature and exposure of substrate to enzyme. The reaction duration, typically 24 to 48 hours, will depend on the amount and concentration of the enzyme and substrate, solvent present, and temperature chosen.

Enzyme may be free in solution, immobilized onto beads or similar mixable scaffolds, or immobilized onto a film or resin over which a solution of isoalpha acids is passed. The purity level of the enzyme may vary from 30 to 90+% depending on the purification method.

Enzyme may be removed from the final product via physical filtering or centrifugation. Enzyme may also be rendered inactive by extreme temperature or pH and remain in the final product.

As used herein ketoreductase includes commercially available ketoreductases such as KRED-P1-B05, KRED-P2-B02, KRED-P2-C02, KRED-P2-C11, KRED-P2-D11, KRED-P2-G03, KRED-P2-G09, KRED-101, KRED-119, KRED-130, KRED-NADH-110, KRED-430, KRED-431, KRED-432, KRED-433, KRED-434, KRED-435, and KRED-436 (available from Codexis, Inc., Redwood City, CA). The invention also contemplates the foregoing ketoreductase which embody one or more differences in amino acid residues, as well as ketoreductase having 99, 95, 90, 85, 80, 75 and/or 70 percent homology with the foregoing ketoreductases.

The invention also includes ketoreductases purposely produced through known mutagenesis methods displaying variable activity on a single or a mixture of isoalpha acids such as SEQ ID NO: 80, SEQ ID NO: 104, SEQ ID NO: 172, SEQ ID NO: 186, SEQ ID NO: 194, SEQ ID NO: 196, SEQ ID NO: 252, SEQ ID NO: 270, SEQ ID NO: 272, SEQ ID NO: 286, SEQ ID NO: 300, SEQ ID NO: 328, SEQ ID NO: 330, SEQ ID NO: 346, SEQ ID NO: 348 SEQ ID NO: 356, SEQ ID NO: 414, and SEQ ID NO: 416. Some variants are significantly improved in substrate tolerance, temperature tolerance, solvent tolerance, substrate specificity (or lack thereof) and/or turnover compared to commercially available ketoreductases.

As used herein, "percentage of sequence homology," "percent homology," and "percent identical" refer to comparisons between polynucleotide sequences or polypeptide sequences, and are determined by comparing two optimally aligned sequences over a comparison window, wherein the portion of the polynucleotide or polypeptide sequence in the comparison window may comprise additions or deletions (i.e., gaps) as compared to the reference sequence for optimal alignment of the two sequences. The percentage is calculated by determining the number of positions at which either the identical nucleic acid base or amino acid residue occurs in both sequences or a nucleic acid base or amino acid residue is aligned with a gap to yield the number of matched positions, dividing the number of matched positions by the total number of positions in the window of comparison and multiplying the result by 100 to yield the percentage of sequence identity. Determination of optimal alignment and percent sequence homology is performed using the BLAST and BLAST 2.0 algorithms (See e.g., Altschul et al., J. Mol. Biol. 215:403-410 [1990]; and Altschul et al., Nucleic Acids Res. 3389-3402 [1977]). Software for performing BLAST analyses is publicly available through the National Center for Biotechnology Information website.

EXAMPLES

The following examples illustrate the invention without limiting its scope.

Example 1

*E. coli* Expression Hosts Containing Recombinant KRED Genes

Figure 3:
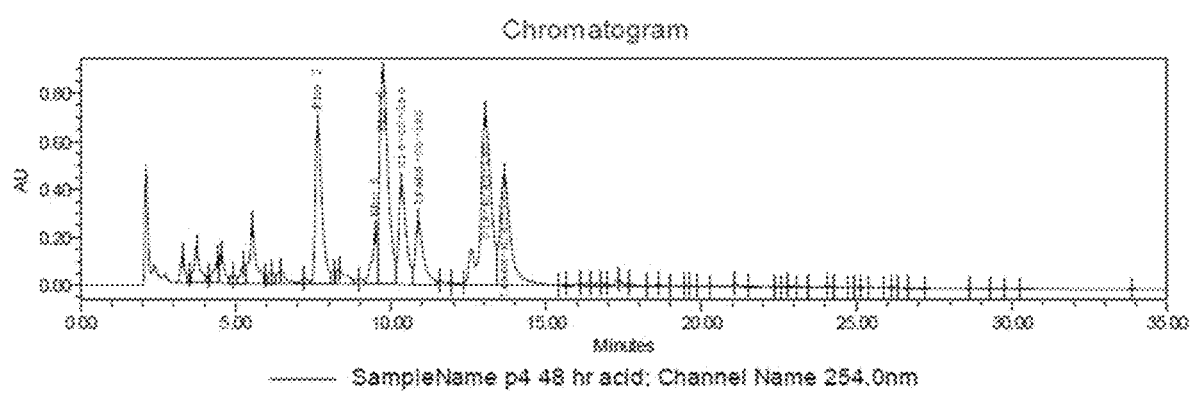
FIG. 3 shows an HPLC chromatogram and peak quantitation for Codexis KRED-P1-B05 (SEQ ID NO: 4) incubated with Isoalpha Acids (acidic solution) for 48 hr at 30° C.

KRED-encoding genes were cloned into the expression vector pCK110900 (See, FIG. 3 of US Pat. Appln. Publn. No. 2006/0195947), operatively linked to the lac promoter under control of the lac1 repressor. The expression vector also contains the P15a origin of replication and a chloramphenicol resistance gene. The resulting plasmids were transformed into *E. coli* W3110, using standard methods known in the art. The transformants were isolated by subjecting the cells to chloramphenicol selection, as known in the art (See e.g., U.S. Pat. No. 8,383,346 and WO2010/144103).

Example 2

Preparation of HTP KRED-Containing Wet Cell Pellets

*E. coli* cells containing recombinant KRED-encoding genes from monoclonal colonies were inoculated into 190 μl Luria-Bertani (LB) broth containing 1% glucose and 30 μg/mL chloramphenicol in the wells of 96-well shallow-well microtiter plates. The plates were sealed with $O_2$-permeable seals, and cultures were grown overnight at 20° C., 200 rpm, and 85% humidity. Then, 20 μl of each of the cell cultures were transferred into the wells of 96-well deep-well plates containing 380 μL Terrific Broth (TB) and 30 μg/mL chloramphenicol (CAM). The deep-well plates were sealed with $O_2$-permeable seals and incubated at 30° C., 250 rpm, and 85% humidity until an $OD_{600}$ of 0.6-0.8 was reached. The cell cultures were then induced by addition of Isopropyl β-d-1-thiogalactopyranoside (IPTG) to a final concentration of 1 mM and incubated overnight under the same conditions as originally used. The cells were then pelleted using centrifugation at 4° C., 4000 rpm for 10 min. The supernatants were discarded, and the pellets frozen at −80° C. prior to lysis.

Example 3

Preparation of HTP KRED-Containing Cell Lysates

First, the cell pellets that were produced as described in Example 2 were lysed by adding 150 μL lysis buffer containing 100 mM pH 8 triethanolamine*$H_2SO_4$ with 2 mM $MgSO_4$ or 100 mM pH 8 Potassium Phosphate with 2 mM $MgSO_4$, 1 g/L lysozyme, and 0.5 g/L polymixin B sulfate (PMBS). Then, the cell pellets were shaken at room temperature for 2 hours on a bench top shaker. The plates were centrifuged at 4000 rpm, for 15 minutes at 4° C. to remove cell debris. The supernatants were then used in biocatalytic reactions to determine their activity levels.

Example 4

Preparation of Lyophilized Lysates from Shake Flask (SF) Cultures

Shake-flask procedures can be used to generate engineered KRED polypeptide shake-flask powders (SFP), which are useful for secondary screening assays and/or use in the biocatalytic processes described herein. Shake flask powder (SFP) preparation of enzymes provides a more purified preparation (e.g., up to 30% of total protein) of the engineered enzyme, as compared to the cell lysate used in high throughput (HTP) assays and also allows for the use of more concentrated enzyme solutions. To start this, selected HTP cultures grown as described above were plated onto LB agar plates with 1% glucose and 30 μg/ml CAM, and grown overnight at 37° C. A single colony from each culture was transferred to 6 ml of LB with 1% glucose and 30 μg/ml CAM. The cultures were grown for 18 h at 30° C. at 250 rpm, and subcultured approximately 1:50 into 250 ml of TB containing 30 μg/ml CAM, to a final $OD_{600}$ of 0.05. The cultures were grown for approximately 3 hours at 30° C. at 250 rpm to an $OD_{600}$ between 0.8-1.0 and induced with 1 mM IPTG. The cultures were then grown for 20 h at 30° C. at 250 rpm. The cultures were centrifuged (4000 rpm for 20 min at 4° C.). The supernatant was discarded, and the pellets were re-suspended in 35 ml of 50 mM pH 8 Potassium Phosphate with 2 mM $MgSO_4$. The re-suspended cells were centrifuged (4000 rpm for 20 min at 4° C.). The supernatant was discarded, and the pellets were re-suspended in 6 ml of 50 mM pH 8 Potassium Phosphate with 2 mM $MgSO_4$, and the cells were lysed using a cell disruptor from Constant Systems (One Shot). The lysates were pelleted (10,000 rpm for 60 min at 4° C.), and the supernatants were frozen and lyophilized to generate shake flask (SF) enzymes.

Example 5

Screening of Commercially Available KRED Enzyme Panel

KRED Screening Assay

Figure 4:
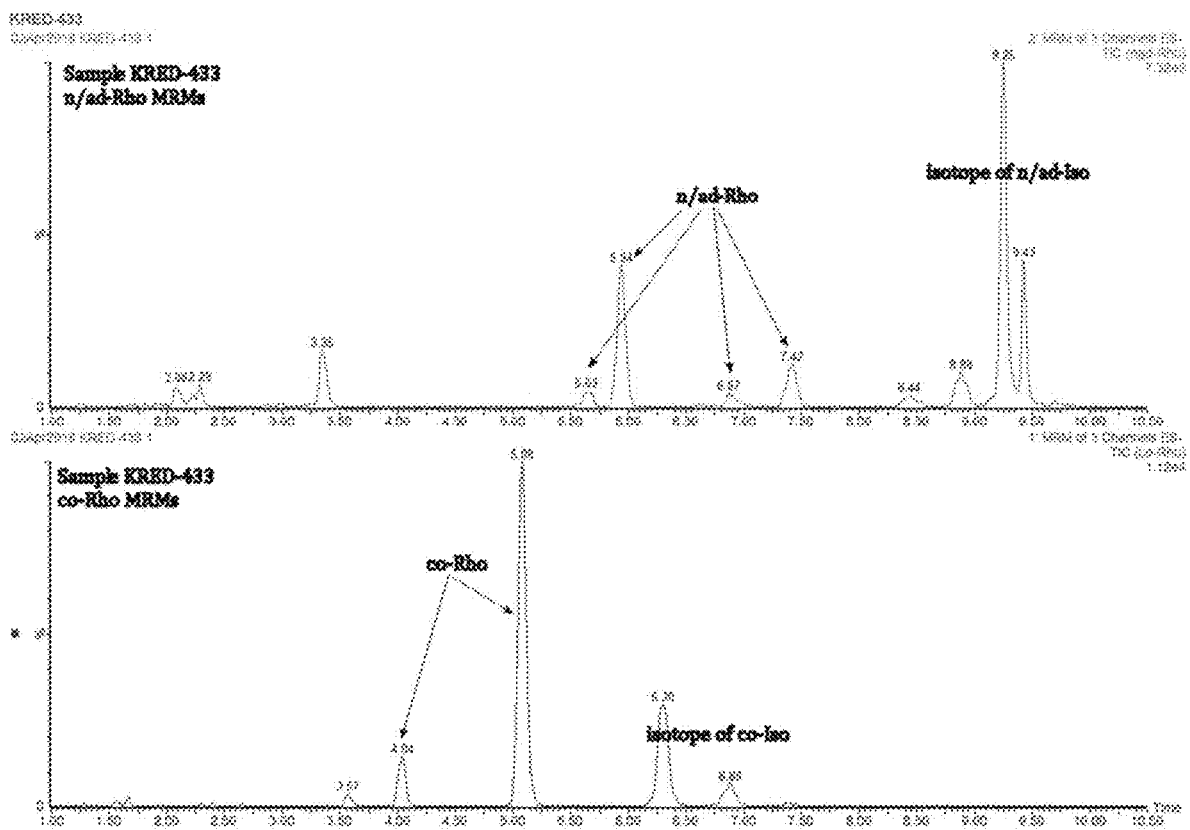
FIG. 4 shows UPLC chromatogram for Codexis KRED-433 incubated with Isoalpha Acids for 24 hr at 30° C.

A set of commercially available ketoreductases were tested for their ability to reduce isoalpha acids using the commercially available "KRED Screening Kits" (Codexis Inc., Redwood City, CA). For a portion of the enzymes in this screening, the enzyme assay was carried out in a 1.5 mL volume tubes, in 1000 μL total volume/tube, which included 10 g/L enzyme powder, 2.9 or 6.9 g/L isoalpha acids substrate, and 0.8 g/L NADP in 30 vol % isopropanol (IPA) in 128 mM pH 7 sodium phosphate with 1.7 mM $MgSO_4$. The tubes were closed and incubated at 30° C. with shaking at 180 rpm for 24-48 hours. The obtained reaction mixture was filtered to remove enzyme using a 10,000 MWCO centrifugal filtration device. Isoalpha acids and dihydro-(rho)-isoalpha acids were quantified by UPLC. See, for example, the chromatogram for Codexis KRED-433 presented in FIG. 4.

For the other portion of the enzymes in this screening, the enzyme assay was carried out in a 1.5 mL volume tubes, in 1000 μL total volume/tube, which included 10 g/L enzyme powder, 1.5 g/L isoalpha acids substrate, 0.8 g/L NADP, 0.7 g/L NAD, 14.4 g/L D-glucose, and 4.3 U/mL glucose dehydrogenase in 263 mM pH 7 sodium phosphate with 1.7 mM $MgSO_4$. The tubes were closed and incubated at 30° C. with shaking at 180 rpm for 24-48 hours. The obtained reaction mixture was filtered to remove enzyme using a 10,000 MWCO centrifugal filtration device. Isoalpha acids and dihydro-(rho)-isoalpha acids were quantified by UPLC.

Ketoreductase Characterization Assay

Ketoreductases that produced detectable quantities of dihydro-(rho)-isoalpha acids were further characterized under various reaction conditions. For this purpose, the enzyme assays were carried out in 2.0 mL volume tubes, in 1000 μL total volume/tube, which included 10-20 g/L enzyme powder, 1.5-6.0 g/L isoalpha acids substrate, 0.8 g/L NADP (optionally, 0.7 g/L NAD, 14.4 g/L D-glucose, 4.3 U/mL glucose dehydrogenase or 30 vol % Isopropanol) in 100-263 mM pH 7-9 sodium phosphate (or alternatively, Tris HCl) with 1.7 mM $MgSO_4$. The tubes were closed and incubated at 30-40° C. with shaking at 180 rpm for 24-48 hours. The obtained reaction mixtures were filtered to remove enzyme. Isoalpha acids and dihydro-(rho)-isoalpha acids were detected by UPLC-MS/MS and HPLC.

Results

KRED Screening Results

Several commercially available enzymes from Codexis' "KRED Screening Kits" are capable of reducing isoalpha acids (Table 1). The original kit was composed of 24 ketoreductases (referred to as KREDs) that have been selected (i.e. natural) or engineered for broad substrate range and enhanced activity by the manufacturer. An additional kit was composed of 7 engineered variants based on the backbone of KRED-130.

TABLE 1

Results from Commercially Available KRED Enzyme Panel

| Ketoreductase Enzyme | Rho Detected?[1] |
|---|---|
| KRED-P1-A04 | − |
| KRED-P1-A12 | − |

TABLE 1-continued

Results from Commercially Available KRED Enzyme Panel

| Ketoreductase Enzyme | Rho Detected?[1] |
|---|---|
| KRED-P1-B02 | − |
| KRED-P1-B05 | + |
| KRED-P1-B10 | − |
| KRED-P1-B12 | − |
| KRED-P1-C01 | − |
| KRED-P1-H08 | − |
| KRED-P2-B02 | + |
| KRED-P2-C02 | + |
| KRED-P2-C11 | + |
| KRED-P2-D03 | − |
| KRED-P2-D11 | + |
| KRED-P2-D12 | − |
| KRED-P2-G03 | + |
| KRED-P2-H07 | − |
| KRED-P3-B03 | − |
| KRED-P3-G09 | + |
| KRED-P3-H12 | − |
| KRED-101 | + |
| KRED-119 | + |
| KRED-130 | + |
| KRED-NADH-101 | − |
| KRED-NADH-110 | + |
| KRED-430 | + |
| KRED-431 | + |
| KRED-432 | + |
| KRED-433 | + |
| KRED-434 | + |
| KRED-435 | + |
| KRED-436 | + |

[1] + = Peaks corresponding to Dihydroisoalpha acids (Rho) observed via UPLC-MS after incubation with enzyme.

Ketoreductase Characterization

Enzymes were determined to reduce isoalpha acids if peaks corresponding to cis/trans-co/ad/n-dihydro-(rho)-isoalpha acid were detected via UPLC at a greater intensity than a control sample lacking enzyme.

Figure 2:
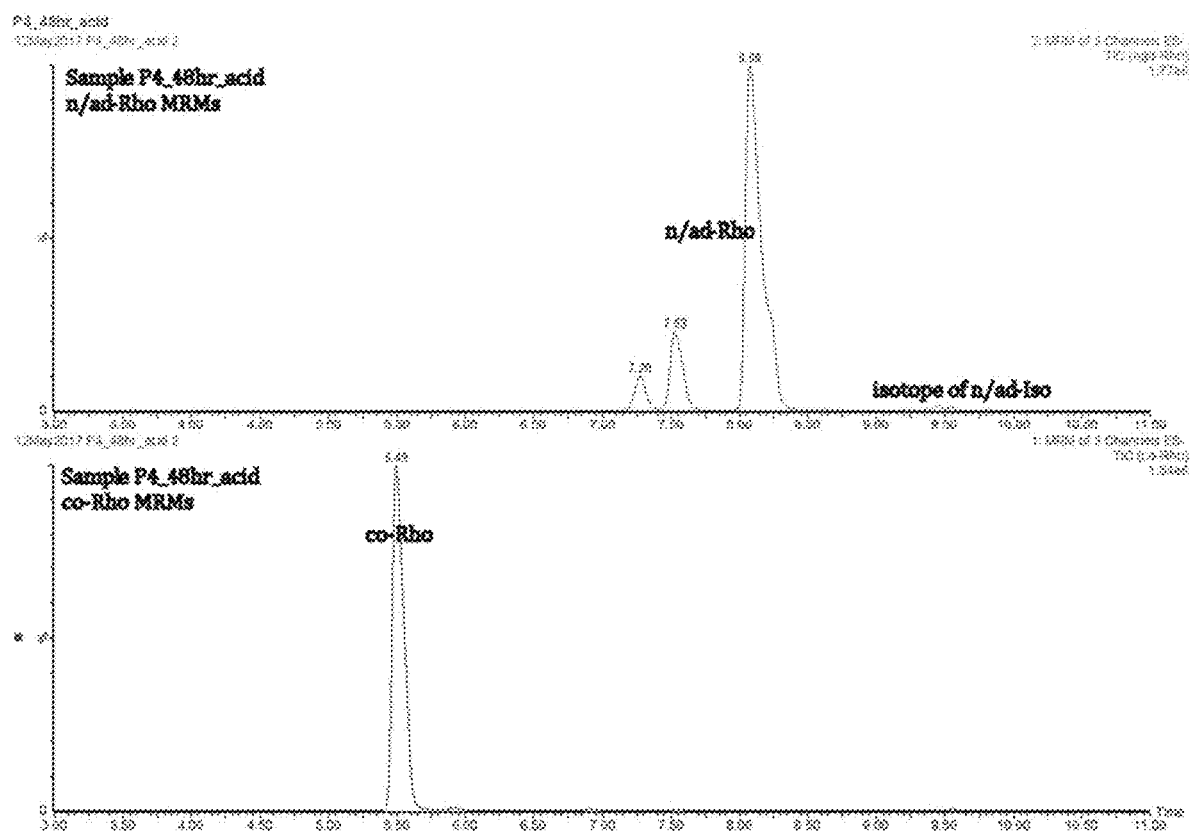
FIG. 2 shows a UPLC chromatogram for Codexis KRED-P1-B05 (SEQ ID NO: 4) incubated with Isoalpha Acids (acidic solution) for 48 hr at 30° C.

KRED-P1-B05 (SEQ ID NO: 4) produced the most dihydro-(rho)-isoalpha acids in a 24 hour period by qualitative comparison of UPLC peak heights (See FIG. 2). KRED-P1-B05 (SEQ ID NO: 4) is derived from an enzyme encoded by a nucleotide (SEQ ID NO: 1) which encodes an amino acid sequence which is a naturally-occurring, wild-type ketoreductase from Lactobacillus kefir (SEQ ID NO: 2). Dihydro-(rho)-isoalpha acids produced by this ketoreductase were present at high enough concentration to be quantified by HPLC. In 24 hour at 30° C., KRED-P1-B05 achieved a yield of 18% dihydro-(rho)-isoalpha acids. The reaction was duplicated with a 48 hour reaction duration, achieving a yield of 42% dihydro-(rho)-isoalpha acids. (See FIG. 3). When the reaction temperature was increased from 30° C. to 37° C. for 48 hours, the yield was 33%.

KRED-P1-B05 activity was initially tested using buffer (128 mM sodium phosphate pH 7 with 1.7 mM magnesium sulfate, 0.8 g/L mM NADP) in addition to 30 vol % isopropanol for cofactor recycling. Multiple reaction conditions (temperature, duration, buffer composition, substrate concentration, etc.) were determined to be adequate for reduction of isoalpha acids.

Substrate Specificity

The ideal ketoreductase for biotransformation purposes shows no substrate specificity for the isohumulone congeners which vary based on side chain composition (conferring n-, ad-, and co-isohumulone). Additionally, the ketoreductase shows no specificity for the isohumulone cis and trans isomers which vary spatially at the C4 tertiary alcohol group proximal to the site of enzymatic reduction. Substrate specificity is dictated by the amino acid sequence and thus the geometry of the substrate binding pocket of an enzyme. Larger binding pockets accommodate larger substrates, as well as a greater variety of substrates, compared to more restricted binding pockets.

Despite the presence of two additional ketone groups on the isoalpha acid molecule, only the desired reduction at the C4 side chain was observed for all characterized ketoreductases.

Example 6

Evolution and Screening of Engineered Polypeptides Derived from SEQ ID NO: 4 for Improved KRED Activity The enzyme of SEQ ID NO: 4 was selected as the parent enzyme based on the results of screening variants for the reduction of the ene-acid substrate. Libraries of engineered genes were produced using well-established techniques (e.g., saturation mutagenesis, and recombination of previously identified beneficial mutations). The polypeptides encoded by each gene were produced in HTP as described in Example 2, and the soluble lysate was generated as described in Example 3.

The engineered polynucleotide of SEQ ID NO: 3 which encodes SEQ ID NO: 4, exhibiting superior KRED activity, was used to generate the further engineered polypeptides of Table 2. These polypeptides displayed improved formation of dihydro-(rho)-isoalpha acids from isoalpha acids, as compared to the starting polypeptide. The engineered polypeptides were generated from the "backbone" amino acid sequence of SEQ ID NO: 4 using directed evolution methods as described above together with the HTP assay and analytical methods described below in Table 2.

TABLE 2

KRED Variant Activity Relative to SEQ ID NO: 4

| SEQ ID NO: (nt/aa) | Percent Conversion Fold Improvement (Relative to SEQ ID NO: 4)[1] |
|---|---|
| 5/6 | ++++ |
| 7/8 | +++ |
| 9/10 | +++ |
| 11/12 | +++ |
| 13/14 | ++ |
| 15/16 | ++ |
| 17/18 | ++ |
| 19/20 | ++ |
| 21/22 | ++ |
| 23/24 | + |
| 25/26 | + |
| 27/28 | + |
| 29/30 | + |
| 31/32 | + |
| 33/34 | + |
| 35/36 | + |
| 37/38 | + |
| 39/40 | + |
| 41/42 | + |
| 43/44 | + |
| 45/46 | + |
| 47/48 | + |
| 49/50 | + |
| 51/52 | + |
| 53/54 | + |
| 55/56 | + |
| 57/58 | + |
| 59/60 | + |
| 61/62 | + |
| 63/64 | + |
| 65/66 | + |

TABLE 2-continued

KRED Variant Activity Relative to SEQ ID NO: 4

| SEQ ID NO:<br>(nt/aa) | Percent Conversion Fold Improvement<br>(Relative to SEQ ID NO: 4)[1] |
|---|---|
| 67/68 | + |
| 69/70 | + |

[1]Levels of increased activity were determined relative to the reference polypeptide of SEQ ID NO: 4 and defined as follows: "+" > 1.0 but <2.0, "++" ≥ 2 but ≤4, "+++" ≥ 4 but ≤8, "++++" ≥ 8

Directed evolution began with the polynucleotide set forth in SEQ ID NO: 3. Engineered polypeptides were then selected as starting "backbone" gene sequences. Libraries of engineered polypeptides were generated using various well-known techniques (e.g., saturation mutagenesis, recombination of previously identified beneficial amino acid differences) and screened using HTP assay and analysis methods that measured the polypeptides ability to convert the isoalpha acids substrates to the desired dihydro-(rho)-isoalpha acids products.

The enzyme assay was carried out in a 96-well format, in 200 UL total volume/well, which included 50% v/v HTP enzyme lysate, 8 g/L isoalpha acids substrate, and 0.1 g/L NADP in 40 vol % isopropanol (IPA) in 100 mM pH 8 triethanolamine*$H_2SO_4$ with 2 mM $MgSO_4$. The plates were sealed and incubated at 40° C. with shaking at 600 rpm for 20-24 hours.

After 20-24 hours, 1000 μL of acetonitrile with 0.1% acetic acid was added. The plates were sealed and centrifuged at 4000 rpm at 4° C. for 10 min. The quenched sample was further diluted 4-5× in 50:50 acetonitrile:water mixture prior to HPLC analysis. The HPLC run parameters are described below in Table 3.

TABLE 3

HPLC Parameters

| Instrument | Agilent 1100 HPLC |
|---|---|
| Column | 30 × 50 mm 2.7 μm Waters XBridge Phenyl column |
| Mobile Phase | A: 0.1% acetic acid in water, B: 0.1% acetic acid in acetonitrile |
| Run parameters | 42:58 A/B for 1 minute; ramp to 10:90 A/B over 1 minute |
| Flow Rate | 1.5 mL/min |
| Run time | 2.0 min |

| Compound | retention time [min] | note |
|---|---|---|
| Peak Retention Times | Iso-1 | 0.6 | mixture of co-Iso isomers |
| | Iso-2 | 0.7 | mixture of n/ad-Iso isomers |
| | Iso-3 | 0.8 | mixture of n/ad-Iso isomers |
| | Rho-1 | 1.0 | mixture of co-Rho isomers |
| | Rho-2 | 1.2 | mixture of n/ad-Rho isomers |
| | Rho-3 | 1.4 | mixture of n/ad-Rho isomers |

| Column Temperature | 50° C. |
|---|---|
| Injection Volume | 10 μL |
| Detection | 260 nm |

Example 7

Evolution and Screening of Engineered Polypeptides Derived from SEQ ID NO: 6 for Improved KRED Activity Libraries of engineered genes were produced using well-established techniques (e.g., saturation mutagenesis, and recombination of previously identified beneficial mutations). The polypeptides encoded by each gene were produced in HTP as described in Example 2, and the soluble lysate was generated as described in Example 3.

The engineered polynucleotide of SEQ ID NO: 5, which encodes the polypeptide of SEQ ID NO: 6, exhibiting superior KRED activity, was used to generate the further engineered polypeptides of Table 4. These polypeptides displayed improved formation of dihydro-(rho)-isoalpha acid from isoalpha acids as compared to the starting polypeptide. The engineered polypeptides were generated from the "backbone" amino acid sequence of SEQ ID NO: 6 using directed evolution methods as described above together with the HTP assay and analytical methods described in Table 3.

TABLE 4

KRED Variant Activity Relative to SEQ ID NO: 6

| SEQ ID NO:<br>(nt/aa) | Percent Conversion Fold Improvement<br>(Relative to SEQ ID NO: 6)[1] |
|---|---|
| 71/72 | ++++ |
| 73/74 | +++ |
| 75/76 | +++ |
| 77/78 | +++ |
| 79/80 | +++ |
| 81/82 | ++ |
| 83/84 | ++ |
| 85/86 | + |
| 87/88 | + |
| 89/90 | + |
| 91/92 | + |
| 93/94 | + |
| 95/96 | + |
| 97/98 | + |

[1]Levels of increased activity were determined relative to the reference polypeptide of SEQ ID NO: 6 and defined as follows: "+" > 1.0 but <2.0, "++" ≥ 2 but ≤4, "+++" ≥ 4 but ≤8, "++++" ≥ 8

Directed evolution began with the polynucleotide set forth in SEQ ID NO: 5. Engineered polypeptides were then selected as starting "backbone" gene sequences. Libraries of engineered polypeptides were generated using various well-known techniques (e.g., saturation mutagenesis, recombination of previously identified beneficial amino acid differences) and screened using HTP assay and analysis methods that measured the polypeptides ability to convert the isoalpha acid substrates to the desired dihydro-(rho)-isoalpha acid products.

The enzyme assay was carried out in a 96-well format, in 200 μL total volume/well, which included 50% v/v HTP enzyme lysate, 16 or 40 g/L of isoalpha acids substrate, and 0.1 g/L NADP in 40 vol % isopropanol (IPA) in 100 mM pH 8 triethanolamine*$H_2SO_4$ with 2 mM $MgSO_4$. The plates were sealed and incubated at 40° C. with shaking at 600 rpm for 20-24 hours.

After 20-24 hours, 1000 μL of acetonitrile with 0.1% acetic acid was added. The plates were sealed and centrifuged at 4000 rpm at 4° C. for 10 min. The quenched sample was further diluted 10-20× in 50:50 acetonitrile:water mixture prior to HPLC analysis. The HPLC run parameters are described in Table 3.

Example 8

Evolution and Screening of Engineered Polypeptides Derived from SEQ ID NO: 80 for Improved KRED Activity Libraries of engineered genes were produced using well-established techniques (e.g., saturation mutagenesis, and recombination of previously identified beneficial mutations). The polypeptides encoded by each gene were produced in HTP as described in Example 2, and the soluble lysate was generated as described in Example 3.

The engineered polynucleotide of SEQ ID NO: 79, which encodes the polypeptide of SEQ ID NO: 80, exhibiting superior KRED activity, was used to generate the further engineered polypeptides of Table 5. These polypeptides displayed improved formation of dihydro-(rho)-isoalpha acids from isoalpha acids as compared to the starting polypeptide. The engineered polypeptides were generated from the "backbone" amino acid sequence of SEQ ID NO: 80 using directed evolution methods as described above together with the HTP assay and analytical methods described below in Table 3.

TABLE 5

KRED Variant Activity Relative to SEQ ID NO: 80

| SEQ ID NO: (nt/aa) | Percent Conversion Fold Improvement (Relative to SEQ ID NO: 80)[1] |
|---|---|
| 99/100 | ++++ |
| 101/102 | ++++ |
| 103/104 | +++ |
| 105/106 | +++ |
| 107/108 | +++ |
| 109/110 | +++ |
| 111/112 | +++ |
| 113/114 | ++ |
| 115/116 | ++ |
| 117/118 | ++ |
| 119/120 | ++ |
| 121/122 | ++ |
| 123/124 | ++ |
| 125/126 | ++ |
| 127/128 | ++ |
| 129/130 | + |
| 131/132 | + |
| 133/134 | + |
| 135/136 | + |
| 137/138 | + |
| 139/140 | + |
| 141/142 | + |

Directed evolution began with the polynucleotide set forth in SEQ ID NO: 79. Engineered polypeptides were then selected as starting "backbone" gene sequences. Libraries of engineered polypeptides were generated using various well-known techniques (e.g., saturation mutagenesis, recombination of previously identified beneficial amino acid differences) and screened using HTP assay and analysis methods that measured the polypeptides ability to convert the isoalpha acid substrates to the desired dihydro-(rho)-isoalpha acid products.

The enzyme assay was carried out in a 96-well format, in 200 μL total volume/well, which included 25% v/v HTP enzyme lysate, 60 or 80 g/L of isoalpha acid substrate, and 0.02 g/L NADP in 40 vol % isopropanol (IPA) in 100 mM pH 8 potassium phosphate with 2 mM MgSO$_4$. The plates were sealed and incubated at 45° C. with shaking at 600 rpm for 20-24 hours.

After 20-24 hours, 1000 μL of acetonitrile with 0.1% acetic acid was added. The plates were sealed and centrifuged at 4000 rpm at 4° C. for 10 min. The quenched sample was further diluted 20-40× in 50:50 acetonitrile:water mixture prior to HPLC analysis. The HPLC run parameters are described in Table 3.

Example 9

Evolution and Screening of Engineered Polypeptides Derived from SEQ ID NO: 80 for Improved KRED Activity at High Substrate Concentration Libraries of engineered genes were produced using well-established techniques (e.g., saturation mutagenesis, and recombination of previously identified beneficial mutations). The polypeptides encoded by each gene were produced in HTP as described in Example 2, and the soluble lysate was generated as described in Example 3.

The engineered polynucleotide of SEQ ID NO: 79, which encodes the polypeptide of SEQ ID NO: 80, exhibiting superior KRED activity, was used to generate the further engineered polypeptides of Table 6. These polypeptides displayed improved formation of dihydro-(rho)-isoalpha acids from isoalpha acids as compared to the starting polypeptide. The engineered polypeptides were generated from the "backbone" amino acid sequence of SEQ ID NO: 80 using directed evolution methods as described above and are described below in Table 3.

TABLE 6

KRED Variant Activity Relative to SEQ ID NO: 80

| SEQ ID NO: (nt/aa) | Percent Conversion Fold Improvement (Relative to SEQ ID NO: 80)[1] |
|---|---|
| 143/144 | ++++ |
| 145/146 | ++++ |
| 147/148 | ++++ |
| 149/150 | ++++ |
| 99/100 | ++++ |
| 151/152 | +++ |
| 153/154 | +++ |
| 155/156 | +++ |
| 103/104 | ++ |
| 157/158 | ++ |
| 159/160 | ++ |
| 139/140 | + |
| 161/162 | + |

Directed evolution began with the polynucleotide set forth in SEQ ID NO: 79. Engineered polypeptides were then selected as starting "backbone" gene sequences. Libraries of engineered polypeptides were generated using various well-known techniques (e.g., saturation mutagenesis, recombination of previously identified beneficial amino acid differences) and screened using HTP assay and analysis methods that measured the polypeptides ability to convert the isoalpha acid substrates to the desired dihydro-(rho)-isoalpha acid products.

The enzyme assay was carried out in a 96-well format, in 200 μL total volume/well, which included 10-20% v/v HTP enzyme lysate, 80 or 160 g/L of isoalpha acid substrate, and 0.02 g/L NADP in 40 vol % isopropanol (IPA) in 100 mM pH 8 potassium phosphate with 2 mM MgSO$_4$. The plates were sealed and incubated at 45° C. with shaking at 600 rpm for 20-24 hours.

After 20-24 hours, 1000 μL of acetonitrile with 0.1% acetic acid was added. The plates were sealed and centrifuged at 4000 rpm at 4° C. for 10 min. The quenched sample was further diluted 20-40× in 50:50 acetonitrile:water mixture prior to HPLC analysis. The HPLC run parameters are described in Table 3.

Example 10

Evolution and Screening of Engineered Polypeptides Derived from SEQ ID NO: 80, 104, 100, 136, 116, 132, 162, 150, 152, 144 and 146 for Improved KRED Activity at High Substrate and Low NADP Concentration A 200 g/L enzyme stock solution was prepared by dissolving 100 mg of enzyme powder in 500 µL of 100 mM pH 8 potassium phosphate buffer with 2 mM $MgSO_4$ and 0.1 g/L of NADP. To a well in a 96 deep-well plate was added 40 µL of the enzyme/NADP stock solution, 80 µL of isopropanol, and 80 µL of 40 wt % aqueous solution of isoalpha acid. The final reaction composition was 40 g/L of enzyme, 160 g/L isoalpha acid, and 0.02 g/L NADP in 40% IPA. The plate was sealed and incubated 40° C. for 24 h and then quenched and analyzed by HPLC-UV. The data are shown in Table 7 and FIG. 5.

TABLE 7

KRED Activity at High Substrate and Low NADPH Concentration

| SEQ ID NO: | % Conversion | | | | | |
|---|---|---|---|---|---|---|
| (nt/aa) | 40 g/L | 20 g/L | 10 g/L | 5 g/L | 2.5 g/L | 1.25 g/L |
| 79/80 | 4.2 | 1.9 | 0.9 | 0.5 | 0.1 | 0.0 |
| 103/104 | 28.2 | 16.5 | 8.7 | 5.2 | 2.2 | 1.2 |
| 99/100 | 23.1 | 11.2 | 6.1 | 3.3 | 1.3 | 0.6 |
| 135/136 | 23.6 | 7.5 | 2.4 | 1.2 | 0.6 | 0.0 |
| 115/116 | 8.5 | 3.2 | 1.2 | 0.7 | 0.2 | 0.0 |
| 131/132 | 5.3 | 2.2 | 0.8 | 0.4 | 0.1 | 0.0 |
| 161/162 | 29.1 | 14.4 | 5.6 | 2.1 | 0.7 | 0.3 |
| 149/150 | 29.0 | 14.9 | 6.0 | 2.4 | 1.0 | 0.2 |
| 151/152 | 30.6 | 17.9 | 7.4 | 3.6 | 2.0 | 1.2 |
| 143/144 | 29.1 | 14.4 | 5.8 | 2.4 | 1.2 | 0.4 |
| 145/146 | 24.3 | 12.3 | 4.7 | 1.9 | 0.8 | 0.1 |
| 157/158 | 3.0 | 1.1 | 0.4 | 0.0 | 0.0 | 0.0 |

Example 11

Enzyme Treatment of Acidified Hop Derived Isoalpha Acids with Cofactor Recycling by Isopropanol Oxidation Isoalpha acids are treated in a manner described in Example 10, where the source of isoalpha acids is a highly concentrated material (68.9% isoalpha acids) having a pH<7.

Example 12

Enzyme Treatment of Hop Derived Isoalpha Acids with Cofactor Recycling by Glucose Dehydrogenase Isoalpha acids are treated in a manner described in Example 10, with the exception that isopropanol is replaced with 4.3 U/mL Glucose Dehydrogenase, 0.7 g/L mM NAD, and 14.4 g/L D-glucose.

Example 13

Enzyme Treatment of Hop Derived Isoalpha Acids without Cofactor Recycling

Isoalpha acids are treated in a manner described in Example 10, with the exception that isopropanol is replaced with an equimolar amount of NADPH as substrate.

Example 14

Enzyme Treatment of Hop Derived Isoalpha Acids with Cofactor Recycling by Ethanol Oxidation Isoalpha acids are treated in a manner described in Example 10, with the exception that isopropanol is replaced with ethanol.

Example 15

Enzyme Treatment of Hop Derived Isoalpha Acids with Immobilized Ketoreductase Via SiO2

A ketoreductase is adsorbed on SiO2 and crosslinked with glutaraldehyde to yield an immobilized ketoreductase material. Isoalpha acids are treated with the immobilized ketoreductase in a manner described in Example 10. The obtained reaction mixture is centrifuged at 10,000 g to remove immobilized enzyme.

Example 16

Enzyme Treatment of Hop Derived Isoalpha Acids with Immobilized Ketoreductase Via DEAE-Cellulose A ketoreductase is crosslinked with glutaraldehyde and adsorbed onto DEAE-cellulose to yield an immobilized ketoreductase material. Isoalpha acids are treated with the immobilized ketoreductase in a manner described in Example 10. The obtained reaction mixture is centrifuged at 10,000 g to remove immobilized enzyme.

Example 17

Enzyme Treatment of Hop Derived Isoalpha Acids with Immobilized Ketoreductase Via PEI-Treated Alumina A ketoreductase is crosslinked with glutaraldehyde and adsorbed onto polyethylimine (PEI)-treated alumina to yield an immobilized ketoreductase material. Isoalpha acids are treated with the immobilized ketoreductase in a manner described in Example 10. The obtained reaction mixture is centrifuged at 10,000 g to remove immobilized enzyme.

Example 18

Enzyme Treatment of Hop Derived Isoalpha Acids with NADH Cofactor Recycling

Enzyme treatment where the NADPH cofactor is substituted with NADH. Isoalpha acids are treated in a manner described in Example 10 but the NADP is replaced with NAD.

Example 19

Enzyme Treatment of Hop Derived Isoalpha Acids Followed by Extraction

Enzyme treatment followed by extraction to increase final concentration of dihydro-(rho)-isoalpha acids is performed. Isoalpha acids are treated in a manner described in Example 10. The obtained reaction mixture is filtered to remove enzyme and extracted with food-grade solvent to achieve a desired concentration of dihydro-(rho)-isoalpha acids.

Example 20

Enzyme Treatment of Hop Derived Isoalpha Acids Followed by Thermal Inactivation

Isoalpha acids are treated in a manner described in Example 10. The reaction is incubated at 30° C. with orbital shaking at 180 rpm for 24 hours. The obtained reaction mixture is heated at 80-100° C. for 10-30 minutes to inactivate enzyme.

Example 21

Enzyme Treatment of Hop Derived Isoalpha Acids Followed by Chemical Inactivation Isoalpha acids are treated in a manner described in Example 10. The reaction is incubated at 30° C. with orbital shaking at 180 rpm for 24 hours. Food-grade ethanol is added to a final concentration of >50% to inactivate enzyme.

Example 22

Enzyme Treatment of Hop Derived Isoalpha Acids with Immobilized Ketoreductase Recycling A ketoreductase is crosslinked with glutaraldehyde and adsorbed onto DEAE-cellulose to yield an immobilized ketoreductase material. Isoalpha acids are then treated with the immobilized ketoreductase in a manner described in Example 10. The obtained reaction mixture is centrifuged at 10,000 g to separate immobilized ketoreductase from the reaction solution. Immobilized ketoreductase is recovered, washed with water or aqueous buffer, and re-used in a new reaction mixture.

Example 23

Isoalpha Acids Reduction using Engineered Polypeptides Derived from SEQ ID NO: 80, 104, 172, 186, 194, 196, 252, 270, 272, 286, 300, 328, 330, and 346 at High Substrate and Low NADP Concentration Libraries of engineered genes were produced using well-established techniques (e.g., saturation mutagenesis, and recombination of previously identified beneficial mutations). The polypeptides encoded by each gene were produced in HTP as described in Example 2, and the soluble lysate was generated as described in Example 3e.

The engineered polynucleotide of SEQ ID NO: 103, which encodes the polypeptide of SEQ ID NO: 104, exhibiting superior KRED activity, was used to generate the further engineered polypeptides of Table 8. These polypeptides displayed improved formation of dihydro-(rho)-isoalpha acid from isoalpha acids as compared to the starting polypeptide. The engineered polypeptides were generated from the "backbone" amino acid sequence of SEQ ID NO: 104 using directed evolution methods as described above together with the HTP assay and analytical methods described in Table 3.

The following procedure can use any of the improved variants (SEQ ID NO: 6, SEQ ID NO: 80, SEQ ID NO: 104, SEQ ID NO: 172, SEQ ID NO: 186, SEQ ID NO: 194, SEQ ID NO: 196, SEQ ID NO: 252, SEQ ID NO: 270, SEQ ID NO: 272, SEQ ID NO: 286, SEQ ID NO: 300, SEQ ID NO: 328, SEQ ID NO: 330, SEQ ID NO: 346, SEQ ID NO: 348, SEQ ID NO: 356, SEQ ID NO: 414, and SEQ ID NO: 416) for production of enzymatically reduced isoalpha acids at commercially viable isoalpha acids concentrations (volumetric productivity) and % conversion (yield). The reaction is performed in a glass vessel, temperature controlled, with mixing. The data are shown in Table 8 and FIG. 6.

Reagents
  a. Isoalpha acids:
    i. Loading is (up to) 160 g/L; 46.000.318; Lot 1014038
    ii. Isoalpha is in the base form (38% by HPLC);
    iii. Use 4210.5 grams
  b. Isopropanol (40% by volume)
  c. RO water
  d. KRED Enzyme (loading is 10 g/L): 100 grams
  e. NADP (loading is 0.125 g/L): 1.25 grams
  f. Magnesium sulfate heptahydrate (91.615, 1 mM in solution; 0.246 g/L; MW=246.4 g/mole): use 2.46 grams
  g. 15% potassium hydroxide (15% KOH)

Procedure
  a. Measure out the 40% by volume of water
  b. Measure out the 40% by volume of isopropanol
  c. Prepare Isoalpha acid solution by adding 15% KOH to pH 8.5 (+/−0.5)
  d. Prepare a 10% "solution" of enzyme-NADP-magnesium sulfate heptahydrate in water
  e. Add enzyme solution to isoalpha acid to start reaction.
  f. Heat reaction to 40° C.
  g. Purge vessel with nitrogen.
  h. Reaction is sampled and pH is recorded at time 0, 24 and 48 hours.

TABLE 8

KRED Variant Activity Relative to SEQ ID NO: 104

| SEQ ID NO: (nt/aa) | Percent Conversion Fold Improvement (Relative to SEQ ID NO: 104)[1] |
|---|---|
| 413/414 | ++++ |
| 415/416 | ++++ |
| 355/356 | ++++ |
| 329/330 | ++++ |
| 327/328 | ++++ |
| 285/286 | ++++ |
| 271/272 | +++ |
| 269/270 | +++ |
| 251/252 | +++ |
| 193/194 | +++ |
| 185/186 | ++ |
| 171/172 | + |

[1]Levels of increased activity were determined relative to the reference polypeptide of SEQ ID NO: 104 and defined as follows: "+" > 1.0 but <10.0, "++" ≥ 10 but ≤20, "+++" ≥ 20 but ≤50, "++++" ≥ 50

Example 24

Isoalpha Acids Reduction using Engineered Polypeptides Derived from SEQ ID NO: 414 and 416 at Higher Substrate Concentration Isoalpha acids are treated in a manner described in Example 23, but where the concentration of isoalpha acids present in the reaction can be increased up to 20% w/v.

CONCLUSIONS 208 ketoreductases have been characterized as transforming isoalpha acids into dihydro-(rho)-isoalpha acids. The ketoreductases characterized in this study possess an enzymatic activity that has not been described previously. The ketoreductases characterized in this study all reduce a ketone group into an alcohol and are thus ketoreductases. These results demonstrate that a ketoreductase biocatalyst may be employed to convert isoalpha acids to dihydro-(rho)-isoalpha acids in a novel biotransformation process. The present invention is intended to replace current processes utilizing sodium borohydride.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All patents, applications, publications, test methods, literature, and other materials cited herein are hereby incorporated by reference.

CITED REFERENCES

1. *Sodium Borohydride*; MSDS No. S9125; Sigma-Aldrich Co.: Saint Louis, MO Nov. 1, 2015. (accessed Jun. 8, 2017).
2. Robinson, P. K., Enzymes: principles and biotechnological applications. Essays Biochem 2015, 59, 1-41.
3. Hult, K.; Berglund, P., Enzyme promiscuity: mechanism and applications. Trends Biotechnol. 2007, 25 (5), 231-238.
4. Nobeli, I.; Favia, A. D.; Thornton, J. M., Protein promiscuity and its implications for biotechnology. Nat. Biotechnol. 2009, 27 (2), 157-167.
5. Pozen, M., Enzymes in Brewing. Ind. Eng. Chem, 1934, 26 (11), 1127-1133.
6. Praet, T.; Opstaele, F.; Jaskula-Goiris, B.; Aerts, G.; De Cooman, L., Biotransformations of hop-derived aroma compounds by *Saccharomyces cerevisiae* upon fermentation. Cerevisia, 2012, 36, 125-132.
7. Wallerstein, L. (1947) Bentonite and Proteolytic Enzyme Treatment of Beer, U.S. Pat. No. 2,433,411.
8. Ghionno, L.; Marconi, O.; Sileoni, V.; De Francesco, G.; Perretti, G., Brewing with prolyl endopeptidase from *Aspergillus niger*: the impact of enzymatic treatment on gluten levels, quality attributes, and sensory profile. Int. J. Food Sci. Technol, 2017, 52 (6), 1367-1374.
9. Gros, J.; Tran, T. T. H.; Collin, S., Enzymatic release of odourant polyfunctional thiols from cysteine conjugates in hop. J. Inst. Brew. 2013, 119 (4), 221-227.

The invention claimed is:

1. A ketoreductase enzyme which comprises the amino acid sequence of SEQ ID NO: 414 or SEQ ID NO: 416.

2. A variant ketoreductase enzyme which comprises an amino acid sequence that is 99 percent homologous to the ketoreductase of SEQ ID NO: 414 or SEQ ID NO: 416.

3. A composition comprising at least one ketoreductase enzyme according to claim 1.

4. A composition comprising at least one variant ketoreductase enzyme according to claim 2.

* * * * *

```
                              SEQUENCE LISTING

Sequence total quantity: 416
SEQ ID NO: 1            moltype = DNA  length = 759
FEATURE                 Location/Qualifiers
misc_feature            1..759
                        note = Wild-Type Kred from Lactobacillus kefir
source                  1..759
                        mol_type = other DNA
                        organism = synthetic construct
SEQUENCE: 1
atgaccgatc gtctgaaggg caaagtagcc atcgtaaccg gcgggactct gggtatcggt    60
ttggcaatcg ccgataaatt tgtagaggag ggtgcgaaag tagttattac tggtcgtcac   120
gcggatgtag gtgaaaaggc cgccaaatca atcggcgtca ctgatgttat tcgctttgtc   180
cagcacgatg catccgatga agcaggctgg acgaaactgt tcgacaccac cgaggaggca   240
ttcggcccgg ttacgaccgt cgtgaacaat gcagggattg cagtttccaa aagcgttgaa   300
gacactacca cggaggaatg gcgtaaactg ctgtccgtta atctggatgg tgttttttc   360
ggcacccgtc tgggcattca gcgcatgaaa aataaaggct tgggcgctag catcatcaat   420
atgagcagta ttgaggggtt cgtaggcgat ccgacgctgg gggcatacaa cgcttccaag   480
ggggcggtac gtatcatgtc gaaaagcgca gcgctggatt gcgcactgaa ggactacgat   540
gtgcgtgtca acacagtaca tccgggctat atcaagaccc cgctggtcga tgatctggaa   600
ggtgctgagg aaatgatgtc acagcgtacg aaaaccccta tgggccacat tggcgaaccg   660
aatgacatcg catggatctg tgtgtacctg gcatctgacg aatcgaaatt tgcgacgggt   720
gcagaatttg tggtcgacgg cgggtatacc gcacagtga                          759

SEQ ID NO: 2            moltype = AA  length = 252
FEATURE                 Location/Qualifiers
REGION                  1..252
                        note = Wild Type Kred from Lactobacillus kefir
source                  1..252
                        mol_type = protein
                        organism = synthetic construct
SEQUENCE: 2
MTDRLKGKVA IVTGGTLGIG LAIADKFVEE GAKVVITGRH ADVGEKAAKS IGGTDVIRFV    60
QHDASDEAGW TKLFDTTEEA FGPVTTVVNN AGIAVSKSVE DTTTEEWRKL LSVNLDGVFF   120
GTRLGIQRMK NKGLGASIIN MSSIEGFVGD PTLGAYNASK GAVRIMSKSA ALDCALKDYD   180
VRVNTVHPGY IKTPLVDDLE GAEEMMSQRT KTPMGHIGEP NDIAWICVYL ASDESKFATG   240
AEFVVDGGYT AQ                                                      252

SEQ ID NO: 3            moltype = DNA  length = 759
FEATURE                 Location/Qualifiers
misc_feature            1..759
                        note = Engineered Variant of Kred from Lactobacillus kefir
source                  1..759
                        mol_type = other DNA
                        organism = synthetic construct
SEQUENCE: 3
atgaccgatc gtctgaagca taaagtagcc atcgtaaccg gcgggacact gggtatcggt    60
ttggcaatcg ccgataaatt tgtagaggag ggtgcgaaag tagttattac tggtcgtcac   120
```

```
gcggatgtag gtgaaaaggc cgccaaatca atcggcggca ctgatgttat tcgctttgtc   180
cagcacgatg cgtccgaaga agcaggctgg acgaaactgt tcgacaccac cgaggaggca   240
ttcggcccgg ttacgaccgt cgtgaacaat gcagggattg gggttattaa aagcgttgaa   300
gacactacca cggaggaatg gcgtaaactg ctgtccgtta atctggatgg tgttttttc    360
ggcacccgtc tgggcattca gcgcatgaaa aataaaggct gggcgctag catcatcaat    420
atgagcagta ttctggggct cgtaggcgat ccgacgctgg gggcatacaa cgcttccaag   480
ggggcggtac gtatcatgtc gaaaagcgca gcgctggatt gcgcactgaa ggactacgat   540
gtgcgtgtca acacagtaca tccgggcccc atcaagaccc cgcggctcga tgatctggaa   600
ggttgggagg aaatgatgtc acagcgtacg ttaaccccta tgggcacat tggcgaaccg    660
aatgacatcg catggatctg tgtgtacctg gcatctgacg aatcgaaatt tgcgacgggt   720
gcagaatttg tggtcgacgg cgggtggacc gcacagtga                          759

SEQ ID NO: 4              moltype = AA  length = 252
FEATURE                   Location/Qualifiers
REGION                    1..252
                          note = Engineered Variant of Kred from Lactobacillus kefir
source                    1..252
                          mol_type = protein
                          organism = synthetic construct
SEQUENCE: 4
MTDRLKHKVA IVTGGTLGIG LAIADKFVEE GAKVVITGRH ADVGEKAAKS IGGTDVIRFV    60
QHDASEEAGW TKLFDTTEEA FGPVTTVVNN AGIGVIKSVE DTTTEEWRKL LSVNLDGVFF   120
GTRLGIQRMK NKGLGASIIN MSSILGLVGD PTLGAYNASK GAVRIMSKSA ALDCALKDYD   180
VRVNTVHPGP IKTPRLDDLE GWEEMMSQRT LTPMGHIGEP NDIAWICVYL ASDESKFATG   240
AEFVVDGGWT AQ                                                      252

SEQ ID NO: 5              moltype = DNA  length = 756
FEATURE                   Location/Qualifiers
misc_feature              1..756
                          note = Engineered Variant of Kred from Lactobacillus kefir
source                    1..756
                          mol_type = other DNA
                          organism = synthetic construct
SEQUENCE: 5
atgaccgatc gtctgaagca taaagtagcc atcgtaaccg gcgggacact gggtatcggt    60
ttggcaatcg ccgataaatt tgtagaggag ggtgcgaaag tagttattac tggtcgtcac   120
gcggatgtag gtgaaaaggc cgccaaatca atcggcggca ctgatgttat tcgctttgtc   180
cagcacgatg cgtccgaaga agcaggctgg acgaaactgt tcgacaccac cgaggaggca   240
ttcggcccgg ttacgaccgt cgtgaacaat gcagggattg gggttattaa aagcgttgaa   300
gacactacca cggaggaatg gcgtaaactg ctgtccgtta atctggatgg tgttttttc    360
ggcacccgtc tgggcattca gcgcatgaaa aataaaggct gggcgctag catcatcaat    420
atgagcagta ttctggggct cgtaggcgat ccgacgctgg gggcatacaa cgcttccaag   480
ggggcggtac gtatcatgtc gaaaagcgca gcgctggatt gcgcactgaa ggactacgat   540
gtgcgtgtca acacagtaca tccgggcccc atcaagaccc gcggaagga tgatctggaa   600
ggttgggagg aaatgatgtc acagcgtacg ttaaccccta tgggcacat tggcgaaccg    660
aatgacatcg catggatctg tgtgtacctg gcatctgacg aatcgaaatt tgcgacgggt   720
gcagaatttg tggtcgacgg cgggtggacc gcacag                            756

SEQ ID NO: 6              moltype = AA  length = 252
FEATURE                   Location/Qualifiers
REGION                    1..252
                          note = Engineered Variant of Kred from Lactobacillus kefir
source                    1..252
                          mol_type = protein
                          organism = synthetic construct
SEQUENCE: 6
MTDRLKHKVA IVTGGTLGIG LAIADKFVEE GAKVVITGRH ADVGEKAAKS IGGTDVIRFV    60
QHDASEEAGW TKLFDTTEEA FGPVTTVVNN AGIGVIKSVE DTTTEEWRKL LSVNLDGVFF   120
GTRLGIQRMK NKGLGASIIN MSSILGLVGD PTLGAYNASK GAVRIMSKSA ALDCALKDYD   180
VRVNTVHPGP IKTPRKDDLE GWEEMMSQRT LTPMGHIGEP NDIAWICVYL ASDESKFATG   240
AEFVVDGGWT AQ                                                      252

SEQ ID NO: 7              moltype = DNA  length = 756
FEATURE                   Location/Qualifiers
misc_feature              1..756
                          note = Engineered Variant of Kred from Lactobacillus kefir
source                    1..756
                          mol_type = other DNA
                          organism = synthetic construct
SEQUENCE: 7
atgaccgatc gtctgaagca taaagtagcc atcgtaaccg gcgggacact gggtatcggt    60
ttggcaatcg ccgataaatt tgtagaggag ggtgcgaaag tagttattac tggtcgtcac   120
gcggatgtag gtgaaaaggc cgccaaatca atcggcggca ctgatgttat tcgctttgtc   180
cagcacgatg cgtccgaaga agcaggctgg acgaaactgt tcgacaccac cgaggaggca   240
ttcggcccgg ttacgaccgt cgtgaacaat gcagggattg gggttattaa aagcgttgaa   300
gacactacca cggaggaatg gcgtaaactg ctgtccgtta atctggatgg tgttttttc    360
ggcacccgtc tgggcattca gcgcatgaaa aataaaggct gggcgctag catcatcaat    420
atgagcagta ttctggggct cgtaggcgat ccgacgctgg gggcatacaa cgcttccaag   480
ggggcggtac gtatcatgtc gaaaagcgca gcgctggatt gcgcactgaa ggactacgat   540
```

```
gtgcgtgtca acacagtaca tccgggcccc atcaagaccc cgcggaggga tgatctggaa    600
ggttgggagg aaatgatgtc acagcgtacg ttaaccccta tgggccacat ggcgaaccg    660
aatgacatcg catggatctg tgtgtacctg gcatctgacg aatcgaaatt tgcgacgggt    720
gcagaatttg tggtcgacgg cgggtggacc gcacag                              756

SEQ ID NO: 8           moltype = AA   length = 252
FEATURE                Location/Qualifiers
REGION                 1..252
                       note = Engineered Variant of Kred from Lactobacillus kefir
source                 1..252
                       mol_type = protein
                       organism = synthetic construct
SEQUENCE: 8
MTDRLKHKVA IVTGGTLGIG LAIADKFVEE GAKVVITGRH ADVGEKAAKS IGGTDVIRFV     60
QHDASEEAGW TKLFDTTEEA FGPVTTVVNN AGIGVIKSVE DTTTEEWRKL LSVNLDGVFF   120
GTRLGIQRMK NKGLGASIIN MSSILGLVGD PTLGAYNASK GAVRIMSKSA ALDCALKDYD   180
VRVNTVHPGP IKTPRRDDLE GWEEMMSQRT LTPMGHIGEP NDIAWICVYL ASDESKFATG   240
AEFVVDGGWT AQ                                                        252

SEQ ID NO: 9           moltype = DNA   length = 756
FEATURE                Location/Qualifiers
misc_feature           1..756
                       note = Engineered Variant of Kred from Lactobacillus kefir
source                 1..756
                       mol_type = other DNA
                       organism = synthetic construct
SEQUENCE: 9
atgaccgatc gtctgaagca taaagtagcc atcgtaaccg gcgggacact gggtatcggt     60
ttggcaatcg ccgataaatt tgtagaggag ggtgcgaaag tagttattac tggtcgtcac   120
gcggatgtag gtgaaaaggc cgccaaatca atcggcggca ctgatgttat tcgctttgtc   180
cagcacgatg cgtccgaaga agcaggctgg acgaaactgt tcgacaccac cgaggaggca   240
ttcggcccgg ttacgaccgt cgtgaacaat gcagggattg gggttattaa aagcgttgaa   300
gacactacca cggaggaatg gcgtaaactg ctgtccgtta atctggatgg tgttttttc   360
ggcacccgtc tgggcattca gcgcatgaaa aataaaggct gggcgctag catcatcaat   420
atgagcagta ttctggggct cgtaggcgat ccgacgaggg gggcatacaa cgcttccaag   480
ggggcggtac gtatcatgtc gaaaagcgca gcgctggatt gcgcactgaa ggactacgat   540
gtgcgtgtca acacagtaca tccgggcccc atcaagaccc cgcggctcga tgatctggaa   600
ggttgggagg aaatgatgtc acagcgtacg ttaaccccta tgggccacat ggcgaaccg   660
aatgacatcg catggatctg tgtgtacctg gcatctgacg aatcgaaatt tgcgacgggt   720
gcagaatttg tggtcgacgg cgggtggacc gcacag                              756

SEQ ID NO: 10          moltype = AA   length = 252
FEATURE                Location/Qualifiers
REGION                 1..252
                       note = Engineered Variant of Kred from Lactobacillus kefir
source                 1..252
                       mol_type = protein
                       organism = synthetic construct
SEQUENCE: 10
MTDRLKHKVA IVTGGTLGIG LAIADKFVEE GAKVVITGRH ADVGEKAAKS IGGTDVIRFV     60
QHDASEEAGW TKLFDTTEEA FGPVTTVVNN AGIGVIKSVE DTTTEEWRKL LSVNLDGVFF   120
GTRLGIQRMK NKGLGASIIN MSSILGLVGD PTRGAYNASK GAVRIMSKSA ALDCALKDYD   180
VRVNTVHPGP IKTPRLDDLE GWEEMMSQRT LTPMGHIGEP NDIAWICVYL ASDESKFATG   240
AEFVVDGGWT AQ                                                        252

SEQ ID NO: 11          moltype = DNA   length = 756
FEATURE                Location/Qualifiers
misc_feature           1..756
                       note = Engineered Variant of Kred from Lactobacillus kefir
source                 1..756
                       mol_type = other DNA
                       organism = synthetic construct
SEQUENCE: 11
atgaccgatc gtctgaagca taaagtagcc atcgtaaccg gcgggacact gggtatcggt     60
ttggcaatcg ccgataaatt tgtagaggag ggtgcgaaag tagttattac tggtcgtcac   120
gcggatgtag gtgaaaaggc cgccaaatca atcggcggca ctgatgttat tcgctttgtc   180
cagcacgatg cgtccgaaga agcaggctgg acgaaactgt tcgacaccac cgaggaggca   240
ttcggcccgg ttacgaccgt cgtgaacaat gcagggattg gggttattaa aagcgttgaa   300
gacactacca cggaggaatg gcgtaaactg ctgtccgtta atctggatgg tgttttttc   360
ggcacccgtc tgggcattca gcgcatgaaa aataaaggct gggcgctag catcatcaat   420
atgagcagta tttctgggct cgtaggcgat ccgacgctgg ggcatacaa cgcttccaag   480
ggggcggtac gtatcatgtc gaaaagcgca gcgctggatt gcgcactgaa ggactacgat   540
gtgcgtgtca acacagtaca tccgggcccc atcaagaccc cgcggctcga tgatctggaa   600
ggttgggagg aaatgatgtc acagcgtacg ttaaccccta tgggccacat ggcgaaccg   660
aatgacatcg catggatctg tgtgtacctg gcatctgacg aatcgaaatt tgcgacgggt   720
gcagaatttg tggtcgacgg cgggtggacc gcacag                              756

SEQ ID NO: 12          moltype = AA   length = 252
FEATURE                Location/Qualifiers
```

| | | |
|---|---|---|
| REGION | 1..252 | |
| | note = Engineered Variant of Kred from Lactobacillus kefir | |
| source | 1..252 | |
| | mol_type = protein | |
| | organism = synthetic construct | |

SEQUENCE: 12

```
MTDRLKHKVA IVTGGTLGIG LAIADKFVEE GAKVVITGRH ADVGEKAAKS IGGTDVIRFV    60
QHDASEEAGW TKLFDTTEEA FGPVTTVVNN AGIGVIKSVE DTTTEEWRKL LSVNLDGVFF   120
GTRLGIQRMK NKGLGASIIN MSSISGLVGD PTLGAYNASK GAVRIMSKSA ALDCALKDYD   180
VRVNTVHPGP IKTPRLDDLE GWEEMMSQRT LTPMGHIGEP NDIAWICVYL ASDESKFATG   240
AEFVVDGGWT AQ                                                      252
```

| | | |
|---|---|---|
| SEQ ID NO: 13 | moltype = DNA  length = 756 | |
| FEATURE | Location/Qualifiers | |
| misc_feature | 1..756 | |
| | note = Engineered Variant of Kred from Lactobacillus kefir | |
| source | 1..756 | |
| | mol_type = other DNA | |
| | organism = synthetic construct | |

SEQUENCE: 13

```
atgaccgatc gtctgaagca taaagtagcc atcgtaaccg gcgggacact gggtatcggt    60
ttggcaatcg ccgataaatt tgtagaggag ggtgcgaaag tagttattac tggtcgtcac   120
gcggatgtag gtgaaaaggc cgccaaatca atcggcggca ctgatgttat tcgctttgtc   180
cagcacgatg cgtccgaaga agcaggctgg acgaaactgt tcgacaccac cgaggaggca   240
ttcggcccgt tacgaccgt cgtgaacaat gcagggattg ggttattaa agcgttgaa     300
gacactacca cggaggaatg gcgtaaactg ctgtccgtta atctggatgg tgttttttc    360
ggcacccgtc tgggcattca gcgcatgaaa aataaaggct tgggcgctag catcatcaat   420
atgagcagta ttctggggct cgtaggcgat ccgggtctgg ggcatacaa cgcttccaag   480
ggggcggtac gtatcatgtc gaaaagcgca gcgctggatt gcgcactgaa ggactacgat   540
gtgcgtgtca acacagtaca tccggggccc atcaagaccc cgcggctcga tgatctggaa   600
ggttgggagg aaatgatgtc acagcgtacg ttaacccta tgggccacat tggcgaaccg    660
aatgacatcg catggatctg tgtgtacctg gcatctgacg aatcgaaatt tgcgacgggt   720
gcagaatttg tggtcgacgg cgggtggacc gcacag                            756
```

| | | |
|---|---|---|
| SEQ ID NO: 14 | moltype = AA  length = 252 | |
| FEATURE | Location/Qualifiers | |
| REGION | 1..252 | |
| | note = Engineered Variant of Kred from Lactobacillus kefir | |
| source | 1..252 | |
| | mol_type = protein | |
| | organism = synthetic construct | |

SEQUENCE: 14

```
MTDRLKHKVA IVTGGTLGIG LAIADKFVEE GAKVVITGRH ADVGEKAAKS IGGTDVIRFV    60
QHDASEEAGW TKLFDTTEEA FGPVTTVVNN AGIGVIKSVE DTTTEEWRKL LSVNLDGVFF   120
GTRLGIQRMK NKGLGASIIN MSSILGLVGD PGLGAYNASK GAVRIMSKSA ALDCALKDYD   180
VRVNTVHPGP IKTPRLDDLE GWEEMMSQRT LTPMGHIGEP NDIAWICVYL ASDESKFATG   240
AEFVVDGGWT AQ                                                      252
```

| | | |
|---|---|---|
| SEQ ID NO: 15 | moltype = DNA  length = 756 | |
| FEATURE | Location/Qualifiers | |
| misc_feature | 1..756 | |
| | note = Engineered Variant of Kred from Lactobacillus kefir | |
| source | 1..756 | |
| | mol_type = other DNA | |
| | organism = synthetic construct | |

SEQUENCE: 15

```
atgaccgatc gtctgaagca taaagtagcc atcgtaaccg gcgggacact gggtatcggt    60
ttggcaatcg ccgataaatt tgtagaggag ggtgcgaaag tagttattac tggtcgtcac   120
gcggatgtag gtgaaaaggc cgccaaatca atcggcggca ctgatgttat tcgctttgtc   180
cagcacgatg cgtccgaaga agcaggctgg acgaaactgt tcgacaccac cgaggaggca   240
ttcggcccgg ttacgaccgt cgtgaacaat gcagggattg ggttattaa agcgttgaa    300
gacactacca cggaggaatg gcgtaaactg ctgtccgtta atctggatgg tgttttttc    360
ggcacccgtc tgggcattca gcgcatgaaa aataaaggct tgggcgctag catcatcaat   420
atgagcagta ttctggggct cgtaggcgat ccgacgctgg ggcatacaa cgcttccaag   480
ggggcggtac gtatcatgtc gaaaagcgca gcgctggatt gcgcactgaa ggactacgat   540
gtgcgtgtca acacagtaca tccggggccc atcaagaccc cgcggcatga tgatctggaa   600
ggttgggagg aaatgatgtc acagcgtacg ttaacccta tgggccacat tggcgaaccg    660
aatgacatcg catggatctg tgtgtacctg gcatctgacg aatcgaaatt tgcgacgggt   720
gcagaatttg tggtcgacgg cgggtggacc gcacag                            756
```

| | | |
|---|---|---|
| SEQ ID NO: 16 | moltype = AA  length = 252 | |
| FEATURE | Location/Qualifiers | |
| REGION | 1..252 | |
| | note = Engineered Variant of Kred from Lactobacillus kefir | |
| source | 1..252 | |
| | mol_type = protein | |
| | organism = synthetic construct | |

SEQUENCE: 16

```
MTDRLKHKVA IVTGGTLGIG LAIADKFVEE GAKVVITGRH ADVGEKAAKS IGGTDVIRFV    60
```

```
QHDASEEAGW TKLFDTTEEA FGPVTTVVNN AGIGVIKSVE DTTTEEWRKL LSVNLDGVFF  120
GTRLGIQRMK NKGLGASIIN MSSILGLVGD PTLGAYNASK GAVRIMSKSA ALDCALKDYD  180
VRVNTVHPGP IKTPRHDDLE GWEEMMSQRT LTPMGHIGEP NDIAWICVYL ASDESKFATG  240
AEFVVDGGWT AQ                                                     252

SEQ ID NO: 17           moltype = DNA   length = 756
FEATURE                 Location/Qualifiers
misc_feature            1..756
                        note = Engineered Variant of Kred from Lactobacillus kefir
source                  1..756
                        mol_type = other DNA
                        organism = synthetic construct
SEQUENCE: 17
atgaccgatc gtctgaagca taaagtagcc atcgtaaccg gcgggacact gggtatcggt   60
ttggcaatcg ccgataaatt tgtagaggag ggtgcgaaag tagttattac tggtcgtcac  120
gcggatgtag gtgaaaaggc cgccaaatca atcggcggca ctgatgttat tcgctttgtc  180
cagcacgatg cgtccgaaga agcaggctgg acgaaactgt tcgacaccac cgaggaggca  240
ttcggcccgg ttacgaccgt cgtgaacaat gcaggggttg gggttattaa aagcgttgaa  300
gacactacca cggaggaatg gcgtaaactg ctgtccgtta atctggatgg tgttttttc   360
ggcacccgtc tgggcattca gcgcatgaaa aataaaggct gggcgctag catcatcaat   420
atgagcagta ttctggggct cgtaggcgat ccgacgctgg ggcatacaa cgcttccaag   480
ggggcggtac gtatcatgtc gaaaagcgca gcgctggatt gcgcactgaa ggactacgat   540
gtgcgtgtca acacagtaca tccgggcccc atcaagaccc cgcggctcga tgatctggaa   600
ggttgggagg aaatgatgtc acagcgtacg ttaaccccta tggcacacat tggcgaaccg   660
aatgacatcg catggatctg tgtgtacctg gcatctgacg aatcgaaatt tgcgacgggt   720
gcagaatttg tggtcgacgg cgggtggacc gcacag                            756

SEQ ID NO: 18           moltype = AA   length = 252
FEATURE                 Location/Qualifiers
REGION                  1..252
                        note = Engineered Variant of Kred from Lactobacillus kefir
source                  1..252
                        mol_type = protein
                        organism = synthetic construct
SEQUENCE: 18
MTDRLKHKVA IVTGGTLGIG LAIADKFVEE GAKVVITGRH ADVGEKAAKS IGGTDVIRFV   60
QHDASEEAGW TKLFDTTEEA FGPVTTVVNN AGVGVIKSVE DTTTEEWRKL LSVNLDGVFF  120
GTRLGIQRMK NKGLGASIIN MSSILGLVGD PTLGAYNASK GAVRIMSKSA ALDCALKDYD  180
VRVNTVHPGP IKTPRLDDLE GWEEMMSQRT LTPMGHIGEP NDIAWICVYL ASDESKFATG  240
AEFVVDGGWT AQ                                                     252

SEQ ID NO: 19           moltype = DNA   length = 756
FEATURE                 Location/Qualifiers
misc_feature            1..756
                        note = Engineered Variant of Kred from Lactobacillus kefir
source                  1..756
                        mol_type = other DNA
                        organism = synthetic construct
SEQUENCE: 19
atgaccgatc gtctgaagca taaagtagcc atcgtaaccg gcgggacact gggtatcggt   60
ttggcaatcg ccgataaatt tgtagaggag ggtgcgaaag tagttattac tggtcgtcac  120
gcggatgtag gtgaaaaggc cgccaaatca atcggcggca ctgatgttat tcgctttgtc  180
cagcacgatg cgtccgaaga agcaggctgg acgaaactgt tcgacaccac cgaggaggca  240
ttcggcccgg ttacgaccgt cgtgaacaat gcagggattg gggttattaa aagcgttgaa  300
gacactacca cggaggaatg gcgtaaactg ctgtccgtta atctggatgg tgttttttc   360
ggcacccgtc tgggcattca gcgcatgaaa aataaaggct gggcgctag catcatcaat   420
atgagcagta ttatggggct cgtaggcgat ccgacgctgg ggcatacaa cgcttccaag   480
ggggcggtac gtatcatgtc gaaaagcgca gcgctggatt gcgcactgaa ggactacgat   540
gtgcgtgtca acacagtaca tccgggcccc atcaagaccc cgcggctcga tgatctggaa   600
ggttgggagg aaatgatgtc acagcgtacg ttaaccccta tggcgcacat tggcgaaccg   660
aatgacatcg catggatctg tgtgtacctg gcatctgacg aatcgaaatt tgcgacgggt   720
gcagaatttg tggtcgacgg cgggtggacc gcacag                            756

SEQ ID NO: 20           moltype = AA   length = 252
FEATURE                 Location/Qualifiers
REGION                  1..252
                        note = Engineered Variant of Kred from Lactobacillus kefir
source                  1..252
                        mol_type = protein
                        organism = synthetic construct
SEQUENCE: 20
MTDRLKHKVA IVTGGTLGIG LAIADKFVEE GAKVVITGRH ADVGEKAAKS IGGTDVIRFV   60
QHDASEEAGW TKLFDTTEEA FGPVTTVVNN AGIGVIKSVE DTTTEEWRKL LSVNLDGVFF  120
GTRLGIQRMK NKGLGASIIN MSSIMGLVGD PTLGAYNASK GAVRIMSKSA ALDCALKDYD  180
VRVNTVHPGP IKTPRLDDLE GWEEMMSQRT LTPMGHIGEP NDIAWICVYL ASDESKFATG  240
AEFVVDGGWT AQ                                                     252

SEQ ID NO: 21           moltype = DNA   length = 756
FEATURE                 Location/Qualifiers
```

| | | |
|---|---|---|
| misc_feature | 1..756 | |
| | note = Engineered Variant of Kred from Lactobacillus kefir | |
| source | 1..756 | |
| | mol_type = other DNA | |
| | organism = synthetic construct | |

SEQUENCE: 21

```
atgaccgatc gtctgaagca taaagtagcc atcgtaaccg gcgggacact gggtatcggt   60
ttggcaatcg ccgataaatt tgtagaggag ggtgcgaaag tagttattac tggtcgtcac  120
gcggatgtag gtgaaaaggc cgccaaatca atcggcggca ctgatgttat tcgctttgtc  180
cagcacgatg cgtccgaaga agcaggctgg acgaaactgt tcgacaccac cgaggaggca  240
ttcggcccgg ttacgaccgt cgtgaacaat gcagggattg ggttattaa aagcgttgaa   300
gacactacca cggaggaatg gcgtaaactg ctgtccgtta atctggatgg tgttttttc   360
ggcacccgtc tgggcattca gcgcatgaaa aataaaggct gggcgctag catcatcaat   420
atgagcagta ttggtgggct cgtaggcgat ccgacgctgg ggcatacaa cgcttccaag   480
ggggcggtac gtatcatgtc gaaaagcgca gcgctggatt gcgcactgaa ggactacgat   540
gtgcgtgtca acacagtaca tccgggcccc atcaagaccc gcggctcga tgatctggaa   600
ggttgggagg aaatgatgtc acagcgtacg ttaaccccta tgggccacat tggcgaaccg   660
aatgacatcg catggatctg tgtgtacctg gcatctgacg aatcgaaatt tgcgacgggt   720
gcagaatttg tggtcgacgg cgggtggacc gcacag                            756
```

| SEQ ID NO: 22 | moltype = AA length = 252 |
|---|---|
| FEATURE | Location/Qualifiers |
| REGION | 1..252 |
| | note = Engineered Variant of Kred from Lactobacillus kefir |
| source | 1..252 |
| | mol_type = protein |
| | organism = synthetic construct |

SEQUENCE: 22

```
MTDRLKHKVA IVTGGTLGIG LAIADKFVEE GAKVVITGRH ADVGEKAAKS IGGTDVIRFV   60
QHDASEEAGW TKLFDTTEEA FGPVTTVVNN AGIGVIKSVE DTTTEEWRKL LSVNLDGVFF  120
GTRLGIQRMK NKGLGASIIN MSSIGGLVGD PTLGAYNASK GAVRIMSKSA ALDCALKDYD  180
VRVNTVHPGP IKTPRLDDLE GWEEMMSQRT LTPMGHIGEP NDIAWICVYL ASDESKFATG  240
AEFVVDGGWT AQ                                                       252
```

| SEQ ID NO: 23 | moltype = DNA length = 756 |
|---|---|
| FEATURE | Location/Qualifiers |
| misc_feature | 1..756 |
| | note = Engineered Variant of Kred from Lactobacillus kefir |
| source | 1..756 |
| | mol_type = other DNA |
| | organism = synthetic construct |

SEQUENCE: 23

```
atgaccgatc gtctgaagca taaagtagcc atcgtaaccg gcgggacact gggtatcggt   60
ttggcaatcg ccgataaatt tgtagaggag ggtgcgaaag tagttattac tggtcgtcac  120
gcggatgtag gtgaaaaggc cgccaaatca atcggcggca ctgatgttat tcgctttgtc  180
cagcacgatg cgtccgaaga agcaggctgg acgaaactgt tcgacaccac cgaggaggca  240
ttcggcccgg ttacgaccgt cgtgaacaat gcagggattg ggttattaa aagcgttgaa   300
gacactacca cggaggaatg gcgtaaactg ctgtccgtta atctggatgg tgttttttc   360
ggcacccgtc tgggcattca gcgcatgaaa aataaaggct gggcgctag catcatcaat   420
atgagcagta tttgtgggct cgtaggcgat ccgacgctgg ggcatacaa cgcttccaag   480
ggggcggtac gtatcatgtc gaaaagcgca gcgctggatt gcgcactgaa ggactacgat   540
gtgcgtgtca acacagtaca tccgggcccc atcaagaccc gcggctcga tgatctggaa   600
ggttgggagg aaatgatgtc acagcgtacg ttaaccccta tgggccacat tggcgaaccg   660
aatgacatcg catggatctg tgtgtacctg gcatctgacg aatcgaaatt tgcgacgggt   720
gcagaatttg tggtcgacgg cgggtggacc gcacag                            756
```

| SEQ ID NO: 24 | moltype = AA length = 252 |
|---|---|
| FEATURE | Location/Qualifiers |
| REGION | 1..252 |
| | note = Engineered Variant of Kred from Lactobacillus kefir |
| source | 1..252 |
| | mol_type = protein |
| | organism = synthetic construct |

SEQUENCE: 24

```
MTDRLKHKVA IVTGGTLGIG LAIADKFVEE GAKVVITGRH ADVGEKAAKS IGGTDVIRFV   60
QHDASEEAGW TKLFDTTEEA FGPVTTVVNN AGIGVIKSVE DTTTEEWRKL LSVNLDGVFF  120
GTRLGIQRMK NKGLGASIIN MSSICGLVGD PTLGAYNASK GAVRIMSKSA ALDCALKDYD  180
VRVNTVHPGP IKTPRLDDLE GWEEMMSQRT LTPMGHIGEP NDIAWICVYL ASDESKFATG  240
AEFVVDGGWT AQ                                                       252
```

| SEQ ID NO: 25 | moltype = DNA length = 756 |
|---|---|
| FEATURE | Location/Qualifiers |
| misc_feature | 1..756 |
| | note = Engineered Variant of Kred from Lactobacillus kefir |
| source | 1..756 |
| | mol_type = other DNA |
| | organism = synthetic construct |

SEQUENCE: 25

```
atgaccgatc gtctgaagca taaagtagcc atcgtaaccg gcgggacact gggtatcggt   60
```

```
ttggcaatcg ccgataaatt tgtagaggag ggtgcgaaag tagttattac tggtcgtcac    120
gcggatgtag gtgaaaaggc cgccaaatca atcggcggca ctgatgttat tcgctttgtc    180
cagcacgatg cgtccgaaga agcaggctgg acgaaactgt tcgacaccac cgaggaggca    240
ttcggcccgg ttacgaccgt cgtgaacaat gcagggattg ggttattaa aagcgttgaa    300
gacactacca cggaggaatg gcgtaaactg ctgtccgtta atctggatgg tgttttttc    360
ggcacccgtc tgggcattca gcgcatgaaa aataaaggct tgggcgctag catcatcaat    420
atgagcagta ttctggggct cgtaggcgat ccgacggttg gggcatacaa cgcttccaag    480
ggggcggtac gtatcatgtc gaaaagcgca gcgctggatt gcgcactgaa ggactacgat    540
gtgcgtgtca acacagtaca tccgggcccc atcaagaccc cgcggctcga tgatctggaa    600
ggttgggagg aaatgatgtc acagcgtacg ttaaccccta tgggccacat tggcgaaccg    660
aatgacatcg catggatctg tgtgtacctg gcatctgacg aatcgaaatt tgcgacgggt    720
gcagaatttg tggtcgacgg cgggtggacc gcacag                              756

SEQ ID NO: 26              moltype = AA   length = 252
FEATURE                    Location/Qualifiers
REGION                     1..252
                           note = Engineered Variant of Kred from Lactobacillus kefir
source                     1..252
                           mol_type = protein
                           organism = synthetic construct SEQUENCE: 26
MTDRLKHKVA IVTGGTLGIG LAIADKFVEE GAKVVITGRH ADVGEKAAKS IGGTDVIRFV     60
QHDASEEAGW TKLFDTTEEA FGPVTTVVNN AGIGVIKSVE DTTTEEWRKL LSVNLDGVFF    120
GTRLGIQRMK NKGLGASIIN MSSILGLVGD PTVGAYNASK GAVRIMSKSA ALDCALKDYD    180
VRVNTVHPGP IKTPRLDDLE GWEEMMSQRT LTPMGHIGEP NDIAWICVYL ASDESKFATG    240
AEFVVDGGWT AQ                                                        252

SEQ ID NO: 27              moltype = DNA   length = 756
FEATURE                    Location/Qualifiers
misc_feature               1..756
                           note = Engineered Variant of Kred from Lactobacillus kefir
source                     1..756
                           mol_type = other DNA
                           organism = synthetic construct SEQUENCE: 27
atgaccgatc gtctgaagca taaagtagcc atcgtaaccg gcgggacact gggtatcggt     60
ttggcaatcg ccgataaatt tgtagaggag ggtgcgaaag tagttattac tggtcgtcac    120
gcggatgtag gtgaaaaggc cgccaaatca atcggcggca ctgatgttat tcgctttgtc    180
cagcacgatg cgtccgaaga agcaggctgg acgaaactgt tcgacaccac cgaggaggca    240
ttcggcccgg ttacgaccgt cgtgaacaat gcagggattg ggttattaa aagcgttgaa    300
gacactacca cggaggaatg gcgtaaactg ctgtccgtta atctggatgg tgttttttc    360
ggcacccgtc tgggcattca gcgcatgaaa aataaaggct tgggcgctag catcatcaat    420
atgagcagta ttctggggct cgtaggcgat ccgacggttg gggcatacaa cgcttccaag    480
ggggcggtac gtatcatgtc gaaaagcgca gcgctggatt gcgcactgaa ggactacgat    540
gtgcgtgtca acacagtaca tccgggcccc atcaagaccc gcggctcag gatctggaa     600
ggttgggagg aaatgatgtc acagcgtacg ttaaccccta tgggccacat tggcgaaccg    660
aatgacatcg catggatctg tgtgtacctg gcatctgacg aatcgaaatt tgcgacgggt    720
gcagaatttg tggtcgacgg cgggtggacc gcacag                              756

SEQ ID NO: 28              moltype = AA   length = 252
FEATURE                    Location/Qualifiers
REGION                     1..252
                           note = Engineered Variant of Kred from Lactobacillus kefir
source                     1..252
                           mol_type = protein
                           organism = synthetic construct SEQUENCE: 28
MTDRLKHKVA IVTGGTLGIG LAIADKFVEE GAKVVITGRH ADVGEKAAKS IGGTDVIRFV     60
QHDASEEAGW TKLFDTTEEA FGPVTTVVNN AGIGVIKSVE DTTTEEWRKL LSVNLDGVFF    120
GTRLGIQRMK NKGLGASIIN MSSILGLVGD PTLGAYNASK GAVRIMSKSA ALDCALKDYD    180
VRVNTVHPGP IKTPRLRDLE GWEEMMSQRT LTPMGHIGEP NDIAWICVYL ASDESKFATG    240
AEFVVDGGWT AQ                                                        252

SEQ ID NO: 29              moltype = DNA   length = 756
FEATURE                    Location/Qualifiers
misc_feature               1..756
                           note = Engineered Variant of Kred from Lactobacillus kefir
source                     1..756
                           mol_type = other DNA
                           organism = synthetic construct SEQUENCE: 29
atgaccgatc gtctgaagca taaagtagcc atcgtaaccg gcgggacact gggtatcggt     60
agggcaatcg ccgataaatt tgtagaggag ggtgcgaaag tagttattac tggtcgtcac    120
gcggatgtag gtgaaaaggc cgccaaatca atcggcggca ctgatgttat tcgctttgtc    180
cagcacgatg cgtccgaaga agcaggctgg acgaaactgt tcgacaccac cgaggaggca    240
ttcggcccgg ttacgaccgt cgtgaacaat gcagggattg ggttattaa aagcgttgaa    300
gacactacca cggaggaatg gcgtaaactg ctgtccgtta atctggatgg tgttttttc    360
ggcacccgtc tgggcattca gcgcatgaaa aataaaggct tgggcgctag catcatcaat    420
atgagcagta ttctggggct cgtaggcgat ccgacgctgg gggcatacaa cgcttccaag    480
```

```
ggggcggtac gtatcatgtc gaaaagcgca gcgctggatt gcgcactgaa ggactacgat   540
gtgcgtgtca acacagtaca tccgggcccc atcaagaccc cgcggctcga tgatctggaa   600
ggttgggagg aaatgatgtc acagcgtacg ttaaccccta tgggccacat tggcgaaccg   660
aatgacatca catggatctg tgtgtacctg gcatctgacg aatcgaaatt tgcgacgggt   720
gcagaatttg tggtcgacgg cgggtggacc gcacag                             756
```

```
SEQ ID NO: 30           moltype = AA   length = 252
FEATURE                 Location/Qualifiers
REGION                  1..252
                        note = Engineered Variant of Kred from Lactobacillus kefir
source                  1..252
                        mol_type = protein
                        organism = synthetic construct
SEQUENCE: 30
MTDRLKHKVA IVTGGTLGIG RAIADKFVEE GAKVVITGRH ADVGEKAAKS IGGTDVIRFV    60
QHDASEEAGW TKLFDTTEEA FGPVTTVVNN AGIGVIKSVE DTTTEEWRKL LSVNLDGVFF   120
GTRLGIQRMK NKGLGASIIN MSSILGLVGD PTLGAYNASK GAVRIMSKSA ALDCALKDYD   180
VRVNTVHPGP IKTPRLDDLE GWEEMMSQRT LTPMGHIGEP NDIAWICVYL ASDESKFATG   240
AEFVVDGGWT AQ                                                      252

SEQ ID NO: 31           moltype = DNA   length = 756
FEATURE                 Location/Qualifiers
misc_feature            1..756
                        note = Engineered Variant of Kred from Lactobacillus kefir
source                  1..756
                        mol_type = other DNA
                        organism = synthetic construct
SEQUENCE: 31
atgaccgatc gtctgaagca taaagtagcc atcgtaaccg gcgggacact gggtatcggt    60
ttggcaatcg ccgataaatt tgtagaggag ggtgcgaaag tagttattac tggtcgtcac   120
gcggatgtag gtgaaaaggc cgccaaatca atcggcggca ctgatgttat tcgctttgtc   180
cagcacgatg cgtccgaaga agcaggctgg acgaaactgt tcgacaccac cgaggaggca   240
ttcggcccgg ttacgaccgt cgtgaacaat gcaggggatg gggttattaa aagcgttgaa   300
gacactacca cggaggaatg gcgtaaactg ctgtccgtta atctggatgg tgtttttttc   360
ggcacccgtc tgggcattca gcgcatgaaa aataaaggct gggcgctag catcatcaat   420
atgagcagta ttctggggct cgtaggcgat ccgacgctgg ggcatacaa cgcttccaag   480
ggggcggtac gtatcatgtc gaaaagcgca gcgctggatt gcgcactgaa ggactacgat   540
gtgcgtgtca acacagtaca tccgggcccc atcaagaccc cgcggctcga tgatctggaa   600
ggttgggagg aaatgatgtc acagcgtacg ttaaccccta tgggccacat tggcgaaccg   660
aatgacatca catggatctg tgtgtacctg gcatctgacg aatcgaaatt tgcgacgggt   720
gcagaatttg tggtcgacgg cgggtggacc gcacag                             756

SEQ ID NO: 32           moltype = AA   length = 252
FEATURE                 Location/Qualifiers
REGION                  1..252
                        note = Engineered Variant of Kred from Lactobacillus kefir
source                  1..252
                        mol_type = protein
                        organism = synthetic construct
SEQUENCE: 32
MTDRLKHKVA IVTGGTLGIG LAIADKFVEE GAKVVITGRH ADVGEKAAKS IGGTDVIRFV    60
QHDASEEAGW TKLFDTTEEA FGPVTTVVNN AGDGVIKSVE DTTTEEWRKL LSVNLDGVFF   120
GTRLGIQRMK NKGLGASIIN MSSILGLVGD PTLGAYNASK GAVRIMSKSA ALDCALKDYD   180
VRVNTVHPGP IKTPRLDDLE GWEEMMSQRT LTPMGHIGEP NDIAWICVYL ASDESKFATG   240
AEFVVDGGWT AQ                                                      252

SEQ ID NO: 33           moltype = DNA   length = 756
FEATURE                 Location/Qualifiers
misc_feature            1..756
                        note = Engineered Variant of Kred from Lactobacillus kefir
source                  1..756
                        mol_type = other DNA
                        organism = synthetic construct
SEQUENCE: 33
atgaccgatc gtctgaagca taaagtagcc atcgtaaccg gcgggacact gggtatcggt    60
ttggcaatcg ccgataaatt tgtagaggag ggtgcgaaag tagttattac tggtcgtcac   120
gcggatgtag gtgaaaaggc cgccaaatca atcggcggca ctgatgttat tcgctttgtc   180
cagcacgatg cgtccgaaga agcaggctgg acgaaactgt tcgacaccac cgaggaggca   240
ttcggcccgg ttacgaccgt cgtgaacaat gcagggattg gggttattaa aagcgttgaa   300
gacactacca cggaggaatg gcgtaaactg ctgtccgtta atctggatgg tgtttttttc   360
ggcacccgtc tgggcattca gcgcatgaaa aataaaggct gggcgctag catcatcaat   420
atgagcagta ttctggggct cattggcgat ccgacgctgg ggcatacaa cgcttccaag   480
ggggcggtac gtatcatgtc gaaaagcgca gcgctggatt gcgcactgaa ggactacgat   540
gtgcgtgtca acacagtaca tccgggcccc atcaagaccc cgcggctcga tgatctggaa   600
ggttgggagg aaatgatgtc acagcgtacg ttaaccccta tgggccacat tggcgaaccg   660
aatgacatcg catggatctg tgtgtacctg gcatctgacg aatcgaaatt tgcgacgggt   720
gcagaatttg tggtcgacgg cgggtggacc gcacag                             756

SEQ ID NO: 34           moltype = AA   length = 252
```

```
FEATURE                 Location/Qualifiers
REGION                  1..252
                        note = Engineered Variant of Kred from Lactobacillus kefir
source                  1..252
                        mol_type = protein
                        organism = synthetic construct
SEQUENCE: 34
MTDRLKHKVA IVTGGTLGIG LAIADKFVEE GAKVVITGRH ADVGEKAAKS IGGTDVIRFV   60
QHDASEEAGW TKLFDTTEEA FGPVTTVVNN AGIGVIKSVE DTTTEEWRKL LSVNLDGVFF  120
GTRLGIQRMK NKGLGASIIN MSSILGLIGD PTLGAYNASK GAVRIMSKSA ALDCALKDYD  180
VRVNTVHPGP IKTPRLDDLE GWEEMMSQRT LTPMGHIGEP NDIAWICVYL ASDESKFATG  240
AEFVVDGGWT AQ                                                     252

SEQ ID NO: 35           moltype = DNA  length = 756
FEATURE                 Location/Qualifiers
misc_feature            1..756
                        note = Engineered Variant of Kred from Lactobacillus kefir
source                  1..756
                        mol_type = other DNA
                        organism = synthetic construct
SEQUENCE: 35
atgaccgatc gtctgaagca taaagtagcc atcgtaaccg gcgggacact gggtatcggt   60
ttggcaatcg ccgataaatt tgtagaggag ggtgcgaaag tagttattac tggtcgtcac  120
gcggatgtag gtgaaaaggc cgccaaatca atcggcggca ctgatgttat tcgctttgtc  180
cagcacgatg cgtccgaaga agcaggctgg acgaaactgt tcgacaccac cgaggaggca  240
ttcggcccgg ttacgaccgt cgtgaacaat gcagggattg ggttattaa aagcgttgaa   300
gacactacca cggaggaatg gcgtaaactg ctgtccgtta atctggatgg tgttttttc   360
ggcacccgtc tgggcattca gcgcatgaaa aataaaggct gggcgctag catcatcaat   420
atgagcagta ttctggggct cgtaggcgat ccgacgtgtg gggcatacaa cgcttccaag  480
ggggcggtac gtatcatgtc gaaaagcgca gcgctggatt gcgcactgaa ggactacgat  540
gtgcgtgtca acacagtaca tccgggcccc atcaagaccc cgcggctcga tgatctggaa  600
ggttgggagg aaatgatgtc acagcgtacg ttaacccta tgggccacat tggcgaaccg  660
aatgacatcg catggatctg tgtgtacctg gcatctgacg aatcgaaatt tgcgacgggt  720
gcagaatttg tggtcgacgg cgggtggacc gcacag                           756

SEQ ID NO: 36           moltype = AA  length = 252
FEATURE                 Location/Qualifiers
REGION                  1..252
                        note = Engineered Variant of Kred from Lactobacillus kefir
source                  1..252
                        mol_type = protein
                        organism = synthetic construct
SEQUENCE: 36
MTDRLKHKVA IVTGGTLGIG LAIADKFVEE GAKVVITGRH ADVGEKAAKS IGGTDVIRFV   60
QHDASEEAGW TKLFDTTEEA FGPVTTVVNN AGIGVIKSVE DTTTEEWRKL LSVNLDGVFF  120
GTRLGIQRMK NKGLGASIIN MSSILGLVGD PTCGAYNASK GAVRIMSKSA ALDCALKDYD  180
VRVNTVHPGP IKTPRLDDLE GWEEMMSQRT LTPMGHIGEP NDIAWICVYL ASDESKFATG  240
AEFVVDGGWT AQ                                                     252

SEQ ID NO: 37           moltype = DNA  length = 756
FEATURE                 Location/Qualifiers
misc_feature            1..756
                        note = Engineered Variant of Kred from Lactobacillus kefir
source                  1..756
                        mol_type = other DNA
                        organism = synthetic construct
SEQUENCE: 37
atgaccgatc gtctgaagca taaagtagcc atcgtaaccg gcgggacact gggtatcggt   60
ttggcaatcg ccgataaatt tgtagaggag ggtgcgaaag tagttattac tggtcgtcac  120
gcggatgtag gtgaaaaggc cgccaaatca atcggcggca ctgatgttat tcgctttgtc  180
cagcacgatg cgtccgaaga agcaggctgg acgaaactgt tcgacaccac cgaggaggca  240
ttcggcccgg ttacgaccgt cgtgaacaat gcagggattg ggttattaa aagcgttgaa   300
gacactacca cggaggaatg gcgtaaactg ctgtccgtta atctggatgg tgttttttc   360
ggcacccgtc tgggcattca gcgcatgaaa aataaaggct gggcgctag catcatcaat   420
atgagcagta ttctggggct cgtaggcgat ccgacgctgg gggcatacaa cgcttccaag  480
ggggcggtac gtatcatgtc gaaaagcgca gcgctggatt gcgcactgaa ggactacgat  540
gtgcgtgtca acacagtaca tccgggcccc atcaagaccc cgcggctcga tgatctgcag  600
ggttgggagg aaatgatgtc acagcgtacg ttaacccta tgggccacat tggcgaaccg  660
aatgacatcg catggatctg tgtgtacctg gcatctgacg aatcgaaatt tgcgacgggt  720
gcagaatttg tggtcgacgg cgggtggacc gcacag                           756

SEQ ID NO: 38           moltype = AA  length = 252
FEATURE                 Location/Qualifiers
REGION                  1..252
                        note = Engineered Variant of Kred from Lactobacillus kefir
source                  1..252
                        mol_type = protein
                        organism = synthetic construct
SEQUENCE: 38
```

```
MTDRLKHKVA IVTGGTLGIG LAIADKFVEE GAKVVITGRH ADVGEKAAKS IGGTDVIRFV    60
QHDASEEAGW TKLFDTTEEA FGPVTTVVNN AGIGVIKSVE DTTTEEWRKL LSVNLDGVFF   120
GTRLGIQRMK NKGLGASIIN MSSILGLVGD PTLGAYNASK GAVRIMSKSA ALDCALKDYD   180
VRVNTVHPGP IKTPRLDDLQ GWEEMMSQRT LTPMGHIGEP NDIAWICVYL ASDESKFATG   240
AEFVVDGGWT AQ                                                       252

SEQ ID NO: 39           moltype = DNA  length = 756
FEATURE                 Location/Qualifiers
misc_feature            1..756
                        note = Engineered Variant of Kred from Lactobacillus kefir
source                  1..756
                        mol_type = other DNA
                        organism = synthetic construct
SEQUENCE: 39
atgaccgatc gtctgaagca taaagtagcc atcgtaaccg gcgggacact gggtatcggt    60
ttggcaatcg ccgataaatt tgtagaggag ggtgcgaaag tagttattac tggtcgtcac   120
gcggatgtag gtgaaaaggc cgccaaatca atcggcggca ctgatgttat tcgctttgtc   180
cagcacgatg cgtccgaaga agcaggctgg acgaaactgt tcgacaccac cgaggaggca   240
ttcggcccgg ttacgaccgt cgtgaacaat gcagggattg gggttattaa aagcgttgaa   300
gacactacca cggaggaatg gcgtaaactg ctgtccgtta atctggatgg tgttttttc   360
ggcacccgtc tgggcattca gcgcatgaaa aataaaggct gggcgctag catcatcaat   420
atgagcagta ttctggggct cgtaggcgat ccgacgctgg gggcatacaa cgcttccaag   480
ggggcggtac gtatcatgtc gaaaagcgca gcgctggatt gcgcactgaa ggactacgat   540
gtgcgtgtca acacagtaca tccgggcccc atcaagacca gcgggctcga tctggaa   600
ggttgggagg aaatgatgtc acagcgtacg ttaaccccta tgggccacat tggcgaaccg   660
aatgacatcg catggatctg tgtgtacctg gcatctgacg aatcgaaatt tgcgacgggt   720
gcagaatttg tggtcgacgg cgggtggacc gcacag                              756

SEQ ID NO: 40           moltype = AA  length = 252
FEATURE                 Location/Qualifiers
REGION                  1..252
                        note = Engineered Variant of Kred from Lactobacillus kefir
source                  1..252
                        mol_type = protein
                        organism = synthetic construct
SEQUENCE: 40
MTDRLKHKVA IVTGGTLGIG LAIADKFVEE GAKVVITGRH ADVGEKAAKS IGGTDVIRFV    60
QHDASEEAGW TKLFDTTEEA FGPVTTVVNN AGIGVIKSVE DTTTEEWRKL LSVNLDGVFF   120
GTRLGIQRMK NKGLGASIIN MSSILGLVGD PTLGAYNASK GAVRIMSKSA ALDCALKDYD   180
VRVNTVHPGP IKTRRLDDLE GWEEMMSQRT LTPMGHIGEP NDIAWICVYL ASDESKFATG   240
AEFVVDGGWT AQ                                                       252

SEQ ID NO: 41           moltype = DNA  length = 756
FEATURE                 Location/Qualifiers
misc_feature            1..756
                        note = Engineered Variant of Kred from Lactobacillus kefir
source                  1..756
                        mol_type = other DNA
                        organism = synthetic construct
SEQUENCE: 41
atgaccgatc gtctgaagca taaagtagcc atcgtaaccg gcgggacact gggtatcggt    60
ttggcaatcg ccgataaatt tgtagaggag ggtgcgaaag tagttattac tggtcgtcac   120
gcggatgtag gtgaaaaggc cgccaaatca atcggcggca ctgatgttat tcgctttgtc   180
cagcacgatg cgtccgaaga agcaggctgg acgaaactgt tcgacaccac cgaggaggca   240
ttcggcccgg ttacgaccgt cgtgaacaat gcagggattg gggttattaa aagcgttgaa   300
gacactacca cggaggaatg gcgtaaactg ctgtccgtta atctggatgg tgttttttc   360
ggcacccgtc tgggcattca gcgcatgaaa aataaaggct gggcgctag catcatcaat   420
atgagcagta ttctggggct cgtaggcgat ccgacgctgg gggcatacaa cgcttccaag   480
ggggcggtac gtatcatgtc gaaaagcgca gcgctggatt gcgcactgaa ggactacgat   540
gtgcgtgtca acacagtaca tccgggcccc atcaagaccc gcggctcga tctgcgg    600
ggttgggagg aaatgatgtc acagcgtacg ttaaccccta tgggccacat tggcgaaccg   660
aatgacatcg catggatctg tgtgtacctg gcatctgacg aatcgaaatt tgcgacgggt   720
gcagaatttg tggtcgacgg cgggtggacc gcacag                              756

SEQ ID NO: 42           moltype = AA  length = 252
FEATURE                 Location/Qualifiers
REGION                  1..252
                        note = Engineered Variant of Kred from Lactobacillus kefir
source                  1..252
                        mol_type = protein
                        organism = synthetic construct
SEQUENCE: 42
MTDRLKHKVA IVTGGTLGIG LAIADKFVEE GAKVVITGRH ADVGEKAAKS IGGTDVIRFV    60
QHDASEEAGW TKLFDTTEEA FGPVTTVVNN AGIGVIKSVE DTTTEEWRKL LSVNLDGVFF   120
GTRLGIQRMK NKGLGASIIN MSSILGLVGD PTLGAYNASK GAVRIMSKSA ALDCALKDYD   180
VRVNTVHPGP IKTPRLDDLR GWEEMMSQRT LTPMGHIGEP NDIAWICVYL ASDESKFATG   240
AEFVVDGGWT AQ                                                       252

SEQ ID NO: 43           moltype = DNA  length = 756
```

```
FEATURE                 Location/Qualifiers
misc_feature            1..756
                        note = Engineered Variant of Kred from Lactobacillus kefir
source                  1..756
                        mol_type = other DNA
                        organism = synthetic construct
SEQUENCE: 43
atgaccgatc gtctgaagca taaagtagcc atcgtaaccg gcgggacact gggtatcggt    60
ttggcaatcg ccgataaatt tgtagaggag ggtgcgaaag tagttattac tggtcgtcac   120
gcggatgtag gtgaaaaggc cgccaaatca atcggcggca ctgatgttat tcgctttgtc   180
cagcacgatg cgtccgaaga agcaggctgg acgaaactgt tcgacaccac cgaggaggca   240
ttcggcccgg ttacgaccgt cgtgaacaat gcagggattg gggttattaa agcgttgaa   300
gacactacca cggaggaatg gcgtaaactg ctgtccgtta atctggatgg tgttttttc   360
ggcacccgtc tgggcattca gcgcatgaaa aataaaggct gggcgctag catcatcaat   420
atgagcagta ttctggggct cgtaggcgat ccgacgctgg gggcatacaa cgcttccaag   480
ggggcggtac gtatcatgtc gaaaagcgca gcgctggatt gcgcactgaa ggactacgat   540
gtgcgtgtca acacagtaca tccgggcccc atcaagaccc cgcggctcga tgatctggaa   600
ggttgggagg aaatggtgtc acagcgtacg ttaacccta tgggcacat tggcgaaccg   660
aatgacatcg catggatctg tgtgtacctg gcatctgacg aatcgaaatt tgcgacgggt   720
gcagaatttg tggtcgacgg cgggtggacc gcacag                             756

SEQ ID NO: 44           moltype = AA  length = 252
FEATURE                 Location/Qualifiers
REGION                  1..252
                        note = Engineered Variant of Kred from Lactobacillus kefir
source                  1..252
                        mol_type = protein
                        organism = synthetic construct
SEQUENCE: 44
MTDRLKHKVA IVTGGTLGIG LAIADKFVEE GAKVVITGRH ADVGEKAAKS IGGTDVIRFV    60
QHDASEEAGW TKLFDTTEEA FGPVTTVVNN AGIGVIKSVE DTTTEEWRKL LSVNLDGVFF   120
GTRLGIQRMK NKGLGASIIN MSSILGLVGD PTLGAYNASK GAVRIMSKSA ALDCALKDYD   180
VRVNTVHPGP IKTPRLDDLE GWEEMVSQRT LTPMGHIGEP NDIAWICVYL ASDESKFATG   240
AEFVVDGGWT AQ                                                       252

SEQ ID NO: 45           moltype = DNA  length = 756
FEATURE                 Location/Qualifiers
misc_feature            1..756
                        note = Engineered Variant of Kred from Lactobacillus kefir
source                  1..756
                        mol_type = other DNA
                        organism = synthetic construct
SEQUENCE: 45
atgaccgatc gtctgaagca taaagtagcc atcgtaaccg gcgggacact gggtatcggt    60
ttggcaatcg ccgataaatt tgtagaggag ggtgcgaaag tagttattac tggtcgtcac   120
gcggatgtag gtgaaaaggc cgccaaatca atcggcggca ctgatgttat tcgctttgtc   180
cagcacgatg cgtccgaaga agcaggctgg acgaaactgt tcgacaccac cgaggaggca   240
ttcggcccgg ttacgaccgt cgtgaacaat gcagggatgg gggttattaa agcgttgaa   300
gacactacca cggaggaatg gcgtaaactg ctgtccgtta atctggatgg tgttttttc   360
ggcacccgtc tgggcattca gcgcatgaaa aataaaggct gggcgctag catcatcaat   420
atgagcagta ttctggggct cgtaggcgat ccgacgctgg gggcatacaa cgcttccaag   480
ggggcggtac gtatcatgtc gaaaagcgca gcgctggatt gcgcactgaa ggactacgat   540
gtgcgtgtca acacagtaca tccgggcccc atcaagaccc cgcggctcga tgatctggaa   600
ggttgggagg aaatgatgtc acagcgtacg ttaacccta tgggcacat tggcgaaccg   660
aatgacatcg catggatctg tgtgtacctg gcatctgacg aatcgaaatt tgcgacgggt   720
gcagaatttg tggtcgacgg cgggtggacc gcacag                             756

SEQ ID NO: 46           moltype = AA  length = 252
FEATURE                 Location/Qualifiers
REGION                  1..252
                        note = Engineered Variant of Kred from Lactobacillus kefir
source                  1..252
                        mol_type = protein
                        organism = synthetic construct
SEQUENCE: 46
MTDRLKHKVA IVTGGTLGIG LAIADKFVEE GAKVVITGRH ADVGEKAAKS IGGTDVIRFV    60
QHDASEEAGW TKLFDTTEEA FGPVTTVVNN AGMGVIKSVE DTTTEEWRKL LSVNLDGVFF   120
GTRLGIQRMK NKGLGASIIN MSSILGLVGD PTLGAYNASK GAVRIMSKSA ALDCALKDYD   180
VRVNTVHPGP IKTPRLDDLE GWEEMMSQRT LTPMGHIGEP NDIAWICVYL ASDESKFATG   240
AEFVVDGGWT AQ                                                       252

SEQ ID NO: 47           moltype = DNA  length = 756
FEATURE                 Location/Qualifiers
misc_feature            1..756
                        note = Engineered Variant of Kred from Lactobacillus kefir
source                  1..756
                        mol_type = other DNA
                        organism = synthetic construct
SEQUENCE: 47
```

```
atgaccgatc gtctgaagca taaagtagcc atcgtaaccg gcgggacact gggtatcggt   60
ttggcaatcg ccgataaatt tgtagaggag ggtgcgaaag tagttattac tggtcgtcac  120
gcggatgtag gtgaaaaggc cgccaaatca atcggcggca ctgatgttat tcgctttgtc  180
cagcacgatg cgtccgaaga agcaggctgg acgaaactgt tcgacaccac cgaggaggca  240
ttcggcccgg ttacgaccgt cgtgaacaat gcagggattg gggttattaa aagcgttgaa  300
gacactacca cggaggaatg gcgtaaactg ctgtccgtta atctggatgg tgttttttc   360
ggcacccgtc tgggcattca gcgcatgaaa aataaaggct gggcgctag catcatcaat   420
atgagcagta ttctggggct cgtaggcgat ccgacgctgg gggcatacaa cgcttccaag  480
ggggcggtac gtatcatgtc gaaaagcgca gcgctggatt gcgcactgaa ggactacgat  540
gtgcgtgtca acacagtaca tccgggcccc atcaagaccc cgggctgcag tgatctgaa   600
ggttgggagg aaatgatgtc acagcgtacg ttaacccta tggcgcacat tggcgaaccg  660
aatgacatcg catggatctg tgtgtacctg gcatctgacg aatcgaaatt tgcgacgggt  720
gcagaatttg tggtcgacgg cgggtggacc gcacag                           756

SEQ ID NO: 48          moltype = AA   length = 252
FEATURE                Location/Qualifiers
REGION                 1..252
                       note = Engineered Variant of Kred from Lactobacillus kefir
source                 1..252
                       mol_type = protein
                       organism = synthetic construct
SEQUENCE: 48
MTDRLKHKVA IVTGGTLGIG LAIADKFVEE GAKVVITGRH ADVGEKAAKS IGGTDVIRFV   60
QHDASEEAGW TKLFDTTEEA FGPVTTVVNN AGIGVIKSVE DTTTEEWRKL LSVNLDGVFF  120
GTRLGIQRMK NKGLGASIIN MSSILGLVGD PTLGAYNASK GAVRIMSKSA ALDCALKDYD  180
VRVNTVHPGP IKTPRLGDLE GWEEMMSQRT LTPMGHIGEP NDIAWICVYL ASDESKFATG  240
AEFVVDGGWT AQ                                                     252

SEQ ID NO: 49          moltype = DNA   length = 756
FEATURE                Location/Qualifiers
misc_feature           1..756
                       note = Engineered Variant of Kred from Lactobacillus kefir
source                 1..756
                       mol_type = other DNA
                       organism = synthetic construct
SEQUENCE: 49
atgaccgatc gtctgaagca taaagtagcc atcgtaaccg gcgggacact gggtatcggt   60
ttggcaatcg ccgataaatt tgtagaggag ggtgcgaaag tagttattac tggtcgtcac  120
gcggatgtag gtgaaaaggc cgccaaatca atcggcggca ctgatgttat tcgctttgtc  180
cagcacgatg cgtccgaaga agcaggctgg acgaaactgt tcgacaccac cgaggaggca  240
ttcggcccgg ttacgaccgt cgtgaacaat gcagggattg gggttattaa aagcgttgaa  300
gacactacca cggaggaatg gcgtaaactg ctgtccgtta atctggatgg tgttttttc   360
ggcacccgtc tgggcattca gcgcatgaaa aataaaggct gggcgctag catcatcaat   420
atgagcagta ttctggggct cgtaggcgat ccgacgctgg gggcatacaa cgcttccaag  480
ggggcggtac gtatcatgtc gaaaagcgca gcgctggatt gcgcactgaa ggactacgat  540
gtgcgtgtca acacagtaca tccgggcccc atcaagacca tcggctcga tgatctgaa   600
ggttgggagg aaatgatgtc acagcgtacg ttaacccta tggcgcacat tggcgaaccg  660
aatgacatcg catggatctg tgtgtacctg gcatctgacg aatcgaaatt tgcgacgggt  720
gcagaatttg tggtcgacgg cgggtggacc gcacag                           756

SEQ ID NO: 50          moltype = AA   length = 252
FEATURE                Location/Qualifiers
REGION                 1..252
                       note = Engineered Variant of Kred from Lactobacillus kefir
source                 1..252
                       mol_type = protein
                       organism = synthetic construct
SEQUENCE: 50
MTDRLKHKVA IVTGGTLGIG LAIADKFVEE GAKVVITGRH ADVGEKAAKS IGGTDVIRFV   60
QHDASEEAGW TKLFDTTEEA FGPVTTVVNN AGIGVIKSVE DTTTEEWRKL LSVNLDGVFF  120
GTRLGIQRMK NKGLGASIIN MSSILGLVGD PTLGAYNASK GAVRIMSKSA ALDCALKDYD  180
VRVNTVHPGP IKTNRLDDLE GWEEMMSQRT LTPMGHIGEP NDIAWICVYL ASDESKFATG  240
AEFVVDGGWT AQ                                                     252

SEQ ID NO: 51          moltype = DNA   length = 756
FEATURE                Location/Qualifiers
misc_feature           1..756
                       note = Engineered Variant of Kred from Lactobacillus kefir
source                 1..756
                       mol_type = other DNA
                       organism = synthetic construct
SEQUENCE: 51
atgaccgatc gtctgaagca taaagtagcc atcgtaaccg gcgggacact gggtatcggt   60
ttggcaatcg ccgataaatt tgtagaggag ggtgcgaaag tagttattac tggtcgtcac  120
gcggatgtag gtgaaaaggc cgccaaatca atcggcggca ctgatgttat tcgctttgtc  180
cagcacgatg cgtccgaaga agcaggctgg acgaaactgt tcgacaccac cgaggaggca  240
ttcggcccgg ttacgaccgt cgtgaacaat gcagggattg gggttattaa aagcgttgaa  300
gacactacca cggaggaatg gcgtaaactg ctgtccgtta atctggatgg tgttttttc   360
ggcacccgtc tgggcattca gcgcatgaaa aataaaggct gggcgctag catcatcaat   420
```

```
atgagcagta ttctggggct cgtaggcgat ccgacgctgg gggcatacaa cgcttccaag   480
ggggcggtac gtatcatgtc gaaaagcgca gcgctggatt gcgcactgaa ggactacgat   540
gtgcgtgtca acacagtaca tccgggcccc atcaagaccc cgcggctcga tgatctgttg   600
ggttgggagg aaatgatgtc acagcgtacg ttaacccca  tgggccacat tggcgaaccg   660
aatgacatcg catggatctg tgtgtacctg gcatctgacg aatcgaaatt tgcgacgggt   720
gcagaatttg tggtcgacgg cgggtggacc gcacag                              756
```

```
SEQ ID NO: 52              moltype = AA   length = 252
FEATURE                    Location/Qualifiers
REGION                     1..252
                           note = Engineered Variant of Kred from Lactobacillus kefir
source                     1..252
                           mol_type = protein
                           organism = synthetic construct
SEQUENCE: 52
MTDRLKHKVA IVTGGTLGIG LAIADKFVEE GAKVVITGRH ADVGEKAAKS IGGTDVIRFV    60
QHDASEEAGW TKLFDTTEEA FGPVTTVVNN AGIGVIKSVE DTTTEEWRKL LSVNLDGVFF   120
GTRLGIQRMK NKGLGASIIN MSSILGLVGD PTLGAYNASK GAVRIMSKSA ALDCALKDYD   180
VRVNTVHPGP IKTPRLDDLL GWEEMMSQRT LTPMGHIGEP NDIAWICVYL ASDESKFATG   240
AEFVVDGGWT AQ                                                       252
```

```
SEQ ID NO: 53              moltype = DNA   length = 756
FEATURE                    Location/Qualifiers
misc_feature               1..756
                           note = Engineered Variant of Kred from Lactobacillus kefir
source                     1..756
                           mol_type = other DNA
                           organism = synthetic construct
SEQUENCE: 53
atgaccgatc gtctgaagca taaagtagcc atcgtaaccg gcgggacact gggtatcggt    60
ttggcaatcg ccgataaatt tgtagaggag ggtgcgaaag tagttattac tggtcgtcac   120
gcggatgtag gtgaaaaggc cgccaaatca atcggcggca ctgatgttat tcgctttgtc   180
cagcacgatg cgtccgaaga agcaggctgg acgaaactgt tcgacaccac cgaggaggca   240
ttcggcccgg ttacgaccgt cgtgaacaat gcagggattg gggttattaa aagcgttgaa   300
gacactacca cggaggaatg gcgtaaaatt ctgtccgtta atctggatgg tgtttttttc   360
ggcacccgtc tgggcattca gcgcatgaaa aataaaggct tgggcgctag catcatcaat   420
atgagcagta ttctggggct cgtaggcgat ccgacgctgg gggcatacaa cgcttccaag   480
ggggcggtac gtatcatgtc gaaaagcgca gcgctggatt gcgcactgaa ggactacgat   540
gtgcgtgtca acacagtaca tccgggcccc atcaagaccc cgcggctcga tgatctggaa   600
ggttgggagg aaatgatgtc acagcgtacg ttaacccca  tgggccacat tggcgaaccg   660
aatgacatcg catggatctg tgtgtacctg gcatctgacg aatcgaaatt tgcgacgggt   720
gcagaatttg tggtcgacgg cgggtggacc gcacag                              756
```

```
SEQ ID NO: 54              moltype = AA   length = 252
FEATURE                    Location/Qualifiers
REGION                     1..252
                           note = Engineered Variant of Kred from Lactobacillus kefir
source                     1..252
                           mol_type = protein
                           organism = synthetic construct
SEQUENCE: 54
MTDRLKHKVA IVTGGTLGIG LAIADKFVEE GAKVVITGRH ADVGEKAAKS IGGTDVIRFV    60
QHDASEEAGW TKLFDTTEEA FGPVTTVVNN AGIGVIKSVE DTTTEEWRKI LSVNLDGVFF   120
GTRLGIQRMK NKGLGASIIN MSSILGLVGD PTLGAYNASK GAVRIMSKSA ALDCALKDYD   180
VRVNTVHPGP IKTPRLDDLE GWEEMMSQRT LTPMGHIGEP NDIAWICVYL ASDESKFATG   240
AEFVVDGGWT AQ                                                       252
```

```
SEQ ID NO: 55              moltype = DNA   length = 756
FEATURE                    Location/Qualifiers
misc_feature               1..756
                           note = Engineered Variant of Kred from Lactobacillus kefir
source                     1..756
                           mol_type = other DNA
                           organism = synthetic construct
SEQUENCE: 55
atgaccgatc gtctgaagca taaagtagcc atcgtaaccg gcgggacact gggtatcggt    60
ttggcaatcg ccgataaatt tgtagaggag ggtgcgaaag tagttattac tggtcgtcac   120
gcggatgtag gtgaaaaggc cgccaaatca atcggcggca ctgatgttat tcgctttgtc   180
cagcacgatg cgtccgaaga agcaggctgg acgaaactgt tcgacaccac cgaggaggca   240
ttcggcccgg ttacgaccgt cgtgaacaat gcagggattg gggttattaa aagcgttgaa   300
gacactacca cggaggaatg gcgtaaactg ctgtccgtta atctggatgg tgtttttttc   360
ggcacccgtc tgggcattca gcgcatgaaa aataaaggct tgggcgctag catcatcaat   420
atgagcagta ttctggggct cgtaggcgat ccgacgctgg gggcatacaa cgcttccaag   480
ggggcggtac gtatcatgtc gaaaagcgca gcgctggatt gcgcactgaa ggactacgat   540
gtgcgtgtca acacagtaca tccgggcccc atcaagaccc cgcggctcga tgatctggaa   600
ggttgggagg aaatgatgtc acagcgtacg ttaacccca  tgggccacat tggcgaaccg   660
aatgacatcg catggatctg tgtgtacctg gcatctgacg aatcgaaatt tgcgacgggt   720
gcagaatttg tggtcgacgg cgggtggacc gcacag                              756
```

```
SEQ ID NO: 56              moltype = AA   length = 252
FEATURE                    Location/Qualifiers
REGION                     1..252
                           note = Engineered Variant of Kred from Lactobacillus kefir
source                     1..252
                           mol_type = protein
                           organism = synthetic construct
SEQUENCE: 56
MTDRLKHKVA IVTGGTLGIG LAIADKFVEE GAKVVITGRH ADVGEKAAKS IGGTDVIRFV    60
QHDASEEAGW TKLFDTTEEA FGPVTTVVNN AGIGVIKSVE DTTTEEWRKL LSVNLDGVFF   120
GTRLGIQRMK NKGLGASIIN MSSILGLVGD PTLGAYNASK GAVRIMSKSA ALDCALKDYD   180
VRVNTVHPGP IKTPRLDDLE GWEEMMSQRT LTPMGHIGEP NDIAWLCVYL ASDESKFATG   240
AEFVVDGGWT AQ                                                      252

SEQ ID NO: 57              moltype = DNA   length = 756
FEATURE                    Location/Qualifiers
misc_feature               1..756
                           note = Engineered Variant of Kred from Lactobacillus kefir
source                     1..756
                           mol_type = other DNA
                           organism = synthetic construct
SEQUENCE: 57
atgaccgatc gtctgaagca taaagtagcc atcgtaaccg gcgggacact gggtatcggt    60
ttggcaatcg ccgataaatt tgtagaggag ggtgcgaaag tagttattac tggtcgtcac   120
gcggatgtag gtgaaaaggc cgccaaatca atcggcggca ctgatgttat tcgctttgtc   180
cagcacgatg cgtccgaaga agcaggctgg acgaaactgt tcgacaccac cgaggaggca   240
ttcggcccgg ttacgaccgt cgtgaacaat gcagggacgg gggttattaa aagcgttgaa   300
gacactacca cggaggaatg gcgtaaactg ctgtccgtta atctggatgg tgttttttc   360
ggcacccgtc tgggcattca gcgcatgaaa aataaaggct gggcgctag catcatcaat   420
atgagcagta ttctggggct cgtaggcgat ccgacgctgg ggcatacaa cgcttccaag   480
ggggcggtac gtatcatgtc gaaaagcgca gcgctggatt gcgcactgaa ggactacgat   540
gtgcgtgtca acacagtaca tccgggcccc atcaagaccc cgcggctcga tgatctggaa   600
ggttgggagg aaatgatgtc acagcgtacg ttaaccccta tgggccacat tggcgaaccg   660
aatgacatcg catggatctg tgtgtacctg gcatctgacg aatcgaaatt tgcgacgggt   720
gcagaatttg tggtcgacgg cgggtggacc gcacag                            756

SEQ ID NO: 58              moltype = AA   length = 252
FEATURE                    Location/Qualifiers
REGION                     1..252
                           note = Engineered Variant of Kred from Lactobacillus kefir
source                     1..252
                           mol_type = protein
                           organism = synthetic construct
SEQUENCE: 58
MTDRLKHKVA IVTGGTLGIG LAIADKFVEE GAKVVITGRH ADVGEKAAKS IGGTDVIRFV    60
QHDASEEAGW TKLFDTTEEA FGPVTTVVNN AGTGVIKSVE DTTTEEWRKL LSVNLDGVFF   120
GTRLGIQRMK NKGLGASIIN MSSILGLVGD PTLGAYNASK GAVRIMSKSA ALDCALKDYD   180
VRVNTVHPGP IKTPRLDDLE GWEEMMSQRT LTPMGHIGEP NDIAWICVYL ASDESKFATG   240
AEFVVDGGWT AQ                                                      252

SEQ ID NO: 59              moltype = DNA   length = 756
FEATURE                    Location/Qualifiers
misc_feature               1..756
                           note = Engineered Variant of Kred from Lactobacillus kefir
source                     1..756
                           mol_type = other DNA
                           organism = synthetic construct
SEQUENCE: 59
atgaccgatc gtctgaagca taaagtagcc atcgtaaccg gcgggacact gggtatcggt    60
ttggcaatcg ccgataaatt tgtagaggag ggtgcgaaag tagttattac tggtcgtcac   120
gcggatgtag gtgaaaaggc cgccaaatca atcggcggca ctgatgttat tcgctttgtc   180
cagcacgatg cgtccgaaga agcaggctgg acgaaactgt tcgacaccac cgaggaggca   240
ttcggcccgg ttacgaccgt cgtgaacaat gcagggattg gggttattaa aagcgttgaa   300
gacactacca cggaggaatg gcgtaaactg ctgtccgtta atctggatgg tgttttttc   360
ggcacccgtc tgggcattca gcgcatgaaa aataaaggct gggcgctag catcatcaat   420
atgagcagta ttctggggct cgtaggcgat ccgacgctgg ggcatacaa cgcttccaag   480
ggggcggtac gtatcatgtc gaaaagcgca gcgctggatt gcgcactgaa ggactacgat   540
gtgcgtgtca acacagtaca tccgggcccc atcaagaccc cgcggctcga tgatctggaa   600
ggttgggagg aaatgatgtc acagcgtacg ttaagtccta tgggccacat tggcgaaccg   660
aatgacatcg catggatctg tgtgtacctg gcatctgacg aatcgaaatt tgcgacgggt   720
gcagaatttg tggtcgacgg cgggtggacc gcacag                            756

SEQ ID NO: 60              moltype = AA   length = 252
FEATURE                    Location/Qualifiers
REGION                     1..252
                           note = Engineered Variant of Kred from Lactobacillus kefir
source                     1..252
                           mol_type = protein
                           organism = synthetic construct
```

```
SEQUENCE: 60
MTDRLKHKVA IVTGGTLGIG LAIADKFVEE GAKVVITGRH ADVGEKAAKS IGGTDVIRFV    60
QHDASEEAGW TKLFDTTEEA FGPVTTVVNN AGIGVIKSVE DTTTEEWRKL LSVNLDGVFF   120
GTRLGIQRMK NKGLGASIIN MSSILGLVGD PTLGAYNASK GAVRIMSKSA ALDCALKDYD   180
VRVNTVHPGP IKTPRLDDLE GWEEMMSQRT LSPMGHIGEP NDIAWICVYL ASDESKFATG   240
AEFVVDGGWT AQ                                                      252

SEQ ID NO: 61           moltype = DNA  length = 756
FEATURE                 Location/Qualifiers
misc_feature            1..756
                        note = Engineered Variant of Kred from Lactobacillus kefir
source                  1..756
                        mol_type = other DNA
                        organism = synthetic construct
SEQUENCE: 61
atgaccgatc gtctgaagca taaagtagcc atcgtaaccg gcgggacact gggtatcggt    60
ttggcaatcg ccgataaatt tgtagaggag ggtgcgaaag tagttattac tggtcgtcac   120
gcggatgtag gtgaaaaggc cgccaaatca atcggcggca ctgatgttat tcgctttgtc   180
cagcacgatg cgtccgaaga agcaggctgg acgaaactgt tcgacaccac cgaggaggca   240
ttcggcccgg ttacgaccgt cgtgaacaat gcagggattg ggttattaa aagcgttgaa    300
gacactacca cggaggaatg gcgtaaactg ctgtccgtta atctggatgg tgttttttc    360
ggcacccgtc tgggcattca gcgcatgaaa aataaaggct gggcgctag catcatcaat    420
atgagcagta ttctggggct cgtaggcgat ccgacgctgg gggcataca cgcttccaag    480
ggggcggtac gtatcatgtc gaaaagcgca gcgctggatt gcgcactgaa ggactacgat   540
gtgcgtgtca acacagtaca tccgggcccc atcaagaccc atcggctcga tgatctgaa    600
ggttgggagg aaatgatgtc acagcgtacg ttaaccccta tgggcacat tggcgaaccg   660
aatgacatcg catggatctg tgtgtacctg gcatctgacg aatcgaaatt tgcgacgggt   720
cagaatttg tggtcgacgg cgggtggacc gcacag                             756

SEQ ID NO: 62           moltype = AA  length = 252
FEATURE                 Location/Qualifiers
REGION                  1..252
                        note = Engineered Variant of Kred from Lactobacillus kefir
source                  1..252
                        mol_type = protein
                        organism = synthetic construct
SEQUENCE: 62
MTDRLKHKVA IVTGGTLGIG LAIADKFVEE GAKVVITGRH ADVGEKAAKS IGGTDVIRFV    60
QHDASEEAGW TKLFDTTEEA FGPVTTVVNN AGIGVIKSVE DTTTEEWRKL LSVNLDGVFF   120
GTRLGIQRMK NKGLGASIIN MSSILGLVGD PTLGAYNASK GAVRIMSKSA ALDCALKDYD   180
VRVNTVHPGP IKTHRLDDLE GWEEMMSQRT LTPMGHIGEP NDIAWICVYL ASDESKFATG   240
AEFVVDGGWT AQ                                                      252

SEQ ID NO: 63           moltype = DNA  length = 756
FEATURE                 Location/Qualifiers
misc_feature            1..756
                        note = Engineered Variant of Kred from Lactobacillus kefir
source                  1..756
                        mol_type = other DNA
                        organism = synthetic construct
SEQUENCE: 63
atgaccgatc gtctgaagca taaagtagcc atcgtaaccg gcgggacact gggtatcggt    60
ttggcaatcg ccgataaatt tgtagaggag ggtgcgaaag tagttattac tggtcgtcac   120
gcggatgtag gtgaaaaggc cgccaaatca atcggcggca ctgatgttat tcgctttgtc   180
cagcacgatg cgtccgaaga agcaggctgg acgaaactgt tcgacaccac cgaggaggca   240
ttcggcccgg ttacgaccgt cgtgaacaat gcagggattg ggttattaa aagcgttgaa    300
gacactacca cggaggaatg gcgtaaactg ctgtccgtta atctggatgg tgttttttc    360
ggcacccgtc tgggcattca gcgcatgaaa aataaaggct gggcgctag catcatcaat    420
atgagcagta ttctggggct cgtaggcgat ccgtctctgg gggcataca cgcttccaag    480
ggggcggtac gtatcatgtc gaaaagcgca gcgctggatt gcgcactgaa ggactacgat   540
gtgcgtgtca acacagtaca tccgggcccc atcaagaccc gcggctcga tgatctgaa    600
ggttgggagg aaatgatgtc acagcgtacg ttaaccccta tgggcacat tggcgaaccg   660
aatgacatcg catggatctg tgtgtacctg gcatctgacg aatcgaaatt tgcgacgggt   720
cagaatttg tggtcgacgg cgggtggacc gcacag                             756

SEQ ID NO: 64           moltype = AA  length = 252
FEATURE                 Location/Qualifiers
REGION                  1..252
                        note = Engineered Variant of Kred from Lactobacillus kefir
source                  1..252
                        mol_type = protein
                        organism = synthetic construct
SEQUENCE: 64
MTDRLKHKVA IVTGGTLGIG LAIADKFVEE GAKVVITGRH ADVGEKAAKS IGGTDVIRFV    60
QHDASEEAGW TKLFDTTEEA FGPVTTVVNN AGIGVIKSVE DTTTEEWRKL LSVNLDGVFF   120
GTRLGIQRMK NKGLGASIIN MSSILGLVGD PSLGAYNASK GAVRIMSKSA ALDCALKDYD   180
VRVNTVHPGP IKTPRLDDLE GWEEMMSQRT LTPMGHIGEP NDIAWICVYL ASDESKFATG   240
AEFVVDGGWT AQ                                                      252
```

```
SEQ ID NO: 65              moltype = DNA  length = 756
FEATURE                    Location/Qualifiers
misc_feature               1..756
                           note = Engineered Variant of Kred from Lactobacillus kefir
source                     1..756
                           mol_type = other DNA
                           organism = synthetic construct
SEQUENCE: 65
atgaccgatc gtctgaagca taaagtagcc atcattaccg gcgggacact gggtatcggt   60
ttggcaatcg ccgataaatt tgtagaggag ggtgcgaaag tagttattac tggtcgtcac  120
gcggatgtag gtgaaaaggc cgccaaatca atcggcggca ctgatgttat tcgctttgtc  180
cagcacgatg cgtccgaaga agcaggctgg acgaaactgt tcgacaccac cgaggaggca  240
ttcggcccgg ttacgaccgt cgtgaacaat gcagggattg gggttattaa aagcgttgaa  300
gacactacca cggaggaatg gcgtaaactg ctgtccgtta atctggatgg tgttttttc  360
ggcacccgtc tgggcattca gcgcatgaaa aataaaggct tgggcgctag catcatcaat  420
atgagcagta ttctggggct cgtaggcgat ccgacgctgg gggcatacaa cgcttccaag  480
ggggcggtac gtatcatgtc gaaaagcgca gcgctggatt gcgcactgaa ggactacgat  540
gtgcgtgtca acacagtaca tccggggccc atcaagaccc cgcggctcga tgatctgaa  600
ggttgggagg aaatgatgtc acagcgtacg ttaaccccta tgggccacat tggcgaaccg  660
aatgacatcg catggatctg tgtgtacctg gcatctgacg aatcgaaatt tgcgacgggt  720
gcagaatttg tggtcgacgg cgggtggacc gcacag                            756

SEQ ID NO: 66              moltype = AA  length = 252
FEATURE                    Location/Qualifiers
REGION                     1..252
                           note = Engineered Variant of Kred from Lactobacillus kefir
source                     1..252
                           mol_type = protein
                           organism = synthetic construct
SEQUENCE: 66
MTDRLKHKVA IITGGTLGIG LAIADKFVEE GAKVVITGRH ADVGEKAAKS IGGTDVIRFV   60
QHDASEEAGW TKLFDTTEEA FGPVTTVVNN AGIGVIKSVE DTTTEEWRKL LSVNLDGVFF  120
GTRLGIQRMK NKGLGASIIN MSSILGLVGD PTLGAYNASK GAVRIMSKSA ALDCALKDYD  180
VRVNTVHPGP IKTPRLDDLE GWEEMMSQRT LTPMGHIGEP NDIAWICVYL ASDESKFATG  240
AEFVVDGGWT AQ                                                      252

SEQ ID NO: 67              moltype = DNA  length = 756
FEATURE                    Location/Qualifiers
misc_feature               1..756
                           note = Engineered Variant of Kred from Lactobacillus kefir
source                     1..756
                           mol_type = other DNA
                           organism = synthetic construct
SEQUENCE: 67
atgaccgatc gtctgaagca taaagtagcc atcgtaaccg gcgggacact gggtatcggt   60
ttggcaatcg ccgataaatt tgtagaggag ggtgcgaaag tagttattac tggtcgtcac  120
gcggatgtag gtgaaaaggc cgccaaatca atcggcggca ctgatgttat tcgctttgtc  180
cagcacgatg cgtccgaaga agcaggctgg acgaaactgt tcgacaccac cgaggaggca  240
ttcggcccgg ttacgaccgt cgtgaacaat gcagggattg gggttattgg agcgttgaa  300
gacactacca cggaggaatg gcgtaaactg ctgtccgtta atctggatgg tgttttttc  360
ggcacccgtc tgggcattca gcgcatgaaa aataaaggct tgggcgctag catcatcaat  420
atgagcagta ttctggggct cgtaggcgat ccgacgctgg gggcatacaa cgcttccaag  480
ggggcggtac gtatcatgtc gaaaagcgca gcgctggatt gcgcactgaa ggactacgat  540
gtgcgtgtca acacagtaca tccggggccc atcaagaccc gcggctcga tgatctgaa  600
ggttgggagg aaatgatgtc acagcgtacg ttaaccccta tgggccacat tggcgaaccg  660
aatgacatcg catggatctg tgtgtacctg gcatctgacg aatcgaaatt tgcgacgggt  720
gcagaatttg tggtcgacgg cgggtggacc gcacag                            756

SEQ ID NO: 68              moltype = AA  length = 252
FEATURE                    Location/Qualifiers
REGION                     1..252
                           note = Engineered Variant of Kred from Lactobacillus kefir
source                     1..252
                           mol_type = protein
                           organism = synthetic construct
SEQUENCE: 68
MTDRLKHKVA IVTGGTLGIG LAIADKFVEE GAKVVITGRH ADVGEKAAKS IGGTDVIRFV   60
QHDASEEAGW TKLFDTTEEA FGPVTTVVNN AGIGVIGSVE DTTTEEWRKL LSVNLDGVFF  120
GTRLGIQRMK NKGLGASIIN MSSILGLVGD PTLGAYNASK GAVRIMSKSA ALDCALKDYD  180
VRVNTVHPGP IKTPRLDDLE GWEEMMSQRT LTPMGHIGEP NDIAWICVYL ASDESKFATG  240
AEFVVDGGWT AQ                                                      252

SEQ ID NO: 69              moltype = DNA  length = 756
FEATURE                    Location/Qualifiers
misc_feature               1..756
                           note = Engineered Variant of Kred from Lactobacillus kefir
source                     1..756
                           mol_type = other DNA
                           organism = synthetic construct
```

```
SEQUENCE: 69
atgaccgatc gtctgaagca taaagtagcc atcgtaaccg gcgggacact gggtatcggt    60
ttggcaatcg ccgataaatt tgtagaggag ggtgcgaaag tagttattac tggtcgtcac   120
gcggatgtag gtgaaaaggc cgccaaatca atcggcggca ctgatgttat tcgctttgtc   180
cagcacgatg cgtccgaaga agcaggctgg acgaaactgt tcgacaccac cgaggaggca   240
ttcggcccgg ttacgacctt ggtgaacaat gcagggattg ggttattaa aagcgttgaa    300
gacactacca cggaggaatg gcgtaaactg ctgtccgtta atctggatgg tgttttttc    360
ggcacccgtc tggcattca gcgcatgaaa aataaaggct tgggcgctag catcatcaat   420
atgagcagta ttctggggct cgtaggcgat ccgacgctgg gggcatacaa cgcttccaag   480
ggggcggtac gtatcatgtc gaaaagcgca gcgctggatt gcgcactgaa ggactacgat   540
gtgcgtgtca acacagtaca tccgggcccc atcaagaccc cgcggctcga tgatctggaa   600
ggttgggagg aaatgatgtc acagcgtacg ttaaccccta tgggccacat tggcgaaccg   660
aatgacatcg catggatctg tgtgtacctg gcatctgacg aatcgaaatt tgcgacgggt   720
gcagaatttg tggtcgacgg cgggtggacc gcacag                             756

SEQ ID NO: 70           moltype = AA  length = 252
FEATURE                 Location/Qualifiers
REGION                  1..252
                        note = Engineered Variant of Kred from Lactobacillus kefir
source                  1..252
                        mol_type = protein
                        organism = synthetic construct
SEQUENCE: 70
MTDRLKHKVA IVTGGTLGIG LAIADKFVEE GAKVVITGRH ADVGEKAAKS IGGTDVIRFV    60
QHDASEEAGW TKLFDTTEEA FGPVTTLVNN AGIGVIKSVE DTTTEEWRKL LSVNLDGVFF   120
GTRLGIQRMK NKGLGASIIN MSSILGLVGD PTLGAYNASK GAVRIMSKSA ALDCALKDYD   180
VRVNTVHPGP IKTPRLDDLE GWEEMMSQRT LTPMGHIGEP NDIAWICVYL ASDESKFATG   240
AEFVVDGGWT AQ                                                      252

SEQ ID NO: 71           moltype = DNA  length = 756
FEATURE                 Location/Qualifiers
misc_feature            1..756
                        note = Engineered Variant of Kred from Lactobacillus kefir
source                  1..756
                        mol_type = other DNA
                        organism = synthetic construct
SEQUENCE: 71
atgaccgatc gtctgaagca taaagtagcc atcattaccg gcgggacact gggtatcggt    60
ttggcaatcg ccgataaatt tgtagaggag ggtgcgaaag tagttattac tggtcgtcac   120
gcggatgtag gtgaaaaggc cgccaaatca atcggcggca ctgatgttat tcgctttgtc   180
cagcacgatg cgtccgaaga agcaggctgg acgaaactgt tcgacaccac cgaggaggca   240
ttcggcccgg ttacgaccgt cgtgaacaat gcagggattg ggttattaa aagcgttgaa    300
gacactacca cggaggaatg gcgtaaactg ctgtccgtta atctggatgg tgttttttc    360
ggcacccgtc tggcattca gcgcatgaaa aataaaggct tgggcgctag catcatcaat   420
atgagcagta ttatggggct cgtaggcgat ccgactctgg gggcatacaa cgcttccaag   480
ggggcggtac gtatcatgtc gaaaagcgca gcgctggatt gcgcactgaa ggactacgat   540
gtgcgtgtca acacagtaca tccgggcccc atcaagaccc cgcggaagga tgatctggaa   600
ggttgggagg aaatgatgtc acagcgtacg ttaaccccta tgggccacat tggcgaaccg   660
aatgacatcg catggatctg tgtgtacctg gcatctgacg aatcgaaatt tgcgacgggt   720
gcagaatttg tggtcgacgg cgggtggacc gcacag                             756

SEQ ID NO: 72           moltype = AA  length = 252
FEATURE                 Location/Qualifiers
REGION                  1..252
                        note = Engineered Variant of Kred from Lactobacillus kefir
source                  1..252
                        mol_type = protein
                        organism = synthetic construct
SEQUENCE: 72
MTDRLKHKVA IITGGTLGIG LAIADKFVEE GAKVVITGRH ADVGEKAAKS IGGTDVIRFV    60
QHDASEEAGW TKLFDTTEEA FGPVTTVVNN AGIGVIKSVE DTTTEEWRKL LSVNLDGVFF   120
GTRLGIQRMK NKGLGASIIN MSSIMGLVGD PTLGAYNASK GAVRIMSKSA ALDCALKDYD   180
VRVNTVHPGP IKTPRKDDLE GWEEMMSQRT LTPMGHIGEP NDIAWICVYL ASDESKFATG   240
AEFVVDGGWT AQ                                                      252

SEQ ID NO: 73           moltype = DNA  length = 756
FEATURE                 Location/Qualifiers
misc_feature            1..756
                        note = Engineered Variant of Kred from Lactobacillus kefir
source                  1..756
                        mol_type = other DNA
                        organism = synthetic construct
SEQUENCE: 73
atgaccgatc gtctgaagca taaagtagcc atcgtaaccg gcgggacact gggtatcggt    60
ttggcaatcg ccgataaatt tgtagaggag ggtgcgaaag tagttattac tggtcgtcac   120
gcggatgtag gtgaaaaggc cgccaaatca atcggcggca ctgatgttat tcgctttgtc   180
cagcacgatg cgtccgaaga agcaggctgg acgaaactgt tcgacaccac cgaggaggca   240
ttcggcccgg ttacgaccgt ggtgaacaat gcagggattg ggttattaa aagcgttgaa    300
gacactacca cggaggaatg gcgtaaactg ctgtccgtta atctggatgg tgttttttc    360
```

```
ggcacccgtc tgggcattca gcgcatgaaa aataaaggct tgggcgctag catcatcaat   420
atgagcagta ttatggggct cgtaggcgat ccgacgctgg gggcatacaa cgcttccaag   480
ggggcggtac gtatcatgtc gaaaagcgca gcgctggatt gcgcactgaa ggactacgat   540
gtgcgtgtca acacagtaca tccgggcccc atcaagaccc gcggaagga tgatctggaa    600
ggttgggagg aaatgatgtc acagcgtacg ttaaccccta tgggcacat tggcgaaccg    660
aatgacatcg catggatctg tgtgtacctg gcatctgacg aatcgaaatt tgcgacgggt   720
gcagaatttg tggtcgacgg cgggtggacc gcacag                             756

SEQ ID NO: 74            moltype = AA  length = 252
FEATURE                  Location/Qualifiers
REGION                   1..252
                         note = Engineered Variant of Kred from Lactobacillus kefir
source                   1..252
                         mol_type = protein
                         organism = synthetic construct
SEQUENCE: 74
MTDRLKHKVA IVTGGTLGIG LAIADKFVEE GAKVVITGRH ADVGEKAAKS IGGTDVIRFV    60
QHDASEEAGW TKLFDTTEEA FGPVTTVVNN AGIGVIKSVE DTTTEEWRKL LSVNLDGVFF   120
GTRLGIQRMK NKGLGASIIN MSSIMGLVGD PTLGAYNASK GAVRIMSKSA ALDCALKDYD   180
VRVNTVHPGP IKTPRKDDLE GWEEMMSQRT LTPMGHIGEP NDIAWICVYL ASDESKFATG   240
AEFVVDGGWT AQ                                                      252

SEQ ID NO: 75            moltype = DNA  length = 756
FEATURE                  Location/Qualifiers
misc_feature             1..756
                         note = Engineered Variant of Kred from Lactobacillus kefir
source                   1..756
                         mol_type = other DNA
                         organism = synthetic construct
SEQUENCE: 75
atgaccgatc gtctgaagca taaagtagcc atcgttaccg gcgggacact gggtatcggt    60
ttggcaatcg ccgataaatt tgtagaggag ggtgcgaaag tagttattac tggtcgtcac   120
gcggatgtag gtgaaaaggc cgccaaatca atcggcggca ctgatgttat tcgctttgtc   180
cagcacgatg cgtccgaaga agcaggctgg acgaaactgt tcgacaccac cgaggaggca   240
ttcggcccgg ttacgaccct ggtgaacaat gcagggattg gggttattaa aagcgttgaa   300
gacactacca cggaggaatg gcgtaaaatc ctgtccgtta atctggatgg tgttttttc   360
ggcacccgtc tgggcattca gcgcatgaaa aataaaggct tgggcgctag catcatcaat   420
atgagcagta ttatggggct cgtaggcgat ccgactctgg gggcatacaa cgcttccaag   480
ggggcggtac gtatcatgtc gaaaagcgca gcgctggatt gcgcactgaa ggactacgat   540
gtgcgtgtca acacagtaca tccgggcccc atcaagaccc tcggaaaga tgatctggaa    600
ggttgggagg aaatgatgtc acagcgtacg ttaaccccta tgggccacat tggcgaaccg   660
aatgacatcg catggatctg tgtgtacctg gcatctgacg aatcgaaatt tgcgacgggt   720
gcagaatttg tggtcgacgg cgggtggacc gcacag                             756

SEQ ID NO: 76            moltype = AA  length = 252
FEATURE                  Location/Qualifiers
REGION                   1..252
                         note = Engineered Variant of Kred from Lactobacillus kefir
source                   1..252
                         mol_type = protein
                         organism = synthetic construct
SEQUENCE: 76
MTDRLKHKVA IVTGGTLGIG LAIADKFVEE GAKVVITGRH ADVGEKAAKS IGGTDVIRFV    60
QHDASEEAGW TKLFDTTEEA FGPVTTLVNN AGIGVIKSVE DTTTEEWRKI LSVNLDGVFF   120
GTRLGIQRMK NKGLGASIIN MSSIMGLVGD PTLGAYNASK GAVRIMSKSA ALDCALKDYD   180
VRVNTVHPGP IKTPRKDDLE GWEEMMSQRT LTPMGHIGEP NDIAWICVYL ASDESKFATG   240
AEFVVDGGWT AQ                                                      252

SEQ ID NO: 77            moltype = DNA  length = 756
FEATURE                  Location/Qualifiers
misc_feature             1..756
                         note = Engineered Variant of Kred from Lactobacillus kefir
source                   1..756
                         mol_type = other DNA
                         organism = synthetic construct
SEQUENCE: 77
atgaccgatc gtctgaagca taaagtagcc atcgttaccg gcgggacact gggtatcggt    60
ttggcaatcg ccgataaatt tgtagaggag ggtgcgaaag tagttattac tggtcgtcac   120
gcggatgtag gtgaaaaggc cgccaaatca atcggcggca ctgatgttat tcgctttgtc   180
cagcacgatg cgtccgaaga agcaggctgg acgaaactgt tcgacaccac cgaggaggca   240
ttcggcccgg ttacgaccgt cgtgaacaat gcagggattg gggttattaa aagcgttgaa   300
gacactacca cggaggaatg cgtaaaactg ctgtccgtta atctggatgg tgttttttc    360
ggcacccgtc tgggcattca gcgcatgaaa aataaaggct tgggcgctag catcatcaat   420
atgagcagta ttatggggct cgtaggcgat ccgggcctgg ggcatacaa cgcttccaag    480
ggggcggtac gtatcatgtc gaaaagcgca gcgctggatt gcgcactgaa ggactacgat   540
gtgcgtgtca acacagtaca tccgggcccc atcaagaccc cgcggaagga tgatctggaa   600
ggttgggagg aaatgatgtc acagcgtacg ttaaccccta tgggccacat tggcgaaccg   660
aatgacatcg catggatctg tgtgtacctg gcatctgacg aatcgaaatt tgcgacgggt   720
gcagaatttg tggtcgacgg cgggtggacc gcacag                             756
```

```
SEQ ID NO: 78            moltype = AA   length = 252
FEATURE                  Location/Qualifiers
REGION                   1..252
                         note = Engineered Variant of Kred from Lactobacillus kefir
source                   1..252
                         mol_type = protein
                         organism = synthetic construct
SEQUENCE: 78
MTDRLKHKVA IVTGGTLGIG LAIADKFVEE GAKVVITGRH ADVGEKAAKS IGGTDVIRFV   60
QHDASEEAGW TKLFDTTEEA FGPVTTVVNN AGIGVIKSVE DTTTEEWRKL LSVNLDGVFF  120
GTRLGIQRMK NKGLGASIIN MSSIMGLVGD PGLGAYNASK GAVRIMSKSA ALDCALKDYD  180
VRVNTVHPGP IKTPRKDDLE GWEEMMSQRT LTPMGHIGEP NDIAWICVYL ASDESKFATG  240
AEFVVDGGWT AQ                                                     252

SEQ ID NO: 79            moltype = DNA   length = 756
FEATURE                  Location/Qualifiers
misc_feature             1..756
                         note = Engineered Variant of Kred from Lactobacillus kefir
source                   1..756
                         mol_type = other DNA
                         organism = synthetic construct
SEQUENCE: 79
atgaccgatc gtctgaagca taaagtagcc atcgttaccg gcgggacact gggtatcggt   60
ttggcaatcg ccgataaatt tgtagaggag ggtgcgaaag tagttattac tggtcgtcac  120
gcggatgtag gtgaaaaggc cgccaaatca atcggcgctg ctgatgttat tcgctttgtc  180
cagcacgatg cgtccgaaga agcaggctgg acgaaactgt tcgacaccac cgaggaggca  240
ttcggcccgg ttacgaccct ggtgaacaat gcagggattg gggttattaa agcgttgaa   300
gacactacca cggaggaatg gcgtaaaatc ctgtccgtta atctggatgg tgttttttc   360
ggcacccgtc tgggcattca gcgcatgaaa aataaaggct gggcgctagc atcatcaat   420
atgagcagta ttatggggct cgtaggcgat ccgactctgg gggcatacaa cgcttccaag   480
ggggcggtac gtatcatgtc gaaaagcgca gcgctggatt gcgcactgaa ggactacgat  540
gtgcgtgtca acacagtaca tccgggcccc atcaagaccc cgcggaagga tgatctgaa   600
ggttgggagg aaatgatgtc acagcgtacg ttaaccccta tgggccacat tggcgaaccg  660
aatgacatcg catggatctg tgtgtacctg gcatctgacg aatcgaaatt tgcgacgggt  720
gcagaatttg tggtcgacgg cgggtggacc gcacag                           756

SEQ ID NO: 80            moltype = AA   length = 252
FEATURE                  Location/Qualifiers
REGION                   1..252
                         note = Engineered Variant of Kred from Lactobacillus kefir
source                   1..252
                         mol_type = protein
                         organism = synthetic construct
SEQUENCE: 80
MTDRLKHKVA IVTGGTLGIG LAIADKFVEE GAKVVITGRH ADVGEKAAKS IGGTDVIRFV   60
QHDASEEAGW TKLFDTTEEA FGPVTTLVNN AGIGVIKSVE DTTTEEWRKI LSVNLDGVFF  120
GTRLGIQRMK NKGLGASIIN MSSIMGLVGD PTLGAYNASK GAVRIMSKSA ALDCALKDYD  180
VRVNTVHPGP IKTPRKDDLE GWEEMMSQRT LTPMGHIGEP NDIAWICVYL ASDESKFATG  240
AEFVVDGGWT AQ                                                     252

SEQ ID NO: 81            moltype = DNA   length = 756
FEATURE                  Location/Qualifiers
misc_feature             1..756
                         note = Engineered Variant of Kred from Lactobacillus kefir
source                   1..756
                         mol_type = other DNA
                         organism = synthetic construct
SEQUENCE: 81
atgaccgatc gtctgaagca taaagtagcc atcattaccg gcgggacact gggtatcggt   60
ttggcaatcg ccgataaatt tgtagaggag ggtgcgaaag tagttattac tggtcgtcac  120
gcggatgtag gtgaaaaggc cgccaaatca atcggcggca ctgatgttat tcgctttgtc  180
cagcacgatg cgtccgaaga agcaggctgg acgaaactgt tcgacaccac cgaggaggca  240
ttcggcccgg ttacgaccgt ggtgaacaat gcagggattg gggttattaa aagcgttgaa  300
gacactacca cggaggaatg gcgtaaaatc ctgtccgtta atctggatgg tgttttttc   360
ggcacccgtc tgggcattca gcgcatgaaa aataaaggct gggcgctagc atcatcaat   420
atgagcagta ttatggggct cgtaggcgat ccggcctggg ggcatacaa cgcttccaag   480
ggggcggtac gtatcatgtc gaaaagcgca gcgctggatt gcgcactgaa ggactacgat  540
gtgcgtgtca acacagtaca tccgggcccc atcaagaccc cgcggaagga tgatctgaa   600
ggttgggagg aaatgatgtc acagcgtacg ttaaccccta tgggccacat tggcgaaccg  660
aatgacatcg catggatctg tgtgtacctg gcatctgacg aatcgaaatt tgcgacgggt  720
gcagaatttg tggtcgacgg cgggtggacc gcacag                           756

SEQ ID NO: 82            moltype = AA   length = 252
FEATURE                  Location/Qualifiers
REGION                   1..252
                         note = Engineered Variant of Kred from Lactobacillus kefir
source                   1..252
                         mol_type = protein
```

```
                        organism = synthetic construct
SEQUENCE: 82
MTDRLKHKVA IITGGTLGIG LAIADKFVEE GAKVVITGRH ADVGEKAAKS IGGTDVIRFV    60
QHDASEEAGW TKLFDTTEEA FGPVTTVVNN AGIGVIKSVE DTTTEEWRKI LSVNLDGVFF   120
GTRLGIQRMK NKGLGASIIN MSSIMGLVGD PGLGAYNASK GAVRIMSKSA ALDCALKDYD   180
VRVNTVHPGP IKTPRKDDLE GWEEMMSQRT LTPMGHIGEP NDIAWICVYL ASDESKFATG   240
AEFVVDGGWT AQ                                                      252

SEQ ID NO: 83          moltype = DNA  length = 756
FEATURE                Location/Qualifiers
misc_feature           1..756
                       note = Engineered Variant of Kred from Lactobacillus kefir
source                 1..756
                       mol_type = other DNA
                       organism = synthetic construct
SEQUENCE: 83
atgaccgatc gtctgaagca taaagtagcc atcgttaccg gcgggacact gggtatcggt    60
ttggcaatcg ccgataaatt tgtagaggag ggtgcgaaag tagttattac tggtcgtcac   120
gcggatgtag gtgaaaaggc cgccaaatca atcggcggca ctgatgttat tcgctttgtc   180
cagcacgatg cgtccgaaga agcaggctgg acgaaactgt tcgacaccac cgaggaggca   240
ttcggcccgt ttacgaccgt ggtgaacaat gcagggattg ggttattaa aagcgttgaa    300
gacactacca cggaggaatg gcgtaaaatc ctgtccgtta atctggatgg tgttttttc    360
ggcacccgtc tgggcattca gcgcatgaaa aataaaggct tgggcgctag catcatcaat   420
atgagcagta ttatggggct cgtaggcgat ccgactctgg gggcatacaa cgcttccaag   480
ggggcggtac gtatcatgtc gaaaagcgca gcgctggatt gcgcactgaa ggactacgat   540
gtgcgtgtca acacagtaca tccgggcccc atcaagaccc ctcggaaaga tgatctggaa   600
ggttgggagg aaatgatgtc acagcgtacg ttaaccccta tgggccacat tggcgaaccg   660
aatgacatcg catggatctg tgtgtacctg gcatctgacg aatcgaaatt tgcgacgggt   720
gcagaatttg tggtcgacgg cgggtggacc gcacag                            756

SEQ ID NO: 84          moltype = AA  length = 252
FEATURE                Location/Qualifiers
REGION                 1..252
                       note = Engineered Variant of Kred from Lactobacillus kefir
source                 1..252
                       mol_type = protein
                       organism = synthetic construct
SEQUENCE: 84
MTDRLKHKVA IVTGGTLGIG LAIADKFVEE GAKVVITGRH ADVGEKAAKS IGGTDVIRFV    60
QHDASEEAGW TKLFDTTEEA FGPVTTVVNN AGIGVIKSVE DTTTEEWRKI LSVNLDGVFF   120
GTRLGIQRMK NKGLGASIIN MSSIMGLVGD PTLGAYNASK GAVRIMSKSA ALDCALKDYD   180
VRVNTVHPGP IKTHRKDDLE GWEEMMSQRT LTPMGHIGEP NDIAWICVYL ASDESKFATG   240
AEFVVDGGWT AQ                                                      252

SEQ ID NO: 85          moltype = DNA  length = 756
FEATURE                Location/Qualifiers
misc_feature           1..756
                       note = Engineered Variant of Kred from Lactobacillus kefir
source                 1..756
                       mol_type = other DNA
                       organism = synthetic construct
SEQUENCE: 85
atgaccgatc gtctgaagca taaagtagcc atcgttaccg gcgggacact gggtatcggt    60
ttggcaatcg ccgataaatt tgtagaggag ggtgcgaaag tagttattac tggtcgtcac   120
gcggatgtag gtgaaaaggc cgccaaatca atcggcggca ctgatgttat tcgctttgtc   180
cagcacgatg cgtccgaaga agcaggctgg acgaaactgt tcgacaccac cgaggaggca   240
ttcggcccgg ttacgaccgt ggtgaacaat gcagggattg ggttattaa aagcgttgaa    300
gacactacca cggaggaatg gcgtaaaatc ctgtccgtta atctggatgg tgttttttc    360
ggcacccgtc tgggcataca gcgcatgaaa aataaaggct tgggcgctag catcatcaat   420
atgagcagta ttatggggct cgtaggcgat ccgggcctgg gggcatacaa cgcttccaag   480
ggggcggtac gtatcatgtc gaaaagcgca gcgctggatt gcgcactgaa ggactacgat   540
gtgcgtgtca acacagtaca tccgggcccc atcaagaccc ctcggaaagg tgatctggaa   600
ggttgggagg aaatgatgtc acagcgtacg ttaaccccta tgggccacat tggcgaaccg   660
aatgacatcg catggatctg tgtgtacctg gcatctgacg aatcgaaatt tgcgacgggt   720
gcagaatttg tggtcgacgg cgggtggacc gcacag                            756

SEQ ID NO: 86          moltype = AA  length = 252
FEATURE                Location/Qualifiers
REGION                 1..252
                       note = Engineered Variant of Kred from Lactobacillus kefir
source                 1..252
                       mol_type = protein
                       organism = synthetic construct
SEQUENCE: 86
MTDRLKHKVA IVTGGTLGIG LAIADKFVEE GAKVVITGRH ADVGEKAAKS IGGTDVIRFV    60
QHDASEEAGW TKLFDTTEEA FGPVTTVVNN AGIGVIKSVE DTTTEEWRKI LSVNLDGVFF   120
GTRLGIQRMK NKGLGASIIN MSSIMGLVGD PGLGAYNASK GAVRIMSKSA ALDCALKDYD   180
VRVNTVHPGP IKTPRKGDLE GWEEMMSQRT LTPMGHIGEP NDIAWICVYL ASDESKFATG   240
AEFVVDGGWT AQ                                                      252
```

```
SEQ ID NO: 87            moltype = DNA  length = 756
FEATURE                  Location/Qualifiers
misc_feature             1..756
                         note = Engineered Variant of Kred from Lactobacillus kefir
source                   1..756
                         mol_type = other DNA
                         organism = synthetic construct
SEQUENCE: 87
atgaccgatc gtctgaagca taaagtagcc atcgtaaccg gcgggacact gggtatcggt    60
ttggcaatcg ccgataaatt tgtagaggag ggtgcgaaag tagttattac tggtcgtcac   120
gcggatgtag gtgaaaaggc cgccaaatca atcggcggca ctgatgttat tcgctttgtc   180
cagcacgatg cgtccgaaga agcaggctgg acgaaactgt tcgacaccac cgaggaggca   240
ttcggcccgg ttacgaccct ggtgaacaat gcagggattg ggttattaa aagcgttgaa    300
gacactacca cggaggaatg gcgtaaaatc ctgtccgtta atctggatgg tgttttttc    360
ggcacccgtc tgggcattca gcgcatgaaa aataaaggct gggcgctag catcatcaat    420
atgagcagta ttatggggct cgtaggcgat ccgactctgg gggcatacaa cgcttccaag   480
ggggcggtac gtatcatgtc gaaaagcgca gcgctggatt gcgcactgaa ggactacgat   540
gtgcgtgtca acacagtaca tccgggcccc atcaagacca accggaaaga tgatctggaa   600
ggttgggagg aaatgatgtc acagcgtacg ttaaccccta tgggccacat tggcgaaccg   660
aatgacatcg catggatctg tgtgtacctg gcatctgacg aatcgaaatt tgcgacgggt   720
gcagaatttg tggtcgacgg cgggtggacc gcacag                             756

SEQ ID NO: 88            moltype = AA  length = 252
FEATURE                  Location/Qualifiers
REGION                   1..252
                         note = Engineered Variant of Kred from Lactobacillus kefir
source                   1..252
                         mol_type = protein
                         organism = synthetic construct
SEQUENCE: 88
MTDRLKHKVA IVTGGTLGIG LAIADKFVEE GAKVVITGRH ADVGEKAAKS IGGTDVIRFV     60
QHDASEEAGW TKLFDTTEEA FGPVTTLVNN AGIGVIKSVE DTTTEEWRKI LSVNLDGVFF   120
GTRLGIQRMK NKGLGASIIN MSSIMGLVGD PTLGAYNASK GAVRIMSKSA ALDCALKDYD   180
VRVNTVHPGP IKTNRKDDLE GWEEMMSQRT LTPMGHIGEP NDIAWICVYL ASDESKFATG   240
AEFVVDGGWT AQ                                                       252

SEQ ID NO: 89            moltype = DNA  length = 756
FEATURE                  Location/Qualifiers
misc_feature             1..756
                         note = Engineered Variant of Kred from Lactobacillus kefir
source                   1..756
                         mol_type = other DNA
                         organism = synthetic construct
SEQUENCE: 89
atgaccgatc gtctgaagca taaagtagcc atcgttaccg gcgggacact gggtatcggt    60
ttggcaatcg ccgataaatt tgtagaggag ggtgcgaaag tagttattac tggtcgtcac   120
gcggatgtag gtgaaaaggc cgccaaatca atcggcggca ctgatgttat tcgctttgtc   180
cagcacgatg cgtccgaaga agcaggctgg acgaaactgt tcgacaccac cgaggaggca   240
ttcggcccgg ttacgaccct ggtgaacaat gcagggattg ggttattaa aagcgttgaa    300
gacactacca cggaggaatg gcgtaaaatc ctgtccgtta atctggatgg tgttttttc    360
ggcacccgtc tgggcattca gcgcatgaaa aataaaggct gggcgctag catcatcaat    420
atgagcagta ttatggggct cgtaggcgat ccgactctgg gggcatacaa cgcttccaag   480
ggggcggtac gtatcatgtc gaaaagcgca gcgctggatt gcgcactgaa ggactacgat   540
gtgcgtgtca acacagtaca tccgggcccc atcaagacca atcggaaaga tgatctggaa   600
ggttgggagg aaatgatgtc acagcgtacg ttaacgccta tgggccacat tggcgaaccg   660
aatgacatcg catggatctg tgtgtacctg gcatctgacg aatcgaaatt tgcgacgggt   720
gcagaatttg tggtcgacgg cgggtggacc gcacag                             756

SEQ ID NO: 90            moltype = AA  length = 252
FEATURE                  Location/Qualifiers
REGION                   1..252
                         note = Engineered Variant of Kred from Lactobacillus kefir
source                   1..252
                         mol_type = protein
                         organism = synthetic construct
SEQUENCE: 90
MTDRLKHKVA IVTGGTLGIG LAIADKFVEE GAKVVITGRH ADVGEKAAKS IGGTDVIRFV     60
QHDASEEAGW TKLFDTTEEA FGPVTTLVNN AGIGVIKSVE DTTTEEWRKI LSVNLDGVFF   120
GTRLGIQRMK NKGLGASIIN MSSIMGLVGD PTLGAYNASK GAVRIMSKSA ALDCALKDYD   180
VRVNTVHPGP IKTHRKDDLE GWEEMMSQRT LTPMGHIGEP NDIAWICVYL ASDESKFATG   240
AEFVVDGGWT AQ                                                       252

SEQ ID NO: 91            moltype = DNA  length = 756
FEATURE                  Location/Qualifiers
misc_feature             1..756
                         note = Engineered Variant of Kred from Lactobacillus kefir
source                   1..756
                         mol_type = other DNA
```

```
                        organism = synthetic construct
SEQUENCE: 91
atgaccgatc gtctgaagca taaagtagcc atcgtaaccg gcgggacact gggtatcggt   60
ttggcaatcg ccgataaatt tgtagaggag ggtgcgaaag tagttattac tggtcgtcac  120
gcggatgtag gtgaaaaggc cgccaaatca atcggcggca ctgatgttat tcgctttgtc  180
cagcacgatg cgtccgaaga agcaggctgg acgaaactgt tcgacaccac cgaggaggca  240
ttcggcccgg ttacgaccgt cgtgaacaat gcagggattg gggttattaa aagcgttgaa  300
gacactacca cggaggaatg gcgtaaactg ctgtccgtta atctggatgg tgttttttc   360
ggcacccgtc tgggcattca gcgcatgaaa aataaaggct tgggcgctag catcatcaat  420
atgagcagta ttctggggct cgtaggcgat ccgagcctgg gggcatacaa cgcttccaag  480
ggggcggtac gtatcatgtc gaaaagcgca gcgctggatt gcgcactgaa ggactacgat  540
gtgcgtgtca acacagtaca tccgggcccc atcaagaccc cgcggaagga tgatctggaa  600
ggttgggagg aaatgatgtc acagcgtacg ttaaccccta tgggccacat tggcgaaccg  660
aatgacatcg catggatctg tgtgtacctg gcatctgacg aatcgaaatt tgcgacgggt  720
gcagaatttg tggtcgacgg cgggtggacc gcacag                             756

SEQ ID NO: 92              moltype = AA   length = 252
FEATURE                    Location/Qualifiers
REGION                     1..252
                           note = Engineered Variant of Kred from Lactobacillus kefir
source                     1..252
                           mol_type = protein
                           organism = synthetic construct
SEQUENCE: 92
MTDRLKHKVA IVTGGTLGIG LAIADKFVEE GAKVVITGRH ADVGEKAAKS IGGTDVIRFV   60
QHDASEEAGW TKLFDTTEEA FGPVTTVVNN AGIGVIKSVE DTTTEEWRKL LSVNLDGVFF  120
GTRLGIQRMK NKGLGASIIN MSSILGLVGD PSLGAYNASK GAVRIMSKSA ALDCALKDYD  180
VRVNTVHPGP IKTPRKDDLE GWEEMMSQRT LTPMGHIGEP NDIAWICVYL ASDESKFATG  240
AEFVVDGGWT AQ                                                      252

SEQ ID NO: 93              moltype = DNA   length = 756
FEATURE                    Location/Qualifiers
misc_feature               1..756
                           note = Engineered Variant of Kred from Lactobacillus kefir
source                     1..756
                           mol_type = other DNA
                           organism = synthetic construct
SEQUENCE: 93
atgaccgatc gtctgaagca taaagtagcc atcgttaccg gcgggacact gggtatcggt   60
ttggcaatcg ccgataaatt tgtagaggag ggtgcgaaag tagttattac tggtcgtcac  120
gcggatgtag gtgaaaaggc cgccaaatca atcggcggca ctgatgttat tcgctttgtc  180
cagcacgatg cgtccgaaga agcaggctgg acgaaactgt tcgacaccac cgaggaggca  240
ttcggcccgg ttacgaccgt ggtgaacaat gcagggattg gggttattaa aagcgttgaa  300
gacactacca cggaggaatg gcgtaaactg ctgtccgtta atctggatgg tgttttttc   360
ggcacccgtc tgggcattca gcgcatgaaa aataaaggct tgggcgctag catcatcaat  420
atgagcagta ttatggggct cgtaggcgat ccgactctgg gggcatacaa cgcttccaag  480
ggggcggtac gtatcatgtc gaaaagcgca gcgctggatt gcgcactgaa ggactacgat  540
gtgcgtgtca acacagtaca tccgggcccc atcaagaccc ctcggaaagg tgatctggaa  600
ggttgggagg aaatgatgtc acagcgtacg ttaaccccta tgggccacat tggcgaaccg  660
aatgacatcg catggctgtg tgtgtacctg gcatctgacg aatcgaaatt tgcgacgggt  720
gcagaatttg tggtcgacgg cgggtggacc gcacag                             756

SEQ ID NO: 94              moltype = AA   length = 252
FEATURE                    Location/Qualifiers
REGION                     1..252
                           note = Engineered Variant of Kred from Lactobacillus kefir
source                     1..252
                           mol_type = protein
                           organism = synthetic construct
SEQUENCE: 94
MTDRLKHKVA IVTGGTLGIG LAIADKFVEE GAKVVITGRH ADVGEKAAKS IGGTDVIRFV   60
QHDASEEAGW TKLFDTTEEA FGPVTTVVNN AGIGVIKSVE DTTTEEWRKL LSVNLDGVFF  120
GTRLGIQRMK NKGLGASIIN MSSIMGLVGD PTLGAYNASK GAVRIMSKSA ALDCALKDYD  180
VRVNTVHPGP IKTPRKGDLE GWEEMMSQRT LTPMGHIGEP NDIAWLCVYL ASDESKFATG  240
AEFVVDGGWT AQ                                                      252

SEQ ID NO: 95              moltype = DNA   length = 756
FEATURE                    Location/Qualifiers
misc_feature               1..756
                           note = Engineered Variant of Kred from Lactobacillus kefir
source                     1..756
                           mol_type = other DNA
                           organism = synthetic construct
SEQUENCE: 95
atgaccgatc gtctgaagca taaagtagcc atcgttaccg gcgggacact gggtatcggt   60
ttggcaatcg ccgataaatt tgtagaggag ggtgcgaaag tagttattac tggtcgtcac  120
gcggatgtag gtgaaaaggc cgccaaatca atcggcggca ctgatgttat tcgctttgtc  180
cagcacgatg cgtccgaaga agcaggctgg acgaaactgt tcgacaccac cgaggaggca  240
ttcggcccgg ttacgaccct ggtgaacaat gcagggattg gggttattaa aagcgttgaa  300
```

```
gacactacca cggaggaatg gcgtaaactg ctgtccgtta atctggatgg tgttttttc    360
ggcacccgtc tgggcattca gcgcatgaaa aataaaggct tgggcgctag catcatcaat   420
atgagcagta ttatggggct cgtaggcgat ccgactctgg gggcatacaa cgcttccaag   480
ggggcggtac gtatcatgtc gaaaagcgca gcgctggatt gcgcactgaa ggactacgat   540
gtgcgtgtca acacagtaca tccgggcccc atcaagaccc atcggaaaga tgatctggaa   600
ggttgggagg aaatgatgtc acagcgtacg ttaaccccta tgggccacat tggcgaaccg   660
aatgacatcg catggatctg tgtgtacctg gcatctgacg aatcgaaatt tgcgacgggt   720
gcagaatttg tggtcgacgg cgggtggacc gcacag                             756

SEQ ID NO: 96           moltype = AA  length = 252
FEATURE                 Location/Qualifiers
REGION                  1..252
                        note = Engineered Variant of Kred from Lactobacillus kefir
source                  1..252
                        mol_type = protein
                        organism = synthetic construct
SEQUENCE: 96
MTDRLKHKVA IVTGGTLGIG LAIADKFVEE GAKVVITGRH ADVGEKAAKS IGGTDVIRFV    60
QHDASEEAGW TKLFDTTEEA FGPVTTLVNN AGIGVIKSVE DTTTEEWRKL LSVNLDGVFF   120
GTRLGIQRMK NKGLGASIIN MSSIMGLVGD PTLGAYNASK GAVRIMSKSA ALDCALKDYD   180
VRVNTVHPGP IKTHRKDDLE GWEEMMSQRT LTPMGHIGEP NDIAWICVYL ASDESKFATG   240
AEFVVDGGWT AQ                                                      252

SEQ ID NO: 97           moltype = DNA  length = 756
FEATURE                 Location/Qualifiers
misc_feature            1..756
                        note = Engineered Variant of Kred from Lactobacillus kefir
source                  1..756
                        mol_type = other DNA
                        organism = synthetic construct
SEQUENCE: 97
atgaccgatc gtctgaagca taaagtagcc atcgttaccg gcgggacact gggtatcggt    60
ttggcaatcg ccgataaatt tgtagaggag ggtgcgaaag tagttattac tggtcgtcac   120
gcggatgtag gtgaaaaggc cgccaaatca atcggcggca ctgatgttat tcgctttgtc   180
cagcacgatg cgtccgaaga agcaggctgg acgaaactgt tcgacaccac cgaggaggca   240
ttcggcccgg ttacgaccgt ggtgaacaat gcagggattg gggttattaa aagcgttgaa   300
gacactacca cggaggaatg gcgtaaaatc ctgtccgtta atctggatgg tgttttttc    360
ggcacccgtc tgggcattca gcgcatgaaa aataaaggct tgggcgctag catcatcaat   420
atgagcagta ttctgggggct cgtaggcgat ccgactctgg gggcatacaa cgcttccaag   480
ggggcggtac gtatcatgtc gaaaagcgca gcgctggatt gcgcactgaa ggactacgat   540
gtgcgtgtca acacagtaca tccgggcccc atcaagaccc ctcggaaaga tgatctggaa   600
ggttgggagg aaatgatgtc acagcgtacg ttaaccccta tgggccacat tggcgaaccg   660
aatgacatcg catggatctg tgtgtacctg gcatctgacg aatcgaaatt tgcgacgggt   720
gcagaatttg tggtcgacgg cgggtggacc gcacag                             756

SEQ ID NO: 98           moltype = AA  length = 252
FEATURE                 Location/Qualifiers
REGION                  1..252
                        note = Engineered Variant of Kred from Lactobacillus kefir
source                  1..252
                        mol_type = protein
                        organism = synthetic construct
SEQUENCE: 98
MTDRLKHKVA IVTGGTLGIG LAIADKFVEE GAKVVITGRH ADVGEKAAKS IGGTDVIRFV    60
QHDASEEAGW TKLFDTTEEA FGPVTTVVNN AGIGVIKSVE DTTTEEWRKI LSVNLDGVFF   120
GTRLGIQRMK NKGLGASIIN MSSILGLVGD PTLGAYNASK GAVRIMSKSA ALDCALKDYD   180
VRVNTVHPGP IKTPRKDDLE GWEEMMSQRT LTPMGHIGEP NDIAWICVYL ASDESKFATG   240
AEFVVDGGWT AQ                                                      252

SEQ ID NO: 99           moltype = DNA  length = 756
FEATURE                 Location/Qualifiers
misc_feature            1..756
                        note = Engineered Variant of Kred from Lactobacillus kefir
source                  1..756
                        mol_type = other DNA
                        organism = synthetic construct
SEQUENCE: 99
atgaccgatc gtctgaagca taaagtagcc atcgttaccg gcgggacact gggtatcggt    60
ttggcaatcg ccgataaatt tgtagaggag ggtgcgaaag tagttattac tggtcgtcac   120
gcggatgtag gtgaaaaggc cgccaaatca atcggcggca ctgatgttat tcgctttgtc   180
cagcacgatg cgtccgaaga agcaggctgg acgaaactgt tcgacaccac cgaggaggca   240
ttcggcccgg ttacgaccct ggtgaacaat gcagggattg gggttattaa aagcgttgaa   300
gacactacca cggaggaatg gcgtaaaatc ctgtccgtta atctggatgg tgttttttc    360
ggcacccgtc tgggcattca gcgcatgaaa aataaaggct tgggcgctag catcatcaat   420
atgagcagta ttatggggct cgtaggcgat ccgactctgg gggcatacaa cgcttccaag   480
ggggcggtac gtatcatgtc gaaaagcgca gcgctggatt gcgcactgaa ggactacgat   540
gtgcgtgtca acacagtaca tccgggcccc atcaagaccc cgcggaagga tgatctggaa   600
ggttgggagg aaatgatgtc acagcgtacg cgtacccccta tgggccacat tggcgaaccg   660
aatgacatcg catggatctg tgtgtacctg gcatctgacg aatcgaaatt tgcgacgggt   720
```

```
gcagaatttg tggtcgacgg cgggtggacc gcacag                              756

SEQ ID NO: 100          moltype = AA  length = 252
FEATURE                 Location/Qualifiers
REGION                  1..252
                        note = Engineered Variant of Kred from Lactobacillus kefir
source                  1..252
                        mol_type = protein
                        organism = synthetic construct
SEQUENCE: 100
MTDRLKHKVA IVTGGTLGIG LAIADKFVEE GAKVVITGRH ADVGEKAAKS IGGTDVIRFV   60
QHDASEEAGW TKLFDTTEEA FGPVTTLVNN AGIGVIKSVE DTTTEEWRKI LSVNLDGVFF  120
GTRLGIQRMK NKGLGASIIN MSSIMGLVGD PTLGAYNASK GAVRIMSKSA ALDCALKDYD  180
VRVNTVHPGP IKTPRKDDLE GWEEMMSQRT RTPMGHIGEP NDIAWICVYL ASDESKFATG  240
AEFVVDGGWT AQ                                                      252

SEQ ID NO: 101          moltype = DNA  length = 756
FEATURE                 Location/Qualifiers
misc_feature            1..756
                        note = Engineered Variant of Kred from Lactobacillus kefir
source                  1..756
                        mol_type = other DNA
                        organism = synthetic construct
SEQUENCE: 101
atgaccgatc gtctgaagca taaagtagcc atcgttaccg gcgggacaag tggtatcggt   60
ttggcaatcg ccgataaatt tgtagaggag ggtgcgaaag tagttattac tggtcgtcac  120
gcggatgtag gtgaaaaggc cgccaaatca atcggcggca ctgatgttat tcgctttgtc  180
cagcacgatg cgtccgaaga agcaggctgg acgaaactgt tcgacaccac cgaggaggca  240
ttcggcccgg ttacgaccct ggtgaacaat gcagggattg ggttattaa aagcgttgaa  300
gacactacca cggaggaatg gcgtaaaatc ctgtccgtta atctggatgg tgttttttc  360
ggcacccgtc tgggcattca gcgcatgaaa aataaaggct gggcgctag catcatcaat  420
atgagcagta ttatggggct cgtaggcgat ccgactctgg gggcatacaa cgcttccaag  480
ggggcggtac gtatcatgtc gaaaagcgca gcgctggatt gcgcactgaa ggactacgat  540
gtgcgtgtca acacagtaca tccgggcccc atcaagaccc cgcggaagga tgatctgaa  600
ggttgggagg aaatgatgtc acagcgtacg ttaacccta tgggccacat tggcgaaccg  660
aatgacatcg catggatctg tgtgtacctg gcatctgacg aatcgaaatt tgcgacgggt  720
gcagaatttg tggtcgacgg cgggtggacc gcacag                            756

SEQ ID NO: 102          moltype = AA  length = 252
FEATURE                 Location/Qualifiers
REGION                  1..252
                        note = Engineered Variant of Kred from Lactobacillus kefir
source                  1..252
                        mol_type = protein
                        organism = synthetic construct
SEQUENCE: 102
MTDRLKHKVA IVTGGTSGIG LAIADKFVEE GAKVVITGRH ADVGEKAAKS IGGTDVIRFV   60
QHDASEEAGW TKLFDTTEEA FGPVTTLVNN AGIGVIKSVE DTTTEEWRKI LSVNLDGVFF  120
GTRLGIQRMK NKGLGASIIN MSSIMGLVGD PTLGAYNASK GAVRIMSKSA ALDCALKDYD  180
VRVNTVHPGP IKTPRKDDLE GWEEMMSQRT LTPMGHIGEP NDIAWICVYL ASDESKFATG  240
AEFVVDGGWT AQ                                                      252

SEQ ID NO: 103          moltype = DNA  length = 756
FEATURE                 Location/Qualifiers
misc_feature            1..756
                        note = Engineered Variant of Kred from Lactobacillus kefir
source                  1..756
                        mol_type = other DNA
                        organism = synthetic construct
SEQUENCE: 103
atgaccgatc gtctgaagca taaagtagcc atcgttaccg gcgggacaca gggtatcggt   60
ttggcaatcg ccgataaatt tgtagaggag ggtgcgaaag tagttattac tggtcgtcac  120
gcggatgtag gtgaaaaggc cgccaaatca atcggcggca ctgatgttat tcgctttgtc  180
cagcacgatg cgtccgaaga agcaggctgg acgaaactgt tcgacaccac cgaggaggca  240
ttcggcccgg ttacgaccct ggtgaacaat gcagggattg ggttattaa aagcgttgaa  300
gacactacca cggaggaatg gcgtaaaatc ctgtccgtta atctggatgg tgttttttc  360
ggcacccgtc tgggcattca gcgcatgaaa aataaaggct gggcgctag catcatcaat  420
atgagcagta ttatggggct cgtaggcgat ccgactctgg gggcatacaa cgcttccaag  480
ggggcggtac gtatcatgtc gaaaagcgca gcgctggatt gcgcactgaa ggactacgat  540
gtgcgtgtca acacagtaca tccgggcccc atcaagaccc cgcggaagga tgatctgaa  600
ggttgggagg aaatgatgtc acagcgtacg ttaacccta tgggccacat tggcgaaccg  660
aatgacatcg catggatctg tgtgtacctg gcatctgacg aatcgaaatt tgcgacgggt  720
gcagaatttg tggtcgacgg cgggtggacc gcacag                            756

SEQ ID NO: 104          moltype = AA  length = 252
FEATURE                 Location/Qualifiers
REGION                  1..252
                        note = Engineered Variant of Kred from Lactobacillus kefir
source                  1..252
```

```
                        mol_type = protein
                        organism = synthetic construct
SEQUENCE: 104
MTDRLKHKVA IVTGGTQGIG LAIADKFVEE GAKVVITGRH ADVGEKAAKS IGGTDVIRFV    60
QHDASEEAGW TKLFDTTEEA FGPVTTLVNN AGIGVIKSAK DTTTEEWRKI LSVNLDGVFF   120
GTRLGIQRMK NKGLGASIIN MSSIMGLVGD PTLGAYNASK GAVRIMSKSA ALDCALKDYD   180
VRVNTVHPGP IKTPRKDDLE GWEEMMSQRT LTPMGHIGEP NDIAWICVYL ASDESKFATG   240
AEFVVDGGWT AQ                                                       252

SEQ ID NO: 105          moltype = DNA  length = 756
FEATURE                 Location/Qualifiers
misc_feature            1..756
                        note = Engineered Variant of Kred from Lactobacillus kefir
source                  1..756
                        mol_type = other DNA
                        organism = synthetic construct
SEQUENCE: 105
atgaccgatc gtctgaagca taaagtagcc atcgttaccg gcgggacact gggtatcggt    60
ttggcaatcg ccgataaatt tgtagaggag ggtgcgaaag tagttattac tggtcgtcac   120
gcggatgtag gtgaaaaggc cgccaaatca atcggcggca ctgatgttat tcgctttgtc   180
cagcacgatg cgtccgaaga agcaggctgg acgaaactgt tcgacaccac cgaggaggca   240
ttcggcccgg ttacgaccct ggtgaacaat gcagggattg ggttattaa aagcgttgaa    300
gacactacca cggaggaatg gcgtaaaatc ctgtccgtta atctggatgg tgtttttttc   360
ggcacccgtc tgggcattca gcgcatgaaa aataaaggct gggcgctag catcatcaat   420
atgagcagta ttatggggct cgtaggcgat ccgactctgg gggcatacaa cgcttccaag   480
ggggcggtac gtatcatgtc gaaaagcgca gcgctggatt gcgcactgaa ggactacgat   540
gtgcgtgtca acacagtaca tccgggcccc atcaagaccc cgcggaagga tgctctggaa   600
ggttgggagg aaatgatgtc acagcgtacg ttaaccccta tgggccacat tggcgaaccg   660
aatgacatcg catggatctg tgtgtacctg gcatctgacg aatcgaaatt tgcgacgggt   720
gcagaatttg tggtcgacgg cgggtggacc gcacag                             756

SEQ ID NO: 106          moltype = AA  length = 252
FEATURE                 Location/Qualifiers
REGION                  1..252
                        note = Engineered Variant of Kred from Lactobacillus kefir
source                  1..252
                        mol_type = protein
                        organism = synthetic construct
SEQUENCE: 106
MTDRLKHKVA IVTGGTLGIG LAIADKFVEE GAKVVITGRH ADVGEKAAKS IGGTDVIRFV    60
QHDASEEAGW TKLFDTTEEA FGPVTTLVNN AGIGVIKSVE DTTTEEWRKI LSVNLDGVFF   120
GTRLGIQRMK NKGLGASIIN MSSIMGLVGD PTLGAYNASK GAVRIMSKSA ALDCALKDYD   180
VRVNTVHPGP IKTPRKDALE GWEEMMSQRT LTPMGHIGEP NDIAWICVYL ASDESKFATG   240
AEFVVDGGWT AQ                                                       252

SEQ ID NO: 107          moltype = DNA  length = 756
FEATURE                 Location/Qualifiers
misc_feature            1..756
                        note = Engineered Variant of Kred from Lactobacillus kefir
source                  1..756
                        mol_type = other DNA
                        organism = synthetic construct
SEQUENCE: 107
atgaccgatc gtctgaagca taaagtagcc atcgttaccg gcgggacact gggtatcggt    60
ttggcaatcg ccgataaatt tgtagaggag ggtgcgaaag tagttattac tggtcgtcac   120
gcggatgtag gtgaaaaggc cgccaaatca atcggcggca ctgatgttat tcgctttgtc   180
cagcacgatg cgtccgaaga agcaggctgg acgaaactgt tcgacaccac cgaggaggca   240
ttcggcccgg ttacgaccct ggtgaacaat gcagggattg ggttattaa aagcgttgaa    300
gacactacca cggaggaatg gcgtaaaatc ctgtccgtta atctggatgg tgtttttttc   360
ggcacccgtc tgggcattca gcgcatgaaa aataaaggct gggcgctag catcatcaat   420
atgagcagta ttatggggct cgtaggcgat ccgaagctgg gggcatacaa cgcttccaag   480
ggggcggtac gtatcatgtc gaaaagcgca gcgctggatt gcgcactgaa ggactacgat   540
gtgcgtgtca acacagtaca tccgggcccc atcaagaccc cgcggaagga tgatctgaa   600
ggttgggagg aaatgatgtc acagcgtacg ttaaccccta tgggccacat tggcgaaccg   660
aatgacatcg catggatctg tgtgtacctg gcatctgacg aatcgaaatt tgcgacgggt   720
gcagaatttg tggtcgacgg cgggtggacc gcacag                             756

SEQ ID NO: 108          moltype = AA  length = 252
FEATURE                 Location/Qualifiers
REGION                  1..252
                        note = Engineered Variant of Kred from Lactobacillus kefir
source                  1..252
                        mol_type = protein
                        organism = synthetic construct
SEQUENCE: 108
MTDRLKHKVA IVTGGTLGIG LAIADKFVEE GAKVVITGRH ADVGEKAAKS IGGTDVIRFV    60
QHDASEEAGW TKLFDTTEEA FGPVTTLVNN AGIGVIKSVE DTTTEEWRKI LSVNLDGVFF   120
GTRLGIQRMK NKGLGASIIN MSSIMGLVGD PKLGAYNASK GAVRIMSKSA ALDCALKDYD   180
VRVNTVHPGP IKTPRKDDLE GWEEMMSQRT LTPMGHIGEP NDIAWICVYL ASDESKFATG   240
```

```
SEQ ID NO: 109          moltype = DNA  length = 756
FEATURE                 Location/Qualifiers
misc_feature            1..756
                        note = Engineered Variant of Kred from Lactobacillus kefir
source                  1..756
                        mol_type = other DNA
                        organism = synthetic construct
SEQUENCE: 109
atgaccgatc gtctgaagca taaagtagcc atcgttaccg gcgggacact gggtatcggt   60
ttggcaatcg ccgataaatt tgtagaggag ggtgcgaaag tagttattac tggtcgtcac  120
gcggatgtag gtgaaaaggc cgccaaatca atcggcggca ctgatgttat tcgctttgtc  180
cagcacgatg cgtccgaaga agcaggctgg acgaaactgt tcgacaccac cgaggaggca  240
ttcggcccgg ttacgaccct ggtgaacaat gcagggattg gggttattaa aagcgttgaa  300
acgactacca cggaggaatg gcgtaaaatc ctgtccgtta atctggatgg tgtttttttc  360
ggcacccgtc tgggcattca gcgcatgaaa aataaaggct gggcgctag catcatcaat  420
atgagcagta ttatggggct cgtaggcgat ccgactctgg ggcatacaa cgcttccaag  480
ggggcggtac gtatcatgtc gaaaagcgca gcgctggatt gcgcactgaa ggactacgat  540
gtgcgtgtca acacagtaca tccgggcccc atcaagaccc cgcggaagga tgatctggaa  600
ggttgggagg aaatgatgtc acagcgtacg ttaacccta tgggccacat tggcgaaccg  660
aatgacatcg catggatctg tgtgtacctg gcatctgacg aatcgaaatt tgcgacgggt  720
gcagaatttg tggtcgacgg cgggtggacc gcacag                            756

SEQ ID NO: 110          moltype = AA  length = 252
FEATURE                 Location/Qualifiers
REGION                  1..252
                        note = Engineered Variant of Kred from Lactobacillus kefir
source                  1..252
                        mol_type = protein
                        organism = synthetic construct
SEQUENCE: 110
MTDRLKHKVA IVTGGTLGIG LAIADKFVEE GAKVVITGRH ADVGEKAAKS IGGTDVIRFV   60
QHDASEEAGW TKLFDTTEEA FGPVTTLVNN AGIGVIKSVE TTTTEEWRKI LSVNLDGVFF  120
GTRLGIQRMK NKGLGASIIN MSSIMGLVGD PTLGAYNASK GAVRIMSKSA ALDCALKDYD  180
VRVNTVHPGP IKTPRKDDLE GWEEMMSQRT LTPMGHIGEP NDIAWICVYL ASDESKFATG  240
AEFVVDGGWT AQ                                                      252

SEQ ID NO: 111          moltype = DNA  length = 756
FEATURE                 Location/Qualifiers
misc_feature            1..756
                        note = Engineered Variant of Kred from Lactobacillus kefir
source                  1..756
                        mol_type = other DNA
                        organism = synthetic construct
SEQUENCE: 111
atgaccgatc gtctgaagca taaagtagcc atcgttaccg gcgggacact gggtatcggt   60
ttggcaatcg ccgataaatt tgtagaggag ggtgcgaaag tagttattac tggtcgtcac  120
gcggatgtag gtgaaaaggc cgccaaatca atcggcggca ctgatgttat tcgctttgtc  180
cagcacgatg cgtccgaaga agcaggctgg acgaaactgt tcgacaccac cgaggaggca  240
ttcggcccgg ttacgaccct ggtgaacaat gcagggattg gggttattaa aagcgttgaa  300
gacactacca cggaggaatg gcgtaaagtg ctgtccgtta atctggatgg tgtttttttc  360
ggcacccgtc tgggcattca gcgcatgaaa aataaaggct gggcgctag catcatcaat  420
atgagcagta ttatggggct cgtaggcgat ccgactctgg gggcatacaa cgcttccaag  480
ggggcggtac gtatcatgtc gaaaagcgca gcgctggatt gcgcactgaa ggactacgat  540
gtgcgtgtca acacagtaca tccgggcccc atcaagaccc cgcggaagga tgatctggaa  600
ggttgggagg aaatgatgtc acagcgtacg ttaacccta tgggccacat tggcgaaccg  660
aatgacatcg catggatctg tgtgtacctg gcatctgacg aatcgaaatt tgcgacgggt  720
gcagaatttg tggtcgacgg cgggtggacc gcacag                            756

SEQ ID NO: 112          moltype = AA  length = 252
FEATURE                 Location/Qualifiers
REGION                  1..252
                        note = Engineered Variant of Kred from Lactobacillus kefir
source                  1..252
                        mol_type = protein
                        organism = synthetic construct
SEQUENCE: 112
MTDRLKHKVA IVTGGTLGIG LAIADKFVEE GAKVVITGRH ADVGEKAAKS IGGTDVIRFV   60
QHDASEEAGW TKLFDTTEEA FGPVTTLVNN AGIGVIKSVE DTTTEEWRKV LSVNLDGVFF  120
GTRLGIQRMK NKGLGASIIN MSSIMGLVGD PTLGAYNASK GAVRIMSKSA ALDCALKDYD  180
VRVNTVHPGP IKTPRKDDLE GWEEMMSQRT LTPMGHIGEP NDIAWICVYL ASDESKFATG  240
AEFVVDGGWT AQ                                                      252

SEQ ID NO: 113          moltype = DNA  length = 756
FEATURE                 Location/Qualifiers
misc_feature            1..756
                        note = Engineered Variant of Kred from Lactobacillus kefir
source                  1..756
```

```
                        mol_type = other DNA
                        organism = synthetic construct
SEQUENCE: 113
atgaccgatc gtctgaagca taaagtagcc atcgttaccg gcgggacact gggtatcggt   60
ttggcaatcg ccgataaatt tgtagaggag ggtgcgaaag tagttattac tggtcgtcac  120
gcggatgtag gtgaaaaggc cgccaaatca atcggcggca ctgatgttat tcgctttgtc  180
cagcacgatg cgtccgaaga agcaggctgg acgaaactgt tcgacaccac cgaggaggca  240
ttcggcccgg ttacgaccct ggtgaacaat gcagggattg ggttattaa aagcgttgaa   300
tgtactacca cggaggaatg gcgtaaaatc ctgtccgtta atctggatgg tgttttttc   360
ggcacccgtc tgggcattca gcgcatgaaa aataaaggct tgggcgctag catcatcaat  420
atgagcagta ttatggggct cgtaggcgat ccgactctgg gggcatacaa cgcttccaag  480
ggggcggtac gtatcatgtc gaaaagcgca gcgctggatt gcgcactgaa ggactacgat  540
gtgcgtgtca acacagtaca tccgggcccc atcaagaccc cgcggaagga tgatctggaa  600
ggttgggagg aaatgatgtc acagcgtacg ttaaccccta tggccacat tggcgaaccg   660
aatgacatcg catggatctg tgtgtacctg gcatctgacg aatcgaaatt tgcgacgggt  720
gcagaatttg tggtcgacgg cgggtggacc gcacag                            756

SEQ ID NO: 114          moltype = AA  length = 252
FEATURE                 Location/Qualifiers
REGION                  1..252
                        note = Engineered Variant of Kred from Lactobacillus kefir
source                  1..252
                        mol_type = protein
                        organism = synthetic construct
SEQUENCE: 114
MTDRLKHKVA IVTGGTLGIG LAIADKFVEE GAKVVITGRH ADVGEKAAKS IGGTDVIRFV   60
QHDASEEAGW TKLFDTTEEA FGPVTTLVNN AGIGVIKSVE CTTTEEWRKI LSVNLDGVFF  120
GTRLGIQRMK NKGLGASIIN MSSIMGLVGD PTLGAYNASK GAVRIMSKSA ALDCALKDYD  180
VRVNTVHPGP IKTPRKDDLE GWEEMMSQRT LTPMGHIGEP NDIAWICVYL ASDESKFATG  240
AEFVVDGGWT AQ                                                      252

SEQ ID NO: 115          moltype = DNA  length = 756
FEATURE                 Location/Qualifiers
misc_feature            1..756
                        note = Engineered Variant of Kred from Lactobacillus kefir
source                  1..756
                        mol_type = other DNA
                        organism = synthetic construct
SEQUENCE: 115
atgaccgatc gtctgaagca taaagtagcc atcgttaccg gcgggacact gggtatcggt   60
ttggcaatcg ccgataaatt tgtagaggag ggtgcgaaag tagttattac tggtcgtcac  120
gcggatgtag gtgaaaaggc cgccaaatca atcggcggca ctgatgttat tcgctttgtc  180
cagcacgatg cgtccgaaga agcaggctgg acgaaactgt tcgacaccac cgaggaggca  240
ttcggcccgg ttacgaccct ggtgaacaat gcagggattg ggttattaa aagcgttgaa   300
gacactacca cggaggaatg gcgtaaaatc ctgtccgtta atctggatgg tgttttttc   360
ggcacccgtc tgggcattca gcgcatgaaa aataaaggct tgggcgctag catcatcaat  420
atgagcagta ttatggggct cgtaggcgat ccgactctgg gggcatacaa cgcttccaag  480
ggggcggtac gtatcatgtc gaaaagcgca gcgctggatt gcgcactgaa ggactacgat  540
gtgcgtgtca acacagtaca tccgggcgcg atcaagaccc cgcggaagga tgatctggaa  600
ggttgggagg aaatgatgtc acagcgtacg ttaaccccta tggccacat tggcgaaccg   660
aatgacatcg catggatctg tgtgtacctg gcatctgacg aatcgaaatt tgcgacgggt  720
gcagaatttg tggtcgacgg cgggtggacc gcacag                            756

SEQ ID NO: 116          moltype = AA  length = 252
FEATURE                 Location/Qualifiers
REGION                  1..252
                        note = Engineered Variant of Kred from Lactobacillus kefir
source                  1..252
                        mol_type = protein
                        organism = synthetic construct
SEQUENCE: 116
MTDRLKHKVA IVTGGTLGIG LAIADKFVEE GAKVVITGRH ADVGEKAAKS IGGTDVIRFV   60
QHDASEEAGW TKLFDTTEEA FGPVTTLVNN AGIGVIKSVE DTTTEEWRKI LSVNLDGVFF  120
GTRLGIQRMK NKGLGASIIN MSSIMGLVGD PTLGAYNASK GAVRIMSKSA ALDCALKDYD  180
VRVNTVHPGA IKTPRKDDLE GWEEMMSQRT LTPMGHIGEP NDIAWICVYL ASDESKFATG  240
AEFVVDGGWT AQ                                                      252

SEQ ID NO: 117          moltype = DNA  length = 756
FEATURE                 Location/Qualifiers
misc_feature            1..756
                        note = Engineered Variant of Kred from Lactobacillus kefir
source                  1..756
                        mol_type = other DNA
                        organism = synthetic construct
SEQUENCE: 117
atgaccgatc gtctgaagca taaagtagcc atcgttaccg gcgggacact gggtatcggt   60
ttggcaatcg ccgataaatt tgtagaggag ggtgcgaaag tagttattac tggtcgtcac  120
gcggatgtag gtgaaaaggc cgccaaatca atcggcggca ctgattgtat tcgctttgtc  180
cagcacgatg cgtccgaaga agcaggctgg acgaaactgt tcgacaccac cgaggaggca  240
```

```
ttcggcccgg ttacgaccct ggtgaacaat gcagggattg ggttattaa aagcgttgaa  300
gacactacca cggaggaatg gcgtaaaatc ctgtccgtta atctggatgg tgttttttc   360
ggcacccgtc tgggcattca gcgcatgaaa aataaaggct tgggcgctag catcatcaat  420
atgagcagta ttatggggct cgtaggcgat ccgactctgg gggcatacaa cgcttccaag  480
gggggcggtac gtatcatgtc gaaaagcgca gcgctggatt gcgcactgaa ggactacgat  540
gtgcgtgtca acacagtaca tccgggcccc atcaagaccc cgcggaagga tgatctggaa  600
ggttgggagg aaatgatgtc acagcgtacg ttaaccccta tgggccacat tggcgaaccg  660
aatgacatcg catggatctg tgtgtacctg gcatctgacg aatcgaaatt tgcgacgggt  720
gcagaatttg tggtcgacgg cgggtggacc gcacag                           756

SEQ ID NO: 118         moltype = AA  length = 252
FEATURE                Location/Qualifiers
REGION                 1..252
                       note = Engineered Variant of Kred from Lactobacillus kefir
source                 1..252
                       mol_type = protein
                       organism = synthetic construct
SEQUENCE: 118
MTDRLKHKVA IVTGGTLGIG LAIADKFVEE GAKVVITGRH ADVGEKAAKS IGGTDCIRFV   60
QHDASEEAGW TKLFDTTEEA FGPVTTLVNN AGIGVIKSVE DTTTEEWRKI LSVNLDGVFF  120
GTRLGIQRMK NKGLGASIIN MSSIMGLVGD PTLGAYNASK GAVRIMSKSA ALDCALKDYD  180
VRVNTVHPGP IKTPRKDDLE GWEEMMSQRT LTPMGHIGEP NDIAWICVYL ASDESKFATG  240
AEFVVDGGWT AQ                                                     252

SEQ ID NO: 119         moltype = DNA  length = 756
FEATURE                Location/Qualifiers
misc_feature           1..756
                       note = Engineered Variant of Kred from Lactobacillus kefir
source                 1..756
                       mol_type = other DNA
                       organism = synthetic construct
SEQUENCE: 119
atgaccgatc gtctgaagca taaagtagcc atcgttaccg gcgggacact gggtatcggt   60
ttggcaatcg ccgataaatt tgtagaggag ggtgcgaaag tagttattac tggtcgtcac  120
gcggatgtag gtgaaaaggc cgccaaatca atcggcggca ctgatgttat tcgcttttgtc  180
cagcacgatg cgtccgaaga agcaggctgg acgaaactgt tcgacaccac cgaggaggca  240
ttcggcccgg ttacgaccct ggtgaacaat gcagggattg ggttattaa aagcgttgaa  300
gacactacca cggaggaatg gcgtaaaatc ctgtccgtta atctggatgg tgttttttc   360
ggcacccgtc tgggcattca gcgcatgaaa aataaaggct tgggcgctag catcatcaat  420
atgagcagta ttatggggct cgtaggcgat ccgactctgg gggcatacaa cgcttccaag  480
gggggcggtac gtatcatgtc gaaaagcgca gcgctggatt gcgcactgaa ggactacgat  540
gtgcgtgtca acacagtaca tccgggcccc atcaagaccc cgcggaagga tgatctggaa  600
ggttgggagg aaatgatgtc acagcgtacg ttaaccccta tgggccacat tggcgaaccg  660
aatgacatcg catggatctg tgtgtacctg gcatctgacg aatcgaaatt tgcgacgggt  720
gcagaatttg tggtcgacgg cgggtggacc gcacag                           756

SEQ ID NO: 120         moltype = AA  length = 252
FEATURE                Location/Qualifiers
REGION                 1..252
                       note = Engineered Variant of Kred from Lactobacillus kefir
source                 1..252
                       mol_type = protein
                       organism = synthetic construct
SEQUENCE: 120
MTDRLKHKVA IVTGGTLGIG LAIADKFVEE GAKVVITGRH ADVGEKAAKS IGGTDVIRFV   60
QHDASEEAGW TKLFDTTEEA FGPVTTLVNN AGIGVIKSVE DTTTEEWRKI LSVNLDGVFF  120
GTRLGIQRMK NKGLGASIIN MSSIMGLVGD PTLGAYNASK GGVRIMSKSA ALDCALKDYD  180
VRVNTVHPGP IKTPRKDDLE GWEEMMSQRT LTPMGHIGEP NDIAWICVYL ASDESKFATG  240
AEFVVDGGWT AQ                                                     252

SEQ ID NO: 121         moltype = DNA  length = 756
FEATURE                Location/Qualifiers
misc_feature           1..756
                       note = Engineered Variant of Kred from Lactobacillus kefir
source                 1..756
                       mol_type = other DNA
                       organism = synthetic construct
SEQUENCE: 121
atgaccgatc gtctgaagca taaagtagcc atcgttaccg gcgggacact gggtatcggt   60
ttggcaatcg ccgataaatt tgtagaggag ggtgcgaaag tagttattac tggtcgtcac  120
gcggatgtag gtgaaaaggc cgccaaatca atcggcggca ctgatgttat tcgcttttgtc  180
cagcacgatg cgtccgaaga agcaggctgg acgaaactgt tcgacaccac cgaggaggca  240
ttcggcccgg ttacgaccct ggtgaacaat gcagggattg ggattattaa aagcgttgaa  300
gacactacca cggaggaatg gcgtaaaatc ctgtccgtta atctggatgg tgttttttc   360
ggcacccgtc tgggcattca gcgcatgaaa aataaaggct tgggcgctag catcatcaat  420
atgagcagta ttatggggct cgtaggcgat ccgactctgg gggcatacaa cgcttccaag  480
ggggcggtac gtatcatgtc gaaaagcgca gcgctggatt gcgcactgaa ggactacgat  540
gtgcgtgtca acacagtaca tccgggcccc atcaagaccc cgcggaagga tgatctggaa  600
ggttgggagg aaatgatgtc acagcgtacg ttaaccccta tgggccacat tggcgaaccg  660
```

```
aatgacatcg catggatctg tgtgtacctg gcatctgacg aatcgaaatt tgcgacgggt   720
gcagaatttg tggtcgacgg cgggtggacc gcacag                              756
```

```
SEQ ID NO: 122            moltype = AA  length = 252
FEATURE                   Location/Qualifiers
REGION                    1..252
                          note = Engineered Variant of Kred from Lactobacillus kefir
source                    1..252
                          mol_type = protein
                          organism = synthetic construct
SEQUENCE: 122
MTDRLKHKVA IVTGGTLGIG LAIADKFVEE GAKVVITGRH ADVGEKAAKS IGGTDVIRFV    60
QHDASEEAGW TKLFDTTEEA FGPVTTLVNN AGIGIIKSVE DTTTEEWRKI LSVNLDGVFF   120
GTRLGIQRMK NKGLGASIIN MSSIMGLVGD PTLGAYNASK GAVRIMSKSA ALDCALKDYD   180
VRVNTVHPGP IKTPRKDDLE GWEEMMSQRT LTPMGHIGEP NDIAWICVYL ASDESKFATG   240
AEFVVDGGWT AQ                                                       252
```

```
SEQ ID NO: 123            moltype = DNA  length = 756
FEATURE                   Location/Qualifiers
misc_feature              1..756
                          note = Engineered Variant of Kred from Lactobacillus kefir
source                    1..756
                          mol_type = other DNA
                          organism = synthetic construct
SEQUENCE: 123
atgaccgatc gtctgaagca taaagtagcc atcgttaccg gcgggacact gggtatcggt    60
ttggcaatcg ccgataaatt tgtagaggag ggtgcgaaag tagttattac tggtcgtcac   120
gcggatgtag gtgaaaaggc cgccaaatca atcggcggca ctgatgttat tcgctttgtc   180
cagcacgatg cgtccgaaga agcaggctgg acgaaactgt tcgacaccac cgaggaggca   240
ttcggcccgg ttacgaccct ggtgaacaat gcagggattg gggttattaa aagcgttgaa   300
gacactacca cggaggaatg gcgtaaaatc ctgtccgtta atctggatgg tgttttttc    360
ggcacccgtc tgggcattca gcgcatgaaa aataaaggct gggcgctag catcatcaat   420
atgagcagta ttatggggct cgtaggcgat ccgactctgg gggcatacaa cgcttccaag   480
ggggcggtac gtatcatgtc gaaaagcgca gcgctggatt gcgcactgaa ggactacgat   540
gtgcgtgtca acacagtaca tccgggcccc atcaagaccc cgcggaagga tgatctggaa   600
ggttgggagg aaatgatgtc acagcgttgg ttaaccccta tgggccacat tggcgaaccg   660
aatgacatcg catggatctg tgtgtacctg gcatctgacg aatcgaaatt tgcgacgggt   720
gcagaatttg tggtcgacgg cgggtggacc gcacag                              756
```

```
SEQ ID NO: 124            moltype = AA  length = 252
FEATURE                   Location/Qualifiers
REGION                    1..252
                          note = Engineered Variant of Kred from Lactobacillus kefir
source                    1..252
                          mol_type = protein
                          organism = synthetic construct
SEQUENCE: 124
MTDRLKHKVA IVTGGTLGIG LAIADKFVEE GAKVVITGRH ADVGEKAAKS IGGTDVIRFV    60
QHDASEEAGW TKLFDTTEEA FGPVTTLVNN AGIGVIKSVE DTTTEEWRKI LSVNLDGVFF   120
GTRLGIQRMK NKGLGASIIN MSSIMGLVGD PTLGAYNASK GAVRIMSKSA ALDCALKDYD   180
VRVNTVHPGP IKTPRKDDLE GWEEMMSQRW LTPMGHIGEP NDIAWICVYL ASDESKFATG   240
AEFVVDGGWT AQ                                                       252
```

```
SEQ ID NO: 125            moltype = DNA  length = 756
FEATURE                   Location/Qualifiers
misc_feature              1..756
                          note = Engineered Variant of Kred from Lactobacillus kefir
source                    1..756
                          mol_type = other DNA
                          organism = synthetic construct
SEQUENCE: 125
atgaccgatc gtctgaagca taaagtagcc atcgttaccg gcgggacact gggtatcggt    60
ttggcaatcg ccgataaatt tgtagaggag ggtgcgaaag tagttattac tggtcgtcac   120
gcggatgtag gtgaaaaggc cgccaaatca atcggcggca ctgatgttat tcgctttgtc   180
cagcacgatg cgtccgaaga agcaggctgg acgaaactgt tcgacaccac cgaggaggca   240
ttcggcccgg ttacgaccct ggtgaacaat gcagggattg gggttattaa aagcgttgaa   300
gacactacca cggaggaatg gcgtaaaatc ctgtccgtta atctggatgg tgttttttc    360
ggcacccgtc tgggcattca gcgcatgaaa aataaaggct gggcgctag catcatcaat   420
atgagcagta ttatggggct cgtaggcgat ccgactctgg gggcatacaa cgcttccaag   480
ggggcggtac gtatcatgtc gaaaagcgca gcgctggatt gcgcactgaa ggactacgat   540
gtgcgtgtca acacagtaca tccgggcccc atcaagaccc cgcggaagga tgatctggaa   600
ggttgggagg aaatgatgtc acagcgtttt ttaaccccta tgggccacat tggcgaaccg   660
aatgacatcg catggatctg tgtgtacctg gcatctgacg aatcgaaatt tgcgacgggt   720
gcagaatttg tggtcgacgg cgggtggacc gcacag                              756
```

```
SEQ ID NO: 126            moltype = AA  length = 252
FEATURE                   Location/Qualifiers
REGION                    1..252
                          note = Engineered Variant of Kred from Lactobacillus kefir
```

| | | |
|---|---|---|
| source | 1..252 | |
| | mol_type = protein | |
| | organism = synthetic construct | |

SEQUENCE: 126
```
MTDRLKHKVA IVTGGTLGIG LAIADKFVEE GAKVVITGRH ADVGEKAAKS IGGTDVIRFV    60
QHDASEEAGW TKLFDTTEEA FGPVTTLVNN AGIGVIKSVE DTTTEEWRKI LSVNLDGVFF   120
GTRLGIQRMK NKGLGASIIN MSSIMGLVGD PTLGAYNASK GAVRIMSKSA ALDCALKDYD   180
VRVNTVHPGP IKTPRKDDLE GWEEMMSQRF LTPMGHIGEP NDIAWICVYL ASDESKFATG   240
AEFVVDGGWT AQ                                                      252
```

| | | |
|---|---|---|
| SEQ ID NO: 127 | moltype = DNA  length = 756 | |
| FEATURE | Location/Qualifiers | |
| misc_feature | 1..756 | |
| | note = Engineered Variant of Kred from Lactobacillus kefir | |
| source | 1..756 | |
| | mol_type = other DNA | |
| | organism = synthetic construct | |

SEQUENCE: 127
```
atgaccgatc gtctgaagca taaagtagcc atcgttaccg gcgggacact gggtatcggt    60
gctgcaatcg ccgataaatt tgtagaggag ggtgcgaaag tagttattac tggtcgtcac   120
gcggatgtag gtgaaaaggc cgccaaatca atcggcggca ctgatgttat tcgctttgtc   180
cagcacgatg cgtccgaaga agcaggctgg acgaaactgt tcgacaccac cgaggaggca   240
ttcggcccgg ttacgaccct ggtgaacaat gcagggattg gggttattaa aagcgttgaa   300
gacactacca cggaggaatg gcgtaaaatc ctgtccgtta atctggatgg tgttttttc   360
ggcacccgtc tgggcattca gcgcatgaaa aataaaggct gggcgctag catcatcaat   420
atgagcagta ttatggggct cgtaggcgat ccgactctgg ggcatacaa cgcttccaag   480
ggggcggtac gtatcatgtc gaaaagcgca gcgctggatt gcgcactgaa ggactacgat   540
gtgcgtgtca acacagtaca tccgggcccc atcaagaccc cgcggaagga tgatctggaa   600
ggttgggagg aaatgatgtc acagcgtacg ttaaccccta tgggccacat tggcgaaccg   660
aatgacatcg catggatctg tgtgtacctg gcatctgacg aatcgaaatt tgcgacgggt   720
gcagaatttg tggtcgacgg cgggtggacc gcacag                            756
```

| | | |
|---|---|---|
| SEQ ID NO: 128 | moltype = AA  length = 252 | |
| FEATURE | Location/Qualifiers | |
| REGION | 1..252 | |
| | note = Engineered Variant of Kred from Lactobacillus kefir | |
| source | 1..252 | |
| | mol_type = protein | |
| | organism = synthetic construct | |

SEQUENCE: 128
```
MTDRLKHKVA IVTGGTLGIG AAIADKFVEE GAKVVITGRH ADVGEKAAKS IGGTDVIRFV    60
QHDASEEAGW TKLFDTTEEA FGPVTTLVNN AGIGVIKSVE DTTTEEWRKI LSVNLDGVFF   120
GTRLGIQRMK NKGLGASIIN MSSIMGLVGD PTLGAYNASK GAVRIMSKSA ALDCALKDYD   180
VRVNTVHPGP IKTPRKDDLE GWEEMMSQRT LTPMGHIGEP NDIAWICVYL ASDESKFATG   240
AEFVVDGGWT AQ                                                      252
```

| | | |
|---|---|---|
| SEQ ID NO: 129 | moltype = DNA  length = 756 | |
| FEATURE | Location/Qualifiers | |
| misc_feature | 1..756 | |
| | note = Engineered Variant of Kred from Lactobacillus kefir | |
| source | 1..756 | |
| | mol_type = other DNA | |
| | organism = synthetic construct | |

SEQUENCE: 129
```
atgaccgatc gtctgaagca taaagtagcc atcgttaccg gcgggacact gggtatcggt    60
ttggcaatcg ccgataaatt tgtagaggag ggtgcgaaag tagttattac tggtcgtcac   120
gcggatgtag gtgaaaaggc cgccaaatca atcggcggca ctgatgttat tcgctttgtc   180
cagcacgatg cgtccgaaga agcaggctgg acgaaactgt tcgacaccac cgaggaggca   240
ttcggcccgg ttacgaccct ggtgaacaat gcagggattg gggttattaa aagcgttgaa   300
gacactacca cggaggaatg gcgtaaaatc ctgtccgtta atctggatgg tgttttttc   360
ggcacccgtc tgggcattca gcgcatgaaa aataaaggct gggcgctag catcatcaat   420
atgagcagta ttatggggct cgtaggcgat ccgactctgg ggcatacaa cgcttccaag   480
ggggcggtac gtatcatgtc gaaaagcgca gcgctggatt gcgcactgaa ggactacgat   540
gtgcgtgtca acacagtaca tccgggcccc atcaagaccc cgcggaagga tgatctggaa   600
ggttgggagg aaatgatgtc acagcgtacg ttaaccccta tgggccacat tggcgaaccg   660
aatgacatcg catggatcgt tgtgtacctg gcatctgacg aatcgaaatt tgcgacgggt   720
gcagaatttg tggtcgacgg cgggtggacc gcacag                            756
```

| | | |
|---|---|---|
| SEQ ID NO: 130 | moltype = AA  length = 252 | |
| FEATURE | Location/Qualifiers | |
| REGION | 1..252 | |
| | note = Engineered Variant of Kred from Lactobacillus kefir | |
| source | 1..252 | |
| | mol_type = protein | |
| | organism = synthetic construct | |

SEQUENCE: 130
```
MTDRLKHKVA IVTGGTLGIG LAIADKFVEE GAKVVITGRH ADVGEKAAKS IGGTDVIRFV    60
QHDASEEAGW TKLFDTTEEA FGPVTTLVNN AGIGVIKSVE DTTTEEWRKI LSVNLDGVFF   120
GTRLGIQRMK NKGLGASIIN MSSIMGLVGD PTLGAYNASK GAVRIMSKSA ALDCALKDYD   180
```

```
VRVNTVHPGP IKTPRKDDLE GWEEMMSQRT LTPMGHIGEP NDIAWIVVYL ASDESKFATG  240
AEFVVDGGWT AQ                                                     252

SEQ ID NO: 131          moltype = DNA  length = 756
FEATURE                 Location/Qualifiers
misc_feature            1..756
                        note = Engineered Variant of Kred from Lactobacillus kefir
source                  1..756
                        mol_type = other DNA
                        organism = synthetic construct
SEQUENCE: 131
atgaccgatc gtctgaagca taaagtagcc atcgttaccg gcgggacact gggtatcggt   60
ttggcaatcg ccgataaatt tgtagaggag ggtgcgaaag tagttattac tggtcgtcac  120
gcggatgtag gtgaagtggc cgccaaatca atcggcggca ctgatgttat tcgctttgtc  180
cagcacgatg cgtccgaaga agcaggctgg acgaaactgt tcgacaccac cgaggaggca  240
ttcggcccgg ttacgaccct ggtgaacaat gcagggattg gggttattaa agcgttgaa   300
gacactacca cggaggaatg gcgtaaaatc ctgtccgtta atctgatgg tgttttttc   360
ggcacccgtc tgggcattca gcgcatgaaa aataaaggct gggcgctag catcatcaat  420
atgagcagta ttatggggct cgtaggcgat ccgactctgg gggcatacaa cgcttccaag  480
ggggcggtac gtatcatgtc gaaaagcgca gcgctggatt gcgcactgaa ggactacgat  540
gtgcgtgtca acacagtaca tccgggcccc atcaagaccc cgcggaagga tgatctgaa   600
ggttgggagg aaatgatgtc acagcgtacg ttaacccta tgggcacat tggcgaaccg   660
aatgacatcg catggatctg tgtgtacctg gcatctgacg aatcgaaatt tgcgacgggt  720
gcagaatttg tggtcgacgg cgggtggacc gcacag                            756

SEQ ID NO: 132          moltype = AA  length = 252
FEATURE                 Location/Qualifiers
REGION                  1..252
                        note = Engineered Variant of Kred from Lactobacillus kefir
source                  1..252
                        mol_type = protein
                        organism = synthetic construct
SEQUENCE: 132
MTDRLKHKVA IVTGGTLGIG LAIADKFVEE GAKVVITGRH ADVGEVAAKS IGGTDVIRFV   60
QHDASEEAGW TKLFDTTEEA FGPVTTLVNN AGIGVIKSVE DTTTEEWRKI LSVNLDGVFF  120
GTRLGIQRMK NKGLGASIIN MSSIMGLVGD PTLGAYNASK GAVRIMSKSA ALDCALKDYD  180
VRVNTVHPGP IKTPRKDDLE GWEEMMSQRT LTPMGHIGEP NDIAWICVYL ASDESKFATG  240
AEFVVDGGWT AQ                                                     252

SEQ ID NO: 133          moltype = DNA  length = 756
FEATURE                 Location/Qualifiers
misc_feature            1..756
                        note = Engineered Variant of Kred from Lactobacillus kefir
source                  1..756
                        mol_type = other DNA
                        organism = synthetic construct
SEQUENCE: 133
atgaccgatc gtctgaagca taaagtagcc atcgttaccg gcgggacact gggtatcggt   60
ttggcaatcg ccgataaatt tgtagaggag ggtgcgaaag tagttattac tggtcgtcac  120
gcggatgtag gtgaaaaggc cgccaaatca atcggcggca ctgatgttat tcgctttgtc  180
cagcacgatg cgtccgaaga agcaggctgg acgaaactgt tcgacaccac cgaggaggca  240
ttcggcccgg ttacgaccct ggtgaacaat gcagggattg gggttattaa agcgttgaa   300
ctgactacca cggaggaatg gcgtaaaatc ctgtccgtta atctgatgg tgttttttc   360
ggcacccgtc tgggcattca gcgcatgaaa aataaaggct gggcgctag catcatcaat  420
atgagcagta ttatggggct cgtaggcgat ccgactctgg gggcatacaa cgcttccaag  480
ggggcggtac gtatcatgtc gaaaagcgca gcgctggatt gcgcactgaa ggactacgat  540
gtgcgtgtca acacagtaca tccgggcccc atcaagaccc cgcggaagga tgatctggaa  600
ggttgggagg aaatgatgtc acagcgtacg ttaacccta tgggcacat tggcgaaccg   660
aatgacatcg catggatctg tgtgtacctg gcatctgacg aatcgaaatt tgcgacgggt  720
gcagaatttg tggtcgacgg cgggtggacc gcacag                            756

SEQ ID NO: 134          moltype = AA  length = 252
FEATURE                 Location/Qualifiers
REGION                  1..252
                        note = Engineered Variant of Kred from Lactobacillus kefir
source                  1..252
                        mol_type = protein
                        organism = synthetic construct
SEQUENCE: 134
MTDRLKHKVA IVTGGTLGIG LAIADKFVEE GAKVVITGRH ADVGEKAAKS IGGTDVIRFV   60
QHDASEEAGW TKLFDTTEEA FGPVTTLVNN AGIGVIKSVE LTTTEEWRKI LSVNLDGVFF  120
GTRLGIQRMK NKGLGASIIN MSSIMGLVGD PTLGAYNASK GAVRIMSKSA ALDCALKDYD  180
VRVNTVHPGP IKTPRKDDLE GWEEMMSQRT LTPMGHIGEP NDIAWICVYL ASDESKFATG  240
AEFVVDGGWT AQ                                                     252

SEQ ID NO: 135          moltype = DNA  length = 756
FEATURE                 Location/Qualifiers
misc_feature            1..756
                        note = Engineered Variant of Kred from Lactobacillus kefir
```

```
source                  1..756
                        mol_type = other DNA
                        organism = synthetic construct
SEQUENCE: 135
atgaccgatc gtctgaagca taaagtagcc atcgttaccg gcgggacact gggtatcggt   60
ttggcaatcg ccgataaatt tgtagaggag ggtgcgaaag tagttattac tggtcgtcac  120
gcggatgtag gtgaaaaggc cgccaaatca atcggcggca ctgatgttat tcgctttgtc  180
cagcacgatg cgtccgaaga agcaggctgg acgaaactgt tcgacaccac cgaggaggca  240
ttcggcccgg ttacgaccct ggtgaacaat gcagggattg gggttattaa aagcgttgaa  300
gacactacca cggaggaatg gcgtaaaatc ctgtccgtta atctggatgg tgttttttc  360
ggcacccgtc tgggcattca gcgcatgaaa aataaaggct gggcgctag catcatcaat  420
atgagcagta ttatggggct cgtaggcgat ccgactctgg ggcatacaa cgcttccaag  480
ggggcggtac gtatcatgtc gaaaagcgca gcgctggatt gcgcactgaa ggactacgat  540
gtgcgtgtca acacagtaca tccggggccc atcaagaccc cgcggaagga tcagctggaa  600
ggttgggagg aaatgatgtc acagcgtacg ttaaccccta tgggccacat tggcgaaccg  660
aatgacatcg catggatctg tgtgtacctg gcatctgacg aatcgaaatt tgcgacgggt  720
gcagaatttg tggtcgacgg cgggtggacc gcacag                             756

SEQ ID NO: 136          moltype = AA   length = 252
FEATURE                 Location/Qualifiers
REGION                  1..252
                        note = Engineered Variant of Kred from Lactobacillus kefir
source                  1..252
                        mol_type = protein
                        organism = synthetic construct
SEQUENCE: 136
MTDRLKHKVA IVTGGTLGIG LAIADKFVEE GAKVVITGRH ADVGEKAAKS IGGTDVIRFV   60
QHDASEEAGW TKLFDTTEEA FGPVTTLVNN AGIGVIKSVE DTTTEEWRKI LSVNLDGVFF  120
GTRLGIQRMK NKGLGASIIN MSSIMGLVGD PTLGAYNASK GAVRIMSKSA ALDCALKDYD  180
VRVNTVHPGP IKTPRKDQLE GWEEMMSQRT LTPMGHIGEP NDIAWICVYL ASDESKFATG  240
AEFVVDGGWT AQ                                                      252

SEQ ID NO: 137          moltype = DNA   length = 756
FEATURE                 Location/Qualifiers
misc_feature            1..756
                        note = Engineered Variant of Kred from Lactobacillus kefir
source                  1..756
                        mol_type = other DNA
                        organism = synthetic construct
SEQUENCE: 137
atgaccgatc gtctgaagca taaagtagcc atcgttaccg gcgggacact gggtatcggt   60
ttggcaatcg ccgataaatt tgtagaggag ggtgcgaaag tagttattac tggtcgtcac  120
gcggatgtag gtgaaaaggc cgccaaatca atcggcggca ctgatgttat tcgctttgtc  180
cagcacgatg cgtccgaaga agcaggctgg acgaaactgt tcgacaccac cgaggaggca  240
ttcggcccgg ttacgaccct ggtgaacaat gcagggattg gggttattaa aagcgttgaa  300
gacactacca cggaggaatg gcgtaaaatc ctgtccgtta atctggatgg tgttttttc   360
ggcacccgtc tgggcattca gcgcatgaaa aataaaggct gggcgctag catcatcaat  420
atgagcagta ttatggggct cgtaggcgat ccgttgctgg ggcatacaa cgcttccaag  480
ggggcggtac gtatcatgtc gaaaagcgca gcgctggatt gcgcactgaa ggactacgat  540
gtgcgtgtca acacagtaca tccggggccc atcaagaccc cgcggaagga tgatctgaa   600
ggttgggagg aaatgatgtc acagcgtacg ttaaccccta tgggccacat tggcgaaccg  660
aatgacatcg catggatctg tgtgtacctg gcatctgacg aatcgaaatt tgcgacgggt  720
gcagaatttg tggtcgacgg cgggtggacc gcacag                             756

SEQ ID NO: 138          moltype = AA   length = 252
FEATURE                 Location/Qualifiers
REGION                  1..252
                        note = Engineered Variant of Kred from Lactobacillus kefir
source                  1..252
                        mol_type = protein
                        organism = synthetic construct
SEQUENCE: 138
MTDRLKHKVA IVTGGTLGIG LAIADKFVEE GAKVVITGRH ADVGEKAAKS IGGTDVIRFV   60
QHDASEEAGW TKLFDTTEEA FGPVTTLVNN AGIGVIKSVE DTTTEEWRKI LSVNLDGVFF  120
GTRLGIQRMK NKGLGASIIN MSSIMGLVGD PLLGAYNASK GAVRIMSKSA ALDCALKDYD  180
VRVNTVHPGP IKTPRKDDLE GWEEMMSQRT LTPMGHIGEP NDIAWICVYL ASDESKFATG  240
AEFVVDGGWT AQ                                                      252

SEQ ID NO: 139          moltype = DNA   length = 756
FEATURE                 Location/Qualifiers
misc_feature            1..756
                        note = Engineered Variant of Kred from Lactobacillus kefir
source                  1..756
                        mol_type = other DNA
                        organism = synthetic construct
SEQUENCE: 139
atgaccgatc gtctgaagca taaagtagcc atcgttaccg gcgggacact gggtatcggt   60
ttggcaatcg ccgataaatt tgtagaggag ggtgcgaaag tagttattac tggtcgtcac  120
gcggatgtag gtgaaaaggc cgccaaatca atcggcggca ctgatgttat tcgctttgtc  180
```

```
cagcacgatg cgtccgaaga agcaggctgg acgaaactgt tcgacaccac cgagttggca    240
ttcggcccgg ttacgaccct ggtgaacaat gcagggattg gggttattaa aagcgttgaa    300
gacactacca cggaggaatg gcgtaaaatc ctgtccgtta atctggatgg tgttttttc     360
ggcacccgtc tgggcattca gcgcatgaaa aataaaggct gggcgctag catcatcaat     420
atgagcagta ttatggggct cgtaggcgat ccgactctgg ggcatacaa cgcttccaag    480
ggggcggtac gtatcatgtc gaaaagcgca gcgctggatt gcgcactgaa ggactacgat    540
gtgcgtgtca acacagtaca tccgggcccc atcaagaccc cgcggaagga tgatctggaa    600
ggttgggagg aaatgatgtc acagcgtacg ttaaccccta tgggccacat tggcgaaccg    660
aatgacatcg catggatctg tgtgtacctg gcatctgacg aatcgaaatt tgcgacgggt    720
gcagaatttg tggtcgacgg cgggtggacc gcacag                              756

SEQ ID NO: 140           moltype = AA   length = 252
FEATURE                  Location/Qualifiers
REGION                   1..252
                         note = Engineered Variant of Kred from Lactobacillus kefir
source                   1..252
                         mol_type = protein
                         organism = synthetic construct
SEQUENCE: 140
MTDRLKHKVA IVTGGTLGIG LAIADKFVEE GAKVVITGRH ADVGEKAAKS IGGTDVIRFV     60
QHDASEEAGW TKLFDTTELA FGPVTTLVNN AGIGVIKSVE DTTTEEWRKI LSVNLDGVFF   120
GTRLGIQRMK NKGLGASIIN MSSIMGLVGD PTLGAYNASK GAVRIMSKSA ALDCALKDYD   180
VRVNTVHPGP IKTPRKDDLE GWEEMMSQRT LTPMGHIGEP NDIAWICVYL ASDESKFATG   240
AEFVVDGGWT AQ                                                      252

SEQ ID NO: 141           moltype = DNA   length = 756
FEATURE                  Location/Qualifiers
misc_feature             1..756
                         note = Engineered Variant of Kred from Lactobacillus kefir
source                   1..756
                         mol_type = other DNA
                         organism = synthetic construct
SEQUENCE: 141
atgaccgatc gtctgaagca taaagtagcc atcgttaccg gcgggacact gggtatcggt     60
ttggcaatcg ccgataaatt tgtagaggag ggtgcgaaag tagttattac tggtcgtcac   120
gcggatgtag gtgaaaaggc cgccaaatca atcggcggca ctgatgttat tcgctttgtc   180
cagcacgatg cgtccgaaga agcaggctgg acggcgctgt tcgacaccac cgaggaggca   240
ttcggcccgg ttacgaccct ggtgaacaat gcagggattg gggttattaa aagcgttgaa   300
gacactacca cggaggaatg gcgtaaaatc ctgtccgtta atctggatgg tgttttttc    360
ggcacccgtc tgggcattca gcgcatgaaa aataaaggct gggcgctag catcatcaat    420
atgagcagta ttatggggct cgtaggcgat ccgactctgg ggcatacaa cgcttccaag   480
ggggcggtac gtatcatgtc gaaaagcgca gcgctggatt gcgcactgaa ggactacgat   540
gtgcgtgtca acacagtaca tccgggcccc atcaagaccc cgcggaagga tgatctggaa   600
ggttgggagg aaatgatgtc acagcgtacg ttaaccccta tgggccacat tggcgaaccg   660
aatgacatcg catggatctg tgtgtacctg gcatctgacg aatcgaaatt tgcgacgggt   720
gcagaatttg tggtcgacgg cgggtggacc gcacag                             756

SEQ ID NO: 142           moltype = AA   length = 252
FEATURE                  Location/Qualifiers
REGION                   1..252
                         note = Engineered Variant of Kred from Lactobacillus kefir
source                   1..252
                         mol_type = protein
                         organism = synthetic construct
SEQUENCE: 142
MTDRLKHKVA IVTGGTLGIG LAIADKFVEE GAKVVITGRH ADVGEKAAKS IGGTDVIRFV     60
QHDASEEAGW TALFDTTEEA FGPVTTLVNN AGIGVIKSVE DTTTEEWRKI LSVNLDGVFF   120
GTRLGIQRMK NKGLGASIIN MSSIMGLVGD PTLGAYNASK GAVRIMSKSA ALDCALKDYD   180
VRVNTVHPGP IKTPRKDDLE GWEEMMSQRT LTPMGHIGEP NDIAWICVYL ASDESKFATG   240
AEFVVDGGWT AQ                                                      252

SEQ ID NO: 143           moltype = DNA   length = 756
FEATURE                  Location/Qualifiers
misc_feature             1..756
                         note = Engineered Variant of Kred from Lactobacillus kefir
source                   1..756
                         mol_type = other DNA
                         organism = synthetic construct
SEQUENCE: 143
atgaccgatc gtctgaagca taaagtagcc atcgttaccg gcgggacact gggtatcggt     60
ttggcaatcg ccgataaatt tgtagaggag ggtgcgaaag tagttattac tggtcgtcac   120
gcggatgtag gtgaaaaggc cgccaaatca atcggcggca ctgatgttat tcgctttgtc   180
cagcacgatg cgtccgaaga agcaggctgg acgaaactgt tcgacaccac cgaggaggca   240
ttcggcccgg ttacgaccct ggtgaacaat gcagggattg gggttattaa aagcgttgaa   300
gacactacca cggaggaatg gcgtaaaatc ctgtccgtta atctggatgg tgttttttc    360
ggcacccgtc tgggcattca gcgcatgaaa aataaaggct gggcgctag catcatcaat    420
atgagcagta ttatggggct cgtaggcgat ccgactctgg ggcatacaa cgcttccaag   480
ggggcggtac gtatcatgtc gaaaagcgca gcgctggatt gcgcactgaa ggactacgat   540
gtgcgtgtca acacagtaca tccgggcgct atcaagaccc agcgcaagga tgatctggaa   600
```

```
ggttgggagg aaatgatgtc acagcgtacg ttaaccccta tgggccacat tggcgaaccg   660
aatgacatcg catggatctg tgtgtacctg gcatctgacg aatcgaaatt tgcgacgggt   720
gcagaatttg tggtcgacgg cgggtggacc gcacag                             756

SEQ ID NO: 144          moltype = AA   length = 252
FEATURE                 Location/Qualifiers
REGION                  1..252
                        note = Engineered Variant of Kred from Lactobacillus kefir
source                  1..252
                        mol_type = protein
                        organism = synthetic construct
SEQUENCE: 144
MTDRLKHKVA IVTGGTLGIG LAIADKFVEE GAKVVITGRH ADVGEKAAKS IGGTDVIRFV    60
QHDASEEAGW TKLFDTTEEA FGPVTTLVNN AGIGVIKSVE DTTTEEWRKI LSVNLDGVFF   120
GTRLGIQRMK NKGLGASIIN MSSIMGLVGD PTLGAYNASK GAVRIMSKSA ALDCALKDYD   180
VRVNTVHPGA IKTERKDDLE GWEEMMSQRT LTPMGHIGEP NDIAWICVYL ASDESKFATG   240
AEFVVDGGWT AQ                                                      252

SEQ ID NO: 145          moltype = DNA   length = 756
FEATURE                 Location/Qualifiers
misc_feature            1..756
                        note = Engineered Variant of Kred from Lactobacillus kefir
source                  1..756
                        mol_type = other DNA
                        organism = synthetic construct
SEQUENCE: 145
atgaccgatc gtctgaagca taaagtagcc atcgttaccg gcgggacact gggtatcggt    60
ttggcaatcg ccgataaatt tgtagaggag ggtgcgaaag tagttattac tggtcgtcac   120
gcggatgtag gtgaaaaggc cgccaaatca atcggcggca ctgatgttat tcgctttgtc   180
cagcacgatg cgtccgaaga agcaggctgg acgaaactgt tcgacaccac cgaggaggca   240
ttcggcccgg ttacgaccct ggtgaacaat gcagggattg gggttattaa aagcgttgaa   300
gacactacca cggaggaatg gcgtaaaatc ctgtccgtta atctggatgg tgttttttc    360
ggcacccgtc tgggcattca gcgcatgaaa aataaaggct gggcgctag catcatcaat    420
atgagcagta ttatggggct cgtaggcgat ccgactctgg gggcatacaa cgcttccaag   480
ggggcggtac gtatcatgtc gaaaagcgca gcgctggatt gcgcactgaa ggactacgat   540
gtgcgtgtca acacagtaca tccgggcccc atcaagaccg agcgcaagga tgatctggaa   600
ggttgggagg aaatgatgtc acagcgtacg ttaaccccta tgggccacat tggcgaaccg   660
aatgacatcg catggatctg tgtgtacctg gcatctgacg aatcgaaatt tgcgacgggt   720
gcagaatttg tggtcgacgg cgggtggacc gcacag                             756

SEQ ID NO: 146          moltype = AA   length = 252
FEATURE                 Location/Qualifiers
REGION                  1..252
                        note = Engineered Variant of Kred from Lactobacillus kefir
source                  1..252
                        mol_type = protein
                        organism = synthetic construct
SEQUENCE: 146
MTDRLKHKVA IVTGGTLGIG LAIADKFVEE GAKVVITGRH ADVGEKAAKS IGGTDVIRFV    60
QHDASEEAGW TKLFDTTEEA FGPVTTLVNN AGIGVIKSVE DTTTEEWRKI LSVNLDGVFF   120
GTRLGIQRMK NKGLGASIIN MSSIMGLVGD PTLGAYNASK GAVRIMSKSA ALDCALKDYD   180
VRVNTVHPGP IKTERKDDLE GWEEMMSQRT LTPMGHIGEP NDIAWICVYL ASDESKFATG   240
AEFVVDGGWT AQ                                                      252

SEQ ID NO: 147          moltype = DNA   length = 756
FEATURE                 Location/Qualifiers
misc_feature            1..756
                        note = Engineered Variant of Kred from Lactobacillus kefir
source                  1..756
                        mol_type = other DNA
                        organism = synthetic construct
SEQUENCE: 147
atgaccgatc gtctgaagca taaagtagcc atcgttaccg gcgggacact gggtatcggt    60
ttggcaatcg ccgataaatt tgtagaggag ggtgcgaaag tagttattac tggtcgtcac   120
gcggatgtag gtgaaaaggc cgccaaatca atcggcggca ctgatgttat tcgctttgtc   180
cagcacgatg cgtccgaaga agcaggctgg acgaaactgt tcgacaccac cgaggaggca   240
ttcggcccgg ttacgaccct ggtgaacaat gcagggattg gggttattaa aagcgttgaa   300
gacactacca cggaggaatg gcgtaaaatc ctgtccgtta atctggatgg tgttttttc    360
ggcacccgtc tgggcattca gcgcatgaaa aataaaggct gggcgctag catcatcaat    420
atgagcagta ttatggggct cgtaggcgat ccgactctgg gggcatactg cgcttccaag   480
ggggcggtac gtatcatgtc gaaaagcgca gcgctggatt gcgcactgaa ggactacgat   540
gtgcgtgtca acacagtaca tccgggcccc atcaagaccc gcggaagga tgatctggaa    600
ggttgggagg aaatgatgtc acagcgtacg ttaaccccta tgggccacat tggcgaaccg   660
aatgacatcg catggatctg tgtgtacctg gcatctgacg aatcgaaatt tgcgacgggt   720
gcagaatttg tggtcgacgg cgggtggacc gcacag                             756

SEQ ID NO: 148          moltype = AA   length = 252
FEATURE                 Location/Qualifiers
REGION                  1..252
```

```
                        note = Engineered Variant of Kred from Lactobacillus kefir
source                  1..252
                        mol_type = protein
                        organism = synthetic construct
SEQUENCE: 148
MTDRLKHKVA IVTGGTLGIG LAIADKFVEE GAKVVITGRH ADVGEKAAKS IGGTDVIRFV    60
QHDASEEAGW TKLFDTTEEA FGPVTTLVNN AGIGVIKSVE DTTTEEWRKI LSVNLDGVFF   120
GTRLGIQRMK NKGLGASIIN MSSIMGLVGD PTLGAYCASK GAVRIMSKSA ALDCALKDYD   180
VRVNTVHPGP IKTPRKDDLE GWEEMMSQRT LTPMGHIGEP NDIAWICVYL ASDESKFATG   240
AEFVVDGGWT AQ                                                      252

SEQ ID NO: 149          moltype = DNA   length = 756
FEATURE                 Location/Qualifiers
misc_feature            1..756
                        note = Engineered Variant of Kred from Lactobacillus kefir
source                  1..756
                        mol_type = other DNA
                        organism = synthetic construct
SEQUENCE: 149
atgaccgatc gtctgaagca taaagtagcc atcgttaccg gcgggacaat gggtatcggt    60
ttggcaatcg ccgataaatt tgtagaggag ggtgcgaaag tagttattac tggtcgtcac   120
gcggatgtag gtgaaaaggc cgccaaatca atcggcggca ctgatgttat tcgctttgtc   180
cagcacgatg cgtccgaaga agcaggctgg acgaaactgt tcgacaccac cgaggaggca   240
ttcggcccgg ttacgaccct ggtgaacaat gcagggattg ggttattaa aagcgttgaa    300
gacactacca cggaggaatg gcgtaaaatc ctgtccgtta atctggatgg tgttttttc    360
ggcacccgtc tgggcattca gcgcatgaaa aataaaggct gggcgctag catcatcaat    420
atgagcagta ttatggggct cgtaggcgat ccgactctgg gggcatacaa cgcttccaag   480
ggggcggtac gtatcatgtc gaaaagcgca gcgctggatt gcgcactgaa ggactacgat   540
gtgcgtgtca acacagtaca tccgggcccc atcaagaccc cgcggaagga tgatctgaa   600
ggttgggagg aaatgatgtc acagcgtacg ttaaccccta tgggccacat tggcgaaccg   660
aatgacatcg catggatctg tgtgtacctg gcatctgacg aatcgaaatt tgcgacgggt   720
gcagaatttg tggtcgacgg cgggtggacc gcacag                            756

SEQ ID NO: 150          moltype = AA    length = 252
FEATURE                 Location/Qualifiers
REGION                  1..252
                        note = Engineered Variant of Kred from Lactobacillus kefir
source                  1..252
                        mol_type = protein
                        organism = synthetic construct
SEQUENCE: 150
MTDRLKHKVA IVTGGTMGIG LAIADKFVEE GAKVVITGRH ADVGEKAAKS IGGTDVIRFV    60
QHDASEEAGW TKLFDTTEEA FGPVTTLVNN AGIGVIKSVE DTTTEEWRKI LSVNLDGVFF   120
GTRLGIQRMK NKGLGASIIN MSSIMGLVGD PTLGAYNASK GAVRIMSKSA ALDCALKDYD   180
VRVNTVHPGP IKTPRKDDLE GWEEMMSQRT LTPMGHIGEP NDIAWICVYL ASDESKFATG   240
AEFVVDGGWT AQ                                                      252

SEQ ID NO: 151          moltype = DNA   length = 756
FEATURE                 Location/Qualifiers
misc_feature            1..756
                        note = Engineered Variant of Kred from Lactobacillus kefir
source                  1..756
                        mol_type = other DNA
                        organism = synthetic construct
SEQUENCE: 151
atgaccgatc gtctgaagca taaagtagcc atcgttaccg gcgggacaag tggtatcggt    60
ttggcaatcg ccgataaatt tgtagaggag ggtgcgaaag tagttattac tggtcgtcac   120
gcggatgtag gtgaaaaggc cgccaaatca atcggcggca ctgatgttat tcgctttgtc   180
cagcacgatg cgtccgaaga agcaggctgg acgaaactgt tcgacaccac cgaggaggca   240
ttcggcccgg ttacgaccct ggtgaacaat gcagggattg gggttattaa aagcgttgaa   300
gacactacca cggaggaatg gcgtaaaatc ctgtccgtta atctggatgg tgttttttc    360
ggcacccgtc tgggcattca gcgcatgaaa aataaaggct gggcgctag catcatcaat    420
atgagcagta ttatggggct cgtaggcgat ccgactctgg gggcatacaa cgcttccaag   480
ggggcggtac gtatcatgtc gaaaagcgca gcgctggatt gcgcactgaa ggactacgat   540
gtgcgtgtca acacagtaca tccgggcccc atcaagaccc cgcggaagga tgatctgaa   600
ggttgggagg aaatgatgtc acagcgtacg ttaaccccta tgggccacat tggcgaaccg   660
aatgacatcg catggatctg tgtgtacctg gcatctgacg aatcgaaatt tgcgacgggt   720
gcagaatttg tggtcgacgg cgggtggacc gcacag                            756

SEQ ID NO: 152          moltype = AA    length = 252
FEATURE                 Location/Qualifiers
REGION                  1..252
                        note = Engineered Variant of Kred from Lactobacillus kefir
source                  1..252
                        mol_type = protein
                        organism = synthetic construct
SEQUENCE: 152
MTDRLKHKVA IVTGGTSGIG LAIADKFVEE GAKVVITGRH ADVGEKAAKS IGGTDVIRFV    60
QHDASEEAGW TKLFDTTEEA FGPVTTLVNN AGIGVIKSVE DTTTEEWRKI LSVNLDGVFF   120
```

```
GTRLGIQRMK NKGLGASIIN MSSIMGLVGD PTLGAYNASK GAVRIMSKSA ALDCALKDYD   180
VRVNTVHPGP IKTPRKDDLE GWEEMMSQRT LTPMGHIGEP NDIAWICVYL ASDESKFATG   240
AEFVVDGGWT AQ                                                      252

SEQ ID NO: 153          moltype = DNA  length = 756
FEATURE                 Location/Qualifiers
misc_feature            1..756
                        note = Engineered Variant of Kred from Lactobacillus kefir
source                  1..756
                        mol_type = other DNA
                        organism = synthetic construct
SEQUENCE: 153
atgaccgatc gtctgaagca taaagtagcc atcgttaccg gcgggacact gggtatcggt   60
ttggcaatcg ccgataaatt tgtagaggag ggtgcgaaag tagttattac tggtcgtcac   120
gcggatgtag gtgaaaaggc cgccaaatca atcggcggca ctgatgttat tcgctttgtc   180
cagcacgatg cgtccgaaga agcaggctgg acgaaactgt tcgacaccac cgaggaggca   240
ttcggcccgg ttacgaccct ggtgaacaat gcagggattg ggttattaa aagcgttgaa    300
gacactacca cggaggaatg gcgtaaaatc ctgtccgtta atctggatgg tgttttttc    360
ggcacccgtc tgggcattca gcgcatgaaa aataaaggct tgggcgctag catcatcaat   420
atgagcagta ttatggggct cgtaggcgat ccgactctgg gggcatacaa cgcttccaag   480
ggggcggtac gtatcatgtc gaaaagcgca gcgctggatt gcgcactgaa ggactacgat   540
gtgcgtgtca acacagtaca tccgggccct accaagaccg agcgcaagga tgatctggaa   600
ggttgggagg aaatgatgtc acagcgtacg ttaaccccta tgggccacat tggcgaaccg   660
aatgacatcg catggatctg tgtgtaccgt gcatctgacg aatcgaaatt tgcgacgggt   720
gcagaatttg tggtcgacgg cgggtggacc gcacag                            756

SEQ ID NO: 154          moltype = AA  length = 252
FEATURE                 Location/Qualifiers
REGION                  1..252
                        note = Engineered Variant of Kred from Lactobacillus kefir
source                  1..252
                        mol_type = protein
                        organism = synthetic construct
SEQUENCE: 154
MTDRLKHKVA IVTGGTLGIG LAIADKFVEE GAKVVITGRH ADVGEKAAKS IGGTDVIRFV   60
QHDASEEAGW TKLFDTTEEA FGPVTTLVNN AGIGVIKSVE DTTTEEWRKI LSVNLDGVFF   120
GTRLGIQRMK NKGLGASIIN MSSIMGLVGD PTLGAYNASK GAVRIMSKSA ALDCALKDYD   180
VRVNTVHPGP TKTERKDDLE GWEEMMSQRT LTPMGHIGEP NDIAWICVYL ASDESKFATG   240
AEFVVDGGWT AQ                                                      252

SEQ ID NO: 155          moltype = DNA  length = 756
FEATURE                 Location/Qualifiers
misc_feature            1..756
                        note = Engineered Variant of Kred from Lactobacillus kefir
source                  1..756
                        mol_type = other DNA
                        organism = synthetic construct
SEQUENCE: 155
atgaccgatc gtctgaagca taaagtagcc atcgttaccg gcgggacact gggtatcggt   60
ttggcaatcg ccgataaatt tgtagaggag ggtgcgaaag tagttattac tggtcgtcac   120
gcggatgtag gtgaaaaggc cgccaaatca atcggcggca ctgatgttat tcgctttgtc   180
cagcacgatg cgtccgaaga agcaggctgg acgaaactgt tcgacaccac cgaggaggca   240
ttcggcccgg ttacgaccct ggtgaacaat gcagggattg ggttattaa aagcgttgaa    300
gacactacca cggaggaatg gcgtaaaatc ctgtccgtta atctggatgg tgttttttc    360
ggcacccgtc tgggcattca gcgcatgaaa aataaaggct tgggcgctag catcatcaat   420
atgagcagta ttatggggct cgtaggcgat ccgactctgg gggcatacaa cgcttccaag   480
ggggcggtac gtatcatgtc gaaaagcgca gcgctggatt gcgcactgaa ggactacgat   540
gtgcgtgtca acacagtaca tccgggcgct accaagaccg agcgcaagga tgatctgaa    600
ggttgggagg aaatgatgtc acagcgtacg ttaaccccta tgggccacat tggcgaaccg   660
aatgacatcg catggatctg tgtgtaccgt gcatctgacg aatcgaaatt tgcgacgggt   720
gcagaatttg tggtcgacgg cgggtggacc gcacag                            756

SEQ ID NO: 156          moltype = AA  length = 252
FEATURE                 Location/Qualifiers
REGION                  1..252
                        note = Engineered Variant of Kred from Lactobacillus kefir
source                  1..252
                        mol_type = protein
                        organism = synthetic construct
SEQUENCE: 156
MTDRLKHKVA IVTGGTLGIG LAIADKFVEE GAKVVITGRH ADVGEKAAKS IGGTDVIRFV   60
QHDASEEAGW TKLFDTTEEA FGPVTTLVNN AGIGVIKSVE DTTTEEWRKI LSVNLDGVFF   120
GTRLGIQRMK NKGLGASIIN MSSIMGLVGD PTLGAYNASK GAVRIMSKSA ALDCALKDYD   180
VRVNTVHPGA TKTERKDDLE GWEEMMSQRT LTPMGHIGEP NDIAWICVYL ASDESKFATG   240
AEFVVDGGWT AQ                                                      252

SEQ ID NO: 157          moltype = DNA  length = 756
FEATURE                 Location/Qualifiers
misc_feature            1..756
```

```
                            note = Engineered Variant of Kred from Lactobacillus kefir
source                      1..756
                            mol_type = other DNA
                            organism = synthetic construct
SEQUENCE: 157
atgaccgatc gtctgaagca taaagtagcc atcgttaccg gcgggacact gggtatcggt   60
ttggcaatcg ccgataaatt tgtagaggag ggtgcgaaag tagttattac tggtcgtcac  120
gcggatgtag gtgaaaaggc cgccaaatca atcggcggca ctgatgttat tcgctttgtc  180
cagcacgatg cgtccgaaga agcaggctgg acgaaactgt tcgacaccac cgaggaggca  240
ttcggcccgg ttacgaccct ggtgaacaat gcagggattg gggttattaa aagcgttgaa  300
gacactacca cggaggaatg gcgtaaaatc ctgtccgtta atctggatgg tgttttttc  360
ggcacccgtc tgggcattca gcgcatgaaa aataaaggct gggcgctag catcatcaat  420
atgagcagta ttatggggct cgtaggcgat ccgactctgg ggcatacaa cgctactaag  480
ggggcggtac gtatcatgtc gaaaagcgca gcgctggatt gcgcactgaa ggactacgat  540
gtgcgtgtca acacagtaca tccgggcccc atcaagaccc cgcggaagga tgatctggaa  600
ggttgggagg aaatgatgtc acagcgtacg ttaaccccta tgggccacat tggcgaaccg  660
aatgacatcg catggatctg tgtgtacctg gcatctgacg aatcgaaatt tgcgacgggt  720
gcagaatttg tggtcgacgg cgggtggacc gcacag                            756

SEQ ID NO: 158              moltype = AA   length = 252
FEATURE                     Location/Qualifiers
REGION                      1..252
                            note = Engineered Variant of Kred from Lactobacillus kefir
source                      1..252
                            mol_type = protein
                            organism = synthetic construct
SEQUENCE: 158
MTDRLKHKVA IVTGGTLGIG LAIADKFVEE GAKVVITGRH ADVGEKAAKS IGGTDVIRFV   60
QHDASEEAGW TKLFDTTEEA FGPVTTLVNN AGIGVIKSVE DTTTEEWRKI LSVNLDGVFF  120
GTRLGIQRMK NKGLGASIIN MSSIMGLVGD PTLGAYNATK GAVRIMSKSA ALDCALKDYD  180
VRVNTVHPGP IKTPRKDDLE GWEEMMSQRT LTPMGHIGEP NDIAWICVYL ASDESKFATG  240
AEFVVDGGWT AQ                                                      252

SEQ ID NO: 159              moltype = DNA   length = 756
FEATURE                     Location/Qualifiers
misc_feature                1..756
                            note = Engineered Variant of Kred from Lactobacillus kefir
source                      1..756
                            mol_type = other DNA
                            organism = synthetic construct
SEQUENCE: 159
atgaccgatc gtctgaagca taaagtagcc atcgttaccg gcgggacact gggtatcggt   60
ttggcaatcg ccgataaatt tgtagaggag ggtgcgaaag tagttattac tggtcgtcac  120
gcggatgtag gtgaaaaggc cgccaaatca atcggcggca ctgatgttat tcgctttgtc  180
cagcacgatg cgtccgaaga agcaggctgg acgaaactgt tcgacaccac cgaggaggca  240
ttcggcccgg ttacgaccct ggtgaacaat gcagggattg gggttattaa aagcgttgaa  300
gacactacca cggaggaatg gcgtaaaatc ctgtccgtta atctggatgg tgttttttc  360
ggcacccgtc tgggcattca gcgcatgaaa aataaaggct gggcgctag catcatcaat  420
atgagcagta ttatggggct cgtaggcgat ccgactctgg ggcatacaa cgcttccaag  480
ggggcggtac gtatcatgtc gaaaagcgca gcgctggatt gcgcactgaa ggactacgat  540
gtgcgtgtca acacagtaca tccgggcccc atcaagaccc cgcggaagga tcagctggaa  600
ggttgggagg aaatgatgtc acagcgtacg ttaaccccta tgggccacat tggcgaaccg  660
aatgacatcg catggatctg tgtgtacctg gcatctgacg aatcgaaatt tgcgacgggt  720
gcagaatttg tggtcgacgg cgggtggacc gcacag                            756

SEQ ID NO: 160              moltype = AA   length = 252
FEATURE                     Location/Qualifiers
REGION                      1..252
                            note = Engineered Variant of Kred from Lactobacillus kefir
source                      1..252
                            mol_type = protein
                            organism = synthetic construct
SEQUENCE: 160
MTDRLKHKVA IVTGGTLGIG LAIADKFVEE GAKVVITGRH ADVGEKAAKS IGGTDVIRFV   60
QHDASEEAGW TKLFDTTEEA FGPVTTLVNN AGIGVIKSVE DTTTEEWRKI LSVNLDGVFF  120
GTRLGIQRMK NKGLGASIIN MSSIMGLVGD PTLGAYNASK GAVRIMSKSA ALDCALKDYD  180
VRVNTVHPGP IKTPRKDQLE GWEEMMSQRT LTPMGHIGEP NDIAWICVYL ASDESKFATG  240
AEFVVDGGWT AQ                                                      252

SEQ ID NO: 161              moltype = DNA   length = 756
FEATURE                     Location/Qualifiers
misc_feature                1..756
                            note = Engineered Variant of Kred from Lactobacillus kefir
source                      1..756
                            mol_type = other DNA
                            organism = synthetic construct
SEQUENCE: 161
atgaccgatc gtctgaagca taaagtagcc atcgttaccg gcgggacact gggtatcggt   60
ttggcaatcg ccgataaatt tgtagaggag ggtgcgaaag tagttattac tggtcgtcac  120
```

```
gcggatgtag gtgaaaaggc cgccaaatca atcggcggca ctgatgttat tcgctttgtc    180
cagcacgatg cgtccgaaga agcaggctgg acgaaactgt tcgacaccac cgaggaggca    240
ttcggcccgg ttacgaccct ggtgaacaat gcagggattg ggttattaa aagcgttgaa     300
gacactacca cggaggaatg gcgtaaaatc ctgtccgtta atctggatgg tgttttttc    360
ggcacccgtc tgggcattca gcgcatgaaa aataaaggct tgggcgctag catcatcaat    420
atgagcagta ttatggggct cgtaggcgat ccgactctgg gggcatacaa cgcttccaag    480
ggggcggtac gtatcatgtc gaaaagcgca gcgctggatt gcgcactgaa ggactacgat    540
gtgcgtgtca acacagtaca tccgggcccc atcaagaccc cgcggaagga tgcgctggaa    600
ggttgggagg aaatgatgtc acagcgtacg ttaaccccta tgggcacat tggcgaaccg    660
aatgacatcg catggatctg tgtgtacctg gcatctgacg aatcgaaatt tgcgacgggt    720
gcagaatttg tggtcgacgg cgggtggacc gcacag                              756

SEQ ID NO: 162          moltype = AA   length = 252
FEATURE                 Location/Qualifiers
REGION                  1..252
                        note = Engineered Variant of Kred from Lactobacillus kefir
source                  1..252
                        mol_type = protein
                        organism = synthetic construct
SEQUENCE: 162
MTDRLKHKVA IVTGGTLGIG LAIADKFVEE GAKVVITGRH ADVGEKAAKS IGGTDVIRFV     60
QHDASEEAGW TKLFDTTEEA FGPVTTLVNN AGIGVIKSVE DTTTEEWRKI LSVNLDGVFF    120
GTRLGIQRMK NKGLGASIIN MSSIMGLVGD PTLGAYNASK GAVRIMSKSA ALDCALKDYD    180
VRVNTVHPGP IKTPRKDALE GWEEMMSQRT LTPMGHIGEP NDIAWICVYL ASDESKFATG    240
AEFVVDGGWT AQ                                                         252

SEQ ID NO: 163          moltype = DNA   length = 756
FEATURE                 Location/Qualifiers
misc_feature            1..756
                        note = Engineered Variant of Kred from Lactobacillus kefir
source                  1..756
                        mol_type = other DNA
                        organism = synthetic construct
SEQUENCE: 163
atgaccgatc gtctgaagca taaagtagcc atcgttaccg gcgggacaat gggtatcggt     60
ttggcaatcg ccgataaatt tgtagaggag ggtgcgaaag tagttattac tggtcgtcac    120
gcggatgtag gtgaaaaggc cgccaaatca atcggcggca ctgatgttat tcgctttgtc    180
cagcacgatg cgtccgaaga agcaggctgg acgaaactgt tcgacaccac cgaggaggca    240
ttcggcccgg ttacgaccct ggtgaacaat gcagggattg ggttattaa aagcgttgaa     300
gacactacca cggaggaatg gcgtaaaatc ctgtccgtta atctggatgg tgttttttc    360
ggcacccgtc tgggcattca gcgcatgaaa aataaaggct tgggcgctag catcatcaat    420
atgagcagta ttatggggct cgtaggcgat ccgactctgg gggcatacaa cgcttccaag    480
ggggcggtac gtatcatgtc gaaaagcgca gcgctggatt gcgcactgaa ggactacgat    540
gtgcgtgtca acacagtaca tccgggcgcg atcaagaccc cacggaagga tgctctggaa    600
ggttgggagg aaatgatgtc acagcgtacg ttaaccccta tgggcacat tggcgaaccg    660
aatgacatcg catggatctg tgtgtacctg gcatctgacg aatcgaaatt tgcgacgggt    720
gcagaatttg tggtcgacgg cgggtggacc gcacag                              756

SEQ ID NO: 164          moltype = AA   length = 252
FEATURE                 Location/Qualifiers
REGION                  1..252
                        note = Engineered Variant of Kred from Lactobacillus kefir
source                  1..252
                        mol_type = protein
                        organism = synthetic construct
SEQUENCE: 164
MTDRLKHKVA IVTGGTMGIG LAIADKFVEE GAKVVITGRH ADVGEKAAKS IGGTDVIRFV     60
QHDASEEAGW TKLFDTTEEA FGPVTTLVNN AGIGVIKSVE DTTTEEWRKI LSVNLDGVFF    120
GTRLGIQRMK NKGLGASIIN MSSIMGLVGD PTLGAYNASK GAVRIMSKSA ALDCALKDYD    180
VRVNTVHPGA IKTPRKDALE GWEEMMSQRT LTPMGHIGEP NDIAWICVYL ASDESKFATG    240
AEFVVDGGWT AQ                                                         252

SEQ ID NO: 165          moltype = DNA   length = 756
FEATURE                 Location/Qualifiers
misc_feature            1..756
                        note = Engineered Variant of Kred from Lactobacillus kefir
source                  1..756
                        mol_type = other DNA
                        organism = synthetic construct
SEQUENCE: 165
atgaccgatc gtctgaagca taaagtagcc atcgttaccg gcgggacaat gggtatcggt     60
ttggcaatcg ccgataaatt tgtagaggag ggtgcgaaag tagttattac tggtcgtcac    120
gcggatgtag gtgaagtagc cgccaaatca atcggcggca ctgatgttat tcgctttgtc    180
cagcacgatg cgtccgaaga agcaggctgg acgaaactgt tcgacaccac cgaggaggca    240
ttcggcccgg ttacgaccct ggtgaacaat gcagggattg ggttattaa aagcgttgaa     300
gacactacca cggaggaatg gcgtaaaatc ctgtccgtta atctggatgg tgttttttc    360
ggcacccgtc tgggcattca gcgcatgaaa aataaaggct tgggcgctag catcatcaat    420
atgagcagta ttatggggct cgtaggcgat ccgactctgg gggcatacaa cgcttccaag    480
ggggcggtac gtatcatgtc gaaaagcgca gcgctggatt gcgcactgaa ggactacgat    540
```

```
gtgcgtgtca acacagtaca tccgggcccc atcaagaccc cgcggaagga tgctctggaa   600
ggttgggagg aaatgatgtc acagcgtacg cgtacccca tgggccacat tggcgaaccg    660
aatgacatcg catggatctg tgtgtacctg gcatctgacg aatcgaaatt tgcgacgggt   720
gcagaatttg tggtcgacgg cgggtggacc gcacag                             756

SEQ ID NO: 166       moltype = AA   length = 252
FEATURE              Location/Qualifiers
REGION               1..252
                     note = Engineered Variant of Kred from Lactobacillus kefir
source               1..252
                     mol_type = protein
                     organism = synthetic construct
SEQUENCE: 166
MTDRLKHKVA IVTGGTMGIG LAIADKFVEE GAKVVITGRH ADVGEVAAKS IGGTDVIRFV    60
QHDASEEAGW TKLFDTTEEA FGPVTTLVNN AGIGVIKSVE DTTTEEWRKI LSVNLDGVFF   120
GTRLGIQRMK NKGLGASIIN MSSIMGLVGD PTLGAYNASK GAVRIMSKSA ALDCALKDYD   180
VRVNTVHPGP IKTPRKDALE GWEEMMSQRT RTPMGHIGEP NDIAWICVYL ASDESKFATG   240
AEFVVDGGWT AQ                                                       252

SEQ ID NO: 167       moltype = DNA   length = 756
FEATURE              Location/Qualifiers
misc_feature         1..756
                     note = Engineered Variant of Kred from Lactobacillus kefir
source               1..756
                     mol_type = other DNA
                     organism = synthetic construct
SEQUENCE: 167
atgaccgatc gtctgaagca taaagtagcc atcgttaccg gcgggacaca gggtatcggt    60
ttggcaatcg ccgataaatt tgtagaggag ggtgcgaaag tagttattac tggtcgtcac   120
gcggatgtag gtgaagtagc cgccaaatca atcggcggga ctgatgttat tcgctttgtc   180
cagcacgatg cgtccgaaga agcaggctgg acgaaactgt tcgacaccac cgaggaggca   240
ttcggcccgg ttacgaccct ggtgaacaat gcagggattg gggttattaa agcgttgaa    300
gacactacca cggaggaatg gcgtaaaatc ctgtccgtta atctggatgg tgttttttc    360
ggcacccgtc tgggcattca gcgcatgaaa aataaaggct gggcgctag catcatcaat    420
atgagcagta ttatggggct cgtaggcgat ccgactctgg gggcatacaa cgcttccaag   480
ggggcggtac gtatcatgtc gaaaagcgca gcgctggatt gcgcactgaa ggactacgat   540
gtgcgtgtca acacagtaca tccgggcccg atcaagaccg agcggaagga tcagctgaa    600
ggttgggagg aaatgatgtc acagcgtacg ttaccccta tgggccacat tggcgaaccg    660
aatgacatcg catggatctg tgtgtacctg gcatctgacg aatcgaaatt tgcgacgggt   720
gcagaatttg tggtcgacgg cgggtggacc gcacag                             756

SEQ ID NO: 168       moltype = AA   length = 252
FEATURE              Location/Qualifiers
REGION               1..252
                     note = Engineered Variant of Kred from Lactobacillus kefir
source               1..252
                     mol_type = protein
                     organism = synthetic construct
SEQUENCE: 168
MTDRLKHKVA IVTGGTQGIG LAIADKFVEE GAKVVITGRH ADVGEVAAKS IGGTDVIRFV    60
QHDASEEAGW TKLFDTTEEA FGPVTTLVNN AGIGVIKSVE DTTTEEWRKI LSVNLDGVFF   120
GTRLGIQRMK NKGLGASIIN MSSIMGLVGD PTLGAYNASK GAVRIMSKSA ALDCALKDYD   180
VRVNTVHPGP IKTERKDQLE GWEEMMSQRT LTPMGHIGEP NDIAWICVYL ASDESKFATG   240
AEFVVDGGWT AQ                                                       252

SEQ ID NO: 169       moltype = DNA   length = 756
FEATURE              Location/Qualifiers
misc_feature         1..756
                     note = Engineered Variant of Kred from Lactobacillus kefir
source               1..756
                     mol_type = other DNA
                     organism = synthetic construct
SEQUENCE: 169
atgaccgatc gtctgaagca taaagtagcc atcgttaccg gcgggacaat gggtatcggt    60
ttggcaatcg ccgataaatt tgtagaggag ggtgcgaaag tagttattac tggtcgtcac   120
gcggatgtag gtgaagtagc cgccaaatca atcggcggca ctgatgttat tcgctttgtc   180
cagcacgatg cgtccgaaga agcaggctgg acgaaactgt tcgacaccac cgaggaggca   240
ttcggcccgg ttacgaccct ggtgaacaat gcagggattg gggttattaa agcgttgaa    300
gacactacca cggaggaatg gcgtaaaatc ctgtccgtta atctggatgg tgttttttc    360
ggcacccgtc tgggcattca gcgcatgaaa aataaaggct gggcgctag catcatcaat    420
atgagcagta ttatggggct cgtaggcgat ccgactctgg gggcatacaa cgcttccaag   480
ggggcggtac gtatcatgtc gaaaagcgca gcgctggatt gcgcactgaa ggactacgat   540
gtgcgtgtca acacagtaca tccgggcgcg atcaagaccc acggaagga tgatctggaa    600
ggttgggagg aaatgatgtc acagcgtacg ttaccccta tgggccacat tggcgaaccg    660
aatgacatcg catggatctg tgtgtacctg gcatctgacg aatcgaaatt tgcgacgggt   720
gcagaatttg tggtcgacgg cgggtggacc gcacag                             756

SEQ ID NO: 170       moltype = AA   length = 252
FEATURE              Location/Qualifiers
```

| | |
|---|---|
| REGION | 1..252 |
| | note = Engineered Variant of Kred from Lactobacillus kefir |
| source | 1..252 |
| | mol_type = protein |
| | organism = synthetic construct |

SEQUENCE: 170
```
MTDRLKHKVA IVTGGTMGIG LAIADKFVEE GAKVVITGRH ADVGEVAAKS IGGTDVIRFV    60
QHDASEEAGW TKLFDTTEEA FGPVTTLVNN AGIGVIKSVE DTTTEEWRKI LSVNLDGVFF   120
GTRLGIQRMK NKGLGASIIN MSSIMGLVGD PTLGAYNASK GAVRIMSKSA ALDCALKDYD   180
VRVNTVHPGA IKTPRKDDLE GWEEMMSQRT LTPMGHIGEP NDIAWICVYL ASDESKFATG   240
AEFVVDGGWT AQ                                                      252
```

| | |
|---|---|
| SEQ ID NO: 171 | moltype = DNA length = 756 |
| FEATURE | Location/Qualifiers |
| misc_feature | 1..756 |
| | note = Engineered Variant of Kred from Lactobacillus kefir |
| source | 1..756 |
| | mol_type = other DNA |
| | organism = synthetic construct |

SEQUENCE: 171
```
atgaccgatc gtctgaagca taaagtagcc atcgttaccg gcgggacaat gggtatcggt    60
ttggcaatcg ccgataaatt tgtagaggag ggtgcgaaag tagttattac tggtcgtcac   120
gcggatgtag gtgaaaaagc cgccaaatca atcggcggca ctgatgttat tcgctttgtc   180
cagcacgatg cgtccgaaga agcaggctgg acgaaactgt tcgacaccac cgaggaggca   240
ttcggcccgg ttacgaccct ggtgaacaat gcagggattg ggttattaa agcgttgaa    300
gacactacca cggaggaatg gcgtaaaatc ctgtccgtta atctggatgg tgttttttc    360
ggcacccgtc tgggcattca gcgcatgaaa aataaaggct tgggcgctag catcatcaat   420
atgagcagta ttatggggct cgtaggcgat ccgactctgg gggcatacaa cgcttccaag   480
ggggcggtac gtatcatgtc gaaaagcgca gcgctggatt gcgcactgaa ggactacgat   540
gtgcgtgtca acacagtaca tccgggcgcg atcaagaccc cacggaagga tcagctggaa   600
ggttgggagg aaatgatgtc acagcgtacg ctgaccccta tgggccacat tggcgaaccg   660
aatgacatcg catggatctg tgtgtacctg gcatctgacg aatcgaaatt tgcgacgggt   720
gcagaatttg tggtcgacgg cgggtggacc gcacag                            756
```

| | |
|---|---|
| SEQ ID NO: 172 | moltype = AA length = 252 |
| FEATURE | Location/Qualifiers |
| REGION | 1..252 |
| | note = Engineered Variant of Kred from Lactobacillus kefir |
| source | 1..252 |
| | mol_type = protein |
| | organism = synthetic construct |

SEQUENCE: 172
```
MTDRLKHKVA IVTGGTMGIG LAIADKFVEE GAKVVITGRH ADVGEKAAKS IGGTDVIRFV    60
QHDASEEAGW TKLFDTTEEA FGPVTTLVNN AGIGVIKSVE DTTTEEWRKI LSVNLDGVFF   120
GTRLGIQRMK NKGLGASIIN MSSIMGLVGD PTLGAYNASK GAVRIMSKSA ALDCALKDYD   180
VRVNTVHPGA IKTPRKDQLE GWEEMMSQRT LTPMGHIGEP NDIAWICVYL ASDESKFATG   240
AEFVVDGGWT AQ                                                      252
```

| | |
|---|---|
| SEQ ID NO: 173 | moltype = DNA length = 756 |
| FEATURE | Location/Qualifiers |
| misc_feature | 1..756 |
| | note = Engineered Variant of Kred from Lactobacillus kefir |
| source | 1..756 |
| | mol_type = other DNA |
| | organism = synthetic construct |

SEQUENCE: 173
```
atgaccgatc gtctgaagca taaagtagcc atcgttaccg gcgggacaca gggtatcggt    60
ttggcaatcg ccgataaatt tgtagaggag ggtgcgaaag tagttattac tggtcgtcac   120
gcggatgtag gtgaagtagc cgccaaatca atcggcggca ctgatgttat tcgctttgtc   180
cagcacgatg cgtccgaaga agcaggctgg acgaaactgt tcgacaccac cgaggaggca   240
ttcggcccgg ttacgaccct ggtgaacaat gcagggattg ggttattaa agcgttgaa    300
gacactacca cggaggaatg gcgtaaaatc ctgtccgtta atctggatgg tgttttttc    360
ggcacccgtc tgggcattca gcgcatgaaa aataaaggct tgggcgctag catcatcaat   420
atgagcagta ttatggggct cgtaggcgat ccgactctgg gggcatacaa cgcttccaag   480
ggggcggtac gtatcatgtc gaaaagcgca gcgctggatt gcgcactgaa ggactacgat   540
gtgcgtgtca acacagtaca tccgggcgcg atcaagaccg agcggaagga tcagctggaa   600
ggttgggagg aaatgatgtc acagcgtacg ttaaccccta tgggccacat tggcgaaccg   660
aatgacatcg catggatctg tgtgtacctg gcatctgacg aatcgaaatt tgcgacgggt   720
gcagaatttg tggtcgacgg cgggtggacc gcacag                            756
```

| | |
|---|---|
| SEQ ID NO: 174 | moltype = AA length = 252 |
| FEATURE | Location/Qualifiers |
| REGION | 1..252 |
| | note = Engineered Variant of Kred from Lactobacillus kefir |
| source | 1..252 |
| | mol_type = protein |
| | organism = synthetic construct |

SEQUENCE: 174
```
MTDRLKHKVA IVTGGTQGIG LAIADKFVEE GAKVVITGRH ADVGEVAAKS IGGTDVIRFV    60
```

```
QHDASEEAGW TKLFDTTEEA FGPVTTLVNN AGIGVIKSVE DTTTEEWRKI LSVNLDGVFF 120
GTRLGIQRMK NKGLGASIIN MSSIMGLVGD PTLGAYNASK GAVRIMSKSA ALDCALKDYD 180
VRVNTVHPGA IKTERKDQLE GWEEMMSQRT LTPMGHIGEP NDIAWICVYL ASDESKFATG 240
AEFVVDGGWT AQ                                                    252

SEQ ID NO: 175          moltype = DNA  length = 756
FEATURE                 Location/Qualifiers
misc_feature            1..756
                        note = Engineered Variant of Kred from Lactobacillus kefir
source                  1..756
                        mol_type = other DNA
                        organism = synthetic construct
SEQUENCE: 175
atgaccgatc gtctgaagca taaagtagcc atcgttaccg gcgggacaat gggtatcggt  60
ttggcaatcg ccgataaatt tgtagaggag ggtgcgaaag tagttattac tggtcgtcac 120
gcggatgtag gtgaaaaagc cgccaaatca atcggcggca ctgatgttat tcgctttgtc 180
cagcacgatg cgtccgaaga agcaggctgg acgaaactgt tcgacaccac cgaggaggca 240
ttcggcccgg ttacgaccct ggtgaacaat gcagggattg gggttgttaa aagcgttgaa 300
gacactacca cggaggaatg gcgtaaaatc ctgtccgtta atctggatgg tgttttttc  360
ggcacccgtc tgggcattca gcgcatgaaa aataaaggct gggcgctag catcatcaat  420
atgagcagta ttatggggct cgtaggcgat ccgactctgg gggcatacaa cgcttccaag  480
ggggcggtac gtatcatgtc gaaaagcgca gcgctggatt gcgcactgaa ggactacgat  540
gtgcgtgtca acacagtaca tccgggcccg atcaagaccg agcggaagga tcagctggaa  600
ggttgggagg aaatgatgtc acagcgtacg ttaaccccta tgggccacat tggcgaaccg  660
aatgacatcg catggatctg tgtgtacctg gcatctgacg aatcgaaatt tgcgacgggt  720
gcagaatttg tggtcgacgg cgggtggacc gcacag                            756

SEQ ID NO: 176          moltype = AA  length = 252
FEATURE                 Location/Qualifiers
REGION                  1..252
                        note = Engineered Variant of Kred from Lactobacillus kefir
source                  1..252
                        mol_type = protein
                        organism = synthetic construct
SEQUENCE: 176
MTDRLKHKVA IVTGGTMGIG LAIADKFVEE GAKVVITGRH ADVGEKAAKS IGGTDVIRFV  60
QHDASEEAGW TKLFDTTEEA FGPVTTLVNN AGIGVVKSVE DTTTEEWRKI LSVNLDGVFF 120
GTRLGIQRMK NKGLGASIIN MSSIMGLVGD PTLGAYNASK GAVRIMSKSA ALDCALKDYD 180
VRVNTVHPGP IKTERKDQLE GWEEMMSQRT LTPMGHIGEP NDIAWICVYL ASDESKFATG 240
AEFVVDGGWT AQ                                                    252

SEQ ID NO: 177          moltype = DNA  length = 756
FEATURE                 Location/Qualifiers
misc_feature            1..756
                        note = Engineered Variant of Kred from Lactobacillus kefir
source                  1..756
                        mol_type = other DNA
                        organism = synthetic construct
SEQUENCE: 177
atgaccgatc gtctgaagca taaagtagcc atcgttaccg gcgggacaat gggtatcggt  60
ttggcaatcg ccgataaatt tgtagaggag ggtgcgaaag tagttattac tggtcgtcac 120
gcggatgtag gtgaaaaagc cgccaaatca atcggcggca ctgatgttat tcgctttgtc 180
cagcacgatg cgtccgaaga agcaggctgg acgaaactgt tcgacaccac cgaggaggca 240
ttcggcccgg ttacgaccct ggtgaacaat gcagggattg gggttattaa aagcgttgaa 300
gacactacca cggaggaatg gcgtaaaatc ctgtccgtta atctggatgg tgttttttc  360
ggcacccgtc tgggcattca gcgcatgaaa aataaaggct gggcgctag catcatcaat  420
atgagcagta ttatggggct cgtaggcgat ccgactctgg gggcatacaa cgcttccaag  480
ggggcggtac gtatcatgtc gaaaagcgca gcgctggatt gcgcactgaa ggactacgat  540
gtgcgtgtca acacagtaca tccgggcgcg atcaagaccc acggaagga tcagctggaa   600
ggttgggagc agatgatgtc acagcgtacg ctgaccccta tgggccacat tggcgaaccg  660
aatgacatcg catggatctg tgtgtacctg gcatctgacg aatcgaaatt tgcgacgggt  720
gcagaatttg tggtcgacgg cgggtggacc gcacag                            756

SEQ ID NO: 178          moltype = AA  length = 252
FEATURE                 Location/Qualifiers
REGION                  1..252
                        note = Engineered Variant of Kred from Lactobacillus kefir
source                  1..252
                        mol_type = protein
                        organism = synthetic construct
SEQUENCE: 178
MTDRLKHKVA IVTGGTMGIG LAIADKFVEE GAKVVITGRH ADVGEKAAKS IGGTDVIRFV  60
QHDASEEAGW TKLFDTTEEA FGPVTTLVNN AGIGVIKSVE DTTTEEWRKI LSVNLDGVFF 120
GTRLGIQRMK NKGLGASIIN MSSIMGLVGD PTLGAYNASK GAVRIMSKSA ALDCALKDYD 180
VRVNTVHPGA IKTPRKDQLE GWEQMMSQRT LTPMGHIGEP NDIAWICVYL ASDESKFATG 240
AEFVVDGGWT AQ                                                    252

SEQ ID NO: 179          moltype = DNA  length = 756
FEATURE                 Location/Qualifiers
```

```
misc_feature            1..756
                        note = Engineered Variant of Kred from Lactobacillus kefir
source                  1..756
                        mol_type = other DNA
                        organism = synthetic construct
SEQUENCE: 179
atgaccgatc gtctgaagca taaagtagcc atcgttaccg gcgggacaat gggtatcggt    60
ttggcaatcg ccgataaatt tgtagaggag ggtgcgaaag tagttattac tggtcgtcac   120
gcggatgtag gtgaaaaagc cgccaaatca atcggcggca ctgatgttat tcgctttgtc   180
cagcacgatg cgtccgaaga agcaggctgg acgaaactgt tcgacaccac cgaggaggca   240
ttcggcccgg ttacgaccct ggtgaacaat gcagggattg ggttattaa aagcgttgaa    300
gacactacca cggaggaatg gcgtaaaatc ctgtccgtta atctggatgg tgttttttc    360
ggcacccgtc tgggcattca gcgcatgaaa aataaaggct gggcgctag catcatcaat    420
atgagcagta ttatggggct cgtaggcgat ccgactctgg ggcatacaa cgcttccaag    480
ggggcggtac gtatcatgtc gaaaagcgca gcgctggatt gcgcactgaa ggactacgat   540
gtgcgtgtca acacagtaca tccgggcgcg atcaagaccc cacggaagga tcagctggaa   600
ggttgggagg aaatgatgtc acagcgtacg ctgaccccta tgggccacat tggcgaaccg   660
aatgacatcg catgggtgtg tgtgtacctg gcatctgacg aatcgaaatt tgcgacgggt   720
gcagaatttg tggtcgacgg cgggtggacc gcacag                             756

SEQ ID NO: 180          moltype = AA length = 252
FEATURE                 Location/Qualifiers
REGION                  1..252
                        note = Engineered Variant of Kred from Lactobacillus kefir
source                  1..252
                        mol_type = protein
                        organism = synthetic construct
SEQUENCE: 180
MTDRLKHKVA IVTGGTMGIG LAIADKFVEE GAKVVITGRH ADVGEKAAKS IGGTDVIRFV    60
QHDASEEAGW TKLFDTTEEA FGPVTTLVNN AGIGVIKSVE DTTTEEWRKI LSVNLDGVFF   120
GTRLGIQRMK NKGLGASIIN MSSIMGLVGD PTLGAYNASK GAVRIMSKSA ALDCALKDYD   180
VRVNTVHPGA IKTPRKDQLE GWEEMMSQRT LTPMGHIGEP NDIAWVCVYL ASDESKFATG   240
AEFVVDGGWT AQ                                                      252

SEQ ID NO: 181          moltype = DNA length = 756
FEATURE                 Location/Qualifiers
misc_feature            1..756
                        note = Engineered Variant of Kred from Lactobacillus kefir
source                  1..756
                        mol_type = other DNA
                        organism = synthetic construct
SEQUENCE: 181
atgaccgatc gtctgaagca taaagtagcc atcgttaccg gcgggacaat gggtatcggt    60
ttggcaatcg ccgataaatt tgtagaggag ggtgcgaaag tagttattac tggtcgtcac   120
gcggatgtag gtgaaaaagc cgccaaatca atcggcggca ctgatgttat tcgctttgtc   180
cagcacgatg cgtccgaaga agcaggctgg acgaaactgt tcgacaccac cgaggaggca   240
ttcggcccgg ttacgaccct ggtgaacaat gcagggattg ggttattaa aagcgttgaa    300
tatactacca cggaggaatg gcgtaaaatc ctgtccgtta atctggatgg tgttttttc    360
ggcacccgtc tgggcattca gcgcatgaaa aataaaggct gggcgctag catcatcaat    420
atgagcagta ttatggggct cgtaggcgat ccgactctgg ggcatacaa cgcttccaag    480
ggggcggtac gtatcatgtc gaaaagcgca gcgctggatt gcgcactgaa ggactacgat   540
gtgcgtgtca acacagtaca tccgggcgcg atcaagaccc cacggaagga tcagctggaa   600
ggttgggagg aaatgatgtc acagcgtacg ctgaccccta tgggccacat tggcgaaccg   660
aatgacatcg catggatctg tgtgtacctg gcatctgacg aatcgaaatt tgcgacgggt   720
gcagaatttg tggtcgacgg cgggtggacc gcacag                             756

SEQ ID NO: 182          moltype = AA length = 252
FEATURE                 Location/Qualifiers
REGION                  1..252
                        note = Engineered Variant of Kred from Lactobacillus kefir
source                  1..252
                        mol_type = protein
                        organism = synthetic construct
SEQUENCE: 182
MTDRLKHKVA IVTGGTMGIG LAIADKFVEE GAKVVITGRH ADVGEKAAKS IGGTDVIRFV    60
QHDASEEAGW TKLFDTTEEA FGPVTTLVNN AGIGVIKSVE YTTTEEWRKI LSVNLDGVFF   120
GTRLGIQRMK NKGLGASIIN MSSIMGLVGD PTLGAYNASK GAVRIMSKSA ALDCALKDYD   180
VRVNTVHPGA IKTPRKDQLE GWEEMMSQRT LTPMGHIGEP NDIAWICVYL ASDESKFATG   240
AEFVVDGGWT AQ                                                      252

SEQ ID NO: 183          moltype = DNA length = 756
FEATURE                 Location/Qualifiers
misc_feature            1..756
                        note = Engineered Variant of Kred from Lactobacillus kefir
source                  1..756
                        mol_type = other DNA
                        organism = synthetic construct
SEQUENCE: 183
atgaccgatc gtctgaagca taaagtagcc atcgttaccg gcgggacaat gggtatcggt    60
```

```
ttggcaatcg ccgataaatt tgtagaggag ggtgcgaaag tagttattac tggtcgtcac    120
gcggatgtag gtgaaaaagc cgccaaatca atcggcggca ctgatgttat tcgctttgtc    180
cagcacgatg cgtccgaaga agcaggctgg acgaaactgt tcgacaccac cgaggaggca    240
ttcggcccgg ttacgaccct ggtgaacaat gcagggattg ggttattaa aagcgttgaa     300
gacactacca cggaggaatg gcgtaaaatc ctgtccgtta atctggatgg tgttttttc     360
ggcacccgtc tgggcattca gcgcatgaaa aataaaggct tgggcgctag catcatcaat    420
atgagcagta ttatggggct cgtaggcgat ccgactctgg gggcatacaa cgcttccaag    480
ggggcggtac gtatcatgtc gaaaagcgca gcgctggatt gcgcactgaa ggacatggat    540
gtgcgtgtca acacagtaca tccgggcgcg atcaagaccc cacggaagga tcagctggaa    600
ggttgggagg aaatgatgtc acagcgtacg ctgaccccta tgggccacat tggcgaaccg    660
aatgacatcg catggatctg tgtgtacctg gcatctgacg aatcgaaatt tgcgacgggt    720
gcagaatttg tggtcgacgg cgggtggacc gcacag                              756

SEQ ID NO: 184        moltype = AA  length = 252
FEATURE               Location/Qualifiers
REGION                1..252
                      note = Engineered Variant of Kred from Lactobacillus kefir
source                1..252
                      mol_type = protein
                      organism = synthetic construct
SEQUENCE: 184
MTDRLKHKVA IVTGGTMGIG LAIADKFVEE GAKVVITGRH ADVGEKAAKS IGGTDVIRFV     60
QHDASEEAGW TKLFDTTEEA FGPVTTLVNN AGIGVIKSVE DTTTEEWRKI LSVNLDGVFF    120
GTRLGIQRMK NKGLGASIIN MSSIMGLVGD PTLGAYNASK GAVRIMSKSA ALDCALKDMD    180
VRVNTVHPGA IKTPRKDQLE GWEEMMSQRT LTPMGHIGEP NDIAWICVYL ASDESKFATG    240
AEFVVDGGWT AQ                                                        252

SEQ ID NO: 185        moltype = DNA  length = 756
FEATURE               Location/Qualifiers
misc_feature          1..756
                      note = Engineered Variant of Kred from Lactobacillus kefir
source                1..756
                      mol_type = other DNA
                      organism = synthetic construct
SEQUENCE: 185
atgaccgatc gtctgaagca taaagtagcc atcgttaccg gcgggacaat gggtatcggt     60
ttggcaatcg ccgataaatt tgtagaggag ggtgcgaaag tagttattac tggtcgtcac    120
gcggatgtag gtgaaaaagc cgccaaatca atcggcggca ctgatgttat tcgctttgtc    180
cagcacgatg cgtccgaaga agcaggctgg acgaaactgt tcgacaccac cgaggaggca    240
ttcggcccgg ttacgaccct ggtgaacaat gcagggattg ggttattaa aagcgttgaa     300
cggactacca cggaggaatg gcgtaaaatc ctgtccgtta atctggatgg tgttttttc     360
ggcacccgtc tgggcattca gcgcatgaaa aataaaggct tgggcgctag catcatcaat    420
atgagcagta ttatggggct cgtaggcgat ccgactctgg gggcatacaa cgcttccaag    480
ggggcggtac gtatcatgtc gaaaagcgca gcgctggatt gcgcactgaa ggactacgat    540
gtgcgtgtca acacagtaca tccgggcgcg atcaagaccc cacggaagga tcagctggaa    600
ggttgggagg aaatgatgtc acagcgtacg ctgaccccta tgggccacat tggcgaaccg    660
aatgacatcg catggatctg tgtgtacctg gcatctgacg aatcgaaatt tgcgacgggt    720
gcagaatttg tggtcgacgg cgggtggacc gcacag                              756

SEQ ID NO: 186        moltype = AA  length = 252
FEATURE               Location/Qualifiers
REGION                1..252
                      note = Engineered Variant of Kred from Lactobacillus kefir
source                1..252
                      mol_type = protein
                      organism = synthetic construct
SEQUENCE: 186
MTDRLKHKVA IVTGGTMGIG LAIADKFVEE GAKVVITGRH ADVGEKAAKS IGGTDVIRFV     60
QHDASEEAGW TKLFDTTEEA FGPVTTLVNN AGIGVIKSVE RTTTEEWRKI LSVNLDGVFF    120
GTRLGIQRMK NKGLGASIIN MSSIMGLVGD PTLGAYNASK GAVRIMSKSA ALDCALKDYD    180
VRVNTVHPGA IKTPRKDQLE GWEEMMSQRT LTPMGHIGEP NDIAWICVYL ASDESKFATG    240
AEFVVDGGWT AQ                                                        252

SEQ ID NO: 187        moltype = DNA  length = 756
FEATURE               Location/Qualifiers
misc_feature          1..756
                      note = Engineered Variant of Kred from Lactobacillus kefir
source                1..756
                      mol_type = other DNA
                      organism = synthetic construct
SEQUENCE: 187
atgaccgatc gtctgaagca taaagtagcc atcgttaccg gcgggacaat gggtatcggt     60
ttggcaatcg ccgataaatt tgtagaggag ggtgcgaaag tagttattac tggtcgtcac    120
gcggatgtag gtgaaaaagc cgccaaatca atcggcggca ctgatgttat tcgctttgtc    180
cagcacgatg cgtccgaaga agcaggctgg acgaaactgt tcgacaccac cgaggaggca    240
ttcggcccgg ttacgaccct ggtgaacaat gcagggattg ggttattaa aagcgttgaa     300
gacactacca cggaggaatg gcgtaaaatc ctgtccgtta atctggatgg tgttttttc     360
ggcacccgtc tgggcattca gcgcatgaaa aataaaggct tgggcgctag catcatcaat    420
atgagcagta ttatggggct cgtaggcgat ccgactctgg gggcatacaa cgcttccaag    480
```

-continued

```
ggggcggtac gtatcatgtc gaaaagcgca gcgctggatt gcgcactgaa ggactacgat    540
gtgcgtgtca acacagtaca tccgggcgcg atcaagaccc cacgaagga tcagctggaa    600
ggttgggagg aaatgatgtc acagcgtacg ctgaccccta tgggccacat tggcgaaccg    660
aatgacatca catggatctg tgtgtacctg ggtctgacg aatcgaaatt tgcgacgggt    720
gcagaatttg tggtcgacgg cgggtggacc gcacag                             756
```

SEQ ID NO: 188          moltype = AA   length = 252
FEATURE                 Location/Qualifiers
REGION                  1..252
                        note = Engineered Variant of Kred from Lactobacillus kefir
source                  1..252
                        mol_type = protein
                        organism = synthetic construct
SEQUENCE: 188
```
MTDRLKHKVA IVTGGTMGIG LAIADKFVEE GAKVVITGRH ADVGEKAAKS IGGTDVIRFV    60
QHDASEEAGW TKLFDTTEEA FGPVTTLVNN AGIGVIKSVE DTTTEEWRKI LSVNLDGVFF   120
GTRLGIQRMK NKGLGASIIN MSSIMGLVGD PTLGAYNASK GAVRIMSKSA ALDCALKDYD   180
VRVNTVHPGA IKTPRKDQLE GWEEMMSQRT LTPMGHIGEP NDIAWICVYL GSDESKFATG   240
AEFVVDGGWT AQ                                                      252
```

SEQ ID NO: 189          moltype = DNA   length = 756
FEATURE                 Location/Qualifiers
misc_feature            1..756
                        note = Engineered Variant of Kred from Lactobacillus kefir
source                  1..756
                        mol_type = other DNA
                        organism = synthetic construct
SEQUENCE: 189
```
atgaccgatc gtctgaagca taaagtagcc atcgttaccg gcgggacaat gggtatcggt    60
ttggcaatcg ccgataaatt tgtagaggag ggtgcgaaag tagttattac tggtcgtcac   120
gcggatgtag gtgaaaaagc cgccaaatca atcggcggca ctgatgttat tcgctttgtc   180
cagcacgatg cgtccgaaga agcaggctgg acgaaactgt tcgacaccac cgaggagca   240
ttcggcccgg ttacgaccct ggtgaacaat gcagggattg gggttattaa aagcgttgaa   300
gacactacca cggaggaatg gcgtaaaatc ctgtccgtta atctggatgg tgttttttc   360
ggcacccgtc tgggcattca gcgcatgaaa aataaaggct gggcgctag catcatcaat   420
atgagcagta ttatgggct cgtaggcgat ccgactctgg ggcatacaa cgcttccaag   480
ggggcggtac gtatcatgtc gaaaagcgca gcgctggatt gcgcactgaa ggactacgat   540
gtgcgtgtca acacagtaca tccgggcgcg atcaagaccc agcggaagga tcagctggaa   600
ggttgggagg aaatgatgtc acagcgtacg ctgaccccta tgggccacat tggcgaaccg   660
aatgacatca catggatctg tgtgtacctg gcatctgacg aatcgaaatt tgcgacgggt   720
gcagaatttg tggtcgacgg cgggtggacc gcacag                             756
```

SEQ ID NO: 190          moltype = AA   length = 252
FEATURE                 Location/Qualifiers
REGION                  1..252
                        note = Engineered Variant of Kred from Lactobacillus kefir
source                  1..252
                        mol_type = protein
                        organism = synthetic construct
SEQUENCE: 190
```
MTDRLKHKVA IVTGGTMGIG LAIADKFVEE GAKVVITGRH ADVGEKAAKS IGGTDVIRFV    60
QHDASEEAGW TKLFDTTEEA FGPVTTLVNN AGIGVIKSVE DTTTEEWRKI LSVNLDGVFF   120
GTRLGIQRMK NKGLGASIIN MSSIMGLVGD PTLGAYNASK GAVRIMSKSA ALDCALKDYD   180
VRVNTVHPGA IKTERKDQLE GWEEMMSQRT LTPMGHIGEP NDIAWICVYL ASDESKFATG   240
AEFVVDGGWT AQ                                                      252
```

SEQ ID NO: 191          moltype = DNA   length = 756
FEATURE                 Location/Qualifiers
misc_feature            1..756
                        note = Engineered Variant of Kred from Lactobacillus kefir
source                  1..756
                        mol_type = other DNA
                        organism = synthetic construct
SEQUENCE: 191
```
atgaccgatc gtctgaagca taaagtagcc atcgttaccg gcgggacaat gggtatcggt    60
ttggcaatcg ccgataaatt tgtagaggag ggtgcgaaag tagttattac tggtcgtcac   120
gcggatgtag gtttgaaggc cgccaaatca atcggcggca ctgatgttat tcgctttgtc   180
cagcacgatg cgtccgaaga agcaggctgg acgaaactgt tcgacaccac cgaggagca   240
ttcggcccgg ttacgaccct ggtgaacaat gcagggattg gggttattaa aagcgttgaa   300
gacactacca cggaggaatg gcgtaaaatc ctgtccgtta atctggatgg tgttttttc   360
ggcacccgtc tgggcattca gcgcatgaaa aataaaggct gggcgctag catcatcaat   420
atgagcagta ttatgggct cgtaggcgat ccgactctgg ggcatacaa cgcttccaag   480
ggggcggtac gtatcatgtc gaaaagcgca gcgctggatt gcgcactgaa ggactacgat   540
gtgcgtgtca acacagtaca tccgggcgcg atcaagaccc cacgaagga tcagctggaa   600
ggttgggagg aaatgatgtc acagcgtacg ctgaccccta tgggccacat tggcgaaccg   660
aatgacatcg catggatctg tgtgtacctg gcatctgacg aatcgaaatt tgcgacgggt   720
gcagaatttg tggtcgacgg cgggtggacc gcacag                             756
```

SEQ ID NO: 192          moltype = AA   length = 252

```
FEATURE                 Location/Qualifiers
REGION                  1..252
                        note = Engineered Variant of Kred from Lactobacillus kefir
source                  1..252
                        mol_type = protein
                        organism = synthetic construct
SEQUENCE: 192
MTDRLKHKVA IVTGGTMGIG LAIADKFVEE GAKVVITGRH ADVGLKAAKS IGGTDVIRFV    60
QHDASEEAGW TKLFDTTEEA FGPVTTLVNN AGIGVIKSVE DTTTEEWRKI LSVNLDGVFF   120
GTRLGIQRMK NKGLGASIIN MSSIMGLVGD PTLGAYNASK GAVRIMSKSA ALDCALKDYD   180
VRVNTVHPGA IKTPRKDQLE GWEEMMSQRT LTPMGHIGEP NDIAWICVYL ASDESKFATG   240
AEFVVDGGWT AQ                                                      252

SEQ ID NO: 193          moltype = DNA  length = 756
FEATURE                 Location/Qualifiers
misc_feature            1..756
                        note = Engineered Variant of Kred from Lactobacillus kefir
source                  1..756
                        mol_type = other DNA
                        organism = synthetic construct
SEQUENCE: 193
atgaccgatc gtctgaagca taaagtagcc atcgttaccg gcgggacaat gggtatcggt    60
ttggcaatcg ccgataaatt tgtagaggag ggtgcgaaag tagttattac tggtcgtcac   120
gcggatgtag gtgaaaaagc cgccaaatca atcggcggca ctgatgttat tcgctttgtc   180
cagcacgatg cgtccgaaga agcaggctgg acgaaactgt tcgacaccac cgaggaggca   240
ttcggcccgg ttacgaccct ggtgaacaat gcagggattg ggtaattaa gagcgttgaa    300
cggactacca cggaggaatg gcgtaaaatc ctgtccgtta atctggatgg tgttttttc    360
ggcacccgtc tgggcattca gcgcatgaaa aataaaggct gggcgctag catcatcaat    420
atgagcagta ttatggggct cgtaggcgct ccgactgcag gggcatacaa cgcttccaag   480
ggggcggtac gtatcatgtc gaaaagcgca gcgctggatt gcgcactgaa ggactacgat   540
gtgcgtgtca acacagtaca tccgggcgcg atcaagaccc cacggaagga tcagctggaa   600
ggttgggagg aagcaatgtc acagcgtacg gcgaccccta tgggccacat tggcgaaccg   660
aatgacatca catggatctg tgtgtacctg gcatctgacg aatcgaaatt tgcgacgggt   720
gcagaatttg tggtcgacgg cgggtggacc gcacag                            756

SEQ ID NO: 194          moltype = AA  length = 252
FEATURE                 Location/Qualifiers
REGION                  1..252
                        note = Engineered Variant of Kred from Lactobacillus kefir
source                  1..252
                        mol_type = protein
                        organism = synthetic construct
SEQUENCE: 194
MTDRLKHKVA IVTGGTMGIG LAIADKFVEE GAKVVITGRH ADVGEKAAKS IGGTDVIRFV    60
QHDASEEAGW TKLFDTTEEA FGPVTTLVNN AGIGVIKSVE RTTTEEWRKI LSVNLDGVFF   120
GTRLGIQRMK NKGLGASIIN MSSIMGLVGA PTAGAYNASK GAVRIMSKSA ALDCALKDYD   180
VRVNTVHPGA IKTPRKDQLE GWEEAMSQRT ATPMGHIGEP NDIAWICVYL ASDESKFATG   240
AEFVVDGGWT AQ                                                      252

SEQ ID NO: 195          moltype = DNA  length = 756
FEATURE                 Location/Qualifiers
misc_feature            1..756
                        note = Engineered Variant of Kred from Lactobacillus kefir
source                  1..756
                        mol_type = other DNA
                        organism = synthetic construct
SEQUENCE: 195
atgaccgatc gtctgaagca taaagtagcc atcgttaccg gcgggacaat gggtatcggt    60
ttggcaatcg ccgataaatt tgtagaggag ggtgcgaaag tagttattac tggtcgtcac   120
gcggatgtag gtgaaaaagc cgccaaatca atcggcggca ctgatgttat tcgctttgtc   180
cagcacgatg cgtccgaaga agcaggctgg acgaaactgt tcgacaccac cgaggaggca   240
ttcggcccgg ttacgaccct ggtgaacaat gcagggattg ggtaattaa gagcgttgaa    300
cggactacca cggaggaatg gcgtaaaatc ctgtccgtta atctggatgg tgttttttc    360
ggcacccgtc tgggcattca gcgcatgaaa aataaaggct gggcgctag catcatcaat    420
atgagcagta ttatggggct cgtaggcgct ccgactgcag gggcatacaa cgcttccaag   480
ggggcggtac gtatcatgtc gaaaagcgca gcgctggatt gcgcactgaa ggactacgat   540
gtgcgtgtca acacagtaca tccgggcgcg atcaagaccc cacggaagga tcagctggaa   600
ggttgggagg aaatgatgtc acagcgtacg gcgaccccta tgggccacat tggcgaaccg   660
aatgacatcg catggatctg tgtgtacctg gcatctgacg aatcgaaatt tgcgacgggt   720
gcagaatttg tggtcgacgg cgggtggacc gcacag                            756

SEQ ID NO: 196          moltype = AA  length = 252
FEATURE                 Location/Qualifiers
REGION                  1..252
                        note = Engineered Variant of Kred from Lactobacillus kefir
source                  1..252
                        mol_type = protein
                        organism = synthetic construct
SEQUENCE: 196
```

```
MTDRLKHKVA IVTGGTMGIG LAIADKFVEE GAKVVITGRH ADVGEKAAKS IGGTDVIRFV    60
QHDASEEAGW TKLFDTTEEA FGPVTTLVNN AGIGVIKSVE RTTTEEWRKI LSVNLDGVFF   120
GTRLGIQRMK NKGLGASIIN MSSIMGLVGA PTAGAYNASK GAVRIMSKSA ALDCALKDYD   180
VRVNTVHPGA IKTPRKDQLE GWEEMMSQRT ATPMGHIGEP NDIAWICVYL ASDESKFATG   240
AEFVVDGGWT AQ                                                       252

SEQ ID NO: 197          moltype = DNA   length = 756
FEATURE                 Location/Qualifiers
misc_feature            1..756
                        note = Engineered Variant of Kred from Lactobacillus kefir
source                  1..756
                        mol_type = other DNA
                        organism = synthetic construct
SEQUENCE: 197
atgaccgatc gtctgaagca taaagtagcc atcgttaccg gcgggacaat gggtatcggt    60
ttggcaatcg ccgataaatt tgtagaggag ggtgcgaaag tagttattac tggtcgtcac   120
gcggatgtag gtgaaaaagc cgccaaatca atcggcggca ctgatgttat tcgctttgtc   180
cagcacgatg cgtccgaaga agcaggctgg acgaaactgt tcgacaccac cgaggaggca   240
ttcggcccgg ttacgaccct ggtgaacaat gcagggattg gggcaattgc gagcgttgaa   300
cggactacca cggaggaatg gcgtaaaatc ctgtccgtta atctggatgg tgttttttc   360
ggcacccgtc tgggcattca gcgcatgaaa aataaaggct gggcgctag catcatcaat   420
atgagcagta ttatgggggct cgtaggcgct ccgactgcag ggcatacaa cgcttccaag   480
ggggcggtac gtatcatgtc gaaaagcgca gcgctggatt gcgcactgaa ggactacgat   540
gtgcgtgtca acacagtaca tccgggcgcg atcaagaccc cacggaagga tcagctggaa   600
ggttgggagg aaatgatgtc acagcgtacg ctgaccccta tgggccacat tggcgaaccg   660
aatgacatcg catggatctg tgtgtacctg gcatctgacg aatcgaaatt tgcgacgggt   720
gcagaatttg tggtcgacgg cgggtggacc gcacag                             756

SEQ ID NO: 198          moltype = AA   length = 252
FEATURE                 Location/Qualifiers
REGION                  1..252
                        note = Engineered Variant of Kred from Lactobacillus kefir
source                  1..252
                        mol_type = protein
                        organism = synthetic construct
SEQUENCE: 198
MTDRLKHKVA IVTGGTMGIG LAIADKFVEE GAKVVITGRH ADVGEKAAKS IGGTDVIRFV    60
QHDASEEAGW TKLFDTTEEA FGPVTTLVNN AGIGAIASVE RTTTEEWRKI LSVNLDGVFF   120
GTRLGIQRMK NKGLGASIIN MSSIMGLVGA PTAGAYNASK GAVRIMSKSA ALDCALKDYD   180
VRVNTVHPGA IKTPRKDQLE GWEEMMSQRT LTPMGHIGEP NDIAWICVYL ASDESKFATG   240
AEFVVDGGWT AQ                                                       252

SEQ ID NO: 199          moltype = DNA   length = 756
FEATURE                 Location/Qualifiers
misc_feature            1..756
                        note = Engineered Variant of Kred from Lactobacillus kefir
source                  1..756
                        mol_type = other DNA
                        organism = synthetic construct
SEQUENCE: 199
atgaccgatc gtctgaagca taaagtagcc atcgttaccg gcgggacaat gggtatcggt    60
ttggcaatcg ccgataaatt tgtagaggag ggtgcgaaag tagttattac tggtcgtcac   120
gcggatgtag gtgaaaaagc cgccaaatca atcggcggca ctgatgttat tcgctttgtc   180
cagcacgatg cgtccgaaga agcaggctgg acgaaactgt tcgacaccac cgaggaggca   240
ttcggcccgg ttacgaccct ggtgaacaat gcagggattg gggcaattga gagcgttgaa   300
cggactacca cggaggaatg gcgtaaaatc ctgtccgtta atctggatgg tgttttttc   360
ggcacccgtc tgggcattca gcgcatgaaa aataaaggct gggcgctag catcatcaat   420
atgagcagta ttatgggggct cgtaggcgct ccgactgcag ggcatacaa cgcttccaag   480
ggggcggtac gtatcatgtc gaaaagcgca gcgctggatt gcgcactgaa ggactacgat   540
gtgcgtgtca acacagtaca tccgggcgcg atcaagaccc cacggaagga tcagctggaa   600
ggttgggagg aagcaatgtc acagcgtacg cgaccccta tgggccacat tggcgaaccg   660
aatgacatcg catggatctg tgtgtacctg gcatctgacg aatcgaaatt tgcgacgggt   720
gcagaatttg tggtcgacgg cgggtggacc gcacag                             756

SEQ ID NO: 200          moltype = AA   length = 252
FEATURE                 Location/Qualifiers
REGION                  1..252
                        note = Engineered Variant of Kred from Lactobacillus kefir
source                  1..252
                        mol_type = protein
                        organism = synthetic construct
SEQUENCE: 200
MTDRLKHKVA IVTGGTMGIG LAIADKFVEE GAKVVITGRH ADVGEKAAKS IGGTDVIRFV    60
QHDASEEAGW TKLFDTTEEA FGPVTTLVNN AGIGAIKSVE RTTTEEWRKI LSVNLDGVFF   120
GTRLGIQRMK NKGLGASIIN MSSIMGLVGA PTAGAYNASK GAVRIMSKSA ALDCALKDYD   180
VRVNTVHPGA IKTPRKDQLE GWEEAMSQRT ATPMGHIGEP NDIAWICVYL ASDESKFATG   240
AEFVVDGGWT AQ                                                       252

SEQ ID NO: 201          moltype = DNA   length = 756
```

```
FEATURE              Location/Qualifiers
misc_feature         1..756
                     note = Engineered Variant of Kred from Lactobacillus kefir
source               1..756
                     mol_type = other DNA
                     organism = synthetic construct
SEQUENCE: 201
atgaccgatc gtctgaagca taaagtagcc atcgttaccg gcgggacaat gggtatcggt    60
ttggcaatcg ccgataaatt tgtagaggag ggtgcgaaag tagttattac tggtcgtcac   120
gcggatgtag gtgaaaaagc cgccaaatca atcggcggca ctgatgttat tcgctttgtc   180
cagcacgatg cgtccgaaga agcaggctgg acgaaactgt tcgacaccac cgaggaggca   240
ttcggcccgg ttacgaccct ggtgaacaat gcagggattg ggttattgc gagcgttgaa    300
cggactacca cggaggaatg gcgtaaaatc ctgtccgtta atctggatgg tgttttttc   360
ggcacccgtc tggcattca gcgcatgaaa aataaaggct gggcgctag catcatcaat    420
atgagcagta ttatggggct cgtaggcgct ccgactgcag ggcatacaa cgcttccaag    480
ggggcggtac gtatcatgtc gaaaagcgca gcgctggatt gcgcactgaa ggactacgat    540
gtgcgtgtca acacagtaca tccgggcgcg atcaagaccc cacggaagga tcagctggaa    600
ggttgggagg aaatgatgtc acagcgtacg ctgaccccta tggccacat ggcgaaccg    660
aatgacatcg catggatctg tgtgtacctg gcatctgacg aatcgaaatt tgcgacgggt    720
gcagaatttg tggtcgacgg cgggtggacc gcacag                             756

SEQ ID NO: 202       moltype = AA  length = 252
FEATURE              Location/Qualifiers
REGION               1..252
                     note = Engineered Variant of Kred from Lactobacillus kefir
source               1..252
                     mol_type = protein
                     organism = synthetic construct
SEQUENCE: 202
MTDRLKHKVA IVTGGTMGIG LAIADKFVEE GAKVVITGRH ADVGEKAAKS IGGTDVIRFV    60
QHDASEEAGW TKLFDTTEEA FGPVTTLVNN AGIGVIASVE RTTTEEWRKI LSVNLDGVFF   120
GTRLGIQRMK NKGLGASIIN MSSIMGLVGA PTAGAYNASK GAVRIMSKSA ALDCALKDYD   180
VRVNTVHPGA IKTPRKDQLE GWEEMMSQRT LTPMGHIGEP NDIAWICVYL ASDESKFATG   240
AEFVVDGGWT AQ                                                        252

SEQ ID NO: 203       moltype = DNA  length = 756
FEATURE              Location/Qualifiers
misc_feature         1..756
                     note = Engineered Variant of Kred from Lactobacillus kefir
source               1..756
                     mol_type = other DNA
                     organism = synthetic construct
SEQUENCE: 203
atgaccgatc gtctgaagca taaagtagcc atcgttaccg gcgggacaat gggtatcggt    60
ttggcaatcg ccgataaatt tgtagaggag ggtgcgaaag tagttattac tggtcgtcac   120
gcggatgtag gtgaaaaagc cgccaaatca atcggcggca ctgatgttat tcgctttgtc   180
cagcacgatg cgtccgaaga agcaggctgg acgaaactgt tcgacaccac cgaggaggca   240
ttcggcccgg ttacgaccct ggtgaacaat gcagggattg ggttattaa agcgttgaa    300
cggactacca cggaggaatg gcgtaaaatc ctgtccgtta atctggatgg tgttttttc   360
ggcacccgtc tggcattca gcgcatgaaa aataaaggct gggcgctag catcatcaat    420
atgagctcga tcgcggggct cgtaggcgat ccgactgcag ggcatacaa cgcttccaag    480
ggggcggtac gtatcatgtc gaaaagcgca gcgctggatt gcgcactgaa ggactacgat    540
gtgcgtgtca acacagtaca tccgggcgcg atcaagaccc cacggaagga tcagctggaa    600
ggttgggagg aaatgatgtc acagcgtacg gcgaccccta tggccacat ggcgaaccg    660
aatgacatcg catggatctg tgtgtacctg gcatctgacg aatcgaaatt tgcgacgggt    720
gcagaatttg tggtcgacgg cgggtggacc gcacag                             756

SEQ ID NO: 204       moltype = AA  length = 252
FEATURE              Location/Qualifiers
REGION               1..252
                     note = Engineered Variant of Kred from Lactobacillus kefir
source               1..252
                     mol_type = protein
                     organism = synthetic construct
SEQUENCE: 204
MTDRLKHKVA IVTGGTMGIG LAIADKFVEE GAKVVITGRH ADVGEKAAKS IGGTDVIRFV    60
QHDASEEAGW TKLFDTTEEA FGPVTTLVNN AGIGVIKSVE RTTTEEWRKI LSVNLDGVFF   120
GTRLGIQRMK NKGLGASIIN MSSIAGLVGD PTAGAYNASK GAVRIMSKSA ALDCALKDYD   180
VRVNTVHPGA IKTPRKDQLE GWEEMMSQRT ATPMGHIGEP NDIAWICVYL ASDESKFATG   240
AEFVVDGGWT AQ                                                        252

SEQ ID NO: 205       moltype = DNA  length = 756
FEATURE              Location/Qualifiers
misc_feature         1..756
                     note = Engineered Variant of Kred from Lactobacillus kefir
source               1..756
                     mol_type = other DNA
                     organism = synthetic construct
SEQUENCE: 205
```

```
atgaccgatc gtctgaagca taaagtagcc atcgttaccg gcgggacaat gggtatcggt    60
ttggcaatcg ccgataaatt tgtagaggag ggtgcgaaag tagttattac tggtcgtcac   120
gcggatgtag gtgaaaaagc cgccaaatca atcggcggca ctgatgttat tcgctttgtc   180
cagcacgatg cgtccgaaga agcaggctgg acgaaactgt tcgacaccac cgaggaggca   240
ttcggcccgg ttacgaccct ggtgaacaat gcagggattg ggtagccaa gagcgttgaa    300
cggactacca cggaggaatg gcgtaaaatc ctgtccgtta atctggatgg tgttttttc    360
ggcacccgtc tgggcattca gcgcatgaaa aataaaggct tgggcgctag catcatcaat   420
atgagcagta ttatgggct cgtaggcgct ccgactgcag gggcatacaa cgcttccaag    480
ggggcggtac gtatcatgtc gaaaagcgca gcgctggatt gcgcactgaa ggactacgat   540
gtgcgtgtca acacagtaca tccgggcgcg atcaagaccc cacggaagga tcagctgaa   600
ggttgggagg aaatgatgtc acagcgtacg ctgaccccta tgggccacat tggcgaaccg   660
aatgacatcg catggatctg tgtgtacctg gcatctgacg aatcgaaatt tgcgacgggt   720
gcagaatttg tggtcgacgg cgggtggacc gcacag                             756

SEQ ID NO: 206           moltype = AA   length = 252
FEATURE                  Location/Qualifiers
REGION                   1..252
                         note = Engineered Variant of Kred from Lactobacillus kefir
source                   1..252
                         mol_type = protein
                         organism = synthetic construct
SEQUENCE: 206
MTDRLKHKVA IVTGGTMGIG LAIADKFVEE GAKVVITGRH ADVGEKAAKS IGGTDVIRFV    60
QHDASEEAGW TKLFDTTEEA FGPVTTLVNN AGIGVAKSVE RTTTEEWRKI LSVNLDGVFF   120
GTRLGIQRMK NKGLGASIIN MSSIMGLVGA PTAGAYNASK GAVRIMSKSA ALDCALKDYD   180
VRVNTVHPGA IKTPRKDQLE GWEEMMSQRT LTPMGHIGEP NDIAWICVYL ASDESKFATG   240
AEFVVDGGWT AQ                                                       252

SEQ ID NO: 207           moltype = DNA   length = 756
FEATURE                  Location/Qualifiers
misc_feature             1..756
                         note = Engineered Variant of Kred from Lactobacillus kefir
source                   1..756
                         mol_type = other DNA
                         organism = synthetic construct
SEQUENCE: 207
atgaccgatc gtctgaagca taaagtagcc atcgttaccg gcgggacaat gggtatcggt    60
ttggcaatcg ccgataaatt tgtagaggag ggtgcgaaag tagttattac tggtcgtcac   120
gcggatgtag gtgaaaaagc cgccaaatca atcggcggca ctgatgttat tcgctttgtc   180
cagcacgatg cgtccgaaga agcaggctgg acgaaactgt tcgacaccac cgaggaggca   240
ttcggcccgg ttacgaccct ggtgaacaat gcagggattg ggtaattgc gagcgttgaa    300
cggactacca cggaggaatg gcgtaaaatc ctgtccgtta atctggatgg tgttttttc    360
ggcacccgtc tgggcattca gcgcatgaaa aataaaggct tgggcgctag catcatcaat   420
atgagcagta ttatgggct cgtaggcgct ccgactgcag gggcatacaa cgcttccaag    480
ggggcggtac gtatcatgtc gaaaagcgca gcgctggatt gcgcactgaa ggactacgat   540
gtgcgtgtca acacagtaca tccgggcgcg atcaagaccc acggaagga tcagctgaa    600
ggttgggagg aagcaatgtc acagcgtacg cgaccccta tgggccacat tggcgaaccg    660
aatgacatcg catggatctg tgtgtacctg gcatctgacg aatcgaaatt tgcgacgggt   720
gcagaatttg tggtcgacgg cgggtggacc gcacag                             756

SEQ ID NO: 208           moltype = AA   length = 252
FEATURE                  Location/Qualifiers
REGION                   1..252
                         note = Engineered Variant of Kred from Lactobacillus kefir
source                   1..252
                         mol_type = protein
                         organism = synthetic construct
SEQUENCE: 208
MTDRLKHKVA IVTGGTMGIG LAIADKFVEE GAKVVITGRH ADVGEKAAKS IGGTDVIRFV    60
QHDASEEAGW TKLFDTTEEA FGPVTTLVNN AGIGVIASVE RTTTEEWRKI LSVNLDGVFF   120
GTRLGIQRMK NKGLGASIIN MSSIMGLVGA PTAGAYNASK GAVRIMSKSA ALDCALKDYD   180
VRVNTVHPGA IKTPRKDQLE GWEEAMSQRT ATPMGHIGEP NDIAWICVYL ASDESKFATG   240
AEFVVDGGWT AQ                                                       252

SEQ ID NO: 209           moltype = DNA   length = 756
FEATURE                  Location/Qualifiers
misc_feature             1..756
                         note = Engineered Variant of Kred from Lactobacillus kefir
source                   1..756
                         mol_type = other DNA
                         organism = synthetic construct
SEQUENCE: 209
atgaccgatc gtctgaagca taaagtagcc atcgttaccg gcgggacaat gggtatcggt    60
ttggcaatcg ccgataaatt tgtagaggag ggtgcgaaag tagttattac tggtcgtcac   120
gcggatgtag gtgaaaaagc cgccaaatca atcggcggca ctgatgttat tcgctttgtc   180
cagcacgatg cgtccgaaga agcaggctgg acgaaactgt tcgacaccac cgaggaggca   240
ttcggcccgg ttacgaccct ggtgaacaat gcagggattg ggcaattaa gagcgttgaa    300
cggactacca cggaggaatg gcgtaaaatc ctgtccgtta atctggatgg tgttttttc    360
ggcacccgtc tgggcattca gcgcatgaaa aataaaggct tgggcgctag catcatcaat   420
```

```
atgagcagta ttatgggct cgtaggcgct ccgactgcag gggcatacaa cgcttccaag   480
ggggcggtac gtatcatgtc gaaaagcgca gcgctggatt gcgcactgaa ggactacgat   540
gtgcgtgtca acacagtaca tccgggcgcg atcaagaccc cacggaagga tcagctggaa   600
ggttgggagg aagcagcttc acagcgtacg gcgacccta tgggccacat tggcgaaccg    660
aatgacatcg catggatctg tgtgtacctg gcatctgacg aatcgaaatt tgcgacgggt   720
gcagaatttg tggtcgacgg cgggtggacc gcacag                             756

SEQ ID NO: 210         moltype = AA  length = 252
FEATURE                Location/Qualifiers
REGION                 1..252
                       note = Engineered Variant of Kred from Lactobacillus kefir
source                 1..252
                       mol_type = protein
                       organism = synthetic construct
SEQUENCE: 210
MTDRLKHKVA IVTGGTMGIG LAIADKFVEE GAKVVITGRH ADVGEKAAKS IGGTDVIRFV    60
QHDASEEAGW TKLFDTTEEA FGPVTTLVNN AGIGAIKSVE RTTTEEWRKI LSVNLDGVFF   120
GTRLGIQRMK NKGLGASIIN MSSIMGLVGA PTAGAYNASK GAVRIMSKSA ALDCALKDYD   180
VRVNTVHPGA IKTPRKDQLE GWEEAASQRT ATPMGHIGEP NDIAWICVYL ASDESKFATG   240
AEFVVDGGWT AQ                                                       252

SEQ ID NO: 211         moltype = DNA  length = 756
FEATURE                Location/Qualifiers
misc_feature           1..756
                       note = Engineered Variant of Kred from Lactobacillus kefir
source                 1..756
                       mol_type = other DNA
                       organism = synthetic construct
SEQUENCE: 211
atgaccgatc gtctgaagca taaagtagcc atcgttaccg gcgggacaat gggtatcggt    60
ttggcaatcg ccgataaatt tgtagaggag ggtgcgaaag tagttattac tggtcgtcac   120
gcggatgtag gtgaaaaagc cgccaaatca atcggcggca ctgatgttat tcgctttgtc   180
cagcacgatg cgtccgaaga agcaggctgg acgaaactgt tcgacaccac cgaggaggca   240
ttcggcccgg ttacgaccct ggtgaacaat gcagggattg ggtaattgc gagcgttgaa    300
cggactacca cggaggaatg gcgtaaaatc ctgtccgtta atctggatgg tgtttttttc   360
ggcacccgtc tgggcattca gcgcatgaaa aataaaggct gggcgctag catcatcaat   420
atgagctcga tcatggggct cgtaggcgct ccgactgcag gggcatacaa cgcttccaag   480
ggggcggtac gtatcatgtc gaaaagcgca gcgctggatt gcgcactgaa ggactacgat   540
gtgcgtgtca acacagtaca tccgggcgcg atcaagaccc cacggaagga tcagctggaa   600
ggttgggagg aagcaatgtc acagcgtacg ctgaccccta tgggccacat tggcgaaccg   660
aatgacatcg catggatctg tgtgtacctg gcatctgacg aatcgaaatt tgcgacgggt   720
gcagaatttg tggtcgacgg cgggtggacc gcacag                             756

SEQ ID NO: 212         moltype = AA  length = 252
FEATURE                Location/Qualifiers
REGION                 1..252
                       note = Engineered Variant of Kred from Lactobacillus kefir
source                 1..252
                       mol_type = protein
                       organism = synthetic construct
SEQUENCE: 212
MTDRLKHKVA IVTGGTMGIG LAIADKFVEE GAKVVITGRH ADVGEKAAKS IGGTDVIRFV    60
QHDASEEAGW TKLFDTTEEA FGPVTTLVNN AGIGVIASVE RTTTEEWRKI LSVNLDGVFF   120
GTRLGIQRMK NKGLGASIIN MSSIMGLVGA PTAGAYNASK GAVRIMSKSA ALDCALKDYD   180
VRVNTVHPGA IKTPRKDQLE GWEEAMSQRT LTPMGHIGEP NDIAWICVYL ASDESKFATG   240
AEFVVDGGWT AQ                                                       252

SEQ ID NO: 213         moltype = DNA  length = 756
FEATURE                Location/Qualifiers
misc_feature           1..756
                       note = Engineered Variant of Kred from Lactobacillus kefir
source                 1..756
                       mol_type = other DNA
                       organism = synthetic construct
SEQUENCE: 213
atgaccgatc gtctgaagca taaagtagcc atcgttaccg gcgggacaat gggtatcggt    60
ttggcaatcg ccgataaatt tgtagaggag ggtgcgaaag tagttattac tggtcgtcac   120
gcggatgtag gtgaaaaagc cgccaaatca atcggcggca ctgatgttat tcgctttgtc   180
cagcacgatg cgtccgaaga agcaggctgg acgaaactgt tcgacaccac cgaggaggca   240
ttcggcccgg ttacgaccct ggtgaacaat gcagggattg ggttattaa agcgttgaa    300
cggactacca cggaggaatg gcgtaaaatc ctgtccgtta atctggatgg tgtttttttc   360
ggcacccgtc tgggcattca gcgcatgaaa aataaaggct gggcgctag catcatcaat   420
atgagctcga tcatggggct cgtaggcgct ccgactgcag gggcatacaa cgcttccaag   480
ggggcggtac gtatcatgtc gaaaagcgca gcgctggatt gcgcactgaa ggactacgat   540
gtgcgtgtca acacagtaca tccgggcgcg atcaagaccc cacggaagga tcagctggaa   600
ggttgggagg aaatggcttc acagcgtacg gcgacccta tgggccacat tggcgaaccg    660
aatgacatcg catggatctg tgtgtacctg gcatctgacg aatcgaaatt tgcgacgggt   720
gcagaatttg tggtcgacgg cgggtggacc gcacag                             756
```

```
SEQ ID NO: 214          moltype = AA  length = 252
FEATURE                 Location/Qualifiers
REGION                  1..252
                        note = Engineered Variant of Kred from Lactobacillus kefir
source                  1..252
                        mol_type = protein
                        organism = synthetic construct
SEQUENCE: 214
MTDRLKHKVA IVTGGTMGIG LAIADKFVEE GAKVVITGRH ADVGEKAAKS IGGTDVIRFV   60
QHDASEEAGW TKLFDTTEEA FGPVTTLVNN AGIGVIKSVE RTTTEEWRKI LSVNLDGVFF  120
GTRLGIQRMK NKGLGASIIN MSSIMGLVGA PTAGAYNASK GAVRIMSKSA ALDCALKDYD  180
VRVNTVHPGA IKTPRKDQLE GWEEMASQRT ATPMGHIGEP NDIAWICVYL ASDESKFATG  240
AEFVVDGGWT AQ                                                     252

SEQ ID NO: 215          moltype = DNA  length = 756
FEATURE                 Location/Qualifiers
misc_feature            1..756
                        note = Engineered Variant of Kred from Lactobacillus kefir
source                  1..756
                        mol_type = other DNA
                        organism = synthetic construct
SEQUENCE: 215
atgaccgatc gtctgaagca taaagtagcc atcgttaccg gcgggacaat gggtatcggt   60
ttggcaatcg ccgataaatt tgtagaggag ggtgcgaaag tagttattac tggtcgtcac  120
gcggatgtag gtgaaaaagc cgccaaatca atcggcggca ctgatgttat tcgctttgtc  180
cagcacgatg cgtccgaaga agcaggctgg acgaaactgt tcgacaccac cgaggaggca  240
ttcggcccgg ttacgaccct ggtgaacaat gcagggattg ggttattaa aagcgttgaa  300
cggactacca cggaggaatg gcgtaaaatc ctgtccgtta atctggatgg tgttttttc  360
ggcacccgtc tgggcattca gcgcatgaaa aataaaggct gggcgctag catcatcaat  420
atgagcagta ttatggggct cgtaggcgct ccgactgcag ggcatacaa cgcttccaag  480
ggggcggtac gtatcatgtc gaaaagcgca gcgctggatt gcgcactgaa ggactacgat  540
gtgcgtgtca acacagtaca tccgggcgcg atcaagaccc cacggaagga tcagctggaa  600
ggttgggagg aaatggcttc acagcgtacg gcgaccccta tgggcacat tggcgaaccg  660
aatgacatcg catggatctg tgtgtacctg gcatctgacg aatcgaaatt tgcgacgggt  720
gcagaatttg tggtcgacgg cgggtggacc gcacag                            756

SEQ ID NO: 216          moltype = AA  length = 252
FEATURE                 Location/Qualifiers
REGION                  1..252
                        note = Engineered Variant of Kred from Lactobacillus kefir
source                  1..252
                        mol_type = protein
                        organism = synthetic construct
SEQUENCE: 216
MTDRLKHKVA IVTGGTMGIG LAIADKFVEE GAKVVITGRH ADVGEKAAKS IGGTDVIRFV   60
QHDASEEAGW TKLFDTTEEA FGPVTTLVNN AGIGVIKSVE RTTTEEWRKI LSVNLDGVFF  120
GTRLGIQRMK NKGLGASIIN MSSIMGLVGA PTAGAYNASK GAVRIMSKSA ALDCALKDYD  180
VRVNTVHPGA IKTPRKDQLE GWEEMASQRT ATPMGHIGEP NDIAWICVYL ASDESKFATG  240
AEFVVDGGWT AQ                                                     252

SEQ ID NO: 217          moltype = DNA  length = 756
FEATURE                 Location/Qualifiers
misc_feature            1..756
                        note = Engineered Variant of Kred from Lactobacillus kefir
source                  1..756
                        mol_type = other DNA
                        organism = synthetic construct
SEQUENCE: 217
atgaccgatc gtctgaagca taaagtagcc atcgttaccg gcgggacaat gggtatcggt   60
ttggcaatcg ccgataaatt tgtagaggag ggtgcgaaag tagttattac tggtcgtcac  120
gcggatgtag gtgaaaaagc cgccaaatca atcggcggca ctgatgttat tcgctttgtc  180
cagcacgatg cgtccgaaga agcaggctgg acgaaactgt tcgacaccac cgaggaggca  240
ttcggcccgg ttacgaccct ggtgaacaat gcagggattg ggcagccgc gagcgttgaa  300
cggactacca cggaggaatg gcgtaaaatc ctgtccgtta atctggatgg tgttttttc  360
ggcacccgtc tgggcattca gcgcatgaaa aataaaggct gggcgctag catcatcaat  420
atgagcagta ttatggggct cgtaggcgct ccgactgcag ggcatacaa cgcttccaag  480
ggggcggtac gtatcatgtc gaaaagcgca gcgctggatt gcgcactgaa ggactacgat  540
gtgcgtgtca acacagtaca tccgggcgcg atcaagaccc cacggaagga tcagctggaa  600
ggttgggagg aagcaatgtc acagcgtacg ctgacccccta tggcacat tggcgaaccg  660
aatgacatcg catggatctg tgtgtacctg gcatctgacg aatcgaaatt tgcgacgggt  720
gcagaatttg tggtcgacgg cgggtggacc gcacag                            756

SEQ ID NO: 218          moltype = AA  length = 252
FEATURE                 Location/Qualifiers
REGION                  1..252
                        note = Engineered Variant of Kred from Lactobacillus kefir
source                  1..252
                        mol_type = protein
                        organism = synthetic construct
```

```
SEQUENCE: 218
MTDRLKHKVA IVTGGTMGIG LAIADKFVEE GAKVVITGRH ADVGEKAAKS IGGTDVIRFV    60
QHDASEEAGW TKLFDTTEEA FGPVTTLVNN AGIGAAASVE RTTTEEWRKI LSVNLDGVFF   120
GTRLGIQRMK NKGLGASIIN MSSIMGLVGA PTAGAYNASK GAVRIMSKSA ALDCALKDYD   180
VRVNTVHPGA IKTPRKDQLE GWEEAMSQRT LTPMGHIGEP NDIAWICVYL ASDESKFATG   240
AEFVVDGGWT AQ                                                      252

SEQ ID NO: 219          moltype = DNA   length = 756
FEATURE                 Location/Qualifiers
misc_feature            1..756
                        note = Engineered Variant of Kred from Lactobacillus kefir
source                  1..756
                        mol_type = other DNA
                        organism = synthetic construct
SEQUENCE: 219
atgaccgatc gtctgaagca taaagtagcc atcgttaccg gcgggacaat gggtatcggt    60
ttggcaatcg ccgataaatt tgtagaggag ggtgcgaaag tagttattac tggtcgtcac   120
gcggatgtag gtgaaaaagc cgccaaatca atcggcggca ctgatgttat tcgctttgtc   180
cagcacgatg cgtccgaaga agcaggctgg acgaaactgt tcgacaccac cgaggaggca   240
ttcggcccgg ttacgaccct ggtgaacaat gcagggattg ggcaattgc gagcgttgaa    300
cggactacca cggaggaatg gcgtaaaatc ctgtccgtta atctggatgg tgttttttc   360
ggcacccgtc tgggcattca gcgcatgaaa aataaaggct gggcgctag catcatcaat   420
atgagcgcga tcgcgggct cgtaggcgct ccgactgcag gggcatacaa cgcttccaag   480
ggggcggtac gtatcatgtc gaaaagcgca gcgctggatt gcgcactgaa ggactacgat   540
gtgcgtgtca acacagtaca tccgggcgcg atcaagaccc cacggaagga tcagctgaa   600
ggtgctgagg aagcaatgtc acagcgtacg ctgaccccta tgggccacat tggcgaaccg   660
aatgacatcg catggatctg tgtgtacctg gcatctgacg aatcgaaatt tgcgacgggt   720
gcagaatttg tggtcgacgg cgggtggacc gcacag                             756

SEQ ID NO: 220          moltype = AA   length = 252
FEATURE                 Location/Qualifiers
REGION                  1..252
                        note = Engineered Variant of Kred from Lactobacillus kefir
source                  1..252
                        mol_type = protein
                        organism = synthetic construct
SEQUENCE: 220
MTDRLKHKVA IVTGGTMGIG LAIADKFVEE GAKVVITGRH ADVGEKAAKS IGGTDVIRFV    60
QHDASEEAGW TKLFDTTEEA FGPVTTLVNN AGIGAIASVE RTTTEEWRKI LSVNLDGVFF   120
GTRLGIQRMK NKGLGASIIN MSAIAGLVGA PTAGAYNASK GAVRIMSKSA ALDCALKDYD   180
VRVNTVHPGA IKTPRKDQLE GAEEAMSQRT LTPMGHIGEP NDIAWICVYL ASDESKFATG   240
AEFVVDGGWT AQ                                                      252

SEQ ID NO: 221          moltype = DNA   length = 756
FEATURE                 Location/Qualifiers
misc_feature            1..756
                        note = Engineered Variant of Kred from Lactobacillus kefir
source                  1..756
                        mol_type = other DNA
                        organism = synthetic construct
SEQUENCE: 221
atgaccgatc gtctgaagca taaagtagcc atcgttaccg gcgggacaat gggtatcggt    60
ttggcaatcg ccgataaatt tgtagaggag ggtgcgaaag tagttattac tggtcgtcac   120
gcggatgtag gtgaaaaagc cgccaaatca atcggcggca ctgatgttat tcgctttgtc   180
cagcacgatg cgtccgaaga agcaggctgg acgaaactgt tcgacaccac cgaggaggca   240
ttcggcccgg ttacgaccct ggtgaacaat gcagggattg ggtaattgc gagcgttgaa    300
cggactacca cggaggaatg gcgtaaaatc ctgtccgtta atctggatgg tgttttttc   360
ggcacccgtc tgggcattca gcgcatgaaa aataaaggct gggcgctag catcatcaat   420
atgagcagta ttatggggct cgtaggcgct ccgactgcag gggcatacaa cgcttccaag   480
ggggcggtac gtatcatgtc gaaaagcgca gcgctggatt gcgcactgaa ggactacgat   540
gtgcgtgtca acacagtaca tccgggcgcg atcaagaccc cacggaagga tcagctgaa   600
ggttgggagg aaatggcttc acagcgtacg ctgaccccta tgggccacat tggcgaaccg   660
aatgacatcg catggatctg tgtgtacctg gcatctgacg aatcgaaatt tgcgacgggt   720
gcagaatttg tggtcgacgg cgggtggacc gcacag                             756

SEQ ID NO: 222          moltype = AA   length = 252
FEATURE                 Location/Qualifiers
REGION                  1..252
                        note = Engineered Variant of Kred from Lactobacillus kefir
source                  1..252
                        mol_type = protein
                        organism = synthetic construct
SEQUENCE: 222
MTDRLKHKVA IVTGGTMGIG LAIADKFVEE GAKVVITGRH ADVGEKAAKS IGGTDVIRFV    60
QHDASEEAGW TKLFDTTEEA FGPVTTLVNN AGIGVIASVE RTTTEEWRKI LSVNLDGVFF   120
GTRLGIQRMK NKGLGASIIN MSSIMGLVGA PTAGAYNASK GAVRIMSKSA ALDCALKDYD   180
VRVNTVHPGA IKTPRKDQLE GWEEMASQRT LTPMGHIGEP NDIAWICVYL ASDESKFATG   240
AEFVVDGGWT AQ                                                      252
```

| SEQ ID NO: 223 | moltype = DNA length = 756 |
|---|---|
| FEATURE | Location/Qualifiers |
| misc_feature | 1..756 |
| | note = Engineered Variant of Kred from Lactobacillus kefir |
| source | 1..756 |
| | mol_type = other DNA |
| | organism = synthetic construct |

SEQUENCE: 223

```
atgaccgatc gtctgaagca taaagtagcc atcgttaccg gcgggacaat gggtatcggt    60
ttggcaatcg ccgataaatt tgtagaggag ggtgcgaaag tagttattac tggtcgtcac   120
gcggatgtag gtgaaaaagc cgccaaatca atcggcggca ctgatgttat tcgctttgtc   180
cagcacgatg cgtccgaaga agcaggctgg acgaaactgt tcgacaccac cgaggaggca   240
ttcggcccgg ttacgaccct ggtgaacaat gcagggattg gggcaattgc gagcgttgaa   300
cggactacca cggaggaatg gcgtaaaatc ctgtccgtta atctggatgg tgttttttc   360
ggcacccgtc tgggcattca gcgcatgaaa aataaaggct ggggcgctag catcatcaat   420
atgagcagta ttatggggct cgtaggcgct ccgactgcag gggcatacaa cgcttccaag   480
ggggcggtac gtatcatgtc gaaaagcgca gcgctggatt gcgcactgaa ggactacgat   540
gtgcgtgtca acacagtaca tccggcgcg atcaagaccc cacggaagga tcagctgaa   600
ggtgctgagg aagcagcttc acagcgtacg ctgaccccta tgggccacat tggcgaaccg   660
aatgacatcg catggatctg tgtgtacctg gcatctgacg aatcgaaatt tgcgacgggt   720
gcagaatttg tggtcgacgg cgggtggacc gcacag                              756
```

| SEQ ID NO: 224 | moltype = AA length = 252 |
|---|---|
| FEATURE | Location/Qualifiers |
| REGION | 1..252 |
| | note = Engineered Variant of Kred from Lactobacillus kefir |
| source | 1..252 |
| | mol_type = protein |
| | organism = synthetic construct |

SEQUENCE: 224

```
MTDRLKHKVA IVTGGTMGIG LAIADKFVEE GAKVVITGRH ADVGEKAAKS IGGTDVIRFV    60
QHDASEEAGW TKLFDTTEEA FGPVTTLVNN AGIGAIASVE RTTTEEWRKI LSVNLDGVFF   120
GTRLGIQRMK NKGLGASIIN MSSIMGLVGA PTAGAYNASK GAVRIMSKSA ALDCALKDYD   180
VRVNTVHPGA IKTPRKDQLE GAEEAASQRT LTPMGHIGEP NDIAWICVYL ASDESKFATG   240
AEFVVDGGWT AQ                                                       252
```

| SEQ ID NO: 225 | moltype = DNA length = 756 |
|---|---|
| FEATURE | Location/Qualifiers |
| misc_feature | 1..756 |
| | note = Engineered Variant of Kred from Lactobacillus kefir |
| source | 1..756 |
| | mol_type = other DNA |
| | organism = synthetic construct |

SEQUENCE: 225

```
atgaccgatc gtctgaagca taaagtagcc atcgttaccg gcgggacaat gggtatcggt    60
ttggcaatcg ccgataaatt tgtagaggag ggtgcgaaag tagttattac tggtcgtcac   120
gcggatgtag gtgaaaaagc cgccaaatca atcggcggca ctgatgttat tcgctttgtc   180
cagcacgatg cgtccgaaga agcaggctgg acgaaactgt tcgacaccac cgaggaggca   240
ttcggcccgg ttacgaccct ggtgaacaat gcagggattg ggtaattaa gagcgttgaa   300
cggactacca cggaggaatg gcgtaaaatc ctgtccgtta atctggatgg tgttttttc   360
ggcacccgtc tgggcattca gcgcatgaaa aataaaggct ggggcgctag catcatcaat   420
atgagcgcgg cggcggggct cgtaggcgct ccgactgcag gggcatacaa cgcttccaag   480
ggggcggtac gtatcatgtc gaaaagcgca gcgctggatt gcgcactgaa ggactacgat   540
gtgcgtgtca acacagtaca tccgggcgcg atcaagaccc acggaagga tcagctgaa    600
ggtgctgagg aagcaatgtc acagcgtacg ctgaccccta tgggccacat tggcgaaccg   660
aatgacatcg catggatctg tgtgtacctg gcatctgacg aatcgaaatt tgcgacgggt   720
gcagaatttg tggtcgacgg cggggcaacc gcacag                             756
```

| SEQ ID NO: 226 | moltype = AA length = 252 |
|---|---|
| FEATURE | Location/Qualifiers |
| REGION | 1..252 |
| | note = Engineered Variant of Kred from Lactobacillus kefir |
| source | 1..252 |
| | mol_type = protein |
| | organism = synthetic construct |

SEQUENCE: 226

```
MTDRLKHKVA IVTGGTMGIG LAIADKFVEE GAKVVITGRH ADVGEKAAKS IGGTDVIRFV    60
QHDASEEAGW TKLFDTTEEA FGPVTTLVNN AGIGVIKSVE RTTTEEWRKI LSVNLDGVFF   120
GTRLGIQRMK NKGLGASIIN MSAAAGLVGA PTAGAYNASK GAVRIMSKSA ALDCALKDYD   180
VRVNTVHPGA IKTPRKDQLE GAEEAMSQRT LTPMGHIGEP NDIAWICVYL ASDESKFATG   240
AEFVVDGGAT AQ                                                       252
```

| SEQ ID NO: 227 | moltype = DNA length = 756 |
|---|---|
| FEATURE | Location/Qualifiers |
| misc_feature | 1..756 |
| | note = Engineered Variant of Kred from Lactobacillus kefir |
| source | 1..756 |
| | mol_type = other DNA |
| | organism = synthetic construct |

```
SEQUENCE: 227
atgaccgatc gtctgaagca taaagtagcc atcgttaccg gcgggacaat gggtatcggt   60
ttggcaatcg ccgataaatt tgtagaggag ggtgcgaaag tagttattac tggtcgtcac  120
gcggatgtag tgaaaaagc cgccaaatca atcggcggca ctgatgttat tcgctttgtc  180
cagcacgatg cgtccgaaga agcaggctgg acgaaactgt tcgacaccac cgaggaggca  240
ttcggcccgg ttacgaccct ggtgaacaat gcagggattg ggttattaa aagcgttgaa  300
cggactacca cggaggaatg gcgtaaaatc ctgtccgtta atctggatgg tgtttttttc  360
ggcacccgtc tggcattca gcgcatgaaa aataaaggct tgggcgctag catcatcaat  420
atgagcgcga tcgcggggct cgtaggcgct ccgactgcag gggcatacaa cgcttccaag  480
ggggcggtac gtatcatgtc gaaaagcgca gcgctggatt gcgcactgaa ggactacgat  540
gtgcgtgtca acacagtaca tccgggcgcg atcaagaccc cacggaagga tcagctggaa  600
ggttgggagg aaatgatgtc acagcgtacg ctgaccccta tgggccacat tggcgaaccg  660
aatgacatcg catggatctg tgtgtacctg gcatctgacg aatcgaaatt tgcgacgggt  720
gcagaatttg tggtcgacgg cgggtggacc gcacag                            756

SEQ ID NO: 228          moltype = AA  length = 252
FEATURE                 Location/Qualifiers
REGION                  1..252
                        note = Engineered Variant of Kred from Lactobacillus kefir
source                  1..252
                        mol_type = protein
                        organism = synthetic construct
SEQUENCE: 228
MTDRLKHKVA IVTGGTMGIG LAIADKFVEE GAKVVITGRH ADVGEKAAKS IGGTDVIRFV   60
QHDASEEAGW TKLFDTTEEA FGPVTTLVNN AGIGVIKSVE RTTTEEWRKI LSVNLDGVFF  120
GTRLGIQRMK NKGLGASIIN MSAIAGLVGA PTAGAYNASK GAVRIMSKSA ALDCALKDYD  180
VRVNTVHPGA IKTPRKDQLE GWEEMMSQRT LTPMGHIGEP NDIAWICVYL ASDESKFATG  240
AEFVVDGGWT AQ                                                      252

SEQ ID NO: 229          moltype = DNA  length = 756
FEATURE                 Location/Qualifiers
misc_feature            1..756
                        note = Engineered Variant of Kred from Lactobacillus kefir
source                  1..756
                        mol_type = other DNA
                        organism = synthetic construct
SEQUENCE: 229
atgaccgatc gtctgaagca taaagtagcc atcgttaccg gcgggacaat gggtatcggt   60
ttggcaatcg ccgataaatt tgtagaggag ggtgcgaaag tagttattac tggtcgtcac  120
gcggatgtag tgaaaaagc cgccaaatca atcggcggca ctgatgttat tcgctttgtc  180
cagcacgatg cgtccgaaga agcaggctgg acgaaactgt tcgacaccac cgaggaggca  240
ttcggcccgg ttacgaccct ggtgaacaat gcagggattg ggcaattgc gagcgttgaa  300
cggactacca cggaggaatg gcgtaaaatc ctgtccgtta atctggatgg tgtttttttc  360
ggcacccgtc tggcattca gcgcatgaaa aataaaggct tgggcgctag catcatcaat  420
atgagcgcga tcgcggggct cgtaggcgct ccgactgcag gggcatacaa cgcttccaag  480
ggggcggtac gtatcatgtc gaaaagcgca gcgctggatt gcgcactgaa ggactacgat  540
gtgcgtgtca acacagtaca tccgggcgcg atcaagaccc cacggaagga tcagctggaa  600
ggttgggagg aaatgatgtc acagcgtacg ctgaccccta tgggccacat tggcgaaccg  660
aatgacatcg catggatctg tgtgtacctg gcatctgacg aatcgaaatt tgcgacgggt  720
gcagaatttg tggtcgacgg cggggcaacc gcacag                            756

SEQ ID NO: 230          moltype = AA  length = 252
FEATURE                 Location/Qualifiers
REGION                  1..252
                        note = Engineered Variant of Kred from Lactobacillus kefir
source                  1..252
                        mol_type = protein
                        organism = synthetic construct
SEQUENCE: 230
MTDRLKHKVA IVTGGTMGIG LAIADKFVEE GAKVVITGRH ADVGEKAAKS IGGTDVIRFV   60
QHDASEEAGW TKLFDTTEEA FGPVTTLVNN AGIGAIASVE RTTTEEWRKI LSVNLDGVFF  120
GTRLGIQRMK NKGLGASIIN MSAIAGLVGA PTAGAYNASK GAVRIMSKSA ALDCALKDYD  180
VRVNTVHPGA IKTPRKDQLE GWEEMMSQRT LTPMGHIGEP NDIAWICVYL ASDESKFATG  240
AEFVVDGGAT AQ                                                      252

SEQ ID NO: 231          moltype = DNA  length = 756
FEATURE                 Location/Qualifiers
misc_feature            1..756
                        note = Engineered Variant of Kred from Lactobacillus kefir
source                  1..756
                        mol_type = other DNA
                        organism = synthetic construct
SEQUENCE: 231
atgaccgatc gtctgaagca taaagtagcc atcgttaccg gcgggacaat gggtatcggt   60
ttggcaatcg ccgataaatt tgtagaggag ggtgcgaaag tagttattac tggtcgtcac  120
gcggatgtag tgaaaaagc cgccaaatca atcggcggca ctgatgttat tcgctttgtc  180
cagcacgatg cgtccgaaga agcaggctgg acgaaactgt tcgacaccac cgaggaggca  240
ttcggcccgg ttacgaccct ggtgaacaat gcagggattg ggtagccaa gagcgttgaa  300
cggactacca cggaggaatg gcgtaaaatc ctgtccgtta atctggatgg tgtttttttc  360
```

```
ggcacccgtc tgggcattca gcgcatgaaa aataaaggct tgggcgctag catcatcaat    420
atgagctcga tcatgggget cgtaggcgct ccgactgcag gggcatacaa cgcttccaag    480
ggggcggtac gtatcatgtc gaaaagcgca gcgctggatt gcgcactgaa ggactacgat    540
gtgcgtgtca acacagtaca tccgggcgcg atcaagaccc cacggaagga tcagctgaa    600
ggtgggagg aaatggcttc acagcgtacg ctgaccccta tgggcacat tggcgaaccg    660
aatgacatcg catggatctg tgtgtacctg gcatctgacg aatcgaaatt tgcgacgggt    720
gcagaatttg tggtcgacgg cgggtggacc gcacag                             756

SEQ ID NO: 232            moltype = AA  length = 252
FEATURE                   Location/Qualifiers
REGION                    1..252
                          note = Engineered Variant of Kred from Lactobacillus kefir
source                    1..252
                          mol_type = protein
                          organism = synthetic construct
SEQUENCE: 232
MTDRLKHKVA IVTGGTMGIG LAIADKFVEE GAKVVITGRH ADVGEKAAKS IGGTDVIRFV     60
QHDASEEAGW TKLFDTTEEA FGPVTTLVNN AGIGVAKSVE RTTTEEWRKI LSVNLDGVFF    120
GTRLGIQRMK NKGLGASIIN MSSIMGLVGA PTAGAYNASK GAVRIMSKSA ALDCALKDYD    180
VRVNTVHPGA IKTPRKDQLE GWEEMASQRT LTPMGHIGEP NDIAWICVYL ASDESKFATG    240
AEFVVDGGWT AQ                                                        252

SEQ ID NO: 233            moltype = DNA  length = 756
FEATURE                   Location/Qualifiers
misc_feature              1..756
                          note = Engineered Variant of Kred from Lactobacillus kefir
source                    1..756
                          mol_type = other DNA
                          organism = synthetic construct
SEQUENCE: 233
atgaccgatc gtctgaagca taaagtagcc atcgttaccg gcgggacaat gggtatcgt     60
ttggcaatcg ccgataaatt tgtagaggag ggtgcgaaag tagttattac tggtcgtcac    120
gcggatgtag gtgaaaaagc cgccaaatca atcggcggca ctgatgttat tcgctttgtc    180
cagcacgatg cgtccgaaga agcaggctgg acgaaactgt tcgacaccac cgaggaggca    240
ttcggcccgg ttacgaccct ggtgaacaat gcagggattg ggtaattaa gagcgttgaa    300
cggactacca cggaggaatg gcgtaaaatc ctgtccgtta atctggatgg tgttttttc    360
ggcacccgtc tgggcattca gcgcatgaaa aataaaggct tgggcgctag catcatcaat    420
atgagctcgg cgatggggct cgtaggcgct ccgactgcag gggcatacaa cgcttccaag    480
ggggcggtac gtatcatgtc gaaaagcgca gcgctggatt gcgcactgaa ggactacgat    540
gtgcgtgtca acacagtaca tccgggcgcg atcaagaccc cacggaagga tcagctggaa    600
ggtgctgagg aagcagcttc acagcgtacg ctgaccccta tgggcacat tggcgaaccg    660
aatgacatcg catggatctg tgtgtacctg gcatctgacg aatcgaaatt tgcgacgggt    720
gcagaatttg tggtcgacgg cgggtggacc gcacag                             756

SEQ ID NO: 234            moltype = AA  length = 252
FEATURE                   Location/Qualifiers
REGION                    1..252
                          note = Engineered Variant of Kred from Lactobacillus kefir
source                    1..252
                          mol_type = protein
                          organism = synthetic construct
SEQUENCE: 234
MTDRLKHKVA IVTGGTMGIG LAIADKFVEE GAKVVITGRH ADVGEKAAKS IGGTDVIRFV     60
QHDASEEAGW TKLFDTTEEA FGPVTTLVNN AGIGVIKSVE RTTTEEWRKI LSVNLDGVFF    120
GTRLGIQRMK NKGLGASIIN MSSAMGLVGA PTAGAYNASK GAVRIMSKSA ALDCALKDYD    180
VRVNTVHPGA IKTPRKDQLE GAEEAASQRT LTPMGHIGEP NDIAWICVYL ASDESKFATG    240
AEFVVDGGWT AQ                                                        252

SEQ ID NO: 235            moltype = DNA  length = 756
FEATURE                   Location/Qualifiers
misc_feature              1..756
                          note = Engineered Variant of Kred from Lactobacillus kefir
source                    1..756
                          mol_type = other DNA
                          organism = synthetic construct
SEQUENCE: 235
atgaccgatc gtctgaagca taaagtagcc atcgttaccg gcgggacaat gggtatcgt     60
ttggcaatcg ccgataaatt tgtagaggag ggtgcgaaag tagttattac tggtcgtcac    120
gcggatgtag gtgaaaaagc cgccaaatca atcggcggca ctgatgttat tcgctttgtc    180
cagcacgatg cgtccgaaga agcaggctgg acgaaactgt tcgacaccac cgaggaggca    240
ttcggcccgg ttacgaccct ggtgaacaat gcagggattg ggcagccaa gagcgttgaa    300
cggactacca cggaggaatg gcgtaaaatc ctgtccgtta atctggatgg tgttttttc    360
ggcacccgtc tgggcattca gcgcatgaaa aataaaggct tgggcgctag catcatcaat    420
atgagcagta ttatgggget cgtaggcgct ccgactgcag gggcatacaa cgcttccaag    480
ggggcggtac gtatcatgtc gaaaagcgca gcgctggatt gcgcactgaa ggactacgat    540
gtgcgtgtca acacagtaca tccgggcgcg atcaagaccc cacggaagga tcagctggaa    600
ggttgggagg aagcagcttc acagcgtacg gcgaccccta tgggcacat tggcgaaccg    660
aatgacatcg catggatctg tgtgtacctg gcatctgacg aatcgaaatt tgcgacgggt    720
gcagaatttg tggtcgacgg cggggcaacc gcacag                             756
```

```
SEQ ID NO: 236          moltype = AA  length = 252
FEATURE                 Location/Qualifiers
REGION                  1..252
                        note = Engineered Variant of Kred from Lactobacillus kefir
source                  1..252
                        mol_type = protein
                        organism = synthetic construct
SEQUENCE: 236
MTDRLKHKVA IVTGGTMGIG LAIADKFVEE GAKVVITGRH ADVGEKAAKS IGGTDVIRFV   60
QHDASEEAGW TKLFDTTEEA FGPVTTLVNN AGIGAAKSVE RTTTEEWRKI LSVNLDGVFF  120
GTRLGIQRMK NKGLGASIIN MSSIMGLVGA PTAGAYNASK GAVRIMSKSA ALDCALKDYD  180
VRVNTVHPGA IKTPRKDQLE GWEEAASQRT ATPMGHIGEP NDIAWICVYL ASDESKFATG  240
AEFVVDGGAT AQ                                                      252

SEQ ID NO: 237          moltype = DNA  length = 756
FEATURE                 Location/Qualifiers
misc_feature            1..756
                        note = Engineered Variant of Kred from Lactobacillus kefir
source                  1..756
                        mol_type = other DNA
                        organism = synthetic construct
SEQUENCE: 237
atgaccgatc gtctgaagca taaagtagcc atcgttaccg gcgggacaat gggtatcggt   60
ttggcaatcg ccgataaatt tgtagaggag ggtgcgaaag tagttattac tggtcgtcac  120
gcggatgtag gtgaaaaagc cgccaaatca atcggcgact ctgatgttat tcgctttgtc  180
cagcacgatg cgtccgaaga agcaggctgg acgaaactgt tcgacaccac cgaggaggca  240
ttcggcccgg ttacgaccct ggtgaacaat gcagggattg gggcaattaa gagcgttgaa  300
cggactacca cggaggaatg gcgtaaaatc ctgtccgtta atctggatgg tgttttttc   360
ggcacccgtc tgggcattca gcgcatgaaa aataaaagct gggcgctag catcatcaat  420
atgagctcga tcatggggct cgtaggcgct ccgactgcag gggcatacaa cgcttccaag  480
ggggcggtac gtatcatgtc gaaaagcgca gcgctggatt gcgcactgaa ggactacgat  540
gtgcgtgtca acacagtaca tccgggcgcg atcaagaccc cacggaagga tcagctgaa   600
ggttgggagg aaatggcttc acagcgtacg ctgaccccta tgggcacat tggcgaaccg  660
aatgacatcg catggatctg tgtgtacctg gcatctgacg aatcgaaatt tgcgacgggt  720
gcagaatttg tggtcgacgg cggggcaacc gcacag                           756

SEQ ID NO: 238          moltype = AA  length = 252
FEATURE                 Location/Qualifiers
REGION                  1..252
                        note = Engineered Variant of Kred from Lactobacillus kefir
source                  1..252
                        mol_type = protein
                        organism = synthetic construct
SEQUENCE: 238
MTDRLKHKVA IVTGGTMGIG LAIADKFVEE GAKVVITGRH ADVGEKAAKS IGGTDVIRFV   60
QHDASEEAGW TKLFDTTEEA FGPVTTLVNN AGIGAAIKSVE RTTTEEWRKI LSVNLDGVFF  120
GTRLGIQRMK NKGLGASIIN MSSIMGLVGA PTAGAYNASK GAVRIMSKSA ALDCALKDYD  180
VRVNTVHPGA IKTPRKDQLE GWEEMASQRT LTPMGHIGEP NDIAWICVYL ASDESKFATG  240
AEFVVDGGAT AQ                                                      252

SEQ ID NO: 239          moltype = DNA  length = 756
FEATURE                 Location/Qualifiers
misc_feature            1..756
                        note = Engineered Variant of Kred from Lactobacillus kefir
source                  1..756
                        mol_type = other DNA
                        organism = synthetic construct
SEQUENCE: 239
atgaccgatc gtctgaagca taaagtagcc atcgttaccg gcgggacaat gggtatcggt   60
ttggcaatcg ccgataaatt tgtagaggag ggtgcgaaag tagttattac tggtcgtcac  120
gcggatgtag gtgaaaaagc cgccaaatca atcggcggca ctgatgttat tcgctttgtc  180
cagcacgatg cgtccgaaga agcaggctgg acgaaactgt tcgacaccac cgaggaggca  240
ttcggcccgg ttacgaccct ggtgaacaat gcagggattg gggttattaa aagcgttgaa  300
cggactacca cggaggaatg gcgtaaaatc ctgtccgtta atctggatgg tgttttttc   360
ggcacccgtc tgggcattca gcgcatgaaa aataaaggct gggcgctag catcatcaat  420
atgagctcgg cggcggggct cgtaggcgct ccgactgcag gggcatacaa cgcttccaag  480
ggggcggtac gtatcatgtc gaaaagcgca gcgctggatt gcgcactgaa ggactacgat  540
gtgcgtgtca acacagtaca tccgggcgcg atcaagaccc cacggaagga tcagctgaa   600
ggttgggagg aagcagcttc acagcgtacg ctgaccccta tgggccacat ggcgaaccg   660
aatgacatcg catggatctg tgtgtacctg gcatctgacg aatcgaaatt tgcgacgggt  720
gcagaatttg tggtcgacgg cgggtggacc gcacag                           756

SEQ ID NO: 240          moltype = AA  length = 252
FEATURE                 Location/Qualifiers
REGION                  1..252
                        note = Engineered Variant of Kred from Lactobacillus kefir
source                  1..252
                        mol_type = protein
```

-continued

```
                            organism = synthetic construct
SEQUENCE: 240
MTDRLKHKVA IVTGGTMGIG LAIADKFVEE GAKVVITGRH ADVGEKAAKS IGGTDVIRFV   60
QHDASEEAGW TKLFDTTEEA FGPVTTLVNN AGIGVIKSVE RTTTEEWRKI LSVNLDGVFF  120
GTRLGIQRMK NKGLGASIIN MSSAAGLVGA PTAGAYNASK GAVRIMSKSA ALDCALKDYD  180
VRVNTVHPGA IKTPRKDQLE GWEEAASQRT LTPMGHIGEP NDIAWICVYL ASDESKFATG  240
AEFVVDGGWT AQ                                                     252

SEQ ID NO: 241          moltype = DNA   length = 756
FEATURE                 Location/Qualifiers
misc_feature            1..756
                        note = Engineered Variant of Kred from Lactobacillus kefir
source                  1..756
                        mol_type = other DNA
                        organism = synthetic construct
SEQUENCE: 241
atgaccgatc gtctgaagca taaagtagcc atcgttaccg gcgggacaat gggtatcggt   60
ttggcaatcg ccgataaatt tgtagaggag ggtgcgaaag tagttattac tggtcgtcac  120
gcggatgtag gtgaaaaagc cgccaaatca atcggcggca ctgatgttat tcgctttgtc  180
cagcacgatg cgtccgaaga agcaggctgg acgaaactgt tcgacaccac cgaggaggca  240
ttcggcccgg ttacgaccct ggtgaacaat gcagggattg ggttattaa aagcgttgaa   300
cggactacca cggaggaatg gcgtaaaatc ctgtccgtta atctggatgg tgttttttc   360
ggcacccgtc tgggcattca gcgcatgaaa aataaaggct tgggcgctag catcatcaat  420
atgagctcga tcgcgggct cgtaggcgct ccgactgcag gggcatacaa cgcttccaag  480
ggggcggtac gtatcatgtc gaaaagcgca gcgctggatt gcgcactgaa ggactacgat  540
gtgcgtgtca acacagtaca tccgggcgcg atcaagaccc cacggaagga tcagctggaa  600
ggttgggagg aaatggcttc acagcgtacg ctgaccccta tgggccacat tggcgaaccg  660
aatgacatcg catggatctg tgtgtacctg gcatctgacg aatcgaaatt tgcgacgggt  720
gcagaatttg tggtcgacgg cggggcaacc gcacag                           756

SEQ ID NO: 242          moltype = AA   length = 252
FEATURE                 Location/Qualifiers
REGION                  1..252
                        note = Engineered Variant of Kred from Lactobacillus kefir
source                  1..252
                        mol_type = protein
                        organism = synthetic construct
SEQUENCE: 242
MTDRLKHKVA IVTGGTMGIG LAIADKFVEE GAKVVITGRH ADVGEKAAKS IGGTDVIRFV   60
QHDASEEAGW TKLFDTTEEA FGPVTTLVNN AGIGVIKSVE RTTTEEWRKI LSVNLDGVFF  120
GTRLGIQRMK NKGLGASIIN MSSIAGLVGA PTAGAYNASK GAVRIMSKSA ALDCALKDYD  180
VRVNTVHPGA IKTPRKDQLE GWEEMASQRT LTPMGHIGEP NDIAWICVYL ASDESKFATG  240
AEFVVDGGAT AQ                                                     252

SEQ ID NO: 243          moltype = DNA   length = 756
FEATURE                 Location/Qualifiers
misc_feature            1..756
                        note = Engineered Variant of Kred from Lactobacillus kefir
source                  1..756
                        mol_type = other DNA
                        organism = synthetic construct
SEQUENCE: 243
atgaccgatc gtctgaagca taaagtagcc atcgttaccg gcgggacaat gggtatcggt   60
ttggcaatcg ccgataaatt tgtagaggag ggtgcgaaag tagttattac tggtcgtcac  120
gcggatgtag gtgaaaaagc cgccaaatca atcggcggca ctgatgttat tcgctttgtc  180
cagcacgatg cgtccgaaga agcaggctgg acgaaactgt tcgacaccac cgaggaggca  240
ttcggcccgg ttacgaccct ggtgaacaat gcagggattg ggttattaa aagcgttgaa   300
cggactacca cggaggaatg gcgtaaaatc ctgtccgtta atctggatgg tgttttttc   360
ggcacccgtc tgggcattca gcgcatgaaa aataaaggct tgggcgctag catcatcaat  420
atgagcagta ttatgggct cgtaggcgct ccgactgcag gggcatacaa cgcttccaag  480
ggggcggtac gtatcatgtc gaaaagcgca gcgctggatt gcgcactgaa ggactacgat  540
gtgcgtgtca acacagtaca tccgggcgcg atcaagaccc cacggaagga tcagctggaa  600
ggttgggagg aaatgatgtc acagcgtacg ctgaccccta tgggccacat tggcgaaccg  660
aatgacatcg catggatctg tgtgtacctg gcatctgacg aatcgaaatt tgcgacgggt  720
gcagaatttg tggtcgacgg cggggcaacc gcacag                           756

SEQ ID NO: 244          moltype = AA   length = 252
FEATURE                 Location/Qualifiers
REGION                  1..252
                        note = Engineered Variant of Kred from Lactobacillus kefir
source                  1..252
                        mol_type = protein
                        organism = synthetic construct
SEQUENCE: 244
MTDRLKHKVA IVTGGTMGIG LAIADKFVEE GAKVVITGRH ADVGEKAAKS IGGTDVIRFV   60
QHDASEEAGW TKLFDTTEEA FGPVTTLVNN AGIGVIKSVE RTTTEEWRKI LSVNLDGVFF  120
GTRLGIQRMK NKGLGASIIN MSSIMGLVGA PTAGAYNASK GAVRIMSKSA ALDCALKDYD  180
VRVNTVHPGA IKTPRKDQLE GWEEMMSQRT LTPMGHIGEP NDIAWICVYL ASDESKFATG  240
AEFVVDGGAT AQ                                                     252
```

```
SEQ ID NO: 245          moltype = DNA  length = 756
FEATURE                 Location/Qualifiers
misc_feature            1..756
                        note = Engineered Variant of Kred from Lactobacillus kefir
source                  1..756
                        mol_type = other DNA
                        organism = synthetic construct
SEQUENCE: 245
atgaccgatc gtctgaagca taaagtagcc atcgttaccg gcgggacaat gggtatcggt   60
ttggcaatcg ccgataaatt tgtagaggag ggtgcgaaag tagttattac tggtcgtcac  120
gcggatgtag gtgaaaaagc cgccaaatca atcggcggca ctgatgttat tcgctttgtc  180
cagcacgatg cgtccgaaga agcaggctgg acgaaactgt tcgacaccac cgaggaggca  240
ttcggcccgg ttacgaccct ggtgaacaat gcagggattg gggttattaa aagcgttgaa  300
cggactacca cggaggaatg gcgtaaaatc ctgtccgtta atctggatgg tgttttttc   360
ggcacccgtc tgggcattca gcgcatgaaa aataaaggct gggcgctag catcatcaat  420
atgagctcgg cgatggggct cgtaggcgct ccgactgcag gggcatacaa cgcttccaag  480
ggggcggtac gtatcatgtc gaaaagcgca gcgctggatt gcgcactgaa ggactacgat  540
gtgcgtgtca acacagtaca tccgggcgcg atcaagaccc cacggaagga tcagctggaa  600
ggttgggagg aaatgatgtc acagcgtacg ctgaccccta tgggccacat tggcgaaccg  660
aatgacatcg catggatctg tgtgtacctg gcatctgacg aatcgaaatt tgcgacgggt  720
gcagaatttg tggtcgacgg cgggtggacc gcacag                            756

SEQ ID NO: 246          moltype = AA  length = 252
FEATURE                 Location/Qualifiers
REGION                  1..252
                        note = Engineered Variant of Kred from Lactobacillus kefir
source                  1..252
                        mol_type = protein
                        organism = synthetic construct
SEQUENCE: 246
MTDRLKHKVA IVTGGTMGIG LAIADKFVEE GAKVVITGRH ADVGEKAAKS IGGTDVIRFV   60
QHDASEEAGW TKLFDTTEEA FGPVTTLVNN AGIGVIKSVE RTTTEEWRKI LSVNLDGVFF  120
GTRLGIQRMK NKGLGASIIN MSSAMGLVGA PTAGAYNASK GAVRIMSKSA ALDCALKDYD  180
VRVNTVHPGA IKTPRKDQLE GWEEMMSQRT LTPMGHIGEP NDIAWICVYL ASDESKFATG  240
AEFVVDGGWT AQ                                                      252

SEQ ID NO: 247          moltype = DNA  length = 756
FEATURE                 Location/Qualifiers
misc_feature            1..756
                        note = Engineered Variant of Kred from Lactobacillus kefir
source                  1..756
                        mol_type = other DNA
                        organism = synthetic construct
SEQUENCE: 247
atgaccgatc gtctgaagca taaagtagcc atcgttaccg gcgggacaat gggtatcggt   60
ttggcaatcg ccgataaatt tgtagaggag ggtgcgaaag tagttattac tggtcgtcac  120
gcggatgtag gtgaaaaagc cgccaaatca atcggcggca ctgatgttat tcgctttgtc  180
cagcacgatg cgtccgaaga agcaggctgg acgaaactgt tcgacaccac cgaggaggca  240
ttcggcccgg ttacgaccct ggtgaacaat gcagggattg gggttattaa aagcgttgaa  300
cggactacca cggaggaatg gcgtaaaatc ctgtccgtta atctggatgg tgttttttc   360
ggcacccgtc tgggcattca gcgcatgaaa aataaaggct gggcgctag catcatcaat  420
atgagcagta ttatggggct cgtaggcgct ccgactgcag gggcatacaa cgcttccaag  480
ggggcggtac gtatcatgtc gaaaagcgca gcgctggatt gcgcactgaa ggactacgat  540
gtgcgtgtca acacagtaca tccgggcgcg atcaagaccc cacggaagga tcagctggaa  600
ggtgctgagg aaatggcttc acagcgtacg ctgaccccta tgggccacat tggcgaaccg  660
aatgacatcg catggatctg tgtgtacctg gcatctgacg aatcgaaatt tgcgacgggt  720
gcagaatttg tggtcgacgg cggggcaacc gcacag                            756

SEQ ID NO: 248          moltype = AA  length = 252
FEATURE                 Location/Qualifiers
REGION                  1..252
                        note = Engineered Variant of Kred from Lactobacillus kefir
source                  1..252
                        mol_type = protein
                        organism = synthetic construct
SEQUENCE: 248
MTDRLKHKVA IVTGGTMGIG LAIADKFVEE GAKVVITGRH ADVGEKAAKS IGGTDVIRFV   60
QHDASEEAGW TKLFDTTEEA FGPVTTLVNN AGIGVIKSVE RTTTEEWRKI LSVNLDGVFF  120
GTRLGIQRMK NKGLGASIIN MSSIMGLVGA PTAGAYNASK GAVRIMSKSA ALDCALKDYD  180
VRVNTVHPGA IKTPRKDQLE GAEEMASQRT LTPMGHIGEP NDIAWICVYL ASDESKFATG  240
AEFVVDGGAT AQ                                                      252

SEQ ID NO: 249          moltype = DNA  length = 756
FEATURE                 Location/Qualifiers
misc_feature            1..756
                        note = Engineered Variant of Kred from Lactobacillus kefir
source                  1..756
                        mol_type = other DNA
```

```
                       organism = synthetic construct
SEQUENCE: 249
atgaccgatc gtctgaagca taaagtagcc atcgttaccg gcgggacaat gggtatcggt    60
ttggcaatcg ccgataaatt tgtagaggag ggtgcgaaag tagttattac tggtcgtcac   120
gcggatgtag gtgaaaaagc cgccaaatca atcggcggca ctgatgttat tcgctttgtc   180
cagcacgatg cgtccgaaga agcaggctgg acgaaactgt tcgacaccac cgaggaggca   240
ttcggcccgg ttacgaccct ggtgaacaat gcagggattg gggcaattaa gagcgttgaa   300
cggactacca cggaggaatg gcgtaaaatc ctgtccgtta atctggatgg tgtttttttc   360
ggcacccgtc tgggcattca gcgcatgaaa aataaaggct gggcgctag catcatcaat   420
atgagcagta ttatggggct cgtaggcgct ccgactgcag ggcatacaa cgcttccaag   480
ggggcggtac gtatcatgtc gaaaagcgca gcgctggatt gcgcactgaa ggactacgat   540
gtgcgtgtca acacagtaca tccgggcgcg atcaagaccc cacggaagga tcagctggaa   600
ggttgggagg aaatggcttc acagcgtacg ctgacccta tgggccacat tggcgaaccg    660
aatgacatcg catggatctg tgtgtacctg gcatctgacg aatcgaaatt tgcgacgggt   720
gcagaatttg tggtcgacgg cggggcaacc gcacag                             756

SEQ ID NO: 250        moltype = AA  length = 252
FEATURE               Location/Qualifiers
REGION                1..252
                      note = Engineered Variant of Kred from Lactobacillus kefir
source                1..252
                      mol_type = protein
                      organism = synthetic construct
SEQUENCE: 250
MTDRLKHKVA IVTGGTMGIG LAIADKFVEE GAKVVITGRH ADVGEKAAKS IGGTDVIRFV    60
QHDASEEAGW TKLFDTTEEA FGPVTTLVNN AGIGAIKSVE RTTTEEWRKI LSVNLDGVFF   120
GTRLGIQRMK NKGLGASIIN MSSIMGLVGA PTAGAYNASK GAVRIMSKSA ALDCALKDYD   180
VRVNTVHPGA IKTPRKDQLE GWEEMASQRT LTPMGHIGEP NDIAWICVYL ASDESKFATG   240
AEFVVDGGAT AQ                                                       252

SEQ ID NO: 251        moltype = DNA  length = 756
FEATURE               Location/Qualifiers
misc_feature          1..756
                      note = Engineered Variant of Kred from Lactobacillus kefir
source                1..756
                      mol_type = other DNA
                      organism = synthetic construct
SEQUENCE: 251
atgaccgatc gtctgaagca taaagtagcc atcgttaccg gcgggacaat gggtatcggt    60
ttggcaatcg ccgataaatt tgtagaggag ggtgcgaaag tagttattac tggtcgtcac   120
gcggatgtag gtgaaaaagc cgccaaatca atcggcggca ctgatgttat tcgctttgtc   180
cagcacgatg cgtccgaaga agcaggctgg acgaaactgt tcgacaccac cgaggaggca   240
ttcggcccgg ttacgaccct ggtgaacaat gcagggattg gggttattaa aagcgttgaa   300
cggactacca cggaggaatg gcgtaaagtt ctgtccgtta atctggatgg tgtttttttc   360
ggcacccgtc tgggcattca gcgcatgaaa aataaaggct gggcgctag catcatcaat   420
atgagcagta ttatggggct cgtaggcgat ccgactctgg ggcatacaa cgcttccaag   480
ggggcggtac gtatcatgtc gaaaagcgca gcgctggatt gcgcactgaa ggacatggat   540
gtgcgtgtca acacagtaca tccgggcgcg atcaagaccc aacggaagga tcagctggaa   600
ggttgggagg aaatgatgtc acagcgtacg ctgacccta tgggccacat tggcgaaccg    660
aatgacatcg catggatctg tgtgtacctg gcgtctgacg aatcgaaatt tgcgacgggt   720
gcagaatttg tggtcgacgg cgggtggacc gcacag                             756

SEQ ID NO: 252        moltype = AA  length = 252
FEATURE               Location/Qualifiers
REGION                1..252
                      note = Engineered Variant of Kred from Lactobacillus kefir
source                1..252
                      mol_type = protein
                      organism = synthetic construct
SEQUENCE: 252
MTDRLKHKVA IVTGGTMGIG LAIADKFVEE GAKVVITGRH ADVGEKAAKS IGGTDVIRFV    60
QHDASEEAGW TKLFDTTEEA FGPVTTLVNN AGIGVIKSVE RTTTEEWRKV LSVNLDGVFF   120
GTRLGIQRMK NKGLGASIIN MSSIMGLVGD PTLGAYNASK GAVRIMSKSA ALDCALKDMD   180
VRVNTVHPGA IKTERKDQLE GWEEMMSQRT LTPMGHIGEP NDIAWICVYL ASDESKFATG   240
AEFVVDGGWT AQ                                                       252

SEQ ID NO: 253        moltype = DNA  length = 756
FEATURE               Location/Qualifiers
misc_feature          1..756
                      note = Engineered Variant of Kred from Lactobacillus kefir
source                1..756
                      mol_type = other DNA
                      organism = synthetic construct
SEQUENCE: 253
atgaccgatc gtctgaagca taaagtagcc atcgttaccg gcgggacaat gggtatcggt    60
ttggcaatcg ccgataaatt tgtagaggag ggtgcgaaag tagttattac tggtcgtcac   120
gcggatgtag gtgaaaaagc cgccaaatca atcggcggca ctgatgttat tcgctttgtc   180
cagcacgatg cgtccgaaga agcaggctgg acgaaactgt tcgacaccac cgaggaggca   240
ttcggcccgg ttacgaccct ggtgaacaat gcagggattg gggttattaa aagcgttgaa   300
```

```
cggactacca cggaggaatg gcgtaaagtg ctgtccgtta atctggatgg tgttttttc    360
ggcacccgtc tgggcattca gcgcatgaaa aataaaggct tgggcgctag catcatcaat   420
atgagcagta ttatggggct cgtaggcgat ccgactctgg gggcatacaa cgcttccaag   480
ggggcggtac gtatcatgtc gaaaagcgca gcgctggatt gcgcactgaa ggactacgat   540
gtgcgtgtca acacagtaca tccgggcgcg atcaagaccc cacggaagga tcagctggaa   600
ggttgggagg aaatgatgtc acagcgtacg ctgaccccta tgggccacat tggcgaaccg   660
aatgacatcg catggatctg tgtgtacctg gcatctgacg aatcgaaatt tgcgacgggt   720
gcagaatttg tggtcgacgg cgggtggacc gcacag                             756

SEQ ID NO: 254          moltype = AA  length = 252
FEATURE                 Location/Qualifiers
REGION                  1..252
                        note = Engineered Variant of Kred from Lactobacillus kefir
source                  1..252
                        mol_type = protein
                        organism = synthetic construct
SEQUENCE: 254
MTDRLKHKVA IVTGGTMGIG LAIADKFVEE GAKVVITGRH ADVGEKAAKS IGGTDVIRFV    60
QHDASEEAGW TKLFDTTEEA FGPVTTLVNN AGIGVIKSVE RTTTEEWRKV LSVNLDGVFF   120
GTRLGIQRMK NKGLGASIIN MSSIMGLVGD PTLGAYNASK GAVRIMSKSA ALDCALKDYD   180
VRVNTVHPGA IKTPRKDQLE GWEEMMSQRT LTPMGHIGEP NDIAWICVYL ASDESKFATG   240
AEFVVDGGWT AQ                                                       252

SEQ ID NO: 255          moltype = DNA  length = 756
FEATURE                 Location/Qualifiers
misc_feature            1..756
                        note = Engineered Variant of Kred from Lactobacillus kefir
source                  1..756
                        mol_type = other DNA
                        organism = synthetic construct
SEQUENCE: 255
atgaccgatc gtctgaagca taaagtagcc atcgttaccg gcgggacaat gggtatcggt    60
ttggcaatcg ccgataaatt tgtagaggag ggtgcgaaag tagttattac tggtcgtcac   120
gcggatgtag gtgaaaaagc cgccaaatca atcggcggca ctgatgttat tcgctttgtc   180
cagcacgatg cgtccgaaga agcaggctgg acgaagctgt tcgacaccac cgaggaggca   240
ttcggcccgg ttacgaccct ggtgaacaat gcagggattg ggttattaa aagcgttgaa   300
cgtactcgca cggaggaatg gcgtaaaatc ctgtccgtta atctggatgg tgttttttc    360
ggcacccgtc tgggcattca gcgcatgaaa aataaaggct tgggcgctag catcatcaat   420
atgagcagta ttatggggat tgtaggcgat ccgactctgg gggcatacaa cgcttccaag   480
ggggcggtac gtatcatgtc gaaaagcgca gcgctggatt gcgcactgaa ggactacgat   540
gtgcgtgtca acacagtaca tccgggcgcg atcaagaccc cacggaagga tcagctggaa   600
ggttgggagg aaatgatgtc acagcgtacg ctgaccccta tgggccacat tggcgaaccg   660
aatgacatcg catggatctg tgtgtacctg gcatctgacg aatcgaaatt tgcgacgggt   720
gcagaatttg tggtcgacgg cgggtggacc gcacag                             756

SEQ ID NO: 256          moltype = AA  length = 252
FEATURE                 Location/Qualifiers
REGION                  1..252
                        note = Engineered Variant of Kred from Lactobacillus kefir
source                  1..252
                        mol_type = protein
                        organism = synthetic construct
SEQUENCE: 256
MTDRLKHKVA IVTGGTMGIG LAIADKFVEE GAKVVITGRH ADVGEKAAKS IGGTDVIRFV    60
QHDASEEAGW TKLFDTTEEA FGPVTTLVNN AGIGVIKSVE RTTEEWRKI LSVNLDGVFF   120
GTRLGIQRMK NKGLGASIIN MSSIMGIVGD PTLGAYNASK GAVRIMSKSA ALDCALKDYD   180
VRVNTVHPGA IKTPRKDQLE GWEEMMSQRT LTPMGHIGEP NDIAWICVYL ASDESKFATG   240
AEFVVDGGWT AQ                                                       252

SEQ ID NO: 257          moltype = DNA  length = 756
FEATURE                 Location/Qualifiers
misc_feature            1..756
                        note = Engineered Variant of Kred from Lactobacillus kefir
source                  1..756
                        mol_type = other DNA
                        organism = synthetic construct
SEQUENCE: 257
atgaccgatc gtctgaagca taaagtagcc atcgttaccg gcgggacaat gggtatcggt    60
ttggcaatcg ccgataaatt tgtagaggag ggtgcgaaag tagttattac tggtcgtcac   120
gcggatgtag gtgaaaaagc cgccaaatca atcggcggca ctgatgttat tcgctttgtc   180
cagcacgatg cgtccgaaga agcaggctgg acgaaactgt tcgacaccac cgaggaggca   240
ttcggcccgg ttacgaccct ggtgaacaat gcagggattg ggttattaa aagcgttgaa   300
cggactacca cggaggaatg gcgtaaagtg ctgtccgtta atctggatgg tgttttttc    360
ggcacccgtc tgggcattca gcgcatgaaa aataaaggct tgggcgctag catcatcaat   420
atgagcagta ttatgggget cgtaggcgat ccgactctgg gggcatacaa cgcttccaag   480
ggggcggtac gtatcatgtc gaaaagcgca gcgctggatt gcgcactgaa ggactacgat   540
gtgcgtgtca acacagtaca tccgggcgcg atcaagaccc cacggaagga tcagctggaa   600
ggttgggagg aaatgatgtc acagcgtacg ctgaccccta tgggccacat tggcgaaccg   660
aatgacatcg catggatctg tgtgtacctg gcatctgacg aatcgaaatt tgcgacgggt   720
```

```
gcagaatttg tggtcgacgg cgggtggacc gcacag                              756

SEQ ID NO: 258           moltype = AA  length = 252
FEATURE                  Location/Qualifiers
REGION                   1..252
                         note = Engineered Variant of Kred from Lactobacillus kefir
source                   1..252
                         mol_type = protein
                         organism = synthetic construct
SEQUENCE: 258
MTDRLKHKVA IVTGGTMGIG LAIADKFVEE GAKVVITGRH ADVGEKAAKS IGGTDVIRFV   60
QHDASEEAGW TKLFDTTEEA FGPVTTLVNN AGIGVIKSVE RTTTEEWRKV LSVNLDGVFF  120
GTRLGIQRMK NKGLGASIIN MSSIMGLVGD PTLGAYNASK GAVRIMSKSA ALDCALKDYD  180
VRVNTVHPGA IKTPRKDQLE GWEEMMSQRT LTPMGHIGEP NDIAWICVYL ASDESKFATG  240
AEFVVDGGWT AQ                                                      252

SEQ ID NO: 259           moltype = DNA  length = 756
FEATURE                  Location/Qualifiers
misc_feature             1..756
                         note = Engineered Variant of Kred from Lactobacillus kefir
source                   1..756
                         mol_type = other DNA
                         organism = synthetic construct
SEQUENCE: 259
atgaccgatc gtctgaagca gaaagtagcc atcgttaccg gcgggacaat gggtatcggt   60
ttggcaatcg ccgataaatt tgtagaggag ggtgcgaaag tagttattac tggtcgtcac  120
gcggatgtag gtgaaaaagc cgccaaatca atcggcggca ctgatgttat tcgctttgtc  180
cagcacgatg cgtccgaaga agcaggctgg acgaagctgt tcgacaccac cgaggaggca  240
ttcggcccgg ttacgaccct ggtgaacaat gcagggattg ggttattaa aagcgttgaa  300
cggactacca cggaggaatg gcgtaaaatc ctgtccgtta atctggatgg tgttttttc  360
ggcacccgtc tgggcattca gcgcatgaaa aataaaggct tgggcgctag catcatcaat  420
atgagcagta ttatggggat tgtaggcgat ccgactctgg gggcatacaa cgcttccaag  480
ggggcggtac gtatcatgtc gaaaagcgca gcgctggatt gcgcactgaa ggactacgat  540
gtgcgtgtca acacagtaca tccgggcgcg atcaagaccc cacggaagga tcagctggaa  600
ggtgggagg aaatgatgtc acagcgtacg ctgaccccta tgggccacat tggcgaaccg  660
aatgacatcg catggatctg tgtgtacctg gcatctgacg aatcgaaatt tgcgacgggt  720
gcagaatttg tggtcgacgg cgggtggacc gcacag                              756

SEQ ID NO: 260           moltype = AA  length = 252
FEATURE                  Location/Qualifiers
REGION                   1..252
                         note = Engineered Variant of Kred from Lactobacillus kefir
source                   1..252
                         mol_type = protein
                         organism = synthetic construct
SEQUENCE: 260
MTDRLKQKVA IVTGGTMGIG LAIADKFVEE GAKVVITGRH ADVGEKAAKS IGGTDVIRFV   60
QHDASEEAGW TKLFDTTEEA FGPVTTLVNN AGIGVIKSVE RTTTEEWRKI LSVNLDGVFF  120
GTRLGIQRMK NKGLGASIIN MSSIMGIVGD PTLGAYNASK GAVRIMSKSA ALDCALKDYD  180
VRVNTVHPGA IKTPRKDQLE GWEEMMSQRT LTPMGHIGEP NDIAWICVYL ASDESKFATG  240
AEFVVDGGWT AQ                                                      252

SEQ ID NO: 261           moltype = DNA  length = 756
FEATURE                  Location/Qualifiers
misc_feature             1..756
                         note = Engineered Variant of Kred from Lactobacillus kefir
source                   1..756
                         mol_type = other DNA
                         organism = synthetic construct
SEQUENCE: 261
atgaccgatc gtctgaagca taaagtagcc atcgttaccg gcgggacaat gggtatcggt   60
ttggcaatcg ccgataaatt tgtagaggag ggtgcgaaag tagttattac tggtcgtcac  120
gcggatgtag gtgaaaaagc cgccaaatca atcggcggca ctgatgttat tcgctttgtc  180
cagcacgatg cgtccgaaga agcaggctgg acgaaactgt tcgacaccac cgaggaggca  240
ttcggcccgg ttacgaccct ggtgaacaat gcagggattg ggttattaa aagcgttgaa  300
cggactacca cggaggaatg gcgtaaaatc ctgtccgtta atctggatgg tgttttttc  360
ggcacccgtc tgggcattca gcgcatgaaa aataaaggct tgggcgctag catcatcaat  420
atgagcagta ttatggggct cgtaggcgat ccgactctgg gggcatacaa cgcttccaag  480
ggggcggtac gtatcatgtc gaaaagcgca gcgctggatt gcgcactgaa ggactacgat  540
gtgcgtgtca acacagtaca tccgggcgcg atcaagaccc cacggaagga tcagctggaa  600
ggtgggagg aaatgatgtc acagcgtacg ctgaccccta tgggccacat tggcgaaccg  660
aatgacatcg catggatctg tgtgtacctg gcatctgacg aatcgaaatt tgcgacgggt  720
gcagaatttg tggtcgacgg cgggtacacc gcacag                              756

SEQ ID NO: 262           moltype = AA  length = 252
FEATURE                  Location/Qualifiers
REGION                   1..252
                         note = Engineered Variant of Kred from Lactobacillus kefir
source                   1..252
```

```
                           mol_type = protein
                           organism = synthetic construct
SEQUENCE: 262
MTDRLKHKVA IVTGGTMGIG LAIADKFVEE GAKVVITGRH ADVGEKAAKS IGGTDVIRFV    60
QHDASEEAGW TKLFDTTEEA FGPVTTLVNN AGIGVIKSRH RTTTEEWRKI LSVNLDGVFF   120
GTRLGIQRMK NKGLGASIIN MSSIMGLVGD PTLGAYNASK GAVRIMSKSA ALDCALKDYD   180
VRVNTVHPGA IKTPRKDQLE GWEEMMSQRT LTPMGHIGEP NDIAWICVYL ASDESKFATG   240
AEFVVDGGYT AQ                                                      252

SEQ ID NO: 263             moltype = DNA  length = 756
FEATURE                    Location/Qualifiers
misc_feature               1..756
                           note = Engineered Variant of Kred from Lactobacillus kefir
source                     1..756
                           mol_type = other DNA
                           organism = synthetic construct
SEQUENCE: 263
atgaccgatc gtctgaagca taaagtagcc atcgttaccg gcgggacaat gggtatcggt    60
ttggcaatcg ccgataaatt tgtagaggag ggtgcgaaag tagttattac tggtcgtcac   120
gcggatgtag gtgaaaaagc cgccaaatca atcggcggca ctgatgttat tcgctttgtc   180
cagcacgatg cgtccgaaga agcaggctgg acgaaactgt tcgacaccac cgaggaggca   240
ttcggcccgg ttacgaccct ggtgaacaat gcagggattg ggttattaa aagcgttgaa    300
cggactacca cggaggaatg gcgtaaaatc ctgtccgtta atctggatgg tgtttttttc   360
ggcacccgtc tgggcattca gcgcatgaaa aataaaggct gggcgctag catcatcaat   420
atgagcagta ttatggggat gtaggcgat ccgactctgg ggcatacaa cgcttccaag    480
ggggcggtac gtatcatgtc gaaaagcgca gcgctggatt gcgcactgaa ggactacgat   540
gtgcgtgtca acacagtaca tccgggcgcg atcaagaccc cacggaagga tcagctggaa   600
ggttgggagg aaatgatgtc acagcgtacg ctgaccccta tgggccacat tggcgaaccg   660
aatgacatcg catggatctg tgtgtacctg gcatctgacg aatcgaaatt tgcgacgggt   720
gcagaatttg tggtcgacgg cgggtggacc gcacag                            756

SEQ ID NO: 264             moltype = AA  length = 252
FEATURE                    Location/Qualifiers
REGION                     1..252
                           note = Engineered Variant of Kred from Lactobacillus kefir
source                     1..252
                           mol_type = protein
                           organism = synthetic construct
SEQUENCE: 264
MTDRLKHKVA IVTGGTMGIG LAIADKFVEE GAKVVITGRH ADVGEKAAKS IGGTDVIRFV    60
QHDASEEAGW TKLFDTTEEA FGPVTTLVNN AGIGVIKSVE RTTTEEWRKI LSVNLDGVFF   120
GTRLGIQRMK NKGLGASIIN MSSIMGIVGD PTLGAYNASK GAVRIMSKSA ALDCALKDYD   180
VRVNTVHPGA IKTPRKDQLE GWEEMMSQRT LTPMGHIGEP NDIAWICVYL ASDESKFATG   240
AEFVVDGGWT AQ                                                      252

SEQ ID NO: 265             moltype = DNA  length = 756
FEATURE                    Location/Qualifiers
misc_feature               1..756
                           note = Engineered Variant of Kred from Lactobacillus kefir
source                     1..756
                           mol_type = other DNA
                           organism = synthetic construct
SEQUENCE: 265
atgaccgatc gtctgaagca caaagtagcc atcatcaccg gcgggacaat gggtatcggt    60
ttggcaatcg ccgataaatt tgtagaggag ggtgcgaaag tagttattac tggtcgtcac   120
gcggatgtag gtgaaaaagc cgccaaatca atcggcggca ctgatgttat tcgctttgtc   180
cagcacgatg cgagcgaaga agcaggctgg acgagtctgt tcgacaccac cgaggaggca   240
ttcggcccgg ttacgaccct ggtgaacaat gcagggattg ggtaattaa gagcgttgaa    300
cggactacca cggaggaatg gcgtaaagtt ctgtccgtta atctggatgg tgtttttttc   360
ggcacccgtc tgggcattca gcgcatgaaa aataaaggct gggcgctag catcatcaat   420
atgagcagta ttatggggat gtaggcgct ccgatggcag ggcatacaa cgcttccaag    480
ggggcggtac gtatcatgtc gaaagcgca gcgctggatt gcgcactgaa ggactacgat   540
gtgcgtgtca acacagtaca tccgggcgcg atcaagaccc cacggaagga tcagctggaa   600
ggttgggagc aggcaatgtc acagcgtacg gcgacccta tgggccacat tggcgaaccg   660
aatgacatcg catggatctg tgtgtacctg gcatctgacg aatcgaaatt tgcgacgggt   720
gcagaatttg tggtcgacgg cgggtggacc gcacag                            756

SEQ ID NO: 266             moltype = AA  length = 252
FEATURE                    Location/Qualifiers
REGION                     1..252
                           note = Engineered Variant of Kred from Lactobacillus kefir
source                     1..252
                           mol_type = protein
                           organism = synthetic construct
SEQUENCE: 266
MTDRLKHKVA IITGGTMGIG LAIADKFVEE GAKVVITGRH ADVGEKAAKS IGGTDVIRFV    60
QHDASEEAGW TSLFDTTEEA FGPVTTLVNN AGIGVIKSVE RTTTEEWRKV LSVNLDGVFF   120
GTRLGIQRMK NKGLGASIIN MSSIMGIVGA PMAGAYNASK GAVRIMSKSA ALDCALKDYD   180
VRVNTVHPGA IKTPRKDQLE GWEQAMSQRT ATPMGHIGEP NDIAWICVYL ASDESKFATG   240
```

```
AEFVVDGGWT AQ                                                        252

SEQ ID NO: 267           moltype = DNA   length = 756
FEATURE                  Location/Qualifiers
misc_feature             1..756
                         note = Engineered Variant of Kred from Lactobacillus kefir
source                   1..756
                         mol_type = other DNA
                         organism = synthetic construct
SEQUENCE: 267
atgaccgacc gtctgaagca caaagtagcc atcatcaccg gcgggacaat gggtatcggt    60
ttggcaatcg ccgataaatt tgtagaggag ggtgcgaaag tagttattac tggtcgtcac   120
gcggatgtag gtgaaaaagc cgccaaatca atcggcggca ctgatgttat tcgctttgtc   180
cagcacgatg cgagcgaaga agcaggctgg acgagtctgt tcgacaccac cgaggaggca   240
ttcggcccgg ttacgaccct ggtgaacaat gcagggattg gggtaattaa gagcgttgaa   300
tatactcaga cggaggaatg gcgtaaagtt ctgtccgtta atctggatgg tgttttttc   360
ggcacccgtc tgggcattca gcgcatgaaa aataaaggct gggcgctag catcatcaat   420
atgagcagta ttatggggct ggtaggcgct ccgatgccgg ggcatacaa cgcttccaag   480
ggggcggtac gtatcatgtc gaaaagcgca gcgctggatt gcgcactgaa ggactacgat   540
gtgcgtgtca acacagtaca tccgggcgcg atcaagaccc cacggaagga tcagctggaa   600
ggttgggagg aagcaatgtc acagcgtacg gcgacccta tgggccacat tggcgaaccg    660
aatgacatcg catggatctg tgtgtacctg gcatctgacg aatcgaaatt tgcgacgggt   720
gcagaatttg tggtcgacgg cgggtacacc gcacag                             756

SEQ ID NO: 268           moltype = AA   length = 252
FEATURE                  Location/Qualifiers
REGION                   1..252
                         note = Engineered Variant of Kred from Lactobacillus kefir
source                   1..252
                         mol_type = protein
                         organism = synthetic construct
SEQUENCE: 268
MTDRLKHKVA IITGGTMGIG LAIADKFVEE GAKVVITGRH ADVGEKAAKS IGGTDVIRFV    60
QHDASEEAGW TSLFDTTEEA FGPVTTLVNN AGIGVIKSVE YTQTEEWRKV LSVNLDGVFF   120
GTRLGIQRMK NKGLGASIIN MSSIMGLVGA PMAGAYNASK GAVRIMSKSA ALDCALKDYD   180
VRVNTVHPGA IKTPRKDQLE GWEEAMSQRT ATPMGHIGEP NDIAWICVYL ASDESKFATG   240
AEFVVDGGYT AQ                                                        252

SEQ ID NO: 269           moltype = DNA   length = 756
FEATURE                  Location/Qualifiers
misc_feature             1..756
                         note = Engineered Variant of Kred from Lactobacillus kefir
source                   1..756
                         mol_type = other DNA
                         organism = synthetic construct
SEQUENCE: 269
atgaccgatc gtctgaagca caaagtagcc atcgtcaccg gcgggacaat gggtatcggt    60
ttggcaatcg ccgataaatt tgtagaggag ggtgcgaaag tagttattac tggtcgtcac   120
gcggatgtag gtctgaaagc cgccaaatca atcggtggca gtgatgttat tcgctttgtc   180
cagcacgatg cgtccgaaga agcaggctgg acgagtctgt tcgacaccac cgaggaggca   240
ttcggcccgg ttacgaccct ggtgaacaat gcagggattg gggtaattaa gagcgttgaa   300
cggactacca cggaggaatg gcgtaaagtt ctgtccgtta atctggatgg tgttttttc   360
ggcacccgtc tgggcattca gcgcatgaaa aataaaggct gggcgctag catcatcaat   420
atgagcagta ttatggggct ggtaggcgct ccgatggcag ggcatacaa cgcttccaag   480
ggggcggtac gtatcatgtc gaaaagcgca gcgctggatt gcgcactgaa ggactacgat   540
gtgcgtgtca acacagtaca tccgggcgcg atcaagaccg agcggaagga tcagctggaa   600
ggttgggagc aggcaatgtc acagcgtacg gcgacccta tgggccacat tggcgaaccg    660
aatgacatcg catggatctg tgtgtacctg gcatctgacg aatcgaaatt tgcgacgggt   720
gcagaatttg tggtcgacgg cgggtggacc gcacag                             756

SEQ ID NO: 270           moltype = AA   length = 252
FEATURE                  Location/Qualifiers
REGION                   1..252
                         note = Engineered Variant of Kred from Lactobacillus kefir
source                   1..252
                         mol_type = protein
                         organism = synthetic construct
SEQUENCE: 270
MTDRLKHKVA IVTGGTMGIG LAIADKFVEE GAKVVITGRH ADVGLKAAKS IGGSDVIRFV    60
QHDASEEAGW TSLFDTTEEA FGPVTTLVNN AGIGVIKSVE RTTTEEWRKV LSVNLDGVFF   120
GTRLGIQRMK NKGLGASIIN MSSIMGLVGA PMAGAYNASK GAVRIMSKSA ALDCALKDYD   180
VRVNTVHPGA IKTERKDQLE GWEQAMSQRT ATPMGHIGEP NDIAWICVYL ASDESKFATG   240
AEFVVDGGWT AQ                                                        252

SEQ ID NO: 271           moltype = DNA   length = 756
FEATURE                  Location/Qualifiers
misc_feature             1..756
                         note = Engineered Variant of Kred from Lactobacillus kefir
source                   1..756
```

```
                        mol_type = other DNA
                        organism = synthetic construct
SEQUENCE: 271
atgaccgacc gtctgaagca caaagtagcc atcattaccg cgggacaat gggtatcggt    60
ttggcaatcg ccgataaatt tgtagaggag ggtgcgaaag tagttattac tggtcgtcac   120
gcggatgtag gtgaaaaagc cgccaaatca atcggtggca gtgatgttat tcgctttgtc   180
cagcacgatg cgtcggaaga agcaggctgg acgacgctgt tcgacaccac cgaggaggca   240
ttcggcccgg ttacgaccct ggtgaacaat gcagggattg gggttattaa agcgttgaa    300
cggactacca cggaggaatg gcgtaaagtt ctgtccgtta atctggatgg tgttttttc    360
ggcacccgtc tgggcattca gcgcatgaaa aataaaggct tgggcgctag catcatcaat   420
atgagcagta ttatggggct cgtaggcgat ccgatgctgg gggcatacaa cgcttccaag   480
ggggcggtac gtatcatgtc gaaaagcgca gcgctggatt gcgcactgaa ggactacgat   540
gtgcgtgtca acacagtaca tccgggcgcg atcaagaccg aacggaagga tcagctggaa   600
ggttgggagg agatgatgtc acagcgtacg ctgaccccta tggccacat tggcgaaccg    660
aatgacatcg catggatctg tgtgtacctg cgtctgacg aatcgaaatt tgcgacgggt    720
gcagaatttg tggtcgacgg cgggtacacc gcacag                             756

SEQ ID NO: 272     moltype = AA   length = 252
FEATURE            Location/Qualifiers
REGION             1..252
                   note = Engineered Variant of Kred from Lactobacillus kefir
source             1..252
                   mol_type = protein
                   organism = synthetic construct
SEQUENCE: 272
MTDRLKHKVA IITGGTMGIG LAIADKFVEE GAKVVITGRH ADVGEKAAKS IGGSDVIRFV    60
QHDASEEAGW TTLFDTTEEA FGPVTTLVNN AGIGVIKSVE RTTTEEWRKV LSVNLDGVFF   120
GTRLGIQRMK NKGLGASIIN MSSIMGLVGD PMLGAYNASK GAVRIMSKSA ALDCALKDYD   180
VRVNTVHPGA IKTERKDQLE GWEEMMSQRT LTPMGHIGEP NDIAWICVYL ASDESKFATG   240
AEFVVDGGYT AQ                                                       252

SEQ ID NO: 273     moltype = DNA   length = 756
FEATURE            Location/Qualifiers
misc_feature       1..756
                   note = Engineered Variant of Kred from Lactobacillus kefir
source             1..756
                   mol_type = other DNA
                   organism = synthetic construct
SEQUENCE: 273
atgaccgacc gtctgaagca caaagtagcc atcgttaccg cgggacaat gggtatcggt    60
ttggcaatcg ccgataaatt tgtagaggag ggtgcgaaag tagttattac tggtcgtcac   120
gcggatgtag gtgaaaaagc cgccaaatca atcggcggca ctgatgttat tcgctttgtc   180
cagcacgatg cgtccgaaga agcaggctgg acgaaactgt tcgacaccac cgaggaggca   240
ttcggcccgg ttacgaccct ggtgaacaat gcagggattg gggttattaa agcgttgaa    300
cggactacca cggaggaatg gcgtaaagtt ctgtccgtta atctggatgg tgttttttc    360
ggcacccgtc tgggcattca gcgcatgaaa aataaaggct tgggcgctag catcatcaat   420
atgagcagta ttatggggct cgtacgcgat ccgacgctgg gggcatacaa cgcttccaag   480
ggggcggtac gtatcatgtc gaaaagcgca gcgctggatt gcgcactgaa ggacatggat   540
gtgcgtgtca acacagtaca tccgggcgcg atcaagaccg aacggaagga tcagctggaa   600
ggttgggagg aaatgatgtc acagcgtacg ctgaccccta tggccacat tggcgaaccg    660
aatgacatcg catggatctg tgtgtacctg cgtctgacg aatcgaaatt tgcgacgggt    720
gcagaatttg tggtcgacgg cgggtacacc gcacag                             756

SEQ ID NO: 274     moltype = AA   length = 252
FEATURE            Location/Qualifiers
REGION             1..252
                   note = Engineered Variant of Kred from Lactobacillus kefir
source             1..252
                   mol_type = protein
                   organism = synthetic construct
SEQUENCE: 274
MTDRLKHKVA IVTGGTMGIG LAIADKFVEE GAKVVITGRH ADVGEKAAKS IGGTDVIRFV    60
QHDASEEAGW TKLFDTTEEA FGPVTTLVNN AGIGVIKSVE RTTTEEWRKV LSVNLDGVFF   120
GTRLGIQRMK NKGLGASIIN MSSIMGLVGD PTLGAYNASK GAVRIMSKSA ALDCALKDMD   180
VRVNTVHPGA IKTERKDQLE GWEEMMSQRT LTPMGHIGEP NDIAWICVYL ASDESKFATG   240
AEFVVDGGYT AQ                                                       252

SEQ ID NO: 275     moltype = DNA   length = 756
FEATURE            Location/Qualifiers
misc_feature       1..756
                   note = Engineered Variant of Kred from Lactobacillus kefir
source             1..756
                   mol_type = other DNA
                   organism = synthetic construct
SEQUENCE: 275
atgaccgacc gtctgaagca gaaagtagcc atcattaccg cgggacaat gggtatcggt    60
ttggcaatcg ccgataaatt tgtagaggag ggtgcgaaag tagttattac tggtcgtcac   120
gcggatgtag gtgaaaaagc cgccaaatca atcggtggca gtgatgttat tcgctttgtc   180
cagcacgatg cgtccgaaga agcaggctgg acgaaactgt tcgacaccac cgaggaggca   240
```

```
ttcggcccgg ttacgaccct ggtgaacaat gcagggattg gggttattaa aagcgttgaa    300
cggactacca cggaggaatg gcgtaaagtt ctgtccgtta atctggatgg tgttttttc     360
ggcaccgtc  tgggcattca gcgcatgaaa aataaaggct tgggcgctag catcatcaat    420
atgagcagta ttatggggct ggtaggcgat ccgacgctgg gggcatacaa cgcttccaag    480
ggggcggtac gtatcatgtc gaaaagcgca gcgctggatt gcgcactgaa ggactacgat    540
gtgcgtgtca acacagtaca tccgggcgcg atcaagaccg aacggaagga tcagctggaa    600
ggttgggagg aaatgatgtc acagcgtacg ctgaccccta tgggccacat tggcgaaccg    660
aatgacatcg catggatctg tgtgtacctg gcgtctgacg aatcgaaatt tgcgacgggt    720
gcagaatttg tggtcgacgg cgggtacacc gcacag                              756

SEQ ID NO: 276          moltype = AA   length = 252
FEATURE                 Location/Qualifiers
REGION                  1..252
                        note = Engineered Variant of Kred from Lactobacillus kefir
source                  1..252
                        mol_type = protein
                        organism = synthetic construct
SEQUENCE: 276
MTDRLKQKVA IITGGTMGIG LAIADKFVEE GAKVVITGRH ADVGEKAAKS IGGSDVIRFV    60
QHDASEEAGW TKLFDTTEEA FGPVTTLVNN AGIGVIKSVE RTTTEEWRKV LSVNLDGVFF    120
GTRLGIQRMK NKGLGASIIN MSSIMGLVGD PTLGAYNASK GAVRIMSKSA ALDCALKDYD    180
VRVNTVHPGA IKTERKDQLE GWEEMMSQRT LTPMGHIGEP NDIAWICVYL ASDESKFATG    240
AEFVVDGGYT AQ                                                        252

SEQ ID NO: 277          moltype = DNA   length = 756
FEATURE                 Location/Qualifiers
misc_feature            1..756
                        note = Engineered Variant of Kred from Lactobacillus kefir
source                  1..756
                        mol_type = other DNA
                        organism = synthetic construct
SEQUENCE: 277
atgaccgatc gtctgaagca caaagtagcc atcgttaccg gcgggacaat gggtatcggt    60
ttggcaatcg ccgataaatt tgtagaggag ggtgcgaaag tagttattac tggtcgtcac    120
gcggatgtag gtgaaaaagc cgccaaatca atcggtggca ctgatgttat tcgcttttgtc   180
cagcacgatg cgtcggaaga agcaggctgg acgtcgctgt tcgacaccac cgaggaggca    240
ttcggcccgg ttacgaccct ggtgaacaat gcagggattg gggttattaa aagcgttgaa    300
cggactacca cggaggaatg gcgtaaagtt ctgtccgtta atctggatgg tgttttttc     360
ggcaccgtc  tgggcattca gcgcatgaaa aataaaggct tgggcgctag catcatcaat    420
atgagcagta ttatggggat ggtaggcgat ccgatgctgg gggcatacaa cgcttccaag    480
ggggcggtac gtatcatgtc gaaaagcgca gcgctggatt gcgcactgaa ggactacgat    540
gtgcgtgtca acacagtaca tccgggcgcg atcaagaccg aacggaagga tcagctggaa    600
ggttgggagg agatgatgtc acagcgtacg ctgaccccta tgggccacat tggcgaaccg    660
aatgacatcg catggatctg tgtgtacctg gcgtctgacg aatcgaaatt tgcgacgggt    720
gcagaatttg tggtcgacgg cgggtacacc gcacag                              756

SEQ ID NO: 278          moltype = AA   length = 252
FEATURE                 Location/Qualifiers
REGION                  1..252
                        note = Engineered Variant of Kred from Lactobacillus kefir
source                  1..252
                        mol_type = protein
                        organism = synthetic construct
SEQUENCE: 278
MTDRLKHKVA IVTGGTMGIG LAIADKFVEE GAKVVITGRH ADVGEKAAKS IGGTDVIRFV    60
QHDASEEAGW TSLFDTTEEA FGPVTTLVNN AGIGVIKSVE RTTTEEWRKV LSVNLDGVFF    120
GTRLGIQRMK NKGLGASIIN MSSIMGMVGD PMLGAYNASK GAVRIMSKSA ALDCALKDYD    180
VRVNTVHPGA IKTERKDQLE GWEEMMSQRT LTPMGHIGEP NDIAWICVYL ASDESKFATG    240
AEFVVDGGYT AQ                                                        252

SEQ ID NO: 279          moltype = DNA   length = 756
FEATURE                 Location/Qualifiers
misc_feature            1..756
                        note = Engineered Variant of Kred from Lactobacillus kefir
source                  1..756
                        mol_type = other DNA
                        organism = synthetic construct
SEQUENCE: 279
atgaccgatc gtctgaagca taaagtagcc atcgttaccg gcgggacaat gggtatcggt    60
ttggcaatcg ccgataaatt tgtagaggag ggtgcgaaag tagttattac tggtcgtgag    120
gcggatgtag gtgaaaaagc cgccaaatca atcggcggca ctgatgttat tcgcttttgtc   180
cagcacgatg cgtccgaaga agcaggctgg acgaaactgt tcgacaccac cgaggaggca    240
ttcggcccgg ttacgaccct ggtgaacaat gcagggattg gggttattaa aagcgttgaa    300
cggactacca cggaggaatg gcgtaaagtt ctgtccgtta atctggatgg tgttttttc     360
ggcaccgtc  tgggcattca gcgcatgaaa aataaaggct tgggcgctag catcatcaat    420
atgagcagta ttatggggct cgtaggcgat ccgactctgg gggcatacaa cgcttccaag    480
ggggcggtac gtatcatgtc gaaaagcgca gcgctggatt gcgcactgaa ggacatgat     540
gtgcgtgtca acacagtaca tccgggcgcg atcaagaccg aacggaagga tcagctggaa    600
ggttgggagg aaatgatgtc acagcgtacg ctgaccccta tgggccacat tggcgaaccg    660
```

```
aatgacatcg catggatctg tgtgtacctg gcgtctgacg aatcgaaatt tgcgacgggt    720
gcagaatttg tggtcgacgg cgggtggacc gcacag                              756

SEQ ID NO: 280          moltype = AA  length = 252
FEATURE                 Location/Qualifiers
REGION                  1..252
                        note = Engineered Variant of Kred from Lactobacillus kefir
source                  1..252
                        mol_type = protein
                        organism = synthetic construct
SEQUENCE: 280
MTDRLKHKVA IVTGGTMGIG LAIADKFVEE GAKVVITGRE ADVGEKAAKS IGGTDVIRFV     60
QHDASEEAGW TKLFDTTEEA FGPVTTLVNN AGIGVIKSVE RTTTEEWRKV LSVNLDGVFF    120
GTRLGIQRMK NKGLGASIIN MSSIMGLVGD PTLGAYNASK GAVRIMSKSA ALDCALKDMD    180
VRVNTVHPGA IKTERKDQLE GWEEMMSQRT LTPMGHIGEP NDIAWICVYL ASDESKFATG    240
AEFVVDGGWT AQ                                                        252

SEQ ID NO: 281          moltype = DNA  length = 756
FEATURE                 Location/Qualifiers
misc_feature            1..756
                        note = Engineered Variant of Kred from Lactobacillus kefir
source                  1..756
                        mol_type = other DNA
                        organism = synthetic construct
SEQUENCE: 281
atgaccgacc gtctgaagca caaagtagcc atcgttaccg gcgggacaat gggtatcggt     60
ttggcaatcg ccgataaatt tgtagaggag ggtgcgaaag tagttattac tggtcgtcac    120
gcggatgtag gtgaaaaagc cgccaaatca atcggtggca gtgatgttat tcgctttgtc    180
cagcacgatg cgtcggaaga agcaggctgg acgtcgctgt tcgacaccac cgaggaggca    240
ttcggcccgg ttacgaccct ggtgaacaat gcagggattg gggttattaa aagcgttgaa    300
cggactacga cggaggaatg gcgtaaagtt ctgtccgtta atctggatgg tgtttttttc    360
ggcacccgtc tgggcattca gcgcatgaaa aataaaggct gggcgctag catcatcaat    420
atgagcagta ttatggggct ggtaggcgat ccgactctgg gggcatacaa cgcttccaag    480
ggggcggtac gtatcatgtc gaaaagcgca gcgctggatt gcgcactgaa ggacatggat    540
gtgcgtgtca acacagtaca tccggggcgg atcaagaccg aacggaagga tcagctggaa    600
ggttgggagg agatgatgtc acagcgtacg ctgaccccta tgggccacat tggcgaaccg    660
aatgacatcg catggatctg tgtgtacctg gcgtctgacg aatcgaaatt tgcgacgggt    720
gcagaatttg tggtcgacgg cgggtggacc gcacag                              756

SEQ ID NO: 282          moltype = AA  length = 252
FEATURE                 Location/Qualifiers
REGION                  1..252
                        note = Engineered Variant of Kred from Lactobacillus kefir
source                  1..252
                        mol_type = protein
                        organism = synthetic construct
SEQUENCE: 282
MTDRLKHKVA IVTGGTMGIG LAIADKFVEE GAKVVITGRH ADVGEKAAKS IGGSDVIRFV     60
QHDASEEAGW TSLFDTTEEA FGPVTTLVNN AGIGVIKSVE RTTTEEWRKV LSVNLDGVFF    120
GTRLGIQRMK NKGLGASIIN MSSIMGLVGD PTLGAYNASK GAVRIMSKSA ALDCALKDMD    180
VRVNTVHPGA IKTERKDQLE GWEEMMSQRT LTPMGHIGEP NDIAWICVYL ASDESKFATG    240
AEFVVDGGWT AQ                                                        252

SEQ ID NO: 283          moltype = DNA  length = 756
FEATURE                 Location/Qualifiers
misc_feature            1..756
                        note = Engineered Variant of Kred from Lactobacillus kefir
source                  1..756
                        mol_type = other DNA
                        organism = synthetic construct
SEQUENCE: 283
atgaccgacc gtctgaagca gaaagtagcc atcgttaccg gcgggacaat gggtatcggt     60
ttggcaatcg ccgataaatt tgtagaggag ggtgcgaaag tagttattac tggtcgtcac    120
gcggatgtag gtgaaaaagc cgccaaatca atcggcggca ctgatgttat tcgctttgtc    180
cagcacgatg cgtccgaaga agcaggctgg acgaaactgt tcgacaccac cgaggaggca    240
ttcggcccgg ttacgaccct ggtgaacaat gcagggattg gggttattaa aagcgttgaa    300
cggactacca cggaggaatg gcgtaaagtt ctgtccgtta atctggatgg tgtttttttc    360
ggcacccgtc tgggcattca gcgcatgaaa aataaaggct gggcgctag catcatcaat    420
atgagcagta ttatggggct ggtaggcgat ccgatgctgg ggcatacaa cgcttccaag    480
ggggcggtac gtatcatgtc gaaaagcgca gcgctggatt gcgcactgaa ggacatggat    540
gtgcgtgtca acacagtaca tccggggcgcg atcaagaccg aacggaagga tcagctggaa    600
ggttgggagg aaatgatgtc acagcgtacg ctgaccccta tgggccacat tggcgaaccg    660
aatgacatcg catggatctg tgtgtacctg gcgtctgacg aatcgaaatt tgcgacgggt    720
gcagaatttg tggtcgacgg cgggtggacc gcacag                              756

SEQ ID NO: 284          moltype = AA  length = 252
FEATURE                 Location/Qualifiers
REGION                  1..252
                        note = Engineered Variant of Kred from Lactobacillus kefir
```

| | | |
|---|---|---|
| source | 1..252 | |
| | mol_type = protein | |
| | organism = synthetic construct | |

SEQUENCE: 284
```
MTDRLKQKVA IVTGGTMGIG LAIADKFVEE GAKVVITGRH ADVGEKAAKS IGGTDVIRFV  60
QHDASEEAGW TKLFDTTEEA FGPVTTLVNN AGIGVIKSVE RTTTEEWRKV LSVNLDGVFF 120
GTRLGIQRMK NKGLGASIIN MSSIMGLVGD PMLGAYNASK GAVRIMSKSA ALDCALKDMD 180
VRVNTVHPGA IKTERKDQLE GWEEMMSQRT LTPMGHIGEP NDIAWICVYL ASDESKFATG 240
AEFVVDGGWT AQ                                                    252
```

| | | |
|---|---|---|
| SEQ ID NO: 285 | moltype = DNA   length = 756 | |
| FEATURE | Location/Qualifiers | |
| misc_feature | 1..756 | |
| | note = Engineered Variant of Kred from Lactobacillus kefir | |
| source | 1..756 | |
| | mol_type = other DNA | |
| | organism = synthetic construct | |

SEQUENCE: 285
```
atgaccgatc gtctgaagca caaagtagcc atcgtcaccg gcgggacaat gggtatcggt  60
ttggcaatcg ccgataaatt tgtagaggag ggtgcgaaag tagttattac tggtcgtcac 120
gcggatgtag gtctgaaagc cgccaaatca atcggtggca gtgatgttat tcgctttgtc 180
cagcacgatg cgtccgaaga agcaggctgg acgagtctgt tcgacaccac cgaggaggca 240
ttcggcccgg ttacgaccct ggtgaacaat gcagggattg gggtaattaa gagcgttgaa 300
cggactacca cggaggaatg gcgtaaagtt ctgtccgtta atctggatgg tgttttttc 360
ggcacccgtc tgggcattca gcgcatgaaa aataaaggct gggcgctag catcatcaat 420
atgagcagta ttatggggct ggtagcgtat ccggcggccg ggcatacaa cgcttccaag 480
ggggcggtac gtatcatgtc gaaaagcgca gcgctggatt gcgcactgaa ggactacgat 540
gtgcgtgtca acacagtaca tccgggcgcg atcaagaccg agcggaagga tcagctggaa 600
ggttgggagc aggcaatgtc acagcgtacg gcgaccccta tgggccacat tggcgaaccg 660
aatgacatcg catggatctg tgtgtacctg gcatctgacg aatcgaaatt tgcgacgggt 720
gcagaatttg tggtcgacgg cgggtggacc gcacag                           756
```

| | | |
|---|---|---|
| SEQ ID NO: 286 | moltype = AA   length = 252 | |
| FEATURE | Location/Qualifiers | |
| REGION | 1..252 | |
| | note = Engineered Variant of Kred from Lactobacillus kefir | |
| source | 1..252 | |
| | mol_type = protein | |
| | organism = synthetic construct | |

SEQUENCE: 286
```
MTDRLKHKVA IVTGGTMGIG LAIADKFVEE GAKVVITGRH ADVGLKAAKS IGGSDVIRFV  60
QHDASEEAGW TSLFDTTEEA FGPVTTLVNN AGIGVIKSVE RTTTEEWRKV LSVNLDGVFF 120
GTRLGIQRMK NKGLGASIIN MSSIMGLVGY PAAGAYNASK GAVRIMSKSA ALDCALKDYD 180
VRVNTVHPGA IKTERKDQLE GWEQAMSQRT ATPMGHIGEP NDIAWICVYL ASDESKFATG 240
AEFVVDGGWT AQ                                                    252
```

| | | |
|---|---|---|
| SEQ ID NO: 287 | moltype = DNA   length = 756 | |
| FEATURE | Location/Qualifiers | |
| misc_feature | 1..756 | |
| | note = Engineered Variant of Kred from Lactobacillus kefir | |
| source | 1..756 | |
| | mol_type = other DNA | |
| | organism = synthetic construct | |

SEQUENCE: 287
```
atgaccgatc gtctgaagca caaagtagcc atcgtcaccg gcgggacaat gggtatcggt  60
ttggcaatcg ccgataaatt tgtagaggag ggtgcgaaag tagttattac tggtcgtcac 120
gcggatgtag gtctgaaagc cgccaaatca atcggtggca gtgatgttat tcgctttgtc 180
cagcacgatg cgtccgaaga agcaggctgg acgagtctgt tcgacaccac cgaggaggca 240
ttcggcccgg ttacgaccct ggtgaacaat gcagggattg gggtaattaa aagcgttgaa 300
cggactacca cggaggaatg gcgtaaagtt ctgtccgtta atctggatgg tgttttttc 360
ggcacccgtc tgggcattca gcgcatgaaa aataaaggct gggcgctag catcatcaat 420
atgagcagta ttatggggct ggtaggctat ccgtcggccg ggcatacaa cgcttccaag 480
ggggcggtac gtatcatgtc gaaaagcgca gcgctggatt gcgcactgaa ggactacgat 540
gtgcgtgtca acacagtaca tccgggcgcg atcaagaccg agcggaagga tcagctggaa 600
ggttgggagc aggcaatgtc acagcgtacg gcgaccccta tgggccacat tggcgaaccg 660
aatgacatcg catggatctg tgtgtacctg gcatctgacg aatcgaaatt tgcgacgggt 720
gcagaatttg tggtcgacgg cgggtggacc gcacag                           756
```

| | | |
|---|---|---|
| SEQ ID NO: 288 | moltype = AA   length = 252 | |
| FEATURE | Location/Qualifiers | |
| REGION | 1..252 | |
| | note = Engineered Variant of Kred from Lactobacillus kefir | |
| source | 1..252 | |
| | mol_type = protein | |
| | organism = synthetic construct | |

SEQUENCE: 288
```
MTDRLKHKVA IVTGGTMGIG LAIADKFVEE GAKVVITGRH ADVGLKAAKS IGGSDVIRFV  60
QHDASEEAGW TSLFDTTEEA FGPVTTLVNN AGIGVIKSVE RTTTEEWRKV LSVNLDGVFF 120
GTRLGIQRMK NKGLGASIIN MSSIMGLVGY PSAGAYNASK GAVRIMSKSA ALDCALKDYD 180
```

```
VRVNTVHPGA IKTERKDQLE GWEQAMSQRT ATPMGHIGEP NDIAWICVYL ASDESKFATG  240
AEFVVDGGWT AQ                                                      252

SEQ ID NO: 289           moltype = DNA  length = 756
FEATURE                  Location/Qualifiers
misc_feature             1..756
                         note = Engineered Variant of Kred from Lactobacillus kefir
source                   1..756
                         mol_type = other DNA
                         organism = synthetic construct
SEQUENCE: 289
atgaccgatc gtctgaagca caaagtagcc atcgtcaccg cgggacaat gggtatcggt   60
ttggcaatcg ccgataaatt tgtagaggag ggtgcgaaag tagttattac tggtcgtcac  120
gcggatgtag gtctgaaagc cgccaaatca atcggtggca gtgatgttat tcgctttgtc  180
cagcacgatg cgtccgaaga agcaggctgg acgagtctgt tcgacaccac cgaggaggca  240
ttcggcccgg ttacgaccct ggtgaacaat gcagggattg gggtaattaa gagcgttgaa  300
cggactacca cggaggaatg gcgtaaagtt ctgtccgtta atctggatgg tgttttttc   360
ggcacccgtc tgggcattca gcgcatgaaa aataaaggct gggcgctag catcatcaat  420
atgagcagta ttatgggct ggtaggcgct ccgatggcag gggcataca cgcttccaag   480
ggggcggtac gtatcatgtc gaaaagcgca gcgctggatt gcgcactgaa ggactacgat  540
gtgcgtgtca acacagtaca tccgggcgcg atcaagacct cggctaaaga tcagctgaa   600
ggttgggagc aggcaatgtc acagcgtacg gcgaccccta tggcacacat ggcgaaccg   660
aatgacatcg catggatctg tgtgtacctg gcatctgacg aatcgaaatt tgcgacgggt  720
gcagaatttg tggtcgacgg cgggtggacc gcacag                            756

SEQ ID NO: 290           moltype = AA  length = 252
FEATURE                  Location/Qualifiers
REGION                   1..252
                         note = Engineered Variant of Kred from Lactobacillus kefir
source                   1..252
                         mol_type = protein
                         organism = synthetic construct
SEQUENCE: 290
MTDRLKHKVA IVTGGTMGIG LAIADKFVEE GAKVVITGRH ADVGLKAAKS IGGSDVIRFV   60
QHDASEEAGW TSLFDTTEEA FGPVTTLVNN AGIGVIKSVE RTTTEEWRKV LSVNLDGVFF  120
GTRLGIQRMK NKGLGASIIN MSSIMGLVGA PMAGAYNASK GAVRIMSKSA ALDCALKDYD  180
VRVNTVHPGA IKTSAKDQLE GWEQAMSQRT ATPMGHIGEP NDIAWICVYL ASDESKFATG  240
AEFVVDGGWT AQ                                                      252

SEQ ID NO: 291           moltype = DNA  length = 756
FEATURE                  Location/Qualifiers
misc_feature             1..756
                         note = Engineered Variant of Kred from Lactobacillus kefir
source                   1..756
                         mol_type = other DNA
                         organism = synthetic construct
SEQUENCE: 291
atgaccgatc gtctgaagca caaagtagcc atcgtcaccg cgggacaat gggtatcggt   60
ttggcaatcg ccgataaatt tgtagaggag ggtgcgaaag tagttattac tggtcgtcac  120
gcggatgtag gtctgaaagc cgccaaatca atcggtggca gtgatgttat tcgctttgtc  180
cagcacgatg cgtccgaaga agcaggctgg acgagtctgt tcgacaccac cgaggaggca  240
ttcggcccgg ttacgaccct ggtgaacaat gcagccgagg cgtcattaa gagcgttgaa   300
cggactacca cggaggaatg gcgtaaagtt ctgtccgtta atctggatgg tgttttttc   360
ggcacccgtc tgggcattca gcgcatgaaa aataaaggct gggcgctag catcatcaat  420
atgagcagta ttatgggct ggtaggcgct ccgatggcag gggcataca cgcttccaag   480
ggggcggtac gtatcatgtc gaaaagcgca gcgctggatt gcgcactgaa ggactacgat  540
gtgcgtgtca acacagtaca tccgggcgcg atcaagaccg agcggaagga tcagctggaa  600
ggttgggagc aggcaatgtc acagcgtacg gcgaccccta tggcacacat ggcgaaccg   660
aatgacatcg catggatctg tgtgtacctg gcatctgacg aatcgaaatt tgcgacgggt  720
gcagaatttg tggtcgacgg cgggtggacc gcacag                            756

SEQ ID NO: 292           moltype = AA  length = 252
FEATURE                  Location/Qualifiers
REGION                   1..252
                         note = Engineered Variant of Kred from Lactobacillus kefir
source                   1..252
                         mol_type = protein
                         organism = synthetic construct
SEQUENCE: 292
MTDRLKHKVA IVTGGTMGIG LAIADKFVEE GAKVVITGRH ADVGLKAAKS IGGSDVIRFV   60
QHDASEEAGW TSLFDTTEEA FGPVTTLVNN AAEGVIKSVE RTTTEEWRKV LSVNLDGVFF  120
GTRLGIQRMK NKGLGASIIN MSSIMGLVGA PMAGAYNASK GAVRIMSKSA ALDCALKDYD  180
VRVNTVHPGA IKTERKDQLE GWEQAMSQRT ATPMGHIGEP NDIAWICVYL ASDESKFATG  240
AEFVVDGGWT AQ                                                      252

SEQ ID NO: 293           moltype = DNA  length = 756
FEATURE                  Location/Qualifiers
misc_feature             1..756
                         note = Engineered Variant of Kred from Lactobacillus kefir
```

```
source                  1..756
                        mol_type = other DNA
                        organism = synthetic construct
SEQUENCE: 293
atgaccgatc gtctgaagca caaagtagcc atcgtcaccg gcgggacaat gggtatcggt    60
ttggcaatcg ccgataaatt tgtagaggag ggtgcgaaag tagttattac tggtcgtcac   120
gcggatgtag gtctgaaagc cgccaaatca atcggtggca gtgatgttat tcgctttgtc   180
cagcacgatg cgtccgaaga agcaggctgg acgagtctgt tcgacaccac cgaggaggca   240
ttcggcccgg ttacgaccct ggtgaacaat gcagggttg gggtaattaa aagcgttgaa    300
cggactacca cggaggaatg gcgtaaagtt ctgtccgtta atctggatgg tgttttttc    360
ggcacccgtc tgggcattca gcgcatgaaa aataaaggct tgggcgctag catcatcaat   420
atgagcagta ttatggggct ggtaggcgat ccggcgctgg ggcatacaa cgcttccaag    480
ggggcggtac gtatcatgtc gaaaagcgca gcgctggatt gcgcactgaa ggactacgat   540
gtgcgtgtca acacagtaca tccgggcgcg atcaagaccg agcggaagga tcagctggaa   600
ggttgggagc aggcaatgtc acagcgtacg gcgaccccta tgggccacat tggcgaaccg   660
aatgacatcg catggatctg tgtgtacctg gcatctgacg aatcgaaatt tgcgacgggt   720
gcagaatttg tggtcgacgg cgggtggacc gcacag                            756

SEQ ID NO: 294         moltype = AA   length = 252
FEATURE                Location/Qualifiers
REGION                 1..252
                       note = Engineered Variant of Kred from Lactobacillus kefir
source                 1..252
                       mol_type = protein
                       organism = synthetic construct
SEQUENCE: 294
MTDRLKHKVA IVTGGTMGIG LAIADKFVEE GAKVVITGRH ADVGLKAAKS IGGSDVIRFV    60
QHDASEEAGW TSLFDTTEEA FGPVTTLVNN AGIGVIKSVE RTTTEEWRKV LSVNLDGVFF   120
GTRLGIQRMK NKGLGASIIN MSSIMGLVGD PALGAYNASK GAVRIMSKSA ALDCALKDYD   180
VRVNTVHPGA IKTERKDQLE GWEQAMSQRT ATPMGHIGEP NDIAWICVYL ASDESKFATG   240
AEFVVDGGWT AQ                                                      252

SEQ ID NO: 295         moltype = DNA   length = 756
FEATURE                Location/Qualifiers
misc_feature           1..756
                       note = Engineered Variant of Kred from Lactobacillus kefir
source                 1..756
                       mol_type = other DNA
                       organism = synthetic construct
SEQUENCE: 295
atgaccgacc gtctgaagca caaagtagcc atcattaccg gcgggacaat gggtatcggt    60
ttggcaatcg ccgataaatt tgtagaggag ggtgcgaaag tagttattac tggtcgtcac   120
gcggatgtag gtgaaaaagc cgccaaatca atcggtggca gtgatgttat tcgctttgtc   180
cagcacgatg cgtcggaaga agcaggctgg acgacgctgt tcgacaccac cgaggaggca   240
ttcggcccgg ttacgaccct ggtgaacaat gcaggtgatg gccgtattaa aagcgttgaa   300
cggactacca cggaggaatg gcgtaaagtt ctgtccgtta atctggatgg tgttttttc    360
ggcacccgtc tgggcattca gcgcatgaaa aataaaggct gggcgctag catcatcaat    420
atgagcagta ttatggggct cgtaggcgat ccgatgctgg ggcatacaa cgcttccaag    480
ggggcggtac gtatcatgtc gaaaagcgca gcgctggatt gcgcactgaa ggactacgat   540
gtgcgtgtca acacagtaca tccgggcgcg atcaagaccg aacggaagga tcagctgaa    600
ggttgggagg agatgatgtc acagcgtacg ctgaccccta tgggccacat tggcgaaccg   660
aatgacatcg catggatctg tgtgtacctg gcgtctgacg aatcgaaatt tgcgacgggt   720
gcagaatttg tggtcgacgg cgggtacacc gcacag                            756

SEQ ID NO: 296         moltype = AA   length = 252
FEATURE                Location/Qualifiers
REGION                 1..252
                       note = Engineered Variant of Kred from Lactobacillus kefir
source                 1..252
                       mol_type = protein
                       organism = synthetic construct
SEQUENCE: 296
MTDRLKHKVA IITGGTMGIG LAIADKFVEE GAKVVITGRH ADVGEKAAKS IGGSDVIRFV    60
QHDASEEAGW TTLFDTTEEA FGPVTTLVNN AGDGRIKSVE RTTTEEWRKV LSVNLDGVFF   120
GTRLGIQRMK NKGLGASIIN MSSIMGLVGD PMLGAYNASK GAVRIMSKSA ALDCALKDYD   180
VRVNTVHPGA IKTERKDQLE GWEEMMSQRT LTPMGHIGEP NDIAWICVYL ASDESKFATG   240
AEFVVDGGYT AQ                                                      252

SEQ ID NO: 297         moltype = DNA   length = 756
FEATURE                Location/Qualifiers
misc_feature           1..756
                       note = Engineered Variant of Kred from Lactobacillus kefir
source                 1..756
                       mol_type = other DNA
                       organism = synthetic construct
SEQUENCE: 297
atgaccgacc gtctgaagca caaagtagcc atcattaccg gcgggacaat gggtatcggt    60
ttggcaatcg ccgataaatt tgtagaggag ggtgcgaaag tagttattac tggtcgtcac   120
gcggatgtag gtgaaaaagc cgccaaatca atcggtggca gtgatgttat tcgctttgtc   180
```

```
cagcacgatg cgtcggaaga agcaggctgg acgacgctgt tcgacaccac cgaggaggca  240
ttcggcccgg ttacgaccct ggtgaacaat gcaggtgctg gcaaaattaa aagcgttgaa  300
cggactacca cggaggaatg gcgtcgtgtt ctgtccgtga atctggatgg tgttttttc   360
ggcacccgtc tgggcattca gcgcatgaaa aataaaggct tgggcgctag catcatcaat  420
atgagcagta ttatggggct cgtaggcgat ccgatgctgg gggcatacaa cgcttccaag  480
ggggcggtac gtatcatgtc gaaaagcgca gcgctggatt gcgcactgaa ggactacgat  540
gtgcgtgtca acacagtaca tccgggcgcg atcaagaccg aacggaagga tcagctggaa  600
ggttgggagg agatgatgtc acagcgtacg ctgaccccta tgggccacat tggcgaaccg  660
aatgacatcg catggatctg tgtgtacctg gcgtctgacg aatcgaaatt tgcgacgggt  720
gcagaatttg tggtcgacgg cgggtacacc gcacag                            756
```

```
SEQ ID NO: 298          moltype = AA  length = 252
FEATURE                 Location/Qualifiers
REGION                  1..252
                        note = Engineered Variant of Kred from Lactobacillus kefir
source                  1..252
                        mol_type = protein
                        organism = synthetic construct
SEQUENCE: 298
MTDRLKHKVA IITGGTMGIG LAIADKFVEE GAKVVITGRH ADVGEKAAKS IGGSDVIRFV   60
QHDASEEAGW TTLFDTTEEA FGPVTTLVNN AGAGKIKSVE RTTTEEWRRV LSVNLDGVFF  120
GTRLGIQRMK NKGLGASIIN MSSIMGLVGD PMLGAYNASK GAVRIMSKSA ALDCALKDYD  180
VRVNTVHPGA IKTERKDQLE GWEEMMSQRT LTPMGHIGEP NDIAWICVYL ASDESKFATG  240
AEFVVDGGYT AQ                                                     252
```

```
SEQ ID NO: 299          moltype = DNA  length = 756
FEATURE                 Location/Qualifiers
misc_feature            1..756
                        note = Engineered Variant of Kred from Lactobacillus kefir
source                  1..756
                        mol_type = other DNA
                        organism = synthetic construct
SEQUENCE: 299
atgaccgacc gtctgaagca caaagtagcc atcattaccg gcgggacaat gggtatcggt   60
ttggcaatcg ccgataaatt tgtagaggag ggtgcgaaag tagttattac tggtcgtcac  120
gcggatgtag gtgaaaaagc cgccaaatca atcggtggca gtgatgttat tcgcttttgtc 180
cagcacgatg cgtcggaaga agcaggctgg acgacgctgt tcgacaccac cgaggaggca  240
ttcggcccgg ttacgaccct ggtgaacaat gcaggtgctg gccgtattaa aagcgttgaa  300
cggactacca cggaggaatg gcgtgatgtt ctgtccgtga atctggatgg tgttttttc   360
ggcacccgtc tgggcattca gcgcatgaaa aataaaggct tgggcgctag catcatcaat  420
atgagcagta ttatggggct cgtaggcgat ccgatgctgg gggcatacaa cgcttccaag  480
ggggcggtac gtatcatgtc gaaaagcgca gcgctggatt gcgcactgaa ggactacgat  540
gtgcgtgtca acacagtaca tccgggcgcg atcaagaccg aacggaagga tcagctggaa  600
ggttgggagg agatgatgtc acagcgtacg ctgaccccta tgggccacat tggcgaaccg  660
aatgacatcg catggatctg tgtgtacctg gcgtctgacg aatcgaaatt tgcgacgggt  720
gcagaatttg tggtcgacgg cgggtacacc gcacag                            756
```

```
SEQ ID NO: 300          moltype = AA  length = 252
FEATURE                 Location/Qualifiers
REGION                  1..252
                        note = Engineered Variant of Kred from Lactobacillus kefir
source                  1..252
                        mol_type = protein
                        organism = synthetic construct
SEQUENCE: 300
MTDRLKHKVA IITGGTMGIG LAIADKFVEE GAKVVITGRH ADVGEKAAKS IGGSDVIRFV   60
QHDASEEAGW TTLFDTTEEA FGPVTTLVNN AGAGRIKSVE RTTTEEWRDV LSVTLDGVFF  120
GTRLGIQRMK NKGLGASIIN MSSIMGLVGD PMLGAYNASK GAVRIMSKSA ALDCALKDYD  180
VRVNTVHPGA IKTERKDQLE GWEEMMSQRT LTPMGHIGEP NDIAWICVYL ASDESKFATG  240
AEFVVDGGYT AQ                                                     252
```

```
SEQ ID NO: 301          moltype = DNA  length = 756
FEATURE                 Location/Qualifiers
misc_feature            1..756
                        note = Engineered Variant of Kred from Lactobacillus kefir
source                  1..756
                        mol_type = other DNA
                        organism = synthetic construct
SEQUENCE: 301
atgaccgacc gtctgaagca caaagtagcc atcattaccg gcgggacaat gggtatcggt   60
ttggcaatcg ccgataaatt tgtagaggag ggtgcgaaag tagttattac tggtcgtcac  120
gcggatgtag gtgaaaaagc cgccaaatca atcggtggca gtgatgttat tcgcttttgtc 180
cagcacgatg cgtcggaaga agcaggctgg acgacgctgt tcgacaccac cgaggaggca  240
ttcggcccgg ttacgaccct ggtgaacaat gcaggtgctg gccgtattaa aagcgttgaa  300
cggactacca cggaggaatg gcgtaaagtt ctgtccgtga cgctggatgg tgttttttc   360
ggcacccgtc tgggcattca gcgcatgaaa aataaaggct tgggcgctag catcatcaat  420
atgagcagta ttatggggct cgtaggcgat ccgatgctgg gggcatacaa cgcttccaag  480
ggggcggtac gtatcatgtc gaaaagcgca gcgctggatt gcgcactgaa ggactacgat  540
gtgcgtgtca acacagtaca tccgggcgcg atcaagaccg aacggaagga tcagctggaa  600
```

```
ggttgggagg agatgatgtc acagcgtacg ctgacccta tgggccacat tggcgaaccg  660
aatgacatcg catggatctg tgtgtacctg gcgtctgacg aatcgaaatt tgcgacgggt  720
gcagaatttg tggtcgacgg cgggtacacc gcacag                            756

SEQ ID NO: 302          moltype = AA   length = 252
FEATURE                 Location/Qualifiers
REGION                  1..252
                        note = Engineered Variant of Kred from Lactobacillus kefir
source                  1..252
                        mol_type = protein
                        organism = synthetic construct
SEQUENCE: 302
MTDRLKHKVA IITGGTMGIG LAIADKFVEE GAKVVITGRH ADVGEKAAKS IGGSDVIRFV   60
QHDASEEAGW TTLFDTTEEA FGPVTTLVNN AGRGAIKSVE RTTTEEWRKV LSVTLDGVFF  120
GTRLGIQRMK NKGLGASIIN MSSIMGLVGD PMLGAYNASK GAVRIMSKSA ALDCALKDYD  180
VRVNTVHPGA IKTERKDQLE GWEEMMSQRT LTPMGHIGEP NDIAWICVYL ASDESKFATG  240
AEFVVDGGYT AQ                                                     252

SEQ ID NO: 303          moltype = DNA   length = 756
FEATURE                 Location/Qualifiers
misc_feature            1..756
                        note = Engineered Variant of Kred from Lactobacillus kefir
source                  1..756
                        mol_type = other DNA
                        organism = synthetic construct
SEQUENCE: 303
atgaccgacc gtctgaagca caaagtagcc atcattaccg gcgggacaat gggtatcggt   60
ttggcaatcg ccgataaatt tgtagaggag ggtgcgaaag tagttattac tggtcgtcac  120
gcggatgtag gtgaaaaagc cgccaaatca atcggtggca gtgatgttat tcgctttgtc  180
cagcacgatg cgtcggaaga agcaggctgg acgacgctgt tcgacaccac cgaggaggca  240
ttcggcccgg ttacgaccct ggtgaacaat gcagggatgg ggttattaa aagcgttgaa   300
cggactacca cggaggaatg gcgtaaagtt ctgtccgtta atctggatgg tgttttttc   360
ggcacccgtc tgggcattca gcgcatgaaa aataaaggct gggcgctag catcatcaat  420
atgagcagta ttatggggct cgtaggcgat ccgatgctgg gggcatacaa cgcttccaag  480
ggggcggtac gtatcatgtc gaaaagcgca gcgctggatt gcgcactgaa ggactacgat  540
gtgcgtgtca acacagtaca tccgggcgcg atcaagaccg aacggaagga tcagctggaa  600
ggttgggagg agatgatgtc acagcgtacg ctgaccccta tgggccacat tggcgaaccg  660
aatgacatcg catggatctg tgtgtacctg gcgtctgacg aatcgaaatt tgcgacgggt  720
gcagaatttg tggtcgacgg cgggtacacc gcacag                            756

SEQ ID NO: 304          moltype = AA   length = 252
FEATURE                 Location/Qualifiers
REGION                  1..252
                        note = Engineered Variant of Kred from Lactobacillus kefir
source                  1..252
                        mol_type = protein
                        organism = synthetic construct
SEQUENCE: 304
MTDRLKHKVA IITGGTMGIG LAIADKFVEE GAKVVITGRH ADVGEKAAKS IGGSDVIRFV   60
QHDASEEAGW TTLFDTTEEA FGPVTTLVNN AGMGVIKSVE RTTTEEWRKV LSVNLDGVFF  120
GTRLGIQRMK NKGLGASIIN MSSIMGLVGD PMLGAYNASK GAVRIMSKSA ALDCALKDYD  180
VRVNTVHPGA IKTERKDQLE GWEEMMSQRT LTPMGHIGEP NDIAWICVYL ASDESKFATG  240
AEFVVDGGYT AQ                                                     252

SEQ ID NO: 305          moltype = DNA   length = 756
FEATURE                 Location/Qualifiers
misc_feature            1..756
                        note = Engineered Variant of Kred from Lactobacillus kefir
source                  1..756
                        mol_type = other DNA
                        organism = synthetic construct
SEQUENCE: 305
atgaccgacc gtctgaagca caaagtagcc atcattaccg gcgggacaat gggtatcggt   60
ttggcaatcg ccgataaatt tgtagaggag ggtgcgaaag tagttattac tggtcgtcac  120
gcggatgtag gtgaaaaagc cgccaaatca atcggtggca gtgatgttat tcgctttgtc  180
cagcacgatg cgtcggaaga agcaggctgg acgacgctgt tcgacaccac cgaggaggca  240
ttcggcccgg ttacgaccct ggtgaacaat gcaggtgagg cgtcattaa aagcgttgaa   300
cggactacca cggaggaatg gcgtcgtgtt ctgtccgtgg cgctggatgg tgttttttc   360
ggcacccgtc tgggcattca gcgcatgaaa aataaaggct gggcgctag catcatcaat  420
atgagcagta ttatggggct cgtaggcgat ccgatgctgg gggcatacaa cgcttccaag  480
ggggcggtac gtatcatgtc gaaaagcgca gcgctggatt gcgcactgaa ggactacgat  540
gtgcgtgtca acacagtaca tccgggcgcg atcaagaccg aacggaagga tcagctggaa  600
ggttgggagg agatgatgtc acagcgtacg ctgaccccta tgggccacat tggcgaaccg  660
aatgacatcg catggatctg tgtgtacctg gcgtctgacg aatcgaaatt tgcgacgggt  720
gcagaatttg tggtcgacgg cgggtacacc gcacag                            756

SEQ ID NO: 306          moltype = AA   length = 252
FEATURE                 Location/Qualifiers
REGION                  1..252
```

```
                        note = Engineered Variant of Kred from Lactobacillus kefir
source                  1..252
                        mol_type = protein
                        organism = synthetic construct
SEQUENCE: 306
MTDRLKHKVA IITGGTMGIG LAIADKFVEE GAKVVITGRH ADVGEKAAKS IGGSDVIRFV    60
QHDASEEAGW TTLFDTTEEA FGPVTTLVNN AGEGVIKSVE RTTTEEWRRV LSVALDGVFF   120
GTRLGIQRMK NKGLGASIIN MSSIMGLVGD PMLGAYNASK GAVRIMSKSA ALDCALKDYD   180
VRVNTVHPGA IKTERKDQLE GWEEMMSQRT LTPMGHIGEP NDIAWICVYL ASDESKFATG   240
AEFVVDGGYT AQ                                                      252

SEQ ID NO: 307          moltype = DNA  length = 756
FEATURE                 Location/Qualifiers
misc_feature            1..756
                        note = Engineered Variant of Kred from Lactobacillus kefir
source                  1..756
                        mol_type = other DNA
                        organism = synthetic construct
SEQUENCE: 307
atgaccgacc gtctgaagca caaagtagcc atcattaccg gcgggacaat gggtatcggt    60
ttggcaatcg ccgataaatt tgtagaggag ggtgcgaaag tagttattac tggtcgtcac   120
gcggatgtag gtgaaaaagc cgccaaatca atcggtggca gtgatgttat tcgctttgtc   180
cagcacgatg cgtcggaaga agcaggctgg acgacgctgt tcgacaccac cgaggaggca   240
ttcggcccgg ttacgaccct ggtgaacaat gcagggattg ggttattaa aagcgttgaa    300
cggactacca cggaggaatg gcgtaaagtt ctgtccgtgg cgctggatgg tgttttttc    360
ggcacccgtc tgggcattca gcgcatgaaa aataaaggct gggcgctag catcatcaat   420
atgagcagta ttatggggct cgtaggcgat ccgatgctgg gggcatacaa cgcttccaag   480
ggggcggtac gtatcatgtc gaaaagcgca gcgctggatt gcgcactgaa ggactacgat   540
gtgcgtgtca acacagtaca tccgggcgcg atcaagaccg aacggaagga tcagctgaa    600
ggttgggagg agatgatgtc acagcgtacg ctgacccta tgggcacat tggcgaaccg    660
aatgacatcg catggatctg tgtgtacctg gcgtctgacg aatcgaaatt tgcgacgggt   720
gcagaatttg tggtcgacgg cgggtacacc gcacag                            756

SEQ ID NO: 308          moltype = AA  length = 252
FEATURE                 Location/Qualifiers
REGION                  1..252
                        note = Engineered Variant of Kred from Lactobacillus kefir
source                  1..252
                        mol_type = protein
                        organism = synthetic construct
SEQUENCE: 308
MTDRLKHKVA IITGGTMGIG LAIADKFVEE GAKVVITGRH ADVGEKAAKS IGGSDVIRFV    60
QHDASEEAGW TTLFDTTEEA FGPVTTLVNN AGIGVIKSVE RTTTEEWRKV LSVALDGVFF   120
GTRLGIQRMK NKGLGASIIN MSSIMGLVGD PMLGAYNASK GAVRIMSKSA ALDCALKDYD   180
VRVNTVHPGA IKTERKDQLE GWEEMMSQRT LTPMGHIGEP NDIAWICVYL ASDESKFATG   240
AEFVVDGGYT AQ                                                      252

SEQ ID NO: 309          moltype = DNA  length = 756
FEATURE                 Location/Qualifiers
misc_feature            1..756
                        note = Engineered Variant of Kred from Lactobacillus kefir
source                  1..756
                        mol_type = other DNA
                        organism = synthetic construct
SEQUENCE: 309
atgaccgacc gtctgaagca caaagtagcc atcattaccg gcgggacaat gggtatcggt    60
ttggcaatcg ccgataaatt tgtagaggag ggtgcgaaag tagttattac tggtcgtcac   120
gcggatgtag gtgaaaaagc cgccaaatca atcggtggca gtgatgttat tcgctttgtc   180
cagcacgatg cgtcggaaga agcaggctgg acgacgctgt tcgacaccac cgaggaggca   240
ttcggcccgg ttacgaccct ggtgaacaat gcagctgatg gcgtattaa aagcgttgaa    300
cggactacca cggaggaatg gcgtaaagtt ctgtccgtta atctggatgg tgttttttc    360
ggcacccgtc tgggcattca gcgcatgaaa aataaaggct gggcgctag catcatcaat   420
atgagcagta ttatggggct cgtaggcgat ccgatgctgg gggcatacaa cgcttccaag   480
ggggcggtac gtatcatgtc gaaaagcgca gcgctggatt gcgcactgaa ggactacgat   540
gtgcgtgtca acacagtaca tccgggcgcg atcaagaccg aacggaagga tcagctgaa    600
ggttgggagg agatgatgtc acagcgtacg ctgacccta tgggcacat tggcgaaccg    660
aatgacatcg catggatctg tgtgtacctg gcgtctgacg aatcgaaatt tgcgacgggt   720
gcagaatttg tggtcgacgg cgggtacacc gcacag                            756

SEQ ID NO: 310          moltype = AA  length = 252
FEATURE                 Location/Qualifiers
REGION                  1..252
                        note = Engineered Variant of Kred from Lactobacillus kefir
source                  1..252
                        mol_type = protein
                        organism = synthetic construct
SEQUENCE: 310
MTDRLKHKVA IITGGTMGIG LAIADKFVEE GAKVVITGRH ADVGEKAAKS IGGSDVIRFV    60
QHDASEEAGW TTLFDTTEEA FGPVTTLVNN AADGRIKSVE RTTTEEWRKV LSVNLDGVFF   120
```

```
GTRLGIQRMK NKGLGASIIN MSSIMGLVGD PMLGAYNASK GAVRIMSKSA ALDCALKDYD     180
VRVNTVHPGA IKTERKDQLE GWEEMMSQRT LTPMGHIGEP NDIAWICVYL ASDESKFATG     240
AEFVVDGGYT AQ                                                        252

SEQ ID NO: 311           moltype = DNA   length = 756
FEATURE                  Location/Qualifiers
misc_feature             1..756
                         note = Engineered Variant of Kred from Lactobacillus kefir
source                   1..756
                         mol_type = other DNA
                         organism = synthetic construct
SEQUENCE: 311
atgaccgatc gtctgaagca caaagtagcc atcgtcaccg gcgggacaat gggtatcggt      60
ttggcaatcg ccgataaatt tgtagaggag ggtgcgaaag tagttattac tggtcgtcac     120
gcggatgtag gtctgaaagc cgccaaatca atcggtggca gtgatgttat tcgctttgtc     180
cagcacgatg cgtccgaaga agcaggctgg acgagtctgt tcgacaccac cgaggaggca     240
ttcggcccgg ttacgaccct ggtgaacaat gcagggattg ggtgtgccaa gagcgttgaa     300
cggactacca cggaggaatg gcgtaaagtt ctgtccgtta atctggatgg tgtttttttc     360
ggcacccgtc tgggcattca gcgcatgaaa aataaaggct tgggcgctag catcatcaat     420
atgagcagta ttatggggct ggtaggctat ccggcggccg gggcatacaa cgcttccaag     480
ggggcggtac gtatcatgtc gaaaagcgca gcgctggatt gcgcactgaa ggactacgat     540
gtgcgtgtca acacagtaca tccgggcgcg atcaagaccg agcggaagga tcagctggaa     600
ggttgggagc aggaaatgtc acagcgtacg gcgacccta tgggccacat tggcgaaccg      660
aatgacatcg catggatctg tgtgtacctg gcatctgacg aatcgaaatt tgcgacgggt     720
gcagaatttg tggtcgacgg cgggtggacc gcacag                              756

SEQ ID NO: 312           moltype = AA   length = 252
FEATURE                  Location/Qualifiers
REGION                   1..252
                         note = Engineered Variant of Kred from Lactobacillus kefir
source                   1..252
                         mol_type = protein
                         organism = synthetic construct
SEQUENCE: 312
MTDRLKHKVA IVTGGTMGIG LAIADKFVEE GAKVVITGRH ADVGLKAAKS IGGSDVIRFV      60
QHDASEEAGW TSLFDTTEEA FGPVTTLVNN AGIGVAKSVE RTTTEEWRKV LSVNLDGVFF     120
GTRLGIQRMK NKGLGASIIN MSSIMGLVGY PAAGAYNASK GAVRIMSKSA ALDCALKDYD     180
VRVNTVHPGA IKTERKDQLE GWEQAMSQRT ATPMGHIGEP NDIAWICVYL ASDESKFATG     240
AEFVVDGGWT AQ                                                        252

SEQ ID NO: 313           moltype = DNA   length = 756
FEATURE                  Location/Qualifiers
misc_feature             1..756
                         note = Engineered Variant of Kred from Lactobacillus kefir
source                   1..756
                         mol_type = other DNA
                         organism = synthetic construct
SEQUENCE: 313
atgaccgatc gtctgaagca caaagtagcc atcgtcaccg gcgggacaat gggtatcggt      60
ttggcaatcg ccgataaatt tgtagaggag ggtgcgaaag tagttattac tggtcgtcac     120
gcggatgtag gtctgaaagc cgccaaatca atcggtggca gtgatgttat tcgctttgtc     180
cagcacgatg cgtccgaaga agcaggctgg acgagtctgt tcgacaccac cgaggaggca     240
ttcggcccgg ttacgaccct ggtgaacaat gcagggattg ggtgatcaa gagcgttgaa      300
cggactacca cggaggaatg gcgtaaagtt ctgtccgtta atctggatgg tgtttttttc     360
ggcacccgtc tgggcattca gcgcatgaaa aataaaggct tgggcgctag catcatcaat     420
atgagctcga tcgcagggct ggtaggcgcc ccggccgccg gggcatacaa cgcttccaag     480
ggggcggtac gtatcatgtc gaaaagcgca gcgctggatt gcgcactgaa ggactacgat     540
gtgcgtgtca acacagtaca tccgggcgcg atcaagaccg agcggaagga tcagctggaa     600
ggttgggagc aggcaatgtc acagcgtacg gcgacccta tgggccacat tggcgaaccg      660
aatgacatcg catggatctg tgtgtacctg gcatctgacg aatcgaaatt tgcgacgggt     720
gcagaatttg tggtcgacgg cgggtggacc gcacag                              756

SEQ ID NO: 314           moltype = AA   length = 252
FEATURE                  Location/Qualifiers
REGION                   1..252
                         note = Engineered Variant of Kred from Lactobacillus kefir
source                   1..252
                         mol_type = protein
                         organism = synthetic construct
SEQUENCE: 314
MTDRLKHKVA IVTGGTMGIG LAIADKFVEE GAKVVITGRH ADVGLKAAKS IGGSDVIRFV      60
QHDASEEAGW TSLFDTTEEA FGPVTTLVNN AGIGVIKSVE RTTTEEWRKV LSVNLDGVFF     120
GTRLGIQRMK NKGLGASIIN MSSIAGLVGA PAAGAYNASK GAVRIMSKSA ALDCALKDYD     180
VRVNTVHPGA IKTERKDQLE GWEQAMSQRT ATPMGHIGEP NDIAWICVYL ASDESKFATG     240
AEFVVDGGWT AQ                                                        252

SEQ ID NO: 315           moltype = DNA   length = 756
FEATURE                  Location/Qualifiers
misc_feature             1..756
```

```
                            note = Engineered Variant of Kred from Lactobacillus kefir
source                      1..756
                            mol_type = other DNA
                            organism = synthetic construct
SEQUENCE: 315
atgaccgatc gtctgaagca caaagtagcc atcatcaccg gcgggacaat gggtatcggt    60
ttggcaatcg ccgataaatt tgtagaggag ggtgcgaaag tagttattac tggtcgtcac   120
gcggatgtag gtgagaaagc cgccaaatca atcggtggca gtgatgttat tcgctttgtc   180
cagcacgatg cgtccgaaga agcaggctgg acgagcctgt tcgacaccac cgaggaggca   240
ttcggcccgg ttacgaccct ggtgaacaat gcagggattg ggtaattaa gagcgttgaa    300
cggactacca cggaggaatg gcgtaaagtt ctgtccgtta atctggatgg tgttttttttc  360
ggcacccgtc tgggcattca gcgcatgaaa aataaaggct tgggcgctag catcatcaat   420
atgagcagta ttatggggct ggtaggctat ccggccgccg gggcatacaa cgcttccaag   480
ggggcggtac gtatcatgtc gaaaagcgca gcgctggatt gcgcactgaa ggactacgat   540
gtgcgtgtca acacagtaca tccgggcgcg atcaagaccg agcggaagga tcagctggaa   600
ggttgggagc aggcaatgtc acagcgtacg gcgaccccta tgggccacat tggcgaaccg   660
aatgacatca catggatctg tgtgtacctg gcatctgacg aatcgaaatt tgcgacgggt   720
gcagaatttg tggtcgacgg cgggtacacc gcacag                             756

SEQ ID NO: 316              moltype = AA  length = 252
FEATURE                     Location/Qualifiers
REGION                      1..252
                            note = Engineered Variant of Kred from Lactobacillus kefir
source                      1..252
                            mol_type = protein
                            organism = synthetic construct
SEQUENCE: 316
MTDRLKHKVA IITGGTMGIG LAIADKFVEE GAKVVITGRH ADVGEKAAKS IGGSDVIRFV    60
QHDASEEAGW TSLFDTTEEA FGPVTTLVNN AGIGVIKSVE RTTTEEWRKV LSVNLDGVFF   120
GTRLGIQRMK NKGLGASIIN MSSIMGLVGY PAAGAYNASK GAVRIMSKSA ALDCALKDYD   180
VRVNTVHPGA IKTERKDQLE GWEQAMSQRT ATPMGHIGEP NDIAWICVYL ASDESKFATG   240
AEFVVDGGYT AQ                                                       252

SEQ ID NO: 317              moltype = DNA  length = 756
FEATURE                     Location/Qualifiers
misc_feature                1..756
                            note = Engineered Variant of Kred from Lactobacillus kefir
source                      1..756
                            mol_type = other DNA
                            organism = synthetic construct
SEQUENCE: 317
atgaccgatc gtctgaagca caaagtagcc atcgtcaccg gcgggacaat gggtatcggt    60
ttggcaatcg ccgataaatt tgtagaggag ggtgcgaaag tagttattac tggtcgtcac   120
gcggatgtag gtgagaaagc cgccaaatca atcggtggca gtgatgttat tcgctttgtc   180
cagcacgatg cgtccgaaga agcaggctgg acgagtctgt tcgacaccac cgaggaggca   240
ttcggcccgg ttacgaccct ggtgaacaat gcagggattg ggtaattaa gagcgttgaa    300
cggactacca cggaggaatg gcgtaaagtt ctgtccgtta atctggatgg tgttttttttc  360
ggcacccgtc tgggcattca gcgcatgaaa aataaaggct tgggcgctag catcatcaat   420
atgagcagta ttatggggct ggtaggctat ccggccgccg gggcatacaa cgcttccaag   480
ggggcggtac gtatcatgtc gaaaagcgca gcgctggatt gcgcactgaa ggactacgat   540
gtgcgtgtca acacagtaca tccgggcgcg atcaagaccg agcggaagga tcagctggaa   600
ggttgggagc aggcaatgtc acagcgtacg gcgaccccta tgggccacat tggcgaaccg   660
aatgacatcg catggatctg tgtgtacctg gcatctgacg aatcgaaatt tgcgacgggt   720
gcagaatttg tggtcgacgg cgggtacacc gcacag                             756

SEQ ID NO: 318              moltype = AA  length = 252
FEATURE                     Location/Qualifiers
REGION                      1..252
                            note = Engineered Variant of Kred from Lactobacillus kefir
source                      1..252
                            mol_type = protein
                            organism = synthetic construct
SEQUENCE: 318
MTDRLKHKVA IVTGGTMGIG LAIADKFVEE GAKVVITGRH ADVGEKAAKS IGGSDVIRFV    60
QHDASEEAGW TSLFDTTEEA FGPVTTLVNN AGIGVIKSVE RTTTEEWRKV LSVNLDGVFF   120
GTRLGIQRMK NKGLGASIIN MSSIMGLVGY PAAGAYNASK GAVRIMSKSA ALDCALKDYD   180
VRVNTVHPGA IKTERKDQLE GWEQAMSQRT ATPMGHIGEP NDIAWICVYL ASDESKFATG   240
AEFVVDGGYT AQ                                                       252

SEQ ID NO: 319              moltype = DNA  length = 756
FEATURE                     Location/Qualifiers
misc_feature                1..756
                            note = Engineered Variant of Kred from Lactobacillus kefir
source                      1..756
                            mol_type = other DNA
                            organism = synthetic construct
SEQUENCE: 319
atgaccgatc gtctgaagca caaagtagcc atcgtcaccg gcgggacaat gggtatcggt    60
ttggcaatcg ccgataaatt tgtagaggag ggtgcgaaag tagttattac tggtcgtcac   120
```

```
gcggatgtag gtgagaaagc cgccaaatca atcggtggca gtgatgttat tcgctttgtc    180
cagcacgatg cgtccgaaga agcaggctgg acgagtctgt tcgacaccac cgaggaggca    240
ttcggcccgg ttacgaccct ggtgaacaat gcagggattg ggtaattaa gagcgttgaa     300
cggactacca cggaggaatg gcgtgatgtt ctgtccgtta atctggatgg tgttttttc     360
ggcacccgtc tgggcattca gcgcatgaaa aataaaggct tgggcgctag catcatcaat    420
atgagcagta ttatggggct ggtaggctat ccggccgccg gggcatacaa cgcttccaag    480
ggggcggtac gtatcatgtc gaaaagcgca gcgctggatt gcgcactgaa ggactacgat    540
gtgcgtgtca acacagtaca tccgggcgcg atcaagaccg agcggaagga tcagctggaa    600
ggttgggagc aagcaatgtc acagcgtacg gcgaccccta tgggcacat tggcgaaccg    660
aatgacatcg catggatctg tgtgtacctg gcatctgacg aatcgaaatt tgcgacgggt    720
gcagaatttg tggtcgacgg cgggtacacc gcacag                              756

SEQ ID NO: 320        moltype = AA   length = 252
FEATURE               Location/Qualifiers
REGION                1..252
                      note = Engineered Variant of Kred from Lactobacillus kefir
source                1..252
                      mol_type = protein
                      organism = synthetic construct
SEQUENCE: 320
MTDRLKHKVA IVTGGTMGIG LAIADKFVEE GAKVVITGRH ADVGEKAAKS IGGSDVIRFV     60
QHDASEEAGW TSLFDTTEEA FGPVTTLVNN AGIGVIKSVE RTTTEEWRDV LSVNLDGVFF    120
GTRLGIQRMK NKGLGASIIN MSSIMGLVGY PAAGAYNASK GAVRIMSKSA ALDCALKDYD    180
VRVNTVHPGA IKTERKDQLE GWEQAMSQRT ATPMGHIGEP NDIAWICVYL ASDESKFATG    240
AEFVVDGGYT AQ                                                        252

SEQ ID NO: 321        moltype = DNA   length = 756
FEATURE               Location/Qualifiers
misc_feature          1..756
                      note = Engineered Variant of Kred from Lactobacillus kefir
source                1..756
                      mol_type = other DNA
                      organism = synthetic construct
SEQUENCE: 321
atgaccgatc gtctgaagca caaagtagcc atcgtcaccg gcgggacaat gggtatcggt     60
ttggcaatcg ccgataaatt tgtagaggag ggtgcgaaag tagttattac tggtcgtcac    120
gcggatgtag gtgagaaagc cgccaaatca atcggtggca gtgatgttat tcgctttgtc    180
cagcacgatg cgtccgaaga agcaggctgg acgaccctgt tcgacaccac cgaggaggca    240
ttcggcccgg ttacgaccct ggtgaacaat gcagggattg ggtaattaa gagcgttgaa     300
cggactacca cggaggaatg gcgtaaagtt ctgtccgtta atctggatgg tgttttttc     360
ggcacccgtc tgggcattca gcgcatgaaa aataaaggct tgggcgctag catcatcaat    420
atgagcagta ttatggggct ggtaggctat ccggccgccg gggcatacaa cgcttccaag    480
ggggcggtac gtatcatgtc gaaaagcgca gcgctggatt gcgcactgaa ggactacgat    540
gtgcgtgtca acacagtaca tccgggcgcg atcaagaccg agcggaagga tcagctggaa    600
ggttgggagc aggcaatgtc acagcgtacg gcgaccccta tgggcacat tggcgaaccg    660
aatgacatcg catggatctg tgtgtacctg gcatctgacg aatcgaaatt tgcgacgggt    720
gcagaatttg tggtcgacgg cgggtacacc gcacag                              756

SEQ ID NO: 322        moltype = AA   length = 252
FEATURE               Location/Qualifiers
REGION                1..252
                      note = Engineered Variant of Kred from Lactobacillus kefir
source                1..252
                      mol_type = protein
                      organism = synthetic construct
SEQUENCE: 322
MTDRLKHKVA IVTGGTMGIG LAIADKFVEE GAKVVITGRH ADVGEKAAKS IGGSDVIRFV     60
QHDASEEAGW TTLFDTTEEA FGPVTTLVNN AGIGVIKSVE RTTTEEWRKV LSVNLDGVFF    120
GTRLGIQRMK NKGLGASIIN MSSIMGLVGY PAAGAYNASK GAVRIMSKSA ALDCALKDYD    180
VRVNTVHPGA IKTERKDQLE GWEQAMSQRT ATPMGHIGEP NDIAWICVYL ASDESKFATG    240
AEFVVDGGYT AQ                                                        252

SEQ ID NO: 323        moltype = DNA   length = 756
FEATURE               Location/Qualifiers
misc_feature          1..756
                      note = Engineered Variant of Kred from Lactobacillus kefir
source                1..756
                      mol_type = other DNA
                      organism = synthetic construct
SEQUENCE: 323
atgaccgatc gtctgaagca caaagtagcc atcatcaccg gcgggacaat gggtatcggt     60
ttggcaatcg ccgataaatt tgtagaggag ggtgcgaaag tagttattac tggtcgtcac    120
gcggatgtag gtgagaaagc cgccaaatca atcggtggca gtgatgttat tcgctttgtc    180
cagcacgatg cgtccgaaga agcaggctgg acgagcctgt tcgacaccac cgaggaggca    240
ttcggcccgg ttacgaccct ggtgaacaat gcagggctg ggtaattaa gagcgttgaa      300
cggactacca cggaggaatg gcgtaaagtt ctgtccgtta atctggatgg tgttttttc     360
ggcacccgtc tgggcattca gcgcatgaaa aataaaggct tgggcgctag catcatcaat    420
atgagcagta ttatggggct ggtaggctat ccggccgccg gggcatacaa cgcttccaag    480
ggggcggtac gtatcatgtc gaaaagcgca gcgctggatt gcgcactgaa ggactacgat    540
```

```
gtgcgtgtca acacagtaca tccgggcgcg atcaagaccg agcggaagga tcagctggaa   600
ggttgggagc aggcaatgtc acagcgtacg gcgacccccta tgggccacat tggcgaaccg   660
aatgacatcg catggatctg tgtgtacctg gcatctgacg aatcgaaatt tgcgacgggt   720
gcagaatttg tggtcgacgg cgggtacacc gcacag                              756

SEQ ID NO: 324        moltype = AA   length = 252
FEATURE               Location/Qualifiers
REGION                1..252
                      note = Engineered Variant of Kred from Lactobacillus kefir
source                1..252
                      mol_type = protein
                      organism = synthetic construct
SEQUENCE: 324
MTDRLKHKVA IITGGTMGIG LAIADKFVEE GAKVVITGRH ADVGEKAAKS IGGSDVIRFV    60
QHDASEEAGW TSLFDTTEEA FGPVTTLVNN AGAGVIKSVE RTTTEEWRKV LSVNLDGVFF   120
GTRLGIQRMK NKGLGASIIN MSSIMGLVGY PAAGAYNASK GAVRIMSKSA ALDCALKDYD   180
VRVNTVHPGA IKTERKDQLE GWEQAMSQRT ATPMGHIGEP NDIAWICVYL ASDESKFATG   240
AEFVVDGGYT AQ                                                       252

SEQ ID NO: 325        moltype = DNA   length = 756
FEATURE               Location/Qualifiers
misc_feature          1..756
                      note = Engineered Variant of Kred from Lactobacillus kefir
source                1..756
                      mol_type = other DNA
                      organism = synthetic construct
SEQUENCE: 325
atgaccgatc gtctgaagca caaagtagcc atcatcaccg gcgggacaat gggtatcggt    60
ttggcaatcg ccgataaatt tgtagaggag ggtgcgaaag tagttattac tggtcgtcac   120
gcggatgtag gtctgaaagc cgccaaatca atcggtggca gtgatgttat tcgctttgtc   180
cagcacgatg cgtccgaaga agcaggctgg acgagtctgt tcgacaccac cgaggaggca   240
ttcggcccgg ttacgaccct ggtgaacaat gcagggattg gggtaattaa gagcgttgaa   300
cggactacca cggaggaatg gcgtgatgtt ctgtccgtta atctggatgg tgtttttttc   360
ggcacccgtc tgggcattca gcgcatgaaa aataaaggct tgggcgctag catcatcaat   420
atgagcagta ttatggggct ggtaggctat ccggccgccg gggcatacaa cgcttccaag   480
ggggcggtac gtatcatgtc gaaaagcgca gcgctggatt gcgcactgaa ggactacgat   540
gtgcgtgtca acacagtaca tccgggcgcg atcaagaccg agcggaagga tcagctggaa   600
ggttgggagc aggcaatgtc acagcgtacg gcgacccccta tgggccacat tggcgaaccg   660
aatgacatcg catggatctg tgtgtacctg gcatctgacg aatcgaaatt tgcgacgggt   720
gcagaatttg tggtcgacgg cgggtacacc gcacag                              756

SEQ ID NO: 326        moltype = AA   length = 252
FEATURE               Location/Qualifiers
REGION                1..252
                      note = Engineered Variant of Kred from Lactobacillus kefir
source                1..252
                      mol_type = protein
                      organism = synthetic construct
SEQUENCE: 326
MTDRLKHKVA IITGGTMGIG LAIADKFVEE GAKVVITGRH ADVGLKAAKS IGGSDVIRFV    60
QHDASEEAGW TSLFDTTEEA FGPVTTLVNN AGIGVIKSVE RTTTEEWRDV LSVNLDGVFF   120
GTRLGIQRMK NKGLGASIIN MSSIMGLVGY PAAGAYNASK GAVRIMSKSA ALDCALKDYD   180
VRVNTVHPGA IKTERKDQLE GWEQAMSQRT ATPMGHIGEP NDIAWICVYL ASDESKFATG   240
AEFVVDGGYT AQ                                                       252

SEQ ID NO: 327        moltype = DNA   length = 756
FEATURE               Location/Qualifiers
misc_feature          1..756
                      note = Engineered Variant of Kred from Lactobacillus kefir
source                1..756
                      mol_type = other DNA
                      organism = synthetic construct
SEQUENCE: 327
atgaccgatc gtctgaagca caaagtagcc atcatcaccg gcgggacaat gggtatcggt    60
ttggcaatcg ccgataaatt tgtagaggag ggtgcgaaag tagttattac tggtcgtcac   120
gcggatgtag gtgagaaagc cgccaaatca atcggtggca gtgatgttat tcgctttgtc   180
cagcacgatg cgtccgaaga agcaggctgg acgaccctgt tcgacaccac cgaggaggca   240
ttcggcccgg ttacgaccct ggtgaacaat gcagggattg gggtaattaa gagcgttgaa   300
cggactacca cggaggaatg gcgtgatgtt ctgtccgtta atctggatgg tgtttttttc   360
ggcacccgtc tgggcattca gcgcatgaaa aataaaggct tgggcgctag catcatcaat   420
atgagcagta ttatggggct ggtaggctat ccggccgccg gggcatacaa cgcttccaag   480
ggggcggtac gtatcatgtc gaaaagcgca gcgctggatt gcgcactgaa ggactacgat   540
gtgcgtgtca acacagtaca tccgggcgcg atcaagaccg agcggaagga tcagctggaa   600
ggttgggagc aggcaatgtc acagcgtacg gcgacccccta tgggccacat tggcgaaccg   660
aatgacatcg catggatctg tgtgtacctg gcatctgacg aatcgaaatt tgcgacgggt   720
gcagaatttg tggtcgacgg cgggtacacc gcacag                              756

SEQ ID NO: 328        moltype = AA   length = 252
FEATURE               Location/Qualifiers
```

| | | |
|---|---|---|
| REGION | 1..252 | |
| | note = Engineered Variant of Kred from Lactobacillus kefir | |
| source | 1..252 | |
| | mol_type = protein | |
| | organism = synthetic construct | |

SEQUENCE: 328
```
MTDRLKHKVA IITGGTMGIG LAIADKFVEE GAKVVITGRH ADVGEKAAKS IGGSDVIRFV   60
QHDASEEAGW TTLFDTTEEA FGPVTTLVNN AGIGVIKSVE RTTTEEWRDV LSVNLDGVFF  120
GTRLGIQRMK NKGLGASIIN MSSIMGLVGY PAAGAYNASK GAVRIMSKSA ALDCALKDYD  180
VRVNTVHPGA IKTERKDQLE GWEQAMSQRT ATPMGHIGEP NDIAWICVYL ASDESKFATG  240
AEFVVDGGYT AQ                                                     252
```

| | | |
|---|---|---|
| SEQ ID NO: 329 | moltype = DNA length = 756 | |
| FEATURE | Location/Qualifiers | |
| misc_feature | 1..756 | |
| | note = Engineered Variant of Kred from Lactobacillus kefir | |
| source | 1..756 | |
| | mol_type = other DNA | |
| | organism = synthetic construct | |

SEQUENCE: 329
```
atgaccgatc gtctgaagca caaagtagcc atcatcaccg gcgggacaat gggtatcggt   60
ttggcaatcg ccgataaatt tgtagaggag ggtgcgaaag tagttattac tggtcgtcac  120
gcggatgtag gtgagaaagc cgccaaatca atcgtggca gtgatgttat tcgctttgtc  180
cagcacgatg cgtccgaaga agcaggctgg acgaccctgt tcgacaccac cgaggaggca  240
ttcggcccgg ttacgaccct ggtgaacaat gcagggattg ggtaattaa gagcgttgaa  300
cggactacca cggaggaatg gcgtgatgtt ctgtccgtta atctggatgg tgtttttttc  360
ggcacccgtc tgggcattca gcgcatgaaa aataaaggct tgggcgctag catcatcaat  420
atgagcagta ttatgggggct ggtaggcgct ccggccgccg ggcatacaa cgcttccaag  480
ggggcggtac gtatcatgtc gaaaagcgca gcgctggatt gcgcactgaa ggactacgat  540
gtgcgtgtca acacagtaca tccgggcgcg atcaagaccg agtcgaagga tcagctggaa  600
ggttgggagc aggcaatgtc acagcgtacg gcgaccccta tgggccacat tggcgaaccg  660
aatgacatcg catggatctg tgtgtacctg gcatctgacg aatcgaaatt tgcgacgggt  720
gcagaatttg tggtcgacgg cgggtacacc gcacag                            756
```

| | | |
|---|---|---|
| SEQ ID NO: 330 | moltype = AA length = 252 | |
| FEATURE | Location/Qualifiers | |
| REGION | 1..252 | |
| | note = Engineered Variant of Kred from Lactobacillus kefir | |
| source | 1..252 | |
| | mol_type = protein | |
| | organism = synthetic construct | |

SEQUENCE: 330
```
MTDRLKHKVA IITGGTMGIG LAIADKFVEE GAKVVITGRH ADVGEKAAKS IGGSDVIRFV   60
QHDASEEAGW TTLFDTTEEA FGPVTTLVNN AGIGVIKSVE RTTTEEWRDV LSVNLDGVFF  120
GTRLGIQRMK NKGLGASIIN MSSIMGLVGA PAAGAYNASK GAVRIMSKSA ALDCALKDYD  180
VRVNTVHPGA IKTESKDQLE GWEQAMSQRT ATPMGHIGEP NDIAWICVYL ASDESKFATG  240
AEFVVDGGYT AQ                                                     252
```

| | | |
|---|---|---|
| SEQ ID NO: 331 | moltype = DNA length = 756 | |
| FEATURE | Location/Qualifiers | |
| misc_feature | 1..756 | |
| | note = Engineered Variant of Kred from Lactobacillus kefir | |
| source | 1..756 | |
| | mol_type = other DNA | |
| | organism = synthetic construct | |

SEQUENCE: 331
```
atgaccgatc gtctgaagca caaagtagcc atcatcaccg gcgggacaat gggtatcggt   60
ttggcaatcg ccgataaatt tgtagaggag ggtgcgaaag tagttattac tggtcgtcac  120
gcggatgtag gtgagaaagc cgccaaatca atcgtggca gtgatgttat tcgctttgtc  180
cagcacgatg cgtccgaaga agcaggctgg acgaccctgt tcgacaccac cgaggaggca  240
ttcggcccgg ttacgaccct ggtgaacaat gcagggattg ggtaattaa gagcgttgaa  300
cggactacca cggaggaatg gcgtgatgtt ctgtccgtta atctggatgg tgtttttttc  360
ggcacccgtc tgggcattca gcgcatgaaa aataaaggct tgggcgctag catcatcaat  420
atgagcagta ttatgggggct ggtaggcgct ccggccgccg ggcatacaa cgcttccaag  480
ggggcggtac gtatcatgtc gaaaagcgca gcgctggatt gcgcactgaa ggactacgat  540
gtgcgtgtca acacagtaca tccgggcgcg atcaagaccg agcggaagga tcagctggaa  600
ggttgggagc aggcaatgtc acagcgtacg gcgaccccta tgggccacat tggcgaaccg  660
aatgacatcg catggatctg tgtgtacctg gcatctgacg aatcgaaatt tgcgacgggt  720
gcagaatttg tggtcgacgg cgggtacacc gcacag                            756
```

| | | |
|---|---|---|
| SEQ ID NO: 332 | moltype = AA length = 252 | |
| FEATURE | Location/Qualifiers | |
| REGION | 1..252 | |
| | note = Engineered Variant of Kred from Lactobacillus kefir | |
| source | 1..252 | |
| | mol_type = protein | |
| | organism = synthetic construct | |

SEQUENCE: 332
```
MTDRLKHKVA IITGGTMGIG LAIADKFVEE GAKVVITGRH ADVGEKAAKS IGGSDVIRFV   60
```

QHDASEEAGW TTLFDTTEEA FGPVTTLVNN AGIGVIKSVE RTTTEEWRDV LSVNLDGVFF 120
GTRLGIQRMK NKGLGASIIN MSSIMGLVGA PAAGAYNASK GAVRIMSKSA ALDCALKDYD 180
VRVNTVHPGA IKTERKDQLE GWEQAMSQRT ATPMGHIGEP NDIAWICVYL ASDESKFATG 240
AEFVVDGGYT AQ 252

```
SEQ ID NO: 333         moltype = DNA   length = 756
FEATURE                Location/Qualifiers
misc_feature           1..756
                       note = Engineered Variant of Kred from Lactobacillus kefir
source                 1..756
                       mol_type = other DNA
                       organism = synthetic construct
SEQUENCE: 333
atgaccgatc gtctgaagca caaagtagcc atcatcaccg gcgggacaat gggtatcggt    60
ttggcaatcg ccgataaatt tgtagaggag ggtgcgaaag tagttattac tggtcgtcac   120
gcggatgtag gtgagaaagc cgccaaatca atcggtggca gtgatgttat tcgctttgtc   180
cagcacgatg cgtccgaaga agcaggctgg acgaccctgt tcgacaccac cgaggaggca   240
ttcggcccgg ttacgaccct ggtgaacaat gcagggattg gggtaattaa gagcgttgaa   300
cggactacca cggaggaatg gcgtgatgtt ctgtccgtta atctggatgg tgttttttc    360
ggcacccgtc tgggcattca gcgcatgaaa aataaaggct gggcgctag catcatcaat   420
atgagcagta ttatggggct ggtaggctat ccggccgccg gggcatacaa cgcttccaag   480
ggggcggtac gtatcatgtc gaaaagcgca gcgctggatt gcgcactgaa ggactacgat   540
gtgcgtgtca acacagtaca tccgggcgcg atcaagaccg agtcgaagga tcagctggaa   600
ggttgggagc aggcaatgtc acagcgtacg gcgacccta tggccacat tggcgaaccg   660
aatgacatcg catggatctg tgtgtacctg gcatctgacg aatcgaaatt tgcgacgggt   720
gcagaatttg tggtcgacgg cgggtacacc gcacag                            756

SEQ ID NO: 334         moltype = AA   length = 252
FEATURE                Location/Qualifiers
REGION                 1..252
                       note = Engineered Variant of Kred from Lactobacillus kefir
source                 1..252
                       mol_type = protein
                       organism = synthetic construct
SEQUENCE: 334
MTDRLKHKVA IITGGTMGIG LAIADKFVEE GAKVVITGRH ADVGEKAAKS IGGSDVIRFV    60
QHDASEEAGW TTLFDTTEEA FGPVTTLVNN AGIGVIKSVE RTTTEEWRDV LSVNLDGVFF   120
GTRLGIQRMK NKGLGASIIN MSSIMGLVGY PAAGAYNASK GAVRIMSKSA ALDCALKDYD   180
VRVNTVHPGA IKTESKDQLE GWEQAMSQRT ATPMGHIGEP NDIAWICVYL ASDESKFATG   240
AEFVVDGGYT AQ                                                      252

SEQ ID NO: 335         moltype = DNA   length = 756
FEATURE                Location/Qualifiers
misc_feature           1..756
                       note = Engineered Variant of Kred from Lactobacillus kefir
source                 1..756
                       mol_type = other DNA
                       organism = synthetic construct
SEQUENCE: 335
atgaccgatc gtctgaagca caaagtagcc atcatcaccg gcgggacaat gggtatcggt    60
ttggcaatcg ccgataaatt tgtagaggag ggtgcgaaag tagttattac tggtcgtcac   120
gcggatgtag gtgagaaagc cgccaaatca atcggtggca gtgatgttat tcgctttgtc   180
cagcacgatg cgtccgaaga agcaggctgg acgaccctgt tcgacaccac cgaggaggca   240
ttcggcccgg ttacgaccct ggtgaacaat gcagggattg gggtaattaa gagcgttgaa   300
cggactacca cggaggaatg gcgtgatgtt ctgtccgtta atctggatgg tgttttttc    360
ggcacccgtc tgggcattca gcgcatgaaa aataaaggct gggcgctag catcatcaat   420
atgagcagta ttatggggct ggtaggctat ccggccgccg gggcatacaa cgcttccaag   480
ggggcggtac gtatcatgtc gaaaagcgca gcgctggatt gcgcactgaa ggactacgat   540
gtgcgtgtca acacagtaca tccgggcgcg atcaagaccg aggcgaagga tcagctggaa   600
ggttgggagc aggcaatgtc acagcgtacg gcgacccta tggccacat tggcgaaccg   660
aatgacatcg catggatctg tgtgtacctg gcatctgacg aatcgaaatt tgcgacgggt   720
gcagaatttg tggtcgacgg cgggtacacc gcacag                            756

SEQ ID NO: 336         moltype = AA   length = 252
FEATURE                Location/Qualifiers
REGION                 1..252
                       note = Engineered Variant of Kred from Lactobacillus kefir
source                 1..252
                       mol_type = protein
                       organism = synthetic construct
SEQUENCE: 336
MTDRLKHKVA IITGGTMGIG LAIADKFVEE GAKVVITGRH ADVGEKAAKS IGGSDVIRFV    60
QHDASEEAGW TTLFDTTEEA FGPVTTLVNN AGIGVIKSVE RTTTEEWRDV LSVNLDGVFF   120
GTRLGIQRMK NKGLGASIIN MSSIMGLVGY PAAGAYNASK GAVRIMSKSA ALDCALKDYD   180
VRVNTVHPGA IKTEAKDQLE GWEQAMSQRT ATPMGHIGEP NDIAWICVYL ASDESKFATG   240
AEFVVDGGYT AQ                                                      252

SEQ ID NO: 337         moltype = DNA   length = 756
FEATURE                Location/Qualifiers
```

```
misc_feature             1..756
                         note = Engineered Variant of Kred from Lactobacillus kefir
source                   1..756
                         mol_type = other DNA
                         organism = synthetic construct
SEQUENCE: 337
atgaccgatc gtctgaagca caaagtagcc atcatcaccg gcgggacaat gggtatcggt    60
ttggcaatcg ccgataaatt tgtagaggag ggtgcgaaag tagttattac tggtcgtcac   120
gcggatgtag gtgagaaagc cgccaaatca atcggtggca gtgatgttat tcgctttgtc   180
cagcacgatg cgtccgaaga agcaggctgg acgaccctgt tcgacaccac cgaggaggca   240
ttcggcccgg ttacgaccct ggtgaacaat gcagggattg gggtaattaa gagcgttgaa   300
cggactacca cggaggaatg gcgtgatgtt ctgtccgtta atctggatgg tgttttttc    360
ggcacccgtc tgggcattca gcgcatgaaa aataaaggct gggcgctag catcatcaat    420
atgagcagta ttatggggct ggtaggctat ccggccgccg gggcatacaa cgcttccaag   480
ggggcggtac gtatcatgtc gaaaagcgca gcgctggatt gcgcactgaa ggactacgat   540
gtgcgtgtca acacagtaca tccgggcgcg atcaagaccg agtcgaagga tcagctggaa   600
ggttgggagc aggcaatgtc acagcgtacg gcgacccta tgggccacat tggcgaaccg    660
aatgacatcg catggatctg tgtgtacctg gcatctgacg aatcgaaatt tgcgacgggt   720
gcagaatttg tggtcgacgg cgggtacacc gcacag                             756

SEQ ID NO: 338           moltype = AA  length = 252
FEATURE                  Location/Qualifiers
REGION                   1..252
                         note = Engineered Variant of Kred from Lactobacillus kefir
source                   1..252
                         mol_type = protein
                         organism = synthetic construct
SEQUENCE: 338
MTDRLKHKVA IITGGTMGIG LAIADKFVEE GAKVVITGRH ADVGEKAAKS IGGSDVIRFV    60
QHDASEEAGW TTLFDTTEEA FGPVTTLVNN AGIGVIKSVE RTTTEEWRDV LSVNLDGVFF   120
GTRLGIQRMK NKGLGASIIN MSSIMGLVGY PAAGAYNASK GAVRIMSKSA ALDCALKDYD   180
VRVNTVHPGA IKTESKDQLE GWEQAMSQRT ATPMGHIGEP NDIAWICVYL ASDESKFATG   240
AEFVVDGGYT AQ                                                       252

SEQ ID NO: 339           moltype = DNA  length = 756
FEATURE                  Location/Qualifiers
misc_feature             1..756
                         note = Engineered Variant of Kred from Lactobacillus kefir
source                   1..756
                         mol_type = other DNA
                         organism = synthetic construct
SEQUENCE: 339
atgaccgatc gtctgaagca caaagtagcc atcatcaccg gcgggacaat gggtatcggt    60
ttggcaatcg ccgataaatt tgtagaggag ggtgcgaaag tagttattac tggtcgtcac   120
gcggatgtag gtgagaaagc cgccaaatca atcggtggca gtgatgttat tcgctttgtc   180
cagcacgatg cgtccgaaga agcaggctgg acgaccctgt tcgacaccac cgaggaggca   240
ttcggcccgg ttacgaccct ggtgaacaat gcagggattg gggtaattaa gagcgttgaa   300
cggactacca cggaggaatg gcgtgatgtt ctgtccgtta atctggatgg tgttttttc    360
ggcacccgtc tgggcattca gcgcatgaaa aataaaggct gggcgctag catcatcaat    420
atgagcagta ttatggggct ggtaggcgct gccgccgccg gggcatacaa cgcttccaag   480
ggggcggtac gtatcatgtc gaaaagcgca gcgctggatt gcgcactgaa ggactacgat   540
gtgcgtgtca acacagtaca tccgggcgcg atcaagaccg agcgcaagga tcagctggaa   600
ggttgggagc aggcaatgtc acagcgtacg gcgacccta tgggccacat tggcgaaccg    660
aatgacatcg catggatctg tgtgtacctg gcatctgacg aatcgaaatt tgcgacgggt   720
gcagaatttg tggtcgacgg cgggtacacc gcacag                             756

SEQ ID NO: 340           moltype = AA  length = 252
FEATURE                  Location/Qualifiers
REGION                   1..252
                         note = Engineered Variant of Kred from Lactobacillus kefir
source                   1..252
                         mol_type = protein
                         organism = synthetic construct
SEQUENCE: 340
MTDRLKHKVA IITGGTMGIG LAIADKFVEE GAKVVITGRH ADVGEKAAKS IGGSDVIRFV    60
QHDASEEAGW TTLFDTTEEA FGPVTTLVNN AGIGVIKSVE RTTTEEWRDV LSVNLDGVFF   120
GTRLGIQRMK NKGLGASIIN MSSIMGLVGA AAAGAYNASK GAVRIMSKSA ALDCALKDYD   180
VRVNTVHPGA IKTERKDQLE GWEQAMSQRT ATPMGHIGEP NDIAWICVYL ASDESKFATG   240
AEFVVDGGYT AQ                                                       252

SEQ ID NO: 341           moltype = DNA  length = 756
FEATURE                  Location/Qualifiers
misc_feature             1..756
                         note = Engineered Variant of Kred from Lactobacillus kefir
source                   1..756
                         mol_type = other DNA
                         organism = synthetic construct
SEQUENCE: 341
atgaccgatc gtctgaagca caaagtagcc atcatcaccg gcgggacaat gggtatcggt    60
```

```
ttggcaatcg ccgataaatt tgtagaggag ggtgcgaaag tagttattac tggtcgtcac   120
gcggatgtag gtgagaaagc cgccaaatca atcggtggca gtgatgttat tcgctttgtc   180
cagcacgatg cgtccgaaga agcaggctgg acgaccctgt tcgacaccac cgaggaggca   240
ttcggcccgt ttacgaccct ggtgaacaat gcagggattg gggtaattaa gagcgttgaa   300
cggactacca cggaggaatg gcgtgatgtt ctgtccgtta atctggatgg tgttttttc   360
ggcacccgtc tgggcattca gcgcatgaaa aataaaggct tgggcgctag catcatcaat   420
atgagcagta ttatggggct ggtaggcgct ccggccgccg gggcatacaa cgcttccaag   480
ggggcggtac gtatcatgtc gaaaagcgca gcgctggatt gcgcactgaa ggactacgat   540
gtgcgtgtca acacagtaca tccgggcgcg atcaagaccg agtcgaagga tcagctggaa   600
ggttgggagc aggcaatgtc acagcgtacg gcgaccccta tgggccacat tggcgaaccg   660
aatgacatcg catggatctg tgtgtacctg gcatctgacg aatcgaaatt tgcgacgggt   720
gcagaatttg tggtcgacgg cgggtacacc gcacag                             756

SEQ ID NO: 342           moltype = AA   length = 252
FEATURE                  Location/Qualifiers
REGION                   1..252
                         note = Engineered Variant of Kred from Lactobacillus kefir
source                   1..252
                         mol_type = protein
                         organism = synthetic construct
SEQUENCE: 342
MTDRLKHKVA IITGGTMGIG LAIADKFVEE GAKVVITGRH ADVGEKAAKS IGGSDVIRFV    60
QHDASEEAGW TTLFDTTEEA FGPVTTLVNN AGIGVIKSVE RTTTEEWRDV LSVNLDGVFF   120
GTRLGIQRMK NKGLGASIIN MSSIMGLVGA PAAGAYNASK GAVRIMSKSA ALDCALKDYD   180
VRVNTVHPGA IKTESKDQLE GWEQAMSQRT ATPMGHIGEP NDIAWICVYL ASDESKFATG   240
AEFVVDGGYT AQ                                                       252

SEQ ID NO: 343           moltype = DNA   length = 756
FEATURE                  Location/Qualifiers
misc_feature             1..756
                         note = Engineered Variant of Kred from Lactobacillus kefir
source                   1..756
                         mol_type = other DNA
                         organism = synthetic construct
SEQUENCE: 343
atgaccgatc gtctgaagca caaagtagcc atcatcaccg gcgggacaat gggtatcggt    60
ttggcaatcg ccgataaatt tgtagaggag ggtgcgaaag tagttattac tggtcgtcac   120
gcggatgtag gtgagaaagc cgccaaatca atcggtggca gtgatgttat tcgctttgtc   180
cagcacgatg cgtccgaaga agcaggctgg acgaccctgt tcgacaccac cgaggaggca   240
ttcggcccgg ttacgaccct ggtgaacaat gcagggatcg gcgtattaa gagcgttgaa    300
cggactacca cggaggaatg gcgtgatgtt ctgtccgtta atctggatgg tgttttttc   360
ggcacccgtc tgggcattca gcgcatgaaa aataaaggct tgggcgctag catcatcaat   420
atgagcagta ttatggggct ggtaggcgct ccggccgccg gggcatacaa cgcttccaag   480
ggggcggtac gtatcatgtc gaaaagcgca gcgctggatt gcgcactgaa ggactacgat   540
gtgcgtgtca acacagtaca tccgggcgcg atcaagaccg agcgcaagga tcagctggaa   600
ggttgggagc aggcaatgtc acagcgtacg gcgaccccta tgggccacat tggcgaaccg   660
aatgacatcg catggatctg tgtgtacctg gcatctgacg aatcgaaatt tgcgacgggt   720
gcagaatttg tggtcgacgg cgggtacacc gcacag                             756

SEQ ID NO: 344           moltype = AA   length = 252
FEATURE                  Location/Qualifiers
REGION                   1..252
                         note = Engineered Variant of Kred from Lactobacillus kefir
source                   1..252
                         mol_type = protein
                         organism = synthetic construct
SEQUENCE: 344
MTDRLKHKVA IITGGTMGIG LAIADKFVEE GAKVVITGRH ADVGEKAAKS IGGSDVIRFV    60
QHDASEEAGW TTLFDTTEEA FGPVTTLVNN AGIGRIKSVE RTTTEEWRDV LSVNLDGVFF   120
GTRLGIQRMK NKGLGASIIN MSSIMGLVGA PAAGAYNASK GAVRIMSKSA ALDCALKDYD   180
VRVNTVHPGA IKTERKDQLE GWEQAMSQRT ATPMGHIGEP NDIAWICVYL ASDESKFATG   240
AEFVVDGGYT AQ                                                       252

SEQ ID NO: 345           moltype = DNA   length = 756
FEATURE                  Location/Qualifiers
misc_feature             1..756
                         note = Engineered Variant of Kred from Lactobacillus kefir
source                   1..756
                         mol_type = other DNA
                         organism = synthetic construct
SEQUENCE: 345
atgaccgatc gtctgaagca caaagtagcc atcatcaccg gcgggacaat gggtatcggt    60
ttggcaatcg ccgataaatt tgtagaggag ggtgcgaaag tagttattac tggtcgtcac   120
gcggatgtag gtgagaaagc cgccaaatca atcggtggca gtgatgttat tcgctttgtc   180
cagcacgatg cgtccgaaga agcaggctgg acgaccctgt tcgacaccac cgaggaggca   240
ttcggcccgg ttacgaccct ggtgaacaat gcagggggcag ggtcattaa gagcgttgaa   300
cggactacca cggaggaatg gcgtgatgtt ctgtccgtta atctggatgg tgttttttc   360
ggcacccgtc tgggcattca gcgcatgaaa aataaaggct tgggcgctag catcatcaat   420
atgagcagta ttatggggct ggtaggcgct ccggccgccg gggcatacaa cgcttccaag   480
```

```
gggggcggtac gtatcatgtc gaaaagcgca gcgctggatt gcgcactgaa ggactacgat   540
gtgcgtgtca acacagtaca tccgggcgcg atcaagaccg agcgcaagga tcagctggaa   600
ggttgggagc aggcaatgtc acagcgtacg gcgacccta tgggccacat tggcgaaccg    660
aatgacatcg catggatctg tgtgtacctg gcatctgacg aatcgaaatt tgcgacgggt   720
gcagaatttg tggtcgacgg cgggtacacc gcacag                             756

SEQ ID NO: 346           moltype = AA   length = 252
FEATURE                  Location/Qualifiers
REGION                   1..252
                         note = Engineered Variant of Kred from Lactobacillus kefir
source                   1..252
                         mol_type = protein
                         organism = synthetic construct
SEQUENCE: 346
MTDRLKHKVA IITGGTMGIG LAIADKFVEE GAKVVITGRH ADVGEKAAKS IGGSDVIRFV    60
QHDASEEAGW TTLFDTTEEA FGPVTTLVNN AGAGVIKSVE RTTTEEWRDV LSVNLDGVFF   120
GTRLGIQRMK NKGLGASIIN MSSIMGLVGA PAAGAYNASK GAVRIMSKSA ALDCALKDYD   180
VRVNTVHPGA IKTERKDQLE GWEQAMSQRT ATPMGHIGEP NDIAWICVYL ASDESKFATG   240
AEFVVDGGYT AQ                                                      252

SEQ ID NO: 347           moltype = DNA   length = 756
FEATURE                  Location/Qualifiers
misc_feature             1..756
                         note = Engineered Variant of Kred from Lactobacillus kefir
source                   1..756
                         mol_type = other DNA
                         organism = synthetic construct
SEQUENCE: 347
atgaccgatc gtctgaagca caaagtagcc atcatcaccg gcgggacaat gggtatcggt    60
ttggcaatcg ccgataaatt tgtagaggag ggtgcgaaag tagttattac tggtcgtcac   120
gcggatgtag gtgagaaagc cgccaaatca atcggtggca gtgatgttat tcgctttgtc   180
cagcacgatg cgtccgaaga agcaggctgg acgaccctgt tcgacaccac cgaggaggca   240
ttcggcccgg ttacgaccct ggtgaacaat gcaggggcag ggcgtattaa gagcgttgaa   300
cggactacca cggaggaatg gcgtgatgtt ctgtccgtta atctggatgg tgttttttc    360
ggcacccgtc tgggcattca gcgcatgaaa aataaaggct tgggcgctag catcatcaat   420
atgagcagta ttgctgggct ggtaggcgct ccggccgccg gggcatacaa cgcttccaag   480
ggggcggtac gtatcatgtc gaaaagcgca gcgctggatt gcgcactgaa ggactacgat   540
gtgcgtgtca acacagtaca tccgggcgcg atcaagaccg agcgcaagga tcagctggaa   600
ggttgggagc aggcaatgtc acagcgtacg gcgaccccta tgggccacat tggcgaaccg   660
aatgacatcg catggatctg tgtgtacctg gcatctgacg aatcgaaatt tgcgacgggt   720
gcagaatttg tggtcgacgg cgggtacacc gcacag                             756

SEQ ID NO: 348           moltype = AA   length = 252
FEATURE                  Location/Qualifiers
REGION                   1..252
                         note = Engineered Variant of Kred from Lactobacillus kefir
source                   1..252
                         mol_type = protein
                         organism = synthetic construct
SEQUENCE: 348
MTDRLKHKVA IITGGTMGIG LAIADKFVEE GAKVVITGRH ADVGEKAAKS IGGSDVIRFV    60
QHDASEEAGW TTLFDTTEEA FGPVTTLVNN AGAGRIKSVE RTTTEEWRDV LSVNLDGVFF   120
GTRLGIQRMK NKGLGASIIN MSSIAGLVGA PAAGAYNASK GAVRIMSKSA ALDCALKDYD   180
VRVNTVHPGA IKTERKDQLE GWEQAMSQRT ATPMGHIGEP NDIAWICVYL ASDESKFATG   240
AEFVVDGGYT AQ                                                      252

SEQ ID NO: 349           moltype = DNA   length = 756
FEATURE                  Location/Qualifiers
misc_feature             1..756
                         note = Engineered Variant of Kred from Lactobacillus kefir
source                   1..756
                         mol_type = other DNA
                         organism = synthetic construct
SEQUENCE: 349
atgaccgatc gtctgaagca caaagtagcc atcatcaccg gcgggacaat gggtatcggt    60
ttggcaatcg ccgataaatt tgtagaggag ggtgcgaaag tagttattac tggtcgtcac   120
gcggatgtag gtgagaaagc cgccaaatca atcggtggca gtgatgttat tcgctttgtc   180
cagcacgatg cgtccgaaga agcaggctgg acgaccctgt tcgacaccac cgaggaggca   240
ttcggcccgg ttacgaccct ggtgaacaat gcaggggcag ggcgtcatta agagcgttga   300
cggactacca cggaggaatg gcgtaaagtt ctgtccgtca ctctggatgg tgttttttc    360
ggcacccgtc tgggcattca gcgcatgaaa aataaaggct tgggcgctag catcatcaat   420
atgagcagta ttgctgggct ggtaggcgct ccggccgccg gggcatacaa cgcttccaag   480
ggggcggtac gtatcatgtc gaaaagcgca gcgctggatt gcgcactgaa ggactacgat   540
gtgcgtgtca acacagtaca tccgggcgcg atcaagaccg agcgcaagga tcagctggaa   600
ggttgggagc aggcaatgtc acagcgtacg gcgaccccta tgggccacat tggcgaaccg   660
aatgacatcg catggatctg tgtgtacctg gcatctgacg aatcgaaatt tgcgacgggt   720
gcagaatttg tggtcgacgg cgggtacacc gcacag                             756

SEQ ID NO: 350           moltype = AA   length = 252
```

```
FEATURE                 Location/Qualifiers
REGION                  1..252
                        note = Engineered Variant of Kred from Lactobacillus kefir
source                  1..252
                        mol_type = protein
                        organism = synthetic construct
SEQUENCE: 350
MTDRLKHKVA IITGGTMGIG LAIADKFVEE GAKVVITGRH ADVGEKAAKS IGGSDVIRFV   60
QHDASEEAGW TTLFDTTEEA FGPVTTLVNN AGAGVIKSVE RTTTEEWRKV LSVTLDGVFF  120
GTRLGIQRMK NKGLGASIIN MSSIAGLVGA PAAGAYNASK GAVRIMSKSA ALDCALKDYD  180
VRVNTVHPGA IKTERKDQLE GWEQAMSQRT ATPMGHIGEP NDIAWICVYL ASDESKFATG  240
AEFVVDGGYT AQ                                                     252

SEQ ID NO: 351          moltype = DNA  length = 756
FEATURE                 Location/Qualifiers
misc_feature            1..756
                        note = Engineered Variant of Kred from Lactobacillus kefir
source                  1..756
                        mol_type = other DNA
                        organism = synthetic construct
SEQUENCE: 351
atgaccgatc gtctgaagca caaagtagcc atcatcaccg gcgggacaat gggtatcggt   60
ttggcaatcg ccgataaatt tgtagaggag ggtgcgaaag tagttattac tggtcgtcac  120
gcggatgtag gtgagaaagc cgccaaatca atcggtggca gtgatgttat tcgctttgtc  180
cagcacgatg cgtccgaaga agcaggctgg acgaccctgt tcgacaccac cgaggaggca  240
ttcggcccgg ttacgaccct ggtgaacaat gcagggattg ggtaattaa gagcgttgaa   300
cggactacca cggaggaatg gcgtgatgtt ctgtccgtta atctggatgg tgttttttc   360
ggcacccgtc tgggcattca gcgcatgaaa aataaaggct gggcgctag catcatcaat   420
atgagcagta ttgctgggct ggtaggcgct ccggccgccg gggcatacaa cgcttccaag   480
ggggcggtac gtatcatgtc gaaaagcgca gcgctggatt gcgcactgaa ggactacgat   540
gtgcgtgtca acacagtaca tccgggcgcg atcaagaccg aggcgaagga tcagctggaa   600
ggttgggagc aggcaatgtc acagcgtacg gcgaccccta tgggccacat tggcgaaccg   660
aatgacatcg catggatctg tgtgtacctg gcatctgacg aatcgaaatt tgcgacgggt   720
gcagaatttg tggtcgacgg cgggtacacc gcacag                            756

SEQ ID NO: 352          moltype = AA  length = 252
FEATURE                 Location/Qualifiers
REGION                  1..252
                        note = Engineered Variant of Kred from Lactobacillus kefir
source                  1..252
                        mol_type = protein
                        organism = synthetic construct
SEQUENCE: 352
MTDRLKHKVA IITGGTMGIG LAIADKFVEE GAKVVITGRH ADVGEKAAKS IGGSDVIRFV   60
QHDASEEAGW TTLFDTTEEA FGPVTTLVNN AGIGVIKSVE RTTTEEWRDV LSVNLDGVFF  120
GTRLGIQRMK NKGLGASIIN MSSIAGLVGA PAAGAYNASK GAVRIMSKSA ALDCALKDYD  180
VRVNTVHPGA IKTEAKDQLE GWEQAMSQRT ATPMGHIGEP NDIAWICVYL ASDESKFATG  240
AEFVVDGGYT AQ                                                     252

SEQ ID NO: 353          moltype = DNA  length = 756
FEATURE                 Location/Qualifiers
misc_feature            1..756
                        note = Engineered Variant of Kred from Lactobacillus kefir
source                  1..756
                        mol_type = other DNA
                        organism = synthetic construct
SEQUENCE: 353
atgaccgatc gtctgaagca caaagtagcc atcatcaccg gcgggacaat gggtatcggt   60
ttggcaatcg ccgataaatt tgtagaggag ggtgcgaaag tagttattac tggtcgtcac  120
gcggatgtag gtgagaaagc cgccaaatca atcggtggca gtgatgttat tcgctttgtc  180
cagcacgatg cgtccgaaga agcaggctgg acgaccctgt tcgacaccac cgaggaggca  240
ttcggcccgg ttacgaccct ggtgaacaat gcagggatcg ggtcattaa gagcgttgaa   300
cggactacca cggaggaatg gcgtgatgtt ctgtccgtta atctggatgg tgttttttc   360
ggcacccgtc tgggcattca gcgcatgaaa aataaaggct gggcgctag catcatcaat   420
atgagcagta ttatggggct ggtaggcgct ccggccgccg gggcatacaa cgcttccaag   480
ggggcggtac gtatcatgtc gaaaagcgca gcgctggatt gcgcactgaa ggactacgat   540
gtgcgtgtca acacagtaca tccgggcgcg atcaagaccg agcgcaagga tcagctgaa   600
ggttgggagc aggcaatgtc acagcgtacg gcgaccccta tgggccacat tggcgaaccg   660
aatgacatcg catggatctg tgtgtacctg gcatctgacg aatcgaaatt tgcgacgggt   720
gcagaatttg tggtcgacgg cgggtacacc gcacag                            756

SEQ ID NO: 354          moltype = AA  length = 252
FEATURE                 Location/Qualifiers
REGION                  1..252
                        note = Engineered Variant of Kred from Lactobacillus kefir
source                  1..252
                        mol_type = protein
                        organism = synthetic construct
SEQUENCE: 354
```

```
MTDRLKHKVA IITGGTMGIG LAIADKFVEE GAKVVITGRH ADVGEKAAKS IGGSDVIRFV   60
QHDASEEAGW TTLFDTTEEA FGPVTTLVNN AGIGVIKSVE RTTTEEWRDV LSVNLNDGVFF  120
GTRLGIQRMK NKGLGASIIN MSSIMGLVGA PAAGAYNASK GAVRIMSKSA ALDCALKDYD  180
VRVNTVHPGA IKTERKDQLE GWEQAMSQRT ATPMGHIGEP NDIAWICVYL ASDESKFATG  240
AEFVVDGGYT AQ                                                     252

SEQ ID NO: 355           moltype = DNA   length = 756
FEATURE                  Location/Qualifiers
misc_feature             1..756
                         note = Engineered Variant of Kred from Lactobacillus kefir
source                   1..756
                         mol_type = other DNA
                         organism = synthetic construct
SEQUENCE: 355
atgaccgatc gtctgaagca caaagtagcc atcatcaccg gcgggacaat gggtatcggt    60
ttggcaatcg ccgataaatt tgtagaggag ggtgcgaaag tagttattac tggtcgtcac   120
gcggatgtag gtgaaaaagc cgccaaatca atcggtggca gtgatgttat tcgctttgtc   180
cagcacgatg cgtccgaaga agcaggctgg acgaagctgt tcgacaccac cgaggaggca   240
ttcggcccgg ttacgaccct ggtgaacaat gcagggattg gggtaattaa gagcgttgaa   300
cggactacca cggaggaatg gcgtgatgtt ctgtccgtta atctggatgg tgttttttc   360
ggcacccgtc tggcattca gcgcatgaaa aataaaggct gggcgctag catcatcaat   420
atgagcagta ttatggggct ggtaggcgct ccggccgccg gggcatacaa cgcttccaag   480
ggggcggtac gtatcatgtc gaaaagcgca gcgctggatt gcgcactgaa ggactacgat   540
gtgcgtgtca acacagtaca tccgggcgcg atcaagaccg agcgcaagga tcagctggaa   600
ggttgggagc aggcaatgtc acagcgtacg gcgacccctA tgggccacat tggcgaaccg   660
aatgacatcg catggatctg tgtgtacctg gcatctgacg aatcgaaatt tgcgacgggt   720
gcagaatttg tggtcgacgg cgggtacacc gcacag                            756

SEQ ID NO: 356           moltype = AA   length = 252
FEATURE                  Location/Qualifiers
REGION                   1..252
                         note = Engineered Variant of Kred from Lactobacillus kefir
source                   1..252
                         mol_type = protein
                         organism = synthetic construct
SEQUENCE: 356
MTDRLKHKVA IITGGTMGIG LAIADKFVEE GAKVVITGRH ADVGEKAAKS IGGSDVIRFV   60
QHDASEEAGW TKLFDTTEEA FGPVTTLVNN AGIGVIKSVE RTTTEEWRDV LSVNLDGVFF  120
GTRLGIQRMK NKGLGASIIN MSSIMGLVGA PMAGAYNASK GAVRIMSKSA ALDCALKDYD  180
VRVNTVHPGA IKTERKDQLE GWEQAMSQRT ATPMGHIGEP NDIAWICVYL ASDESKFATG  240
AEFVVDGGYT AQ                                                     252

SEQ ID NO: 357           moltype = DNA   length = 756
FEATURE                  Location/Qualifiers
misc_feature             1..756
                         note = Engineered Variant of Kred from Lactobacillus kefir
source                   1..756
                         mol_type = other DNA
                         organism = synthetic construct
SEQUENCE: 357
atgaccgatc gtctgaagca caaagtagcc atcgtcaccg gcgggacaat gggtatcggt    60
ttggcaatcg ccgataaatt tgtagaggag ggtgcgaaag tagttattac tggtcgtcac   120
gcggatgtag gtgaaaaagc cgccaaatca atcggtggca gtgatgttat tcgctttgtc   180
cagcacgatg cgtccgaaga agcaggctgg acgtcgctgt tcgacaccac cgaggaggca   240
ttcggcccgg ttacgaccct ggtgaacaat gcagggattg gggtaattaa gagcgttgaa   300
cggactacca cggaggaatg gcgtaaggtt ctgtccgtta atctggatgg tgttttttc   360
ggcacccgtc tggcattca gcgcatgaaa aataaaggct gggcgctag catcatcaat   420
atgagcagta ttatggggct ggtaggcgct ccggccgccg gggcatacaa cgcttccaag   480
ggggcggtac gtatcatgtc gaaaagcgca gcgctggatt gcgcactgaa ggactacgat   540
gtgcgtgtca acacagtaca tccgggcgcg atcaagaccg agcgcaagga tcagctggaa   600
ggttgggagc aggcaatgtc acagcgtacg gcgacccctA tgggccacat tggcgaaccg   660
aatgacatcg catggatctg tgtgtacctg gcatctgacg aatcgaaatt tgcgacgggt   720
gcagaatttg tggtcgacgg cgggtacacc gcacag                            756

SEQ ID NO: 358           moltype = AA   length = 252
FEATURE                  Location/Qualifiers
REGION                   1..252
                         note = Engineered Variant of Kred from Lactobacillus kefir
source                   1..252
                         mol_type = protein
                         organism = synthetic construct
SEQUENCE: 358
MTDRLKHKVA IVTGGTMGIG LAIADKFVEE GAKVVITGRH ADVGEKAAKS IGGSDVIRFV   60
QHDASEEAGW TSLFDTTEEA FGPVTTLVNN AGIGVIKSVE RTTTEEWRKV LSVNLDGVFF  120
GTRLGIQRMK NKGLGASIIN MSSIMGLVGA PAAGAYNASK GAVRIMSKSA ALDCALKDYD  180
VRVNTVHPGA IKTERKDQLE GWEQAMSQRT ATPMGHIGEP NDIAWICVYL ASDESKFATG  240
AEFVVDGGYT AQ                                                     252

SEQ ID NO: 359           moltype = DNA   length = 756
```

```
FEATURE            Location/Qualifiers
misc_feature       1..756
                   note = Engineered Variant of Kred from Lactobacillus kefir
source             1..756
                   mol_type = other DNA
                   organism = synthetic construct
SEQUENCE: 359
atgaccgatc gtctgaagca caaagtagcc atcatcaccg gcgggacaat gggtatcggt   60
ttggcaatcg ccgataaatt tgtagaggag ggtgcgaaag tagttattac tggtcgtcac  120
gcggatgtag gtgaaaaagc cgccaaatca atcggtggca gtgatgttat tcgctttgtc  180
cagcacgatg cgtccgaaga agcaggctgg acgtcgctgt tcgacaccac cgaggaggca  240
ttcggcccgg ttacgaccct ggtgaacaat gcagggattg ggtaattaa gagcgttgaa   300
cggactacca cggaggaatg gcgtaaggtt ctgtccgtta atctggatgg tgttttttc   360
ggcacccgtc tgggcattca gcgcatgaaa aataaaggct tgggcgctag catcatcaat  420
atgagcagta ttatggggct ggtaggcgct ccgatggccg gggcatacaa cgcttccaag  480
ggggcggtac gtatcatgtc gaaaagcgca gcgctggatt gcgcactgaa ggactacgat  540
gtgcgtgtca acacagtaca tccgggcgcg atcaagaccg agcgcaagga tcagctggaa  600
ggttgggagc aggcaatgtc acagcgtacg gcgaccccta tgggcacat tggcgaaccg   660
aatgacatcg catggatctg tgtgtacctg gcatctgacg aatcgaaatt tgcgacgggt  720
gcagaatttg tggtcgacgg cgggtacacc gcacag                            756

SEQ ID NO: 360     moltype = AA   length = 252
FEATURE            Location/Qualifiers
REGION             1..252
                   note = Engineered Variant of Kred from Lactobacillus kefir
source             1..252
                   mol_type = protein
                   organism = synthetic construct
SEQUENCE: 360
MTDRLKHKVA IITGGTMGIG LAIADKFVEE GAKVVITGRH ADVGEKAAKS IGGSDVIRFV   60
QHDASEEAGW TSLFDTTEEA FGPVTTLVNN AGIGVIKSVE RTTTEEWRKV LSVNLDGVFF  120
GTRLGIQRMK NKGLGASIIN MSSIMGLVGA PMAGAYNASK GAVRIMSKSA ALDCALKDYD  180
VRVNTVHPGA IKTERKDQLE GWEQAMSQRT ATPMGHIGEP NDIAWICVYL ASDESKFATG  240
AEFVVDGGYT AQ                                                      252

SEQ ID NO: 361     moltype = DNA   length = 756
FEATURE            Location/Qualifiers
misc_feature       1..756
                   note = Engineered Variant of Kred from Lactobacillus kefir
source             1..756
                   mol_type = other DNA
                   organism = synthetic construct
SEQUENCE: 361
atgaccgatc gtctgaagca caaagtagcc atcatcaccg gcgggacaat gggtatcggt   60
ttggcaatcg ccgataaatt tgtagaggag ggtgcgaaag tagttattac tggtcgtcac  120
gcggatgtag gtgaaaaagc cgccaaatca atcggtggca gtgatgttat tcgctttgtc  180
cagcacgatg cgtccgaaga agcaggctgg acgtcgctgt tcgacaccac cgaggaggca  240
ttcggcccgg ttacgaccct ggtgaacaat gcagggattg ggtaattaa gagcgttgaa   300
cggactacca cggaggaatg gcgtaaggtt ctgtccgtta atctggatgg tgttttttc   360
ggcacccgtc tgggcattca gcgcatgaaa aataaaggct tgggcgctag catcatcaat  420
atgagcagta ttatggggct ggtaggcgct ccggccgccg gggcatacaa cgcttccaag  480
ggggcggtac gtatcatgtc gaaaagcgca gcgctggatt gcgcactgaa ggactacgat  540
gtgcgtgtca acacagtaca tccgggcgcg atcaagaccg agcgcaagga tcagctggaa  600
ggttgggagc aggcaatgtc acagcgtacg gcgaccccta tgggcacat tggcgaaccg   660
aatgacatcg catggatctg tgtgtacctg gcatctgacg aatcgaaatt tgcgacgggt  720
gcagaatttg tggtcgacgg cgggtacacc gcacag                            756

SEQ ID NO: 362     moltype = AA   length = 252
FEATURE            Location/Qualifiers
REGION             1..252
                   note = Engineered Variant of Kred from Lactobacillus kefir
source             1..252
                   mol_type = protein
                   organism = synthetic construct
SEQUENCE: 362
MTDRLKHKVA IITGGTMGIG LAIADKFVEE GAKVVITGRH ADVGEKAAKS IGGSDVIRFV   60
QHDASEEAGW TSLFDTTEEA FGPVTTLVNN AGIGVIKSVE RTTTEEWRKV LSVNLDGVFF  120
GTRLGIQRMK NKGLGASIIN MSSIMGLVGA PAAGAYNASK GAVRIMSKSA ALDCALKDYD  180
VRVNTVHPGA IKTERKDQLE GWEQAMSQRT ATPMGHIGEP NDIAWICVYL ASDESKFATG  240
AEFVVDGGYT AQ                                                      252

SEQ ID NO: 363     moltype = DNA   length = 756
FEATURE            Location/Qualifiers
misc_feature       1..756
                   note = Engineered Variant of Kred from Lactobacillus kefir
source             1..756
                   mol_type = other DNA
                   organism = synthetic construct
SEQUENCE: 363
```

```
atgaccgatc gtctgaagca caaagtagcc atcatcaccg gcgggacaat gggtatcggt   60
ttggcaatcg ccgataaatt tgtagaggag ggtgcgaaag tagttattac tggtcgtcac  120
gcggatgtag gtgaaaaagc cgccaaatca atcggtggca gtgatgttat tcgctttgtc  180
cagcacgatg cgtccgaaga agcaggctgg acgaagctgt tcgacaccac cgaggaggca  240
ttcggcccgg ttacgaccct ggtgaacaat gcagggattg ggtaattaa gagcgttgaa  300
cggactacca cggaggaatg gcgtgatgtt ctgtccgtta atctggatgg tgtttttttc  360
ggcacccgtc tgggcattca gcgcatgaaa aataaaggct tgggcgctag catcatcaat  420
atgagcagta ttatggggct ggtaggcgct ccggccgccg gggcatacaa cgcttccaag  480
ggggcggtac gtatcatgtc gaaaagcgca gcgctggatt gcgcactgaa ggactacgat  540
gtgcgtgtca acacagtaca tccgggcgcg atcaagaccg agcgcaagga tcagctggaa  600
ggttgggagc aggcaatgtc acagcgtacg gcgaccccta tgggccacat tggcgaaccg  660
aatgacatcg catggatctg tgtgtacctg gcatctgacg aatcgaaatt tgcgacgggt  720
gcagaatttg tggtcgacgg cgggtacacc gcacag                            756

SEQ ID NO: 364          moltype = AA  length = 252
FEATURE                 Location/Qualifiers
REGION                  1..252
                        note = Engineered Variant of Kred from Lactobacillus kefir
source                  1..252
                        mol_type = protein
                        organism = synthetic construct
SEQUENCE: 364
MTDRLKHKVA IITGGTMGIG LAIADKFVEE GAKVVITGRH ADVGEKAAKS IGGSDVIRFV   60
QHDASEEAGW TKLFDTTEEA FGPVTTLVNN AGIGVIKSVE RTTTEEWRDV LSVNLDGVFF  120
GTRLGIQRMK NKGLGASIIN MSSIMGLVGA PAAGAYNASK GAVRIMSKSA ALDCALKDYD  180
VRVNTVHPGA IKTERKDQLE GWEQAMSQRT ATPMGHIGEP NDIAWICVYL ASDESKFATG  240
AEFVVDGGYT AQ                                                     252

SEQ ID NO: 365          moltype = DNA  length = 756
FEATURE                 Location/Qualifiers
misc_feature            1..756
                        note = Engineered Variant of Kred from Lactobacillus kefir
source                  1..756
                        mol_type = other DNA
                        organism = synthetic construct
SEQUENCE: 365
atgaccgatc gtctgaagca caaagtagcc atcatcaccg gcgggacaat gggtatcggt   60
ttggcaatcg ccgataaatt tgtagaggag ggtgcgaaag tagttattac tggtcgtcac  120
gcggatgtag gtgagaaagc cgccaaatca atcggtggca gtgatgttat tcgctttgtc  180
cagcacgatg cgtccgaaga agcaggctgg acgaccctgt tcgacaccac cgaggaggca  240
ttcggcccgg ttacgaccct ggtgaacaat gcaggggccg gggtaattaa gagcgttgaa  300
cggactacca cggaggaatg gcgtgatgtt ctgtccgtta atctggatgg tgtttttttc  360
ggcacccgtc tgggcattca gcgcatgaaa aataaaggct tgggcgctag catcatcaat  420
atgagcagta ttatggggct ggtaggcgct ccggccgccg gggcatacaa cgcttccaag  480
ggggcggtac gtatcatgtc gaaaagcgca gcgctggatt gcgcactgaa ggactacgat  540
gtgcgtgtca acacagtaca tccgggcgcg atcaagaccg agtcgaagga tcagctggaa  600
ggttgggagc aggcaatgtc acagcgtacg gcgaccccta tgggccacat tggcgaaccg  660
aatgacatcg catggatctg tgtgtacctg gcatctgacg aatcgaaatt tgcgacgggt  720
gcagaatttg tggtcgacgg cgggtacacc gcacag                            756

SEQ ID NO: 366          moltype = AA  length = 252
FEATURE                 Location/Qualifiers
REGION                  1..252
                        note = Engineered Variant of Kred from Lactobacillus kefir
source                  1..252
                        mol_type = protein
                        organism = synthetic construct
SEQUENCE: 366
MTDRLKHKVA IITGGTMGIG LAIADKFVEE GAKVVITGRH ADVGEKAAKS IGGSDVIRFV   60
QHDASEEAGW TTLFDTTEEA FGPVTTLVNN AGAGVIKSVE RTTTEEWRDV LSVNLDGVFF  120
GTRLGIQRMK NKGLGASIIN MSSIMGLVGA PAAGAYNASK GAVRIMSKSA ALDCALKDYD  180
VRVNTVHPGA IKTESKDQLE GWEQAMSQRT ATPMGHIGEP NDIAWICVYL ASDESKFATG  240
AEFVVDGGYT AQ                                                     252

SEQ ID NO: 367          moltype = DNA  length = 756
FEATURE                 Location/Qualifiers
misc_feature            1..756
                        note = Engineered Variant of Kred from Lactobacillus kefir
source                  1..756
                        mol_type = other DNA
                        organism = synthetic construct
SEQUENCE: 367
atgaccgatc gtctgaagca caaagtagcc atcatcaccg gcgggacaat gggtatcggt   60
ttggcaatcg ccgataaatt tgtagaggag ggtgcgaaag tagttattac tggtcgtcac  120
gcggatgtag gtgagaaagc cgccaaatca atcggtggca gtgatgttat tcgctttgtc  180
cagcacgatg cgtccgaaga agcaggctgg acgaccctgt tcgacaccac cgaggaggca  240
ttcggcccgg ttacgaccct ggtgaacaat gcagggattg ggtaattaa gagcgttgaa  300
cggactacca cggaggaatg gcgtgatgtt ctgtccgtta atctggatgg tgtttttttc  360
ggcacccgtc tgggcattca gcgcatgaaa aataaaggct tgggcgctag catcatcaat  420
```

```
atgagcagta ttatggggct ggtaggcgct ccggccgccg gggcatacaa cgcttccaag  480
ggggcggtac gtatcatgtc gaaaagcgca gcgctggatt gcgcactgaa ggactacgat  540
gttcgtgtca acacagtaca tccgggcgcg atcaagacca actcgaagga tcagctggag  600
ggttgggagc aggcaatgtc acagcgtacg gcgacccta tgggccacat tggcgaaccg   660
aatgacatcg catggatctg tgtgtacctg gcatctgacg aatcgaaatt tgcgacgggt  720
gcagaatttg tggtcgacgg cgggtacacc gcacag                             756

SEQ ID NO: 368           moltype = AA  length = 252
FEATURE                  Location/Qualifiers
REGION                   1..252
                         note = Engineered Variant of Kred from Lactobacillus kefir
source                   1..252
                         mol_type = protein
                         organism = synthetic construct
SEQUENCE: 368
MTDRLKHKVA IITGGTMGIG LAIADKFVEE GAKVVITGRH ADVGEKAAKS IGGSDVIRFV   60
QHDASEEAGW TTLFDTTEEA FGPVTTLVNN AGIGVIKSVE RTTTEEWRDV LSVNLDGVFF  120
GTRLGIQRMK NKGLGASIIN MSSIMGLVGA PAAGAYNASK GAVRIMSKSA ALDCALKDYD  180
VRVNTVHPGA IKTNSKDQLE GWEQAMSQRT ATPMGHIGEP NDIAWICVYL ASDESKFATG  240
AEFVVDGGYT AQ                                                      252

SEQ ID NO: 369           moltype = DNA  length = 756
FEATURE                  Location/Qualifiers
misc_feature             1..756
                         note = Engineered Variant of Kred from Lactobacillus kefir
source                   1..756
                         mol_type = other DNA
                         organism = synthetic construct
SEQUENCE: 369
atgaccgatc gtctgaagca caaagtagcc atcatcaccg gcgggacaat gggtatcggt   60
ttggcaatcg ccgataaatt tgtagaggag ggtgcgaaag tagttattac tggtcgtcac  120
gcggatgtag gtgagaaagc cgccaaatca atcggtggca gtgatgttat tcgctttgtc  180
cagcacgatg cgtccgaaga agcaggctgg acgaccctgt tcgacaccac cgaggaggca  240
ttcggcccgg ttacgaccct ggtgaacaat gcagggattg gggtaattaa gagcgttgaa  300
cggactacca cggaggaatg gcgtgatgtt ctgtccgtta atctggatgg tgttttttc   360
ggcacccgtc tgggcattca gcgcatgaaa aataaaggct tgggcgctag catcatcaat  420
atgagcagta ttatggggct ggtaggcgct ccggccgccg gggcatacaa cgcttccaag  480
ggggcggtac gtatcatgtc gaaaagcgca gcgctggatt gcgcactgaa ggactacgat  540
gttcgtgtca acacagtaca tccgggcgcg atcaagacca actcgaagga tcagctggag  600
ggttgggagc aggcaatgtc acagcgtacg gcgacccta tgggccacat tggcgaaccg   660
aatgacatcg catggatctg tgtgtacctg gcatctgacg aatcgaaatt tgcgacgggt  720
gcagaatttg tggtcgacgg cgggtacacc gcacag                             756

SEQ ID NO: 370           moltype = AA  length = 252
FEATURE                  Location/Qualifiers
REGION                   1..252
                         note = Engineered Variant of Kred from Lactobacillus kefir
source                   1..252
                         mol_type = protein
                         organism = synthetic construct
SEQUENCE: 370
MTDRLKHKVA IITGGTMGIG LAIADKFVEE GAKVVITGRH ADVGEKAAKS IGGSDVIRFV   60
QHDASEEAGW TTLFDTTEEA FGPVTTLVNN AGIGVIKSVE RTTTEEWRDV LSVNLDGVFF  120
GTRLGIQRMK NKGLGASIIN MSSIMGLVGA PAAGAYNASK GAVRIMSKSA ALDCALKDYD  180
VRVNTVHPGA IKTNSKDQLP GWEQAMSQRT ATPMGHIGEP NDIAWICVYL ASDESKFATG  240
AEFVVDGGYT AQ                                                      252

SEQ ID NO: 371           moltype = DNA  length = 756
FEATURE                  Location/Qualifiers
misc_feature             1..756
                         note = Engineered Variant of Kred from Lactobacillus kefir
source                   1..756
                         mol_type = other DNA
                         organism = synthetic construct
SEQUENCE: 371
atgaccgatc gtctgaagca caaagtagcc atcatcaccg gcgggacaat gggtatcggt   60
ttggcaatcg ccgataaatt tgtagaggag ggtgcgaaag tagttattac tggtcgtcac  120
gcggatgtag gtgagaaagc cgccaaatca atcggtggca gtgatgttat tcgctttgtc  180
cagcacgatg cgtccgaaga agcaggctgg acgaccctgt tcgacaccac cgaggaggca  240
ttcggcccgg ttacgaccct ggtgaacaat gcagggattg gggtaattaa gagcgttgaa  300
cggactacca cggaggaatg gcgtgatgtt ctgtccgtta atctggatgg tgttttttc   360
ggcacccgtc tgggcattca gcgcatgaaa aataaaggct tgggcgctag catcatcaat  420
atgagcagta ttatggggct ggtaggcgct ccggccgccg gggcatacaa cgcttccaag  480
ggggcggtac gtatcatgtc gaaaagcgca gcgctggatt gcgcactgaa ggactacgat  540
gtgcgtgtca acacagtaca tccgggcgcg atcaagaccg aatcgaagga tcagctgcca  600
ggttgggagc aggcaatgtc acagcgtacg gcgacccta tgggccacat tggcgaaccg   660
aatgacatcg catggatctg tgtgtacctg gcatctgacg aatcgaaatt tgcgacgggt  720
gcagaatttg tggtcgacgg cgggtacacc gcacag                             756
```

```
SEQ ID NO: 372            moltype = AA   length = 252
FEATURE                   Location/Qualifiers
REGION                    1..252
                          note = Engineered Variant of Kred from Lactobacillus kefir
source                    1..252
                          mol_type = protein
                          organism = synthetic construct
SEQUENCE: 372
MTDRLKHKVA IITGGTMGIG LAIADKFVEE GAKVVITGRH ADVGEKAAKS IGGSDVIRFV   60
QHDASEEAGW TTLFDTTEEA FGPVTTLVNN AGIGVIKSVE RTTTEEWRDV LSVNLDGVFF  120
GTRLGIQRMK NKGLGASIIN MSSIMGLVGA PAAGAYNASK GAVRIMSKSA ALDCALKDYD  180
VRVNTVHPGA IKTESKDQLP GWEQAMSQRT ATPMGHIGEP NDIAWICVYL ASDESKFATG  240
AEFVVDGGYT AQ                                                     252

SEQ ID NO: 373            moltype = DNA   length = 756
FEATURE                   Location/Qualifiers
misc_feature              1..756
                          note = Engineered Variant of Kred from Lactobacillus kefir
source                    1..756
                          mol_type = other DNA
                          organism = synthetic construct
SEQUENCE: 373
atgaccgatc gtctgaagca caaagtagcc atcatcaccg gcgggacaat gggtatcggt   60
ttggcaatcg ccgataaatt tgtagaggag ggtgcgaaag tagttattac tggtcgtcac  120
gcggatgtag gtgagaaagc cgccaaatca atcggtggca gtgatgttat tcgctttgtc  180
cagcacgatg cgtccgaaga agcaggctgg acgaccctgt tcgacaccac cgaggaggca  240
ttcggcccgg ttacgaccct ggtgaacaat gcagggattg ggtaattaa gagcgttgaa   300
cggactacca cggaggaatg gcgtgatgtt ctgtccgtta atctggatgg tgttttttc   360
ggcacccgtc tgggcattca gcgcatgaaa aataaaggct tgggcgctag catcatcaat  420
atgagcagta ttatggggct ggtaggcgct ccggccgccg ggcatacaa cgcttccaag   480
ggggcggtac gtatcatgtc gaaaagcgca gcgctggatt gcgcactgaa ggactacgat  540
gtgcgtgtca acacagtaca tccgggcgcg atcaagaccg agtcgaagga tcagctggaa  600
ggttgggagc aggcaatgtc acagcgtacg gcgacccta tggcacacat tggcgaaccg   660
aatgacatcg catggatctg tgtgtacctg gcatctgacg aatcgaaatt tgcgacgggt  720
gcagaatttg tggtcgacgg cgggtacacc gcacag                            756

SEQ ID NO: 374            moltype = AA   length = 252
FEATURE                   Location/Qualifiers
REGION                    1..252
                          note = Engineered Variant of Kred from Lactobacillus kefir
source                    1..252
                          mol_type = protein
                          organism = synthetic construct
SEQUENCE: 374
MTDRLKHKVA IITGGTMGIG LAIADKFVEE GAKVVITGRH ADVGEKAAKS IGGSDVIRFV   60
QHDASEEAGW TTLFDTTEAA FGPVTTLVNN AGIGVIKSVE RTTTEEWRDV LSVNLDGVFF  120
GTRLGIQRMK NKGLGASIIN MSSIMGLVGA PAAGAYNASK GAVRIMSKSA ALDCALKDYD  180
VRVNTVHPGA IKTESKDQLE GWEQAMSQRT ATPMGHIGEP NDIAWICVYL ASDESKFATG  240
AEFVVDGGYT AQ                                                     252

SEQ ID NO: 375            moltype = DNA   length = 756
FEATURE                   Location/Qualifiers
misc_feature              1..756
                          note = Engineered Variant of Kred from Lactobacillus kefir
source                    1..756
                          mol_type = other DNA
                          organism = synthetic construct
SEQUENCE: 375
atgaccgatc gtctgaagca caaagtagcc atcatcaccg gcgggacaat gggtatcggt   60
ttggcaatcg ccgataaatt tgtagaggag ggtgcgaaag tagttattac tggtcgtcac  120
gcggatgtag gtgagaaagc cgccaaatca atcggtggca gtgatgttat tcgctttgtc  180
cagcacgatg cgtccgaaga agcaggctgg acgaccctgt cgacaccac cgaggaggca   240
ttcggcccgg ttacgaccct ggtgaacaat gcagggattg ggttccgaa gagcgttgaa   300
cggactacca cggaggaatg gcgtgatgtt ctgtccgtta atctggatgg tgttttttc   360
ggcacccgtc tgggcattca gcgcatgaaa aataaaggct tgggcgctag catcatcaat  420
atgagcagta ttatggggct ggtaggcgct ccggccgccg ggcatacaa cgcttccaag   480
ggggcggtac gtatcatgtc gaaaagcgca gcgctggatt gcgcactgaa ggactacgat  540
gtgcgtgtca acacagtaca tccgggcgcg atcaagacca actcgaagga tcagctgcca  600
ggttgggagc aggcaatgtc acagcgtacg gcgacccta tggcgcacat tggcgaaccg   660
aatgacatcg catggatctg tgtgtacctg gcatctgacg aatcgaaatt tgcgacgggt  720
gcagaatttg tggtcgacgg cgggtacacc gcacag                            756

SEQ ID NO: 376            moltype = AA   length = 252
FEATURE                   Location/Qualifiers
REGION                    1..252
                          note = Engineered Variant of Kred from Lactobacillus kefir
source                    1..252
                          mol_type = protein
                          organism = synthetic construct
```

```
SEQUENCE: 376
MTDRLKHKVA IITGGTMGIG LAIADKFVEE GAKVVITGRH ADVGEKAAKS IGGSDVIRFV    60
QHDASEEAGW TTLFDTTEEA FGPVTTLVNN AGIGVPKSVE RTTTEEWRDV LSVNLDGVFF   120
GTRLGIQRMK NKGLGASIIN MSSIMGLVGA PAAGAYNASK GAVRIMSKSA ALDCALKDYD   180
VRVNTVHPGA IKTNSKDQLP GWEQAMSQRT ATPMGHIGEP NDIAWICVYL ASDESKFATG   240
AEFVVDGGYT AQ                                                      252

SEQ ID NO: 377          moltype = DNA  length = 756
FEATURE                 Location/Qualifiers
misc_feature            1..756
                        note = Engineered Variant of Kred from Lactobacillus kefir
source                  1..756
                        mol_type = other DNA
                        organism = synthetic construct
SEQUENCE: 377
atgaccgatc gtctgaagca caaagtagcc atcatcaccg gcgggacaat gggtatcggt    60
ttggcaatcg ccgataaatt tgtagaggag ggtgcgaaag tagttattac tggtcgtcac   120
gcggatgtag gtgagaaagc cgccaaatca atcggtggca gtgatgttat tcgctttgtc   180
cagcacgatg cgtccgaaga agcaggctgg acgaccctgt tcgacaccac cgaggaggca   240
ttcggcccgg ttacgaccct ggtgaacaat gcagggattg ggttccgaa gagcgttgaa    300
cggactacca cggaggaatg gagtgatgtt ctgtccgtta atctggatgg tgttttttc    360
ggcacccgtc tgggcattca gcgcatgaaa aataaaggct gggcgctag catcatcaat   420
atgagcagta ttatggggat cgtaggcgct ccggccgccg gggcataaca cgcttccaag   480
ggggcggtac gtatcatgtc gaaaagcgca gcgctggatt gcgcactgaa ggactacgat   540
gtgcgtgtca acacagtaca tccgggcgcg atcaagaccc aatcgaagga tcagctgcca   600
ggttgggagc aggcaatgtc acagcgtacg gcgaccccta tgggcacat tggcgaaccg    660
aatgacatcg catggatctg tgtgtacctg gcatctgacg aatcgaaatt tgcgacgggt   720
gcagaatttg tggtcgacgg cgggtacacc gcacag                            756

SEQ ID NO: 378          moltype = AA  length = 252
FEATURE                 Location/Qualifiers
REGION                  1..252
                        note = Engineered Variant of Kred from Lactobacillus kefir
source                  1..252
                        mol_type = protein
                        organism = synthetic construct
SEQUENCE: 378
MTDRLKHKVA IITGGTMGIG LAIADKFVEE GAKVVITGRH ADVGEKAAKS IGGSDVIRFV    60
QHDASEEAGW TTLFDTTEEA FGPVTTLVNN AGIGVPKSVE RTTTEEWSDV LSVNLDGVFF   120
GTRLGIQRMK NKGLGASIIN MSSIMGIVGA PAAGAYNASK GAVRIMSKSA ALDCALKDYD   180
VRVNTVHPGA IKTESKDQLP GWEQAMSQRT ATPMGHIGEP NDIAWICVYL ASDESKFATG   240
AEFVVDGGYT AQ                                                      252

SEQ ID NO: 379          moltype = DNA  length = 756
FEATURE                 Location/Qualifiers
misc_feature            1..756
                        note = Engineered Variant of Kred from Lactobacillus kefir
source                  1..756
                        mol_type = other DNA
                        organism = synthetic construct
SEQUENCE: 379
atgaccgatc gtctgaagca caaagtagcc atcatcaccg gcgggacaat gggtatcggt    60
ttggcaatcg ccgataaatt tgtagaggag ggtgcgaaag tagttattac tggtcgtcac   120
gcggatgtag gtgagaaagc cgccaaatca atcggtggca gtgatgttat tcgctttgtc   180
cagcacgatg cgtccgaaga agcaggctgg acgaccctgt tcgacaccac cgaggaggca   240
ttcggcccgg ttacgaccct ggtgaacaat gcagggattg ggtaattaa gagcgttgaa    300
cggactacca cggaggaatg gcgtgatgtt ctgtccgtta atctggatgg tgttttttc    360
ggcacccgtc tgggcattca gcgcatgaaa aataaaggct gggcgctag catcatcaat   420
atgagcagta ttatggggct ggtaggcgct ccggccgccg gggcataaca cgcttccaag   480
ggggcggtac gtatcatgtc gaaaagcgca gcgctggatt gcgcactgaa ggactacgat   540
gtgcgtgtca acacagtaca tcccgggcgcg atccgcaccg agtcgaagga tcagctggaa  600
ggttgggagc aggcaatgtc acagcgtacg gcgaccccta tgggcacat tggcgaaccg    660
aatgacatcg catggatctg tgtgtacctg gcatctgacg aatcgaaatt tgcgacgggt   720
gcagaatttg tggtcgacgg cgggtacacc gcacag                            756

SEQ ID NO: 380          moltype = AA  length = 252
FEATURE                 Location/Qualifiers
REGION                  1..252
                        note = Engineered Variant of Kred from Lactobacillus kefir
source                  1..252
                        mol_type = protein
                        organism = synthetic construct
SEQUENCE: 380
MTDRLKHKVA IITGGTMGIG LAIADKFVEE GAKVVITGRH ADVGEKAAKS IGGSDVIRFV    60
QHDASEEAGW TTLFDTTEEA FGPVTTLVNN AGIVIKSVE RTTTEEWRDV LSVNLDGVFF    120
GTRLGIQRMK NKGLGASIIN MSSIMGLVGA PAAGAYNASK GAVRIMSKSA ALDCALKDYD   180
VRVNTVHPGA IRTESKDQLE GWEQAMSQRT ATPMGHIGEP NDIAWICVYL ASDESKFATG   240
AEFVVDGGYT AQ                                                      252
```

| SEQ ID NO: 381 | moltype = DNA length = 756 |
|---|---|
| FEATURE | Location/Qualifiers |
| misc_feature | 1..756 |
| | note = Engineered Variant of Kred from Lactobacillus kefir |
| source | 1..756 |
| | mol_type = other DNA |
| | organism = synthetic construct |

SEQUENCE: 381

| | | |
|---|---|---|
| atgaccgatc gtctgaagca caaagtagcc atcatcaccg gcgggacaat gggtatcggt | 60 |
| ttggcaatcg ccgataaatt tgtagaggag ggtgcgaaag tagttattac tggtcgtcac | 120 |
| gcggatgtag gtgagaaagc cgccaaatca atcggtggca gtgatgttat tcgctttgtc | 180 |
| cagcacgatg cgtccgaaga agcaggctgg acgaccctgt tcgacaccac cgaggaggca | 240 |
| ttcggcccgg ttacgaccct ggtgaacaat gcagggattg ggtaattaa gagcgttgaa | 300 |
| cggactacca cggaggaatg gcgtgatgtt ctgtccgtta atctggatgg tgttttttc | 360 |
| ggcacccgtc tgggcattca gcgcatgaaa aataaaggct tgggcgctag catcatcaat | 420 |
| atgagcagta ttatggggat cgtaggcgct ccggccgccg gggcatacaa cgcttccaag | 480 |
| ggggcggtac gtatcatgtc gaaaagcgca gcgctggatt gcgcactgaa ggactacgat | 540 |
| gtgcgtgtca acacagtaca tccgggcgcg atcaagaccg agtcgaagga tcagctgaa | 600 |
| ggttgggagc aggcaatgtc acagcgtacg gcgacccta tgggccacat tggcgaaccg | 660 |
| aatgacatcg catggatctg tgtgtacctg gcatctgacg aatcgaaatt tgcgacgggt | 720 |
| gcagaatttg tggtcgacgg cgggtacacc gcacag | 756 |

| SEQ ID NO: 382 | moltype = AA length = 252 |
|---|---|
| FEATURE | Location/Qualifiers |
| REGION | 1..252 |
| | note = Engineered Variant of Kred from Lactobacillus kefir |
| source | 1..252 |
| | mol_type = protein |
| | organism = synthetic construct |

SEQUENCE: 382

| | |
|---|---|
| MTDRLKHKVA IITGGTMGIG LAIADKFVEE GAKVVITGRH ADVGEKAAKS IGGSDVIRFV | 60 |
| QHDASEEAGW TTLFDTTEEA FGPVTTLVNN AGIGVIKSVE RTTTEEWRDV LSVNLDGVFF | 120 |
| GTRLGIQRMK NKGLGASIIN MSSIMGIVGA PAAGAYNASK GAVRIMSKSA ALDCALKDYD | 180 |
| VRVNTVHPGA IKTESKDQLE GWEQAMSQRT ATPMGHIGEP NDIAWICVYL ASDESKFATG | 240 |
| AEFVVDGGYT AQ | 252 |

| SEQ ID NO: 383 | moltype = DNA length = 756 |
|---|---|
| FEATURE | Location/Qualifiers |
| misc_feature | 1..756 |
| | note = Engineered Variant of Kred from Lactobacillus kefir |
| source | 1..756 |
| | mol_type = other DNA |
| | organism = synthetic construct |

SEQUENCE: 383

| | |
|---|---|
| atgaccgatc gtctgaagca caaagtagcc atcatcaccg gcgggacaat gggtatcggt | 60 |
| ttggcaatcg ccgataaatt tgtagaggag ggtgcgaaag tagttattac tggtcgtcac | 120 |
| gcggatgtag gtgagaaagc cgccaaatca atcggtggca gtgatgttat tcgctttgtc | 180 |
| cagcacgatg cgtccgaaga agcaggctgg acgaccctgt tcgacaccac cgaggaggca | 240 |
| ttcggcccgg ttacgaccct ggtgaacaat gcagggattg ggtaattaa gagcgttgaa | 300 |
| cgcactacca cggaggaatg gcgtgatgtt ctgtccgtta atctggatgg tgttttttc | 360 |
| ggcacccgtc tgggcattca gcgcatgaaa aataaaggct tgggcgctag catcatcaat | 420 |
| atgagcagta ttatggggat cgtaggcgct ccggccgccg gggcatacaa cgcttccaag | 480 |
| ggggcggtac gtatcatgtc gaaaagcgca gcgctggatt gcgcactgaa ggactacgat | 540 |
| gtgcgtgtca acacagtaca tccgggcgcg atcaagaccg aatcgaagga tcagctgcca | 600 |
| ggttgggagc aggcaatgtc acagcgtacg gcgacccta tgggccacat tggcgaaccg | 660 |
| aatgacatcg catggatctg tgtgtacctg gcatctgacg aatcgaaatt tgcgacgggt | 720 |
| gcagaatttg tggtcgacgg cgggtacacc gcacag | 756 |

| SEQ ID NO: 384 | moltype = AA length = 252 |
|---|---|
| FEATURE | Location/Qualifiers |
| REGION | 1..252 |
| | note = Engineered Variant of Kred from Lactobacillus kefir |
| source | 1..252 |
| | mol_type = protein |
| | organism = synthetic construct |

SEQUENCE: 384

| | |
|---|---|
| MTDRLKHKVA IITGGTMGIG LAIADKFVEE GAKVVITGRH ADVGEKAAKS IGGSDVIRFV | 60 |
| QHDASEEAGW TTLFDTTEEA FGPVTTLVNN AGIGVIKSVE RTTTEEWRDV LSVNLDGVFF | 120 |
| GTRLGIQRMK NKGLGASIIN MSSIMGIVGA PAAGAYNASK GAVRIMSKSA ALDCALKDYD | 180 |
| VRVNTVHPGA IKTESKDQLP GWEQAMSQRT ATPMGHIGEP NDIAWICVYL ASDESKFATG | 240 |
| AEFVVDGGYT AQ | 252 |

| SEQ ID NO: 385 | moltype = DNA length = 756 |
|---|---|
| FEATURE | Location/Qualifiers |
| misc_feature | 1..756 |
| | note = Engineered Variant of Kred from Lactobacillus kefir |
| source | 1..756 |
| | mol_type = other DNA |
| | organism = synthetic construct |

-continued

```
SEQUENCE: 385
atgaccgatc gtctgaagca caaagtagcc atcatcaccg gcgggacaat gggtatcggt    60
ttggcaatcg ccgataaatt tgtagaggag ggtgcgaaag tagttattac tggtcgtcac   120
gcggatgtag gtgagaaagc cgccaaatca atcggtggca gtgatgttat tcgctttgtc   180
cagcacgatg cgtccgaaga agcaggctgg acgaccgtgt tcgacaccac cgaggaggca   240
ttcggcccgg ttacgaccct ggtgaacaat gcagggattg ggttaattaa gagcgttgaa   300
cggactacca cggaggaatg gcgtgatgtt ctgtccgtta atctggatgg tgttttttc   360
ggcacccgtc tggcattca gcgcatgaaa aataaaggct tgggcgctag catcatcaat   420
atgagcagta ttatgggct ggtaggcgct ccggccgccg gggcatacaa cgcttccaag   480
ggggcggtac gtatcatgtc gaaaagcgca gcgctggatt gcgcactgaa ggactacgat   540
gtgcgtgtca acacagtaca tccgggcgcg atcaagaccg aatcgaagga tcagctggag   600
ggttgggagc aggcaatgtc acagcgtacg gcgaccccta tgggccacat tggcgaaccg   660
aatgacatcg catggatctg tgtgtacctg gcatctgacg aatcgaaatt tgcgacgggt   720
gcagaatttg tggtcgacgg cgggtacacc gcacag                              756

SEQ ID NO: 386         moltype = AA   length = 252
FEATURE                Location/Qualifiers
REGION                 1..252
                       note = Engineered Variant of Kred from Lactobacillus kefir
source                 1..252
                       mol_type = protein
                       organism = synthetic construct
SEQUENCE: 386
MTDRLKHKVA IITGGTMGIG LAIADKFVEE GAKVVITGRH ADVGEKAAKS IGGSDVIRFV    60
QHDASEEAGW TTVFDTTEEA FGPVTTLVNN AGIGVIKSVE RTTTEEWRDV LSVNLDGVFF   120
GTRLGIQRMK NKGLGASIIN MSSIMGLVGA PAAGAYNASK GAVRIMSKSA ALDCALKDYD   180
VRVNTVHPGA IKTESKDQLE GWEQAMSQRT ATPMGHIGEP NDIAWICVYL ASDESKFATG   240
AEFVVDGGYT AQ                                                      252

SEQ ID NO: 387         moltype = DNA   length = 756
FEATURE                Location/Qualifiers
misc_feature           1..756
                       note = Engineered Variant of Kred from Lactobacillus kefir
source                 1..756
                       mol_type = other DNA
                       organism = synthetic construct
SEQUENCE: 387
atgaccgatc gtctgaagca caaagtagcc atcatcaccg gcgggacaat gggtatcggt    60
ttggcaatcg ccgataaatt tgtagaggag ggtgcgaaag tagttattac tggtcgtcac   120
gcggatgtag gtgagaaagc cgccaaatca atcggtggca gtgatgttat tcgctttgtc   180
cagcacgatg cgtccgaaga agcaggctgg acgaccgtgt tcgacaccac cgaggaggca   240
ttcggcccgg ttacgaccct ggtgaacaat gcagggattg ggttatcaa gagcgttgaa   300
cgcactacca cggaggaatg gcgtgatgtt ctgtccgtta atctggatgg tgttttttc   360
ggcacccgtc tggcattca gcgcatgaaa aataaaggct tgggcgctag catcatcaat   420
atgagcagta ttatggggat cgtaggcgct ccggccgccg gggcatacaa cgcttccaag   480
ggggcggtac gtatcatgtc gaaaagcgca gcgctggatt gcgcactgaa ggactacgat   540
gtgcgtgtca acacagtaca tccgggcgcg atcaagaccg aatcgaagga tcagctggag   600
ggttgggagc aggcaatgtc acagcgtacg gcgaccccta tgggccacat tggcgaaccg   660
aatgacatcg catggatctg tgtgtacctg gcatctgacg aatcgaaatt tgcgacgggt   720
gcagaatttg tggtcgacgg cgggtacacc gcacag                              756

SEQ ID NO: 388         moltype = AA   length = 252
FEATURE                Location/Qualifiers
REGION                 1..252
                       note = Engineered Variant of Kred from Lactobacillus kefir
source                 1..252
                       mol_type = protein
                       organism = synthetic construct
SEQUENCE: 388
MTDRLKHKVA IITGGTMGIG LAIADKFVEE GAKVVITGRH ADVGEKAAKS IGGSDVIRFV    60
QHDASEEAGW TTVFDTTEEA FGPVTTLVNN AGIGVIKSVE RTTTEEWRDV LSVNLDGVFF   120
GTRLGIQRMK NKGLGASIIN MSSIMGIVGA PAAGAYNASK GAVRIMSKSA ALDCALKDYD   180
VRVNTVHPGA IKTESKDQLE GWEQAMSQRT ATPMGHIGEP NDIAWICVYL ASDESKFATG   240
AEFVVDGGYT AQ                                                      252

SEQ ID NO: 389         moltype = DNA   length = 756
FEATURE                Location/Qualifiers
misc_feature           1..756
                       note = Engineered Variant of Kred from Lactobacillus kefir
source                 1..756
                       mol_type = other DNA
                       organism = synthetic construct
SEQUENCE: 389
atgaccgatc gtctgaagca caaagtagcc atcatcaccg gcgggacagc cggtatcggt    60
ttggcaatcg ccgataaatt tgtagaggag ggtgcgaaag tagttattac tggtcgtcac   120
gcggatgtag gtgagaaagc cgccaaatca atcggtggca gtgatgttat tcgctttgtc   180
cagcacgatg cgtccgaaga agcaggctgg acgaccctgt tcgacaccac cgaggaggca   240
ttcggcccgg ttacgaccct ggtgaacaat gcagggattg ggttaattaa gagcgttgaa   300
cggactacca cggaggaatg gcgtgatgtt ctgtccgtta atcaggatgg tgttttttc   360
```

```
ggcacccgtc tgggcattca gcgcatgaaa aataaaggct tgggcgctag catcatcaat    420
atgagcagta ttatggggct ggtaggcgct ccggccgccg gggcatacaa cgcttccaag    480
ggggcggtac gtatcatgtc gaaaagcgca gcgctggatt gcgcactgaa ggactacgat    540
gtgcgtgtca acacagtaca tccgggcgcg atcaagaccg agtcgaagga tcagctgaa     600
ggttgggagc aggcaatgtc acagcgtacg gcgacccca tgggcacat tggcgaaccg      660
aatgacatcg catggatctg tgtgtacctg gcatctgacg aatcgaaatt tgcgacgggt    720
gcagaatttg tggtcgacgg cgggtacacc gcacag                              756

SEQ ID NO: 390          moltype = AA  length = 252
FEATURE                 Location/Qualifiers
REGION                  1..252
                        note = Engineered Variant of Kred from Lactobacillus kefir
source                  1..252
                        mol_type = protein
                        organism = synthetic construct
SEQUENCE: 390
MTDRLKHKVA IITGGTAGIG LAIADKFVEE GAKVVITGRH ADVGEKAAKS IGGSDVIRFV     60
QHDASEEAGW TTLFDTTEEA FGPVTTLVNN AGIGVIKSVE RTTTEEWRDV LSVNQDGVFF    120
GTRLGIQRMK NKGLGASIIN MSSIMGLVGA PAAGAYNASK GAVRIMSKSA ALDCALKDYD    180
VRVNTVHPGA IKTESKDQLE GWEQAMSQRT ATPMGHIGEP NDIAWICVYL ASDESKFATG    240
AEFVVDGGYT AQ                                                       252

SEQ ID NO: 391          moltype = DNA  length = 756
FEATURE                 Location/Qualifiers
misc_feature            1..756
                        note = Engineered Variant of Kred from Lactobacillus kefir
source                  1..756
                        mol_type = other DNA
                        organism = synthetic construct
SEQUENCE: 391
atgaccgatc gtctgaagca caaagtagcc atcatcaccg gcgggacagc cggtatcggt     60
ttggcaatcg ccgataaatt tgtagaggag ggtgcgaaag tagttattac tggtcgtcac    120
gcggatgtag gtgagaaagc cgccaaatca atcggtggca gtgatgttat tcgctttgtc    180
cagcacgatg cgtccgaaga agcaggctgg acgaccgtgt tcgacaccac cgaggaggca    240
ttcggcccgg ttacgacccc tggtgaacaa tgcagggattg ggtaattaa gagcgtttgaa   300
cggactacca cggaggaatg gcgtgatgtt ctgtccgtta atctggatgg tgttttttc     360
ggcacccgtc tgggcattca gcgcatgaaa aataaaggct tgggcgctag catcatcaat    420
atgagcagta ttatggggct ggtaggcgct ccggccgccg gggcatacaa cgcttccaag    480
ggggcggtac gtatcatgtc gaaaagcgca gcgctgatt gcgcactgaa ggactacgat     540
gtgcgtgtca acacagtaca tccgggcgcg atcaagaccg aatcgaagga tcagctgcca    600
ggttgggagc aggcaatgtc acagcgtacg gcgacccta tgggcacat tggcgaaccg      660
aatgacatcg catggatctg tgtgtacctg gcatctgacg aatcgaaatt tgcgacgggt    720
gcagaatttg tggtcgacgg cgggtacacc gcacag                              756

SEQ ID NO: 392          moltype = AA  length = 252
FEATURE                 Location/Qualifiers
REGION                  1..252
                        note = Engineered Variant of Kred from Lactobacillus kefir
source                  1..252
                        mol_type = protein
                        organism = synthetic construct
SEQUENCE: 392
MTDRLKHKVA IITGGTAGIG LAIADKFVEE GAKVVITGRH ADVGEKAAKS IGGSDVIRFV     60
QHDASEEAGW TTVFDTTEEA FGPVTTLVNN AGIGVIKSVE RTTTEEWRDV LSVNLDGVFF    120
GTRLGIQRMK NKGLGASIIN MSSIMGLVGA PAAGAYNASK GAVRIMSKSA ALDCALKDYD    180
VRVNTVHPGA IKTESKDQLP GWEQAMSQRT ATPMGHIGEP NDIAWICVYL ASDESKFATG    240
AEFVVDGGYT AQ                                                       252

SEQ ID NO: 393          moltype = DNA  length = 756
FEATURE                 Location/Qualifiers
misc_feature            1..756
                        note = Engineered Variant of Kred from Lactobacillus kefir
source                  1..756
                        mol_type = other DNA
                        organism = synthetic construct
SEQUENCE: 393
atgaccgatc gtctgaagca caaagtagcc atcatcaccg gcgggacaat gggtatcggt     60
ttggcaatcg ccgataaatt tgtagaggag ggtgcgaaag tagttattac tggtcgtcac    120
gcggatgtag gtgagaaagc cgccaaatca atcggtggca gtgatgttat tcgctttgtc    180
cagcacgatg cgtccgaaga agcaggctgg acgaccctgt tcgacaccac cgaggaggca    240
ttcggcccgg ttacgacccc tggtgaacaa tgcagggattg ggtaattaa gagcgttgaa    300
cggactacca cggaggaatg gcgtgatgtt ctgtccgtta atctggatgg tgttttttc     360
ggcacccgtc tgggcattca gcgcatgaaa aataaaggct tgggcgctag catcatcaat    420
atgagcagta ttatggggct ggtaggcgct ccggccgccg gggcatacaa cgcttccaag    480
ggggcggtac gtatcatgtc gaaaagcgca gcgctggatt gcgcactgaa ggactacgat    540
gtgcgtgtca acacagtaca tccgggcgcg atcaagaccg agtcgaagga tggcctgaa    600
ggttgggagc aggcaatgtc acagcgtacg gcgacccta tgggcacat tggcgaaccg      660
aatgacatcg catggatctg tgtgtacctg gcatctgacg aatcgaaatt tgcgacgggt    720
gcagaatttg tggtcgacgg cgggtacacc gcacag                              756
```

```
SEQ ID NO: 394          moltype = AA  length = 252
FEATURE                 Location/Qualifiers
REGION                  1..252
                        note = Engineered Variant of Kred from Lactobacillus kefir
source                  1..252
                        mol_type = protein
                        organism = synthetic construct
SEQUENCE: 394
MTDRLKHKVA IITGGTMGIG LAIADKFVEE GAKVVITGRH ADVGEKAAKS IGGSDVIRFV   60
QHDASEEAGW TTLFDTTEEA FGPVTTLVNN AGIGVIKSVE RTTTEEWRDV LSVNLDGVFF  120
GTRLGIQRMK NKGLGASIIN MSSIMGLVGA PAAGAYNASK GAVRIMSKSA ALDCALKDYD  180
VRVNTVHPGA IKTESKDGLE GWEQAMSQRT ATPMGHIGEP NDIAWICVYL ASDESKFATG  240
AEFVVDGGYT AQ                                                      252

SEQ ID NO: 395          moltype = DNA  length = 756
FEATURE                 Location/Qualifiers
misc_feature            1..756
                        note = Engineered Variant of Kred from Lactobacillus kefir
source                  1..756
                        mol_type = other DNA
                        organism = synthetic construct
SEQUENCE: 395
atgaccgatc gtctgaagca caaagtagcc atcatcaccg gcgggacaat gggtatcggt   60
ttggcaatcg ccgataaatt tgtagaggag ggtgcgaaag tagttattac tggtcgtcac  120
gcggatgtag gtgagaaagc cgccaaatca atcggtggca gtgatgttat tcgctttgtc  180
cagcacgatg cgtccgaaga agcaggctgg acgaccctgt tcgacaccac cgaggaggca  240
ttcggcccgg ttacgaccct ggtgaacaat gcagggattg gggtaattaa gagcgttgaa  300
cggactacca cggaggaatg gcgtgatgtt ctgtccgtta atctggatgg tgttttttc   360
ggcacccgtc tgggcattca gcgcatgaaa aataaaggct gggcgctag catcatcaat   420
atgagcagta ttatggggct ggtaggcgct ccgccgccg gggcatacaa cgcttccaag   480
ggggcggtac gtatcatgtc gaaaagcgca gcgctggatt gcgcactgaa ggactacgat   540
gtgcgtgtca acacagtaca tccgggcgcg atcaagaccg agtcgaagga tcgcctggaa  600
ggttgggagc aggcaatgtc acagcgtacg gcgacccta tggcacat tggcgaaccg   660
aatgacatcg catggatctg tgtgtacctg gcatctgacg aatcgaaatt tgcgacgggt  720
gcagaatttg tggtcgacgg cgggtacacc gcacag                            756

SEQ ID NO: 396          moltype = AA  length = 252
FEATURE                 Location/Qualifiers
REGION                  1..252
                        note = Engineered Variant of Kred from Lactobacillus kefir
source                  1..252
                        mol_type = protein
                        organism = synthetic construct
SEQUENCE: 396
MTDRLKHKVA IITGGTMGIG LAIADKFVEE GAKVVITGRH ADVGEKAAKS IGGSDVIRFV   60
QHDASEEAGW TTLFDTTEEA FGPVTTLVNN AGIGVIKSVE RTTTEEWRDV LSVNLDGVFF  120
GTRLGIQRMK NKGLGASIIN MSSIMGLVGA PAAGAYNASK GAVRIMSKSA ALDCALKDYD  180
VRVNTVHPGA IKTESKDRLE GWEQAMSQRT ATPMGHIGEP NDIAWICVYL ASDESKFATG  240
AEFVVDGGYT AQ                                                      252

SEQ ID NO: 397          moltype = DNA  length = 756
FEATURE                 Location/Qualifiers
misc_feature            1..756
                        note = Engineered Variant of Kred from Lactobacillus kefir
source                  1..756
                        mol_type = other DNA
                        organism = synthetic construct
SEQUENCE: 397
atgaccgatc gtctgaagca caaagtagcc atcatcaccg gcgggacaat gggtatcggt   60
ttggcaatcg ccgataaatt tgtagaggag ggtgcgaaag tagttattac tggtcgtcac  120
gcggatgtag gtgagaaagc cgccaaatca atcggtggca gtgatgttat tcgctttgtc  180
cagcacgatg cgtccgaaga acgtggctgg acggaccctgt tcgacaccac cgaggaggca  240
ttcggcccgg ttacgaccct ggtgaacaat gcagggattg gggtaattaa gagcgttgaa  300
caaactacta cggaggaatg gcgtgatgtt ctgtccgtta atctggatgg tgttttttc   360
ggcacccgtc tgggcattca gcgcatgaaa aataaaggct gggcgctag catcatcaat   420
atgagcagta ttatggggct ggtaggcgct ccgcaggccg gggcatacaa cgcttccaag   480
ggggcggtac gtatcatgtc gaaaagcgca gcgctggatt gcgcactgaa ggactacgat   540
gtgcgtgtca acacagtaca tccgggcgcg atcaagaccg agtcgaagga tcagctggaa  600
ggttgggagc agctgatgtc acagcgtacg gcgacccta tggccacat tggcgaaccg   660
aatgacatcg catggatctg tgtgtacctg gcatctgacg aatcgaaatt tgcgacgggt  720
gcagaatttg tggtcgacgg cgggtacacc gcacag                            756

SEQ ID NO: 398          moltype = AA  length = 252
FEATURE                 Location/Qualifiers
REGION                  1..252
                        note = Engineered Variant of Kred from Lactobacillus kefir
source                  1..252
                        mol_type = protein
```

```
                        organism = synthetic construct
SEQUENCE: 398
MTDRLKHKVA IITGGTMGIG LAIADKFVEE GAKVVITGRH ADVGEKAAKS IGGSDVIRFV    60
QHDASEERGW TDLFDTTEEA FGPVTTLVNN AGIGVIKSVE QTTTEEWRDV LSVNLDGVFF   120
GTRLGIQRMK NKGLGASIIN MSSIMGLVGA PQAGAYNASK GAVRIMSKSA ALDCALKDYD   180
VRVNTVHPGA IKTESKDQLE GWEQLMSQRT ATPMGHIGEP NDIAWICVYL ASDESKFATG   240
AEFVVDGGYT AQ                                                      252

SEQ ID NO: 399          moltype = DNA  length = 756
FEATURE                 Location/Qualifiers
misc_feature            1..756
                        note = Engineered Variant of Kred from Lactobacillus kefir
source                  1..756
                        mol_type = other DNA
                        organism = synthetic construct
SEQUENCE: 399
atgaccgatc gtctgaagca caaagtagcc atcatcaccg gcgggacaat gggtatcggt    60
ttggcaatcg ccgataaatt tgtagaggag ggtgcgaaag tagttattac tggtcgtcac   120
gcggatgtag gtgagaaagc cgccaaatca atcggtggca gtgatgttat tcgctttgtc   180
cagcacgatg cgtccgaaga gaggggctgg acggacctgt tcgacaccac cgaggaggca   240
ttcggcccgt tacgaccct ggtgaacaat gcagggattg ggtaattaa gagcgttgaa    300
aagactacta cggaggaatg gcgtgatgtt ctgtccgtta atctggatgg tgtttttttc   360
ggcacccgtc tgggcattca gcgcatgaaa aataaaggct tgggcgctag catcatcaat   420
atgagcagta ttatggggct ggtaggcgct ccgcaggccg gggcatacaa cgcttccaag   480
ggggcggtac gtatcatgtc gaaaagcgca gcgctggatt gcgcactgaa ggactacgat   540
gtgcgtgtca acacagtaca tccgggcgcg atcaagaccg agtcgaagga tcagctggaa   600
ggttgggagc agctgatgtc acagcgtacg gcgaccccta tgggccacat tggcgaaccg   660
aatgacatcg catggatctg tgtgtacctg gcatctgacg aatcgaaatt tgcgacgggt   720
gcagaatttg tggtcgacgg cgggtacacc gcacag                            756

SEQ ID NO: 400          moltype = AA  length = 252
FEATURE                 Location/Qualifiers
REGION                  1..252
                        note = Engineered Variant of Kred from Lactobacillus kefir
source                  1..252
                        mol_type = protein
                        organism = synthetic construct
SEQUENCE: 400
MTDRLKHKVA IITGGTMGIG LAIADKFVEE GAKVVITGRH ADVGEKAAKS IGGSDVIRFV    60
QHDASEEEGW TDLFDTTEEA FGPVTTLVNN AGIGVIKSVE KTTTEEWRDV LSVNLDGVFF   120
GTRLGIQRMK NKGLGASIIN MSSIMGLVGA PQAGAYNASK GAVRIMSKSA ALDCALKDYD   180
VRVNTVHPGA IKTESKDQLE GWEQLMSQRT ATPMGHIGEP NDIAWICVYL ASDESKFATG   240
AEFVVDGGYT AQ                                                      252

SEQ ID NO: 401          moltype = DNA  length = 756
FEATURE                 Location/Qualifiers
misc_feature            1..756
                        note = Engineered Variant of Kred from Lactobacillus kefir
source                  1..756
                        mol_type = other DNA
                        organism = synthetic construct
SEQUENCE: 401
atgaccgatc gtctgaagca caaagtagcc atcatcaccg gcgggacaat gggtatcggt    60
ttggcaatcg ccgataaatt tgtagaggag ggtgcgaaag tagttattac tggtcgtcac   120
gcggatgtag gtgagaaagc cgccaaatca atcggtggca gtgatgttat tcgctttgtc   180
cagcacgatg cgtccgaaga agcgggctgg acgacgctgt tcgacaccac cgaggaggca   240
ttcggcccgg ttacgaccct ggtgaacaat gcagggattg ggtaattaa gagcgttgaa    300
atgactacta cggaggaatg gcgtgatgtt ctgtccgtta atctggatgg tgtttttttc   360
ggcacccgtc tgggcattca gcgcatgaaa aataaaggct tgggcgctag catcatcaat   420
atgagcagta ttatgggct ggtaggcgct ccggccgccg gggcatacaa cgcttccaag    480
ggggcggtac gtatcatgtc gaaaagcgca gcgctggatt gcgcactgaa ggactacgat   540
gtgcgtgtca acacagtaca tccgggcgcg atcaagaccg agtcgaagga tcagctggaa   600
ggttgggagc agctgatgtc acagcgtacg gcgaccccta tgggccacat tggcgaaccg   660
aatgacatcg catggatctg tgtgtacctg gcatctgacg aatcgaaatt tgcgacgggt   720
gcagaatttg tggtcgacgg cgggtacacc gcacag                            756

SEQ ID NO: 402          moltype = AA  length = 252
FEATURE                 Location/Qualifiers
REGION                  1..252
                        note = Engineered Variant of Kred from Lactobacillus kefir
source                  1..252
                        mol_type = protein
                        organism = synthetic construct
SEQUENCE: 402
MTDRLKHKVA IITGGTMGIG LAIADKFVEE GAKVVITGRH ADVGEKAAKS IGGSDVIRFV    60
QHDASEEAGW TTLFDTTEEA FGPVTTLVNN AGIGVIKSVE MTTTEEWRDV LSVNLDGVFF   120
GTRLGIQRMK NKGLGASIIN MSSIMGLVGA PAAGAYNASK GAVRIMSKSA ALDCALKDYD   180
VRVNTVHPGA IKTESKDQLE GWEQLMSQRT ATPMGHIGEP NDIAWICVYL ASDESKFATG   240
AEFVVDGGYT AQ                                                      252
```

```
SEQ ID NO: 403            moltype = DNA  length = 756
FEATURE                   Location/Qualifiers
misc_feature              1..756
                          note = Engineered Variant of Kred from Lactobacillus kefir
source                    1..756
                          mol_type = other DNA
                          organism = synthetic construct
SEQUENCE: 403
atgaccgatc gtctgaagca caaagtagcc atcatcaccg gcgggacaat gggtatcggt   60
ttggcaatcg ccgataaatt tgtagaggag ggtgcgaaag tagttattac tggtcgtcac  120
gcggatgtag gtgagaaagc cgccaaatca atcggtggca gtgatgttat tcgctttgtc  180
cagcacgatg cgtccgaaga acgtggctgg acgcgcctgt tcgacaccac cgaggaggca  240
ttcggcccgg ttacgaccct ggtgaacaat gcagggattg ggtaattaa gagcgttgaa   300
cggactacca cggaggaatg gcgtgatgtt ctgtccgtta atctggatgg tgttttttc   360
ggcacccgtg agggcattca gcgcatgaaa aataaaggct gggcgctag catcatcaat  420
atgagcagta ttatggggct ggtaggcgct ccggccgccg ggcatacaa cgcttccaag  480
ggggcggtac gtatcatgtc gaaaagcgca gcgctggatt gcgcactgaa ggactacgat  540
gtgcgtgtca acacagtaca tccgggcgcg atcaagaccg agtcgaagga tcagctggaa  600
ggttgggagc aggcaatgtc acagcgtacg gcgacccta tgggccacat tggcgaaccg   660
aatgacatcg catggatctg tgtgtacctg gcatctgacg aatcgaaatt tgcgacgggt  720
gcagaatttg tggtcgacgg cgggtacacc gcacag                             756

SEQ ID NO: 404            moltype = AA  length = 252
FEATURE                   Location/Qualifiers
REGION                    1..252
                          note = Engineered Variant of Kred from Lactobacillus kefir
source                    1..252
                          mol_type = protein
                          organism = synthetic construct
SEQUENCE: 404
MTDRLKHKVA IITGGTMGIG LAIADKFVEE GAKVVITGRH ADVGEKAAKS IGGSDVIRFV   60
QHDASEERGW TRLFDTTEEA FGPVTTLVNN AGIGVIKSVE RTTTEEWRDV LSVNLDGVFF  120
GTREGIQRMK NKGLGASIIN MSSIMGLVGA PAAGAYNASK GAVRIMSKSA ALDCALKDYD  180
VRVNTVHPGA IKTESKDQLE GWEQAMSQRT ATPMGHIGEP NDIAWICVYL ASDESKFATG  240
AEFVVDGGYT AQ                                                       252

SEQ ID NO: 405            moltype = DNA  length = 756
FEATURE                   Location/Qualifiers
misc_feature              1..756
                          note = Engineered Variant of Kred from Lactobacillus kefir
source                    1..756
                          mol_type = other DNA
                          organism = synthetic construct
SEQUENCE: 405
atgaccgatc gtctgaagca caaagtagcc atcatcaccg gcgggacaat gggtatcggt   60
ttggcaatcg ccgataaatt tgtagaggag ggtgcgaaag tagttattac tggtcgtcac  120
gcggatgtag gtgagaaagc cgccaaatca atcggtggca gtgatgttat tcgctttgtc  180
cagcacgatg cgtccgaaga acgtggctgg acgcgcctgt tcgacaccac cgaggaggca  240
ttcggcccgg ttacgaccct ggtgaacaat gcagggattg ggtaattaa gagcgttgaa   300
cgcactacta cggaggaatg gcgtgatgtt ctgtccgtta atctggatgg tgttttttc   360
ggcacccgtg agggcattca gcgcatgaaa aataaaggct gggcgctag catcatcaat  420
atgagcagta ttatggggct ggtaggcgct ccggcaggccg ggcatacaa cgcttccaag  480
ggggcggtac gtatcatgtc gaaaagcgca gcgctggatt gcgcactgaa ggactacgat  540
gtgcgtgtca acacagtaca tccgggcgcg atcaagaccg agtcgaagga tcagctggaa  600
ggttgggagc aggcaatgtc acagcgtacg gcgacccta tgggccacat tggcgaaccg   660
aatgacatcg catggatctg tgtgtacctg gcatctgacg aatcgaaatt tgcgacgggt  720
gcagaatttg tggtcgacgg cgggtacacc gcacag                             756

SEQ ID NO: 406            moltype = AA  length = 252
FEATURE                   Location/Qualifiers
REGION                    1..252
                          note = Engineered Variant of Kred from Lactobacillus kefir
source                    1..252
                          mol_type = protein
                          organism = synthetic construct
SEQUENCE: 406
MTDRLKHKVA IITGGTMGIG LAIADKFVEE GAKVVITGRH ADVGEKAAKS IGGSDVIRFV   60
QHDASEERGW TRLFDTTEEA FGPVTTLVNN AGIGVIKSVE RTTTEEWRDV LSVNLDGVFF  120
GTREGIQRMK NKGLGASIIN MSSIMGLVGA PQAGAYNASK GAVRIMSKSA ALDCALKDYD  180
VRVNTVHPGA IKTESKDQLE GWEQAMSQRT ATPMGHIGEP NDIAWICVYL ASDESKFATG  240
AEFVVDGGYT AQ                                                       252

SEQ ID NO: 407            moltype = DNA  length = 756
FEATURE                   Location/Qualifiers
misc_feature              1..756
                          note = Engineered Variant of Kred from Lactobacillus kefir
source                    1..756
                          mol_type = other DNA
```

```
                        organism = synthetic construct
SEQUENCE: 407
atgaccgatc gtctgaagca caaagtagcc atcatcaccg gcgggacaat gggtatcggt    60
ttggcaatcg ccgataaatt tgtagaggag ggtgcgaaag tagttattac tggtcgtcac   120
gcggatgtag gtgagaaagc cgccaaatca atcggtggca gtgatgttat tcgctttgtc   180
cagcacgatg cgtccgaaga gcgggctgg acggacctgt tcgacaccac cgaggaggca    240
ttcggcccgg ttacgaccct ggtgaacaat gcagggattg ggtaattaa gagcgttgaa    300
cggactacca cggaggaatg gcgtgatgtt ctgtccgtta atctggatgg tgttttttc    360
ggcacccgtc tgggcattca gcgcatgaaa aataaaggct gggcgctag catcatcaat    420
atgagcagta ttatggggct ggtaggcgct ccgcaggccg gggcatacaa cgcttccaag    480
ggggcggtac gtatcatgtc gaaaagcgca gcgctggatt gcgcactgaa ggactacgat    540
gtgcgtgtca acacagtaca tccgggcgcg atcaagaccg agtcgaagga tcagctggaa    600
ggttgggagc aggcaatgtc acagcgtacg gcgaccccta tgggccacat tggcgaaccg    660
aatgacatcg catggatctg tgtgtacctg gcatctgacg aatcgaaatt tgcgacgggt    720
gcagaatttg tggtcgacgg cgggtacacc gcacag                              756

SEQ ID NO: 408         moltype = AA  length = 252
FEATURE                Location/Qualifiers
REGION                 1..252
                       note = Engineered Variant of Kred from Lactobacillus kefir
source                 1..252
                       mol_type = protein
                       organism = synthetic construct
SEQUENCE: 408
MTDRLKHKVA IITGGTMGIG LAIADKFVEE GAKVVITGRH ADVGEKAAKS IGGSDVIRFV    60
QHDASEEAGW TDLFDTTEEA FGPVTTLVNN AGIGVIKSVE RTTTEEWRDV LSVNLDGVFF   120
GTRLGIQRMK NKGLGASIIN MSSIMGLVGA PQAGAYNASK GAVRIMSKSA ALDCALKDYD   180
VRVNTVHPGA IKTESKDQLE GWEQAMSQRT ATPMGHIGEP NDIAWICVYL ASDESKFATG   240
AEFVVDGGYT AQ                                                        252

SEQ ID NO: 409         moltype = DNA  length = 756
FEATURE                Location/Qualifiers
misc_feature           1..756
                       note = Engineered Variant of Kred from Lactobacillus kefir
source                 1..756
                       mol_type = other DNA
                       organism = synthetic construct
SEQUENCE: 409
atgaccgatc gtctgaagca caaagtagcc atcatcaccg gcgggacaat gggtatcggt    60
ttggcaatcg ccgataaatt tgtagaggag ggtgcgaaag tagttattac tggtcgtcac   120
gcggatgtag gtgagaaagc cgccaaatca atcggtggca gtgatgttat tcgctttgtc   180
cagcacgatg cgtccgaaga acgtggctgg acgacgctgt tcgacaccac cgaggaggca    240
ttcggcccgg ttacgaccct ggtgaacaat gcagggattg ggtaattaa gagcgttgaa    300
cggactacca cggaggaatg gcgtgatgtt ctgtccgtta atctggatgg tgttttttc    360
ggcacccgtg agggcattca gcgcatgaaa aataaaggct gggcgctag catcatcaat    420
atgagcagta ttatggggct ggtaggcgct ccggccgccg gggcatacaa cgcttccaag    480
ggggcggtac gtatcatgtc gaaaagcgca gcgctggatt gcgcactgaa ggactacgat    540
gtgcgtgtca acacagtaca tccgggcgcg atcaagaccg agtcgaagga tcagctggaa    600
ggttgggagc agctgatgtc acagcgtacg gcgaccccta tgggccacat tggcgaaccg    660
aatgacatcg catggatctg tgtgtacctg gcatctgacg aatcgaaatt tgcgacgggt    720
gcagaatttg tggtcgacgg cgggtacacc gcacag                              756

SEQ ID NO: 410         moltype = AA  length = 252
FEATURE                Location/Qualifiers
REGION                 1..252
                       note = Engineered Variant of Kred from Lactobacillus kefir
source                 1..252
                       mol_type = protein
                       organism = synthetic construct
SEQUENCE: 410
MTDRLKHKVA IITGGTMGIG LAIADKFVEE GAKVVITGRH ADVGEKAAKS IGGSDVIRFV    60
QHDASEERGW TTLFDTTEEA FGPVTTLVNN AGIGVIKSVE RTTTEEWRDV LSVNLDGVFF   120
GTREGIQRMK NKGLGASIIN MSSIMGLVGA PAAGAYNASK GAVRIMSKSA ALDCALKDYD   180
VRVNTVHPGA IKTESKDQLE GWEQLMSQRT ATPMGHIGEP NDIAWICVYL ASDESKFATG   240
AEFVVDGGYT AQ                                                        252

SEQ ID NO: 411         moltype = DNA  length = 756
FEATURE                Location/Qualifiers
misc_feature           1..756
                       note = Engineered Variant of Kred from Lactobacillus kefir
source                 1..756
                       mol_type = other DNA
                       organism = synthetic construct
SEQUENCE: 411
atgaccgatc gtctgaagca caaagtagcc atcatcaccg gcgggacaat gggtatcggt    60
ttggcaatcg ccgataaatt tgtagaggag ggtgcgaaag tagttattac tggtcgtcac   120
gcggatgtag gtgagaaagc cgccaaatca atcggtggca gtgatgttat tcgctttgtc   180
cagcacgatg cgtccgaaga acgtggctgg acgacgctgt tcgacaccac cgaggaggca    240
ttcggcccgg ttacgaccct ggtgaacaat gcagggattg ggtaattaa gagcgttgaa    300
```

```
caaactacta cggaggaatg gcgtgatgtt ctgtccgtta atctggatgg tgttttttc    360
ggcacccgtg agggcattca gcgcatgaaa aataaaggct tgggcgctag catcatcaat   420
atgagcagta ttatggggct ggtaggcgct ccgcaggccg gggcatacaa cgcttccaag   480
ggggcggtac gtatcatgtc gaaaagcgca gcgctggatt gcgcactgaa ggactacgat   540
gtgcgtgtca acacagtaca tccgggcgcg atcaagaccg agtcgaagga tcagctggaa   600
ggttgggagc agctgatgtc acagcgtacg gcgacccta tgggccacat tggcgaaccg    660
aatgacatcg catggatctg tgtgtacctg gcatctgacg aatcgaaatt tgcgacgggt   720
gcagaatttg tggtcgacgg cgggtacacc gcacag                             756

SEQ ID NO: 412          moltype = AA  length = 252
FEATURE                 Location/Qualifiers
REGION                  1..252
                        note = Engineered Variant of Kred from Lactobacillus kefir
source                  1..252
                        mol_type = protein
                        organism = synthetic construct
SEQUENCE: 412
MTDRLKHKVA IITGGTMGIG LAIADKFVEE GAKVVITGRH ADVGEKAAKS IGGSDVIRFV    60
QHDASEERGW TTLFDTTEEA FGPVTTLVNN AGIGVIKSVE QTTTEEWRDV LSVNLDGVFF   120
GTREGIQRMK NKGLGASIIN MSSIMGLVGA PQAGAYNASK GAVRIMSKSA ALDCALKDYD   180
VRVNTVHPGA IKTESKDQLE GWEQLMSQRT ATPMGHIGEP NDIAWICVYL ASDESKFATG   240
AEFVVDGGYT AQ                                                       252

SEQ ID NO: 413          moltype = DNA  length = 756
FEATURE                 Location/Qualifiers
misc_feature            1..756
                        note = KRED Variants
source                  1..756
                        mol_type = other DNA
                        organism = synthetic construct
SEQUENCE: 413
atgaccgatc gtctgaagca caaagtagcc atcatcaccg gcgggacaat gggtatcggt    60
ttggcaatcg ccgataaatt tgtagaggag ggtgcgaaag tagttattac tggtcgtcac   120
gcggatgtag gtgagaaagc cgccaaatca atcggtggca gtgatgttat tcgctttgtc   180
cagcacgatg cgtccgaaga agcaggctgg acgaccctgt tcgacaccac cgaggaggca   240
ttcggcccgg ttacgaccct ggtgaacaat gcaggggcag ggtcattaa gagcgttgaa    300
cggactacca cggaggaatg gcgtgatgtt ctgtccgtta atctggatgg tgttttttc    360
ggcacccgtc tgggcattca gcgcatgaaa aataaaggct tgggcgctag catcatcaat   420
atgagcagta ttatggggct ggtaggcgct ccggccgccg gggcatacaa cgcttccaag   480
ggggcggtac gtatcatgtc gaaaagcgca gcgctggatt gcgcactgaa ggactacgat   540
gtgcgtgtca acacagtaca tccgggcgcg atcaagaccg agcgcaagga tcagctggat   600
ggttgggagc aggcaatgtc acagcgtacg gcgacccta tgggccacat tggcgaaccg    660
aatgacatcg catggatctg tgtgtacctg gcatctgacg aatcgaaatt tgcgacgggt   720
gcagaatttg tggtcgacgg cgggtacacc gcacag                             756

SEQ ID NO: 414          moltype = AA  length = 252
FEATURE                 Location/Qualifiers
REGION                  1..252
                        note = KRED Variants
source                  1..252
                        mol_type = protein
                        organism = synthetic construct
SEQUENCE: 414
MTDRLKHKVA IITGGTMGIG LAIADKFVEE GAKVVITGRH ADVGEKAAKS IGGSDVIRFV    60
QHDASEEAGW TTLFDTTEEA FGPVTTLVNN AGAGVIKSVE RTTTEEWRDV LSVNLDGVFF   120
GTRLGIQRMK NKGLGASIIN MSSIMGLVGA PAAGAYNASK GAVRIMSKSA ALDCALKDYD   180
VRVNTVHPGA IKTERKDQLD GWEQAMSQRT ATPMGHIGEP NDIAWICVYL ASDESKFATG   240
AEFVVDGGYT AQ                                                       252

SEQ ID NO: 415          moltype = DNA  length = 756
FEATURE                 Location/Qualifiers
misc_feature            1..756
                        note = KRED Variants
source                  1..756
                        mol_type = other DNA
                        organism = synthetic construct
SEQUENCE: 415
atgaccgatc gtctgaagca caaagtagcc atcgtcaccg gcgggacagc gggtatcggt    60
ttggcaatcg ccgataaatt tgtagaggag ggtgcgaaag tagttattac tggtcgtcac   120
gcggatgtag gtgagaaagc cgccaaatca atcggtggca gtgatgttat tcgctttgtc   180
cagcacgatg cgtccgaaga agcaggctgg acgagcctgt tcgacaccac cgaggaagca   240
ttcggcccgg ttacgaccct ggtgaacaat gcaggggcag ggtcatcaa gagcgttgaa    300
cggactacca cggaggaatg gcgtgatgtt ctgtccgtta atctggatgg tgttttttc    360
ggcacccgtc tgggcattca gcgcatgaaa aataaaggct tgggcgctag catcatcaat   420
atgagcagta ttatggggct ggtaggcgct ccgatggccg ggcatacaa cgcttccaag    480
ggggcggtac gtatcatgtc gaaaagcgca gcgctggatt gcgcactgaa ggactacgat   540
gtgcgtgtca acacagtaca tccgggcgcg atcaagaccg aggctaagga tcagctggat   600
ggttgggagc aggcaatgtc acagcgtacg gcgacccta tgggccacat tggcgaaccg    660
aatgacatcg catggatctg tgtgtacctg gcatctgacg aatcgaaatt tgcgacgggt   720
```

```
gcagaatttg tggtcgacgg cgggtacacc gcacag                         756

SEQ ID NO: 416        moltype = AA  length = 252
FEATURE               Location/Qualifiers
REGION                1..252
                      note = KRED Variants
source                1..252
                      mol_type = protein
                      organism = synthetic construct
SEQUENCE: 416
MTDRLKHKVA IVTGGTAGIG LAIADKFVEE GAKVVITGRH ADVGEKAAKS IGGSDVIRFV   60
QHDASEEAGW TSLFDTTEEA FGPVTTLVNN AGAGVIKSVE RTTTEEWRDV LSVNLDGVFF  120
GTRLGIQRMK NKGLGASIIN MSSIMGLVGA PMAGAYNASK GAVRIMSKSA ALDCALKDYD  180
VRVNTVHPGA IKTEAKDQLD GWEQAMSQRT ATPMGHIGEP NDIAWICVYL ASDESKFATG  240
AEFVVDGGYT AQ                                                     252
```